(12) United States Patent
Iacone et al.

(10) Patent No.: US 10,519,450 B2
(45) Date of Patent: Dec. 31, 2019

(54) ANTISENSE OLIGONUCLEOTIDES FOR MODULATING HTRA1 EXPRESSION

(71) Applicant: F. HOFFMANN-LA ROCHE AG, Basel (CH)

(72) Inventors: Roberto Iacone, Basel (CH); Peter Hagedorn, Hørsholm (DK); Susanne Kammler, Hørsholm (DK); Soren Ottosen, Hørsholm (DK); Sindri Traustason, Hørsholm (DK); Heidi Hudlebusch, Hørsholm (DK); Lykke Pedersen, Hørsholm (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/635,629

(22) Filed: Jun. 28, 2017

(65) Prior Publication Data
US 2018/0002701 A1    Jan. 4, 2018

(30) Foreign Application Priority Data

Jul. 1, 2016 (EP) .................................. 16177508
May 9, 2017 (EP) .................................. 17170129

(51) Int. Cl.
| A61K 48/00 | (2006.01) |
| C07H 21/02 | (2006.01) |
| C07H 21/04 | (2006.01) |
| C12N 15/11 | (2006.01) |
| C12N 15/113 | (2010.01) |

(52) U.S. Cl.
CPC ...... *C12N 15/1137* (2013.01); *C12N 2310/11* (2013.01); *C12N 2310/315* (2013.01); *C12N 2310/3231* (2013.01); *C12N 2310/3341* (2013.01); *C12N 2310/344* (2013.01); *C12N 2310/346* (2013.01); *C12N 2310/351* (2013.01)

(58) Field of Classification Search
CPC ... C12N 15/11; C12N 15/113; C12N 15/1137; C12N 2310/11; C12N 2310/315; C12N 2310/341; C12N 2310/3341; C12N 2310/3231; C12N 2310/346; C12N 2310/351
See application file for complete search history.

(56) References Cited

U.S. PATENT DOCUMENTS

| 2010/0303832 A1 | 12/2010 | Hegeman |
| 2015/0141320 A1 | 5/2015 | Krieg et al. |
| 2019/0055564 A1 | 2/2019 | Sanchez et al. |

FOREIGN PATENT DOCUMENTS

| WO | WO9839352 | 9/1998 |
| WO | WO9914226 | 3/1999 |
| WO | WO00047599 | 8/2000 |

(Continued)

OTHER PUBLICATIONS

Bakay et al., "A web-accessible complete transcriptome of normal human and DMD muscle," Neuromuscul. Disord., Oct. 2002, 12(Suppl. 1):125-141.

(Continued)

*Primary Examiner* — Terra C Gibbs
(74) *Attorney, Agent, or Firm* — Fish & Richardson P.C.

(57) ABSTRACT

The present invention relates to antisense oligonucleotides (oligomers) that are complementary to HTRA1, leading to modulation of the expression of HTRA1. Modulation of HTRA1 expression is beneficial for a range of medical disorders, such as macular degeneration, e.g. age-related macular degeneration.

42 Claims, 16 Drawing Sheets
Specification includes a Sequence Listing.

(56) References Cited

FOREIGN PATENT DOCUMENTS

| | | |
|---|---|---|
| WO | WO0066604 | 11/2000 |
| WO | WO0123613 | 4/2001 |
| WO | WO2004046160 | 6/2004 |
| WO | WO2006127913 | 11/2006 |
| WO | WO2007031091 | 3/2007 |
| WO | WO2007090071 | 8/2007 |
| WO | WO2007134181 | 11/2007 |
| WO | WO 2008013893 | 1/2008 |
| WO | WO 2008067040 | 6/2008 |
| WO | WO 2008094370 | 8/2008 |
| WO | WO2008150729 | 12/2008 |
| WO | WO2008154401 | 12/2008 |
| WO | WO 2009006460 | 1/2009 |
| WO | WO2009006478 | 1/2009 |
| WO | WO2009067647 | 5/2009 |
| WO | WO10036698 | 4/2010 |
| WO | WO2010077578 | 7/2010 |
| WO | WO2011017521 | 2/2011 |
| WO | WO2011156202 | 12/2011 |
| WO | WO0008134 | 2/2012 |
| WO | WO2012038668 | 3/2012 |
| WO | WO2013036868 | 3/2013 |
| WO | WO2013154798 | 10/2013 |
| WO | WO2014076195 | 5/2014 |
| WO | WO2017075212 | 5/2017 |
| WO | WO2018002105 | 1/2018 |
| WO | 2018087200 | 5/2018 |

OTHER PUBLICATIONS

Baldi et al., "The HtrA1 serine protease is down-regulated during human melanoma progression and represses growth of metastatic melanoma cells," Oncogene, Sep. 2002, 21(43):6684-6688.
Chien et al., "A candidate tumor suppressor HtrA1 is downregulated in ovarian cancer," Oncogene, Feb. 2004, 23(8):1636-1644.
Deleavey and Damha, "Designing chemically modified oligonucleotides for targeted gene silencing," Chemistry and Biology, Aug. 2012, 19(8), 937-954.
Dewan et al., "HTRA1 promoter polymorphism in wet age-related macular degenerat," Science, Nov. 2006, 314(5801):989-992.
Freier & Altmann, "The ups and downs of nucleic acid duplex stability: structure-stability studies on chemically-modified DNA:RNA duplexes," Nucl. Acid Res., Nov. 1997, 25(22):4429-4443.
Fritsche, et al., "Seven new loci associated with age-related macular degeneration," Nat Gen, Apr. 2013, 45(4):433-9.
Grau et al., "Implications of the serine protease HtrA1 in amyloid precursor protein processing," Proc. Nat. Acad. Sci. USA., Apr. 2005, 102(17):6021-6026.
Grau et al., "The role of human HtrA1 in arthritic disease," J. Biol. Chem., Mar. 2006, 281(10):6124-6129.
Hou et al., "The Secreted Serine Protease xHtrA1 Stimulates Long-Range FGF Signaling in the Early Xenopus Embryo," Developmental Cell, Aug. 2007, 13(2):226-241.
International Search Report and Written Opinion for International Application No. PCT/EP2017/065937, dated Sep. 11, 2017, 11 pages.
Jones et al., "Increased expression of multifunctional serine protease, HTRA1, in retinal pigment epithelium induces polypoidal choroidal vasculopathy in mice," Proceedings of the National Academy of Sciences, Aug. 2011, 108(35):14578-14583.
Kumar et al., "Angiographic Features of Transgenic Mice With Increased Expression of Human Serine Protease HTRA1 in Retinal Pigment Epithelium," Invest. Ophthalmol Vis. Sci., May 2014, 55(6):3842-3850.
Nakayama et al., "Overexpression of HtrA1 and Exposure to Mainstream Cigarette Smoke Leads to Choroidal Neovascularization and Subretinal Deposits in Aged Mice," Invest. Ophthalmol Vis. Sci., Sep. 2014, 55(10):6514-6523.

Oka et al., "HtrA1 serine protease inhibits signaling mediated by Tgfbeta family proteins," Development, Mar. 2004, 131(5):1041-1053.
Uhlmann, "Recent advances in the medicinal chemistry of antisense oligonucleotides," Curr. Opinion in Drug Development, Mar. 2000, 3(2), 203-213.
Vierkotten et al., "Overexpression of HTRA1 leads to ultrastructural changes in the elastic layer of Bruch's membrane via cleavage of extracellular matrix components," PlosOne, Aug. 2011, 6(8):e22959.
Xueting et al., "Inhibition of cell proliferation and migration afterHTRA1 knockdown in retinal pigment epithelial cells," Graefe's Archive for Clinical and Experimental Ophthalmology, Dec. 2014, 253(4):565-572.
Yang et al., "A variant of the HTRA1 gene increases susceptibility to age-related macular degeneration," Science, Nov. 2006, 314(5801):992-993.
Zumbrunn and Trueb, "Primary structure of a putative serine protease specific for IGF-binding proteins," FEES Letters, Dec. 1996, 398(2-3):189-192.
GenBank Accession No. NC_022280.1, "Macaca fascicularis chromosome 9, Macaca_fascicularis_5.0, whole genome shotgun sequence," Jan. 25, 2016, 2 pages.
GenBank Accession No. NM_002775.4, "*Homo sapiens* HtrA serine peptidase 1 (HTRA1), mRNA," Apr. 30, 2016, 5 pages.
International Search Report and Written Opinion for International Application No. PCT/EP2018/064221, dated Jul. 30, 2018, 18 pages.
Mitsuoka et al., "A bridged nucleic acid, 2',4'-BNA COC: synthesis of fully modified oligonucleotides bearing thymine, 5-methylcytosine, adenine and guanine 2',4'-BNA COC monomers and RNA-selective nucleic-acid recognition," Nucleic Acids Research, Mar. 2009, 37(4):1225-1238.
Pei et al., "Inhibition of cell proliferation and migration after HTRA1 knockdown in retinal pigment epithelial cells," Graefe's Archive for Clinical and Experimental Ophthalmology, Dec. 31, 2014, 253(4):565-572.
SantaLucia, Jr., "A unified view of polymer, dumbbell, and oligonucleotide DNA nearest-neighbor thermodynamics," Proc Natl Acad Sci USA, Feb. 1998, 95(4):1460-1465.
Seth at al., "Synthesis and biophysical evaluation of 2',4'-constrained 2'O-methoxyethyl and 2',4'-constrained 2'O-ethyl nucleic acid analogues," J. Org. Chem., Mar. 2010, 75(5):1569-1581.
Shirui Hou et al., "The Secreted Serine Protease xHtrA1 Stumulates Long-Range FGF Signalling in the Early Xenopus Embryo," Developmental Cell, Aug. 6, 2007, 13(2):226-241.
Bergstrom, "Unnatural Nucleosides with Unusual Base Pairing Properties," Current Protocols in Nucleic Acid Chemistry Jun. 2009, 37(1):1.4.1-1.4.32.
Caruthers et al, "Chemical synthesis of deoxyoligonucleotides by the phosphoramidite method," Methods in Enzymology, Jan. 1987, 154:287-313.
Hansen et al., "Entropy titration. A calorimetric method for the determination of $\Delta G°(K)$, $\Delta H°$ and $\Delta S°$," Chemical Communications (London), 1965, (3):36-38.
Hirao et al., "Natural versus Artificial Creation of Base Pairs in DNA: Origin of Nucleobases from the Perspectives of Unnatural Base Pair Studies," Accounts of Chemical Research, Jan. 2012, 45(12):2055-2065.
Holdgate et al., "Measurements of binding thermodynamics in drug discovery," Drug Discov Today, Nov. 2005, 10(22):1543-1550.
McTigue et al., "Sequence-dependent thermodynamic parameters for locked nucleic acid (LNA)-DNA duplex formation," Biochemistry, May 2004, 43(18):5388-5405.
Mergny and Lacroix, "Analysis of thermal melting curves," Oligonucleotides, Dec. 2003, 13(6):515-537.
Morita et al, "2'-O,4'-C-ethylene-bridged nucleic acids (ENA): highly nuclease-resistant and thermodynamically stable oligonucleotides for antisense drug," Bioorganic & Med.Chem. Lett., Jan. 2002, 12(1):73-76.
Sugimoto et al., "Thermodynamic Parameters to Predict Stability of RNA/DNA Hybrid Duplexes," Biochemistry, Sep. 1995, 34(35):11211-11216.

(56) References Cited

OTHER PUBLICATIONS

Tosi et al., "HTRA1 and TGF-β1 Concentrations in the Aqueous Humor of Patients With Neovascular Age-Related Macular Degeneration," Invest Ophthalmol Vis Sci., Jan. 1, 2017, 58(1):163-167.

| Treatment | Rat # | LE / RE | rnHTRA1 mRNA (ISH) +, ++, +++ | comment total / partly | GFAP (IHC) +, ++, +++ | comment total / partly |
|---|---|---|---|---|---|---|
| PBS | 91 | LE | +++ | | + | |
| | | RE | +++ | | + | |
| | 92 | LE | +++ | | + | |
| | | RE | +++ | | + | |
| 140.1 50 µg/eye | 33 | LE | + | partly ++ | + | |
| | | RE | + | | + | |
| | 34 | LE | + | partly ++ | + | |
| | | RE | + | | + | |
| 143.1 50 µg/eye | 67 | LE | + | | + | partly ++ |
| | | RE | + | | + | |
| | 68 | LE | + | | + | |
| | | RE | + | | + | partly ++ |

Rat In vivo efficacy, dose response Retina, qPCR

Rat groups, n=10 eyes

SEQUENCE LISTING

```
<160> NUMBER OF SEQ ID NOS: 156

<210> SEQ ID NO 1
<211> LENGTH: 2138
<212> TYPE: DNA
<213> ORGANISM: homo sapiens

<400> SEQUENCE: 1
caatgggctg ggccgcgcgg ccgcgcgcac tcgcacccgc tgccccgag   gccctcctgc      60 actctccccg gcgccgctct ccggccctcg ccctgtccgc cgccaccgcc gccgccgcca     120
gagtcgccat gcagatcccg cgcgccgctc ttctcccgct gctgctgctg ctgctggcgg     180
cgcccgcctc ggcgcagctg tcccgggccg gccgctcggc gcctttggcc gccgggtgcc     240
cagaccgctg cgagccggcg cgctgccgc cgcagccgga gcactgcgag ggcggccggg      300
cccgggacgc gtgcggctgc tgcgaggtgt gcggcgcgc cgagggcgcc gcgtgcggcc     360
tgcaggaggg cccgtgcggc gagggctgc agtgcgtggt gccttcggg gtgccagcct      420 cggccacggt gcggcgcgc gcgcaggccg gcctctgtgt gtgcgccagc agcgagccgg     480
tgtgcggcag cgacgccaac acctacgcca acctgtgcca gctgcgcgcc gccagccgcc     540
gctccgagag gctgcaccgg ccgccggtca tcgtcctgca gcgcggagcc tgcggccaag    600
ggcaggaaga tcccaacagt ttgcgccata aatataactt tatcgcggac gtggtggaga     660
agatcgcccc tgccgtggtt catatcgaat tgtttcgcaa gcttccgttt tctaaacgag     720
aggtgccggt ggctagtggg tctgggttta ttgtgtcgga agatggactg atcgtgacaa     780
atgcccacgt ggtgaccaac aagcaccggg tcaaagttga gctgaagaac ggtgccactt     840
acgaagccaa aatcaaggat gtggatgaga aagcagacat cgcactcatc aaaattgacc     900
accagggcaa gctgcctgtc ctgctgcttg gccgctcctc agagctgcgg ccgggagagt     960
tcgtggtcgc catcggaagc ccgttttccc ttcaaaacac agtcaccacc gggatcgtga    1020
gcaccaccca gcgaggcggc aaagagctgg ggctccgcaa ctcagacatg gactacatcc    1080
agaccgacgc catcatcaac tatggaaact cgggaggccc gttagtaaac ctggacggtg    1140
aagtgattgg aattaacact ttgaaagtga cagctggaat ctcctttgca atcccatctg    1200
ataagattaa aaagttcctc acggagtccc atgaccgaca ggccaaagga aaagccatca    1260
ccaagaagaa gtatattggt atccgaatga tgtcactcac gtccagcaaa gccaaagagc    1320
tgaaggaccg gcacgggac ttcccagacg tgatctcagg agcgtatata attgaagtaa    1380
ttcctgatac cccagcagaa gctggtggtc tcaaggaaaa cgacgtcata atcagcatca    1440
atggacagtc cgtggtctcc gccaatgatg tcagcgacgt cattaaaagg gaaagcaccc    1500
tgaacatggt ggtccgcagg ggtaatgaag atatcatgat cacagtgatt cccgaagaaa    1560
ttgacccata ggcagaggca tgagctggac ttcatgtttc cctcaaagac tctcccgtgg    1620
atgacggatg aggactctgg gctgctggaa taggacactc aagactttg  actgccattt    1680
```

| | | |
|---|---|---|
| tgtttgttca gtggagactc cctggccaac agaatccttc ttgatagttt gcaggcaaaa | 1740 |
| caaatgtaat gttgcagatc cgcaggcaga agctctgccc ttctgtatcc tatgtatgca | 1800 |
| gtgtgctttt tcttgccagc ttgggccatt cttgcttaga cagtcagcat ttgtctcctc | 1860 |
| ctttaactga gtcatcatct tagtccaact aatgcagtcg atacaatgcg tagatagaag | 1920 |
| aagccccacg ggagccagga tgggactggt cgtgtttgtg cttttctcca agtcagcacc | 1980 |
| caaaggtcaa tgcacagaga ccccgggtgg gtgagcgctg gcttctcaaa cggccgaagt | 2040 |
| tgcctctttt aggaatctct ttggaattgg gagcacgatg actctgagtt tgagctatta | 2100 |
| aagtacttct tacacattgc aaaaaaaaaa aaaaaaaa | 2138 |

```
<210> SEQ ID NO 2
<211> LENGTH: 53384
<212> TYPE: DNA
<213> ORGANISM: homo sapiens

<400> SEQUENCE: 2
```

| | | |
|---|---|---|
| caatgggctg ggccgcgcgg ccgcgcgcac tcgcacccgc tgcccccgag gccctcctgc | 60 |
| actctccccg gcgccgctct ccggccctcg ccctgtccgc cgccaccgcc gccgccgcca | 120 |
| gagtcgccat gcagatcccg cgcgccgctc ttctcccgct gctgctgctg ctgctggcgg | 180 |
| cgcccgcctc ggcgcagctg tcccgggccg gcgctcggc gcctttggcc gccgggtgcc | 240 |
| cagaccgctg cgagccggcg cgctgcccgc cgcagccgga gcactgcgag ggcggccggg | 300 |
| cccgggacgc gtgcggctgc tgcgaggtgt gcggcgcgcc cgaggcgcc cgtgcggcc | 360 |
| tgcaggaggg cccgtgcggc gagggctgc agtgcgtggt gcccttcggg gtgccagcct | 420 |
| cggccacggt gcggcggcgc gcgcaggccg gcctctgtgt gtgcgccagc agcgagccgg | 480 |
| tgtgcggcag cgacgccaac acctacgcca acctgtgcca gctgcgcgcc gccagccgcc | 540 |
| gctccgagag gctgcaccgg ccgccggtca tcgtcctgca gcgcggagcc tgcggccaag | 600 |
| gtactccgcc gcgctcctgg gcagctcccc actctctcca tcccagctcg gacctgcttc | 660 |
| tgcgggactg gtgggcaggt tgaggggcag cgaagcgttg tggggtggcc agggcaactc | 720 |
| tcggggacag gcaggtgggc cccggggtgg cggatttccg cgggctgcct cggaaccgag | 780 |
| cttcgcgccc agcccggggc cggttctgcg cccagacgat gccagtacgc ccggcctgca | 840 |
| ctctggggct cgagacgccg ggcgaccggc catggagtgc cctgagggca accacacagc | 900 |
| gcggggaccc caggacaaat aagaggaatg ggggcataaa ggaaggagag aagttcagga | 960 |
| ctgggaattg gcgcctcgca gagcggcttc aggaccacaa gaagtcattt cggttgctt | 1020 |
| ttcttctatt tacgtcctcc gtccccttta aaattcactg ctttgatcac gggaccgctc | 1080 |
| agtgaaaact gtatgtaact cttttggaaa ggaacagtgt ttgccggccc gccccggagt | 1140 |
| ttctccaaaa agtctacccc gagcagggaa cggtttggca ccgctctcgt ttcggcggcg | 1200 |
| ttgctgcctg tcttgctttc ctcgttttga gccagcccta caaaaatgaa agtggctcct | 1260 |
| tttgaataag ctgaatcggg cttttggatca cgaaatctgc agaggcggag aagggaccgg | 1320 |
| gttagtgatg aggaagaagt ctaccctct gttcctacag ccgcacacag gacctgttct | 1380 |
| ggcaggggag acgtggtga tggggaagg agtggaatga agcaatgtct aactctctcg | 1440 |
| cgggaccttc cggagagatg ctcctcatct tcaggcagag gccatgtgga aaaataatat | 1500 |
| cgagttcagc agcggccagc cccgcgttgt aggaaccaga cagcggggct tggcagtgcg | 1560 |
| cttgggcgca gccgtgccgc tgctgccgga ccccagtgct gcctcctcaa cacgggcagt | 1620 |

```
gccaggagag gggcataggg gagcacagtg cagagggact ggtctagagt ttactttata   1680
ggaatatggt tcggtgtgac caactagggc ttagcatagt ttggcttacg tggacgggaa   1740
gatgccagag ccgaactggg tgaaattcga gattgcgtat tcaccaaca caggagcaca    1800
gccctcggga aactcagcct agtcaggcag tagagagttg tcccggagag aagtgatcct   1860
gcagactcga aagggcat gatgatagca cacgtctgtt gagcacccag tctgtgtgcc     1920
gggtgtgtta cctctgtgac ctcatttggt caaacgagga ggcagttgct cctctctctc   1980
tcttttttt tcttaagaga cagggtctcc ctctgtcgcc catgctggag tgtagtggtg    2040
tgatcatggc tcactgcagc ctccgacccc tgggctcaat gattctcctg cttcagcctc   2100
ccaagtggct gggactacag gcggatgcca ccacacccag cttctcattc ccgttttaca   2160
gatagcggag ctaaggttga aaaacttgcc caaggtcatt cagctggaat ttaaacccag   2220
acagcctcat tcagaggagt cagcccagca cttaactcca agggtgtggg agagggtca    2280
ggtgctgtaa atttcctggt gggctggacg tgcatccccc tcagagctgg aacagcata    2340
cacaaagcct aagacttgtt tggaggtgaa tagatcagtg tggctgggga acgttttggg   2400
agggcagcag gagtgagcca ggctggtggc ccagagtccc agggctgaag aggctggctg   2460
tgccccgtgc cctgtgcgca gatgttcttg aactggcagca actcaaagcc tagtgtagtg  2520
tagggctgac ctagcagtgg agtgcggaat gcatccaggg tggagagttt agactactgc   2580
aataatctgg gtgtgaggcg acaacattga aaaagcatgt ttttgtccaa acaagccag    2640
ctgttactgg tctcgctgtt tgtggtctca tcgcacgggg tcctgagttg ctggcaccat   2700
gcgagccgcc taatttattg ctagtgaggc aagttgctta acaagttttg gagttggctg   2760
agtccctgtg tggaggaaaa caggtccccc attggccatc gggctcacag cgggcccccg   2820
gtgtaccagt gaggggacag ccacagaggg ataagcatgg tggctttgaa aggagggaga   2880
gacagagtgg gtacaatgct tttcttatcc ctccctcctt cttttgcaaa tatttattga   2940
gctctgtagg gtgtctgaca ccgtttgcat gtttgtctgt ctggcacatc ggaggtactt   3000
ggtacgagtg gattagtgaa tgaataaatg aatgaatgaa gacaaacggg aggtgcttgc   3060
gatacacagc cattctgttt ttccttagtg gaaggcactg cttttgctgcg cccctctct   3120
ggatctcaca ctccaccctt gacttttcgg aggtgtttcc gaggacaggc gcctgggagc   3180
cagcagactt cattcagtcc aagccaggct ccaggactca acagctggtg cccacgggca   3240
ggtcacttga cgtcactgtt aaatgaggtg aattggctgc ctgctctggc tggaagattg   3300
gcgggagagt cactttagct gccatggaca tgagccttt ctaggggtgc cacttgacta    3360
gaggcctgga gttggagcaa gtcatacacg gatctggaga cagagctctc gaggcaggag   3420
cgggtgctgc gatttcaaat attataaggt ggctttgtct ggggcagagc atgccagggg   3480
atgagaggta gaaatgtcat cagatcaggg gtccccaggg aggtgactag cactttgggt   3540
cacagtagat ctttggatag aggaacatgt caccattcaa aggaaagcac tttcatctgt   3600
aagctgttta ttgaatagac ctcagagaac atctctgctc accgctctgg aaatgaaggc   3660
aaatcatcta tttcagaagt caatgcactg gcagggtttg gatgggaaag tatacaattc   3720
agctagagaa caaagatctg tcatctccag ctgtactggt cagatgatta caaaaagaa    3780
aggaattgaa atactaatag ggtactaata atgagggcta acatatatgt tgtgcttatt   3840
ctatgccggg tgcatactaa ttcatttgat cctccggaca gtcctatgag tgagtgctgt   3900
agtcttccct gggttacagc tgggcagcta agtcacagaa aagtaccttg ctcaggactg   3960
gtggtcccac acaactggat ggagagcctc gttcataacc accatgctgt gctgttgaca   4020
```

```
gagcaacaga gattttaaac caaccccagc taagccccag ctaatagctg aaataaacag    4080
ggctccagat ggctgtggct tagagatgga acaggacaga tcacagcctt cactctgcag    4140
gctcaggagc ctgaagacaa ggttgcctcc agttgccgtc agtgcagccc tcactaaaga    4200
aaagcaaaaa gagccgaggg actgtaggaa ggctgtttcc aagccagaga tccagacaaa    4260
ctgctcttga agagagaaag cccttccaga ttcccccatg tcccaaaaga ccagccggga    4320
ttccggacct ctgctaaaac atggacaaga agccaggaac gagacctgaa acagacttcc    4380
caaacagcag aagcctcatc catttctcct gctagtacat cctccaggaa agcccaccct    4440
actccatgca gcagcccaga caagcttgga ggtctgcaag ctgcaggggt gcccagaaac    4500
tccacccctg gaggttttta ggatcgcctg ctcctggtct caccccagag cctctaaagg    4560
cagaggctgt atgtacatac ctggtgaaga accaagggct tagatggttg ctttacttct    4620
tggagccctg gaatgtttgt aaaatttact tttttttttg agacagtgtc tcgttctgtc    4680
gcctacgctg gagtgcagtg gcgcgatctc ggctcactgc aagctccacc tcccgggttc    4740
atgccattct cctgccttag cctccagagt agctgggact acaggcaccc gccaccacgc    4800
ccagctaatt tttttgtatt ttttggtaga cggggtttt caccgtgtta gccaggatgg     4860
tctccatctc ctgaccttgt gatccgcccg ctttggcctc ccaaagtgct gggattacag    4920
gagtgagcca ctgcacccgt gccaaaatgt actttattta ggtgactctt tcgtgggaac    4980
ctcaaacaag caatcattgc tagctgagtg ctgaccctgt actgagctct ggggagacag    5040
ggttgaataa aacaaagtca ctgcccacag gtaacttata ttcaatacaa tgggggaaaa    5100
tacaatcact gcttccctgg ggttgtattt ttccattgtt aaagtgggca gtttgctcga    5160
gagtcatttt cactattggc aattcaaata caccttttgt cagttaaaaa acaagtgtgc    5220
cagggacctg agcttcatct tagggcaggg tgggtggaaa catttgtgag tctccagctt    5280
ttagtcacct gaaacttgga aacttggagg tcttttgagc agtttatgag tctctgcctg    5340
ctctggtcgg ctgccttctt ttattgctct gttggttttg ctaaagagtt aaaatattaa    5400
ggcttcataa aattaggaag ttaacaagct caaaaaccaa gtgtttgagt tacttcattc    5460
cactgagaga gctgtaaatg ggttgcattg aacttaaaa taactgcatt gagtaagtga     5520
tggtggcggg caccatgagc taactgtggt cagaagcctg atggcctccg ctttggggct    5580
ggattctccg tttggagctg tgtgatcctg atgagtttc atgccttgga ttcagaaatc     5640
agactttcca tgagcttata tttcaagtga ataaatagct ctggtcaggc ttaatttgaa    5700
gaagaagtaa gcttggcagt gggtgagggt tccttggaag gccaactggg gcggaggggc    5760
tgagggcaag cggctctggc ccttcctggg gtgttacctg accaggtaac agctccctcg    5820
acctctcgga gcctcggcag tgaggggatt gggccagttg atctctgagg ctccttttaa    5880
ctagaatggt ctgggatttt tctaagaaaa caagtctttg aggaggttgt ggtcacctca    5940
ttcctaattt aaagcctggg gaggcttcct tatgagctac ttcttttttcc taaattattg   6000 atggttaaag ccaaggctgg catcgaatag atgtgatcca tcttgagcct ggttgctttg    6060
tgtttcagct ttgtactggc tgctgaagtc cccgggagac cacaggggtg acatgttcat    6120
ctccaagaga tgagcttcca cgagactcat accccttgct ccttccctgg ggctccaagg    6180
cctttgggtc atctgaagtg agatacccct gtgtcatttc atctttttcct tctccacctt    6240 ctctgccgtt aaaaaaaaaa gaagaaagag aaaaatccta ttaatagaga aaccgagaag    6300
tgtagccatt ctgaatgtgt ttccaaaagg ctcctggaag tggcatggaa gttacagtga    6360
```

```
ttcagcacta cttggtgacg tgtgcctaga accacagggg gacattagcc aggacaacac    6420
gcctcaggac agaagtaagt ggctgcgaag aggcatgtcc atcactgccg gaaagatgca    6480
gagttcagtt tttggagtca gtgctgagag ttccatttct aaattcattc agagcattta    6540
tttaacacct actgtgtgct cagaagtgta tcaggtatgg ggactcagag gtaagggctg    6600
gtggcccctg atctcaaggt actcgtggta gatagtatga tgctcagctt aagggctggg    6660
cttctgaagt cggattgcca ttttctggat gtgtggtgtt tcttgggtga cttcatctct    6720
aagtctcagt ttccccatca gtaagataag agaagtaata gcagatacat acgtagctct    6780
tagggcattg cagaatggaa ggacctcctt atatgaaacg caaagcactg tgcctgatgc    6840
attgctagaa ctcaggcaat attagcgtgt tgtcattgtc atcatcatca tcatcatcat    6900
catcatcatc atcatcatct tcaaggcact gacaaaggag tcagctgtgt gggaggagtg    6960
ctgggacact cttgtctccc tggggatgag gtgggtgggt gggttaggaa atcttcacag    7020
agaaggaggg tgatgtgaga cttctgtccg ggagctgact cggaatttgc catctaatat    7080
gttggaaaag gttctctggg cagaggtatc caaagtcact ttgcctgtca cccttttgagg   7140 tcccagttgt tgcctatatc atgtgaccag tgtgtggctt ctcttgaatt aagagctgca    7200
tgtctggact gcctgggatt ttacagatgt catctcgtta actctccctg gagcttgtga    7260
cacccaggag atggcagttt atagaagccc tggcaccttc ttgaatgatg cttggtttgg    7320
tttctatgca ctgggaattc ctcacaagga aagatttgtc acatcttaag gaaggaaaaa    7380
aaggcaaatt tgggagtcca tggataccct attattttag attccaggac aaattgtcga    7440
ataagcacgt ttcataaaaa caatcctccg cagcatcccg tgacagcagc tggtccctcg    7500
ccacaggata attatgtctc cttgtgcaca caaaagtctc cgagggcata ttgttgtggc    7560
tggagtttct gataatttcc aaattgaaca acctcagtcc taatgagtca gaggcttgtg    7620
caatattttc aaacctcagg aacatctttt tcattagttg tgcaataaag atggtaggcc    7680
tatctctgtg atgagctgtt ttttttttctc aaagtttgat gagattcgcc gtagaattcc    7740
ttctcacata gtcttgggca agattttacc cgatcttcca acacatgagt catctcatat    7800
cctgtgacta agaagagctg tctctttggt gccagttttc taagtgcagt caccacttga    7860
tggagacgga tggacacagt tgggattgcc caggcagatg ggcaatcttg ccagctagac    7920
ataggggagg gaagcctcaa tgttcagcgg tcacatctgc ttttctgtgg cacagagtga    7980
gctatacagg aatattgtat tctccaggac agttagggca gtgggaaatg tcatcaaaca    8040
gaacagtgac ccaaagagcc actgccactg ggtgctctgt gggagctggg cactgtgctc    8100
attgtgttat gggccttgct ttgttcttac cttgtagcca cccagagagg cagggcatta    8160
tccttgcttc ctagctgagg ccacagaaga ggctcctaga ggttagctgt aacttgtcca    8220
aggccagcca gtgcaaggag gcagagccag gatttgagcc catgtctgtt tcactcccaa    8280
actattcttc agatttcttt aagtcaagtg ttatttagaa atgttttgtt tattcatcaa    8340
atatttggtg ggtgtttcca gctatctttc tgttattaat ttctagtttta attctattgt   8400 gggctgagaa tatattttgt atgatttcta ttctattacg tttgttaggg tgtattttct    8460
ggtctagaat gtggtctgtc ttggtgagtg ttccctgtgt gcttgagagg aatgtgtgtt    8520
ctgtcattgt tgaatggagt gttctataaa tgtcacttag gtctagtgga ttgatagtgc    8580
ggttcaggtc aactgtatcc ttcctgattt tctgcctact gatctatcaa ttcctgaaag    8640
agaagtgttg acgtctcctg agtctattct gaaacactga attgcggtct ccatgatgaa    8700
ccactagagt tagaaaacct gggtcctagc cccatttggg cctttgggat gactcccttc    8760
```

```
tgcctcagtt tcctcatcta caacaggggg acaatgatgc tgcctaggag acatcagcag    8820
gatactgtga aagtccagtg gcataagggg tatggaggag cttcgtcaac tcctaaagct    8880
tcagtgctag gaatcctaaa gcattgaaat ccaaagatat aaggaatatg aaggagtttt    8940
gtcaattcct aatgcttcag tgctaggaat cctaaagcat taaagtccaa tgatataagg    9000
aatatgaagg agctttgtca actcctaaag cttcaatgct aggaatccta aagcattgaa    9060
gtccagtgat ataaggaata tgaaggagtt ttatcaactc ccaatgcttc agtgctagga    9120
atcctaaagc actgaagtcc aatgatacaa ggaatatgaa ggagctttgt caactcctaa    9180
agcttcagtg ctttaggagt cctaaagcat gaagctgta agagattagg acctctagtt     9240
ggcaattcca gactcttcca ggactcctga tagagccaac accaagaata gtgaagccag    9300
aaggatggaa atagtaaaat gcctcctggg tgtcaaagca tgggtctcct ctgggcatgt    9360
tctcttgtcc tactgagaca tgatagctct tggccaaagt gactgaactt gaccctctgt    9420
ttcaggaagg ccaaatgcag ggttcactac catcatgtcc aagggcagat gcgttggtcc    9480
agaacatcag catcccaatc attataccaa gcaaacagcc gtctctgcct gcaccgtgga    9540
gagcacacgc tcctcctggg gtggcctgca tcctgtgttc ttctcaggcc gactttctgt    9600
ttaatgtttg ctggtcagga aatggcctga gctgaggttc ttcagatccc agtctgacct    9660
ttctccacca gcatttgtgg ctctgaaaaa tatagcccag tgtggtttag ccccactgga    9720
tgaaacccag taggaaaagt ctgataatag cagaagacgc acaggaggaa gagtgaggat    9780
ttgagagcat ctgggaagga ccatgtgcct ggatatcgtt ctgtctgtgg gattctgtga    9840
cacttgtcat ttacagtctg ttcccatgga attctcatca ttggccaaac atatagtcct    9900
tctgtcctct gaaaaatatc attctgctcc gacctttcac acccatctct gaccacatca    9960
actccctgtt tgcatgcatc ttgtggatga aggacaccac tttacctgta aagacactgg   10020
tggcttccca aagccaccaa ctgacttgta gagaagacag aatcccagag tatgaaacct   10080
gagggtgaag ggtcctggca ggtcctagag ctcaacccctt cacttcacag gtggggaaac   10140
tgagggagcc aatgggaaca tgactctcac aagctgcaca gctcatctgt aggggccagt   10200
gtggagtctg tttgtcctga gacccagggc tgagcctttg agccctccgc atctcagccg   10260
catcctcctg ttggagcagt taggtgtttg ggagaggcca cggtccatgc tcatggtttt   10320
cctgtaaggc tggagaaaca ggccttgttc ccttagtctc tctaatcaaa atgaggttgc   10380
agaaaaccct tctccctact tctccctaaa ataatttcct tgggttagaa gatgactaaa   10440
agactattca tccgatgact gatgtctccc ttcaagagtt ataagcacat ataaatgcct   10500
ttgaatggta attataataa ttttgctgaa gggaaaatat cagtataaat atcatggtgg   10560
acacatggaa tgaggactga gatgcttcca tgtcttttca gctgtggtta gattttcttt   10620
aagcagaata tacaagtttt tcctctccta gcataaggac tctttttttt tgtatctttt   10680
ctctctactt tttagacatg atggaaaatg catttataca tttgatgaca tattgtacta   10740
tctcagttgt ttaaaattat aaatgtaatt taatcatatg aaaaattaag aaaagaagat   10800
tcatatttca ccatcatctc cccagaaata tcatttcttt attactatta ttattattat   10860
tattattatt attattatta ttattatttt gagacagggt cttgctccat cacccaggct   10920
ggagtaaggg gcacgatctt gactcctgc aacctccacc tcccaggttc aagcagttct    10980
catgcctcag cctcctcagt agctgggatt acaggcctgc accaccacac ccagctacct   11040
tttatatttt taagtagaga cagtttcgcc atgttggcca gactggtctc gaactcctgg   11100
```

```
cctcaagtga ttggcctgct tcagcctccc aaagtgtggg gattacaggc atgagctacc   11160
atgcctggcc taattccatc atttctgtcc caagtgttgc caccgtttgg ttaactgttc   11220
ccctgttcac atccatttgg gccaaggttg caatgttaaa caatcctgag atggacattt   11280
tcatgtttat ggctatttct gtatctaggg tcattctctt aggagaggta ctaaggagta   11340
caaaaactgg gaagaaggat atggaatttt tatggatctg gtataaattg ccaaattatt   11400
ttccagaagg gttgtagcca tatttgttgc catcagctct agaatttcaa cctcgtaagt   11460
cactgaaaga aattctccca aaatcaatcc ttcaggaata atggaagaag atggtgccaa   11520
accccagcca ttctgctcac tgttagattc ctttttggt cttacaggtt acttttattc    11580
tcaggttgat ggctcttaga gttgagcaat gtttgggta gaataacgag cacttttaaa    11640
acttggttct acctggggag ggggtgagtt gtgatcacag acagtctcac ctgggagggg   11700
cttgggtgtt tgtcggcttg tccttctaac actcgtgtct caggcgagca gcctgggacc   11760
agtgaggtga cctgaaggct ggaggtcaca agctaagagg cgacagagaa cccaggtctc   11820
aggaagccca gcccagagct cgctgcactg agcctctcgg atgccagctc tgtccaggat   11880
gcgggaggag gccagactga tttggtctgt tttgaaaagt gatgaaaata tttattcaaa   11940
tgttttgtac tcataggcag aagtataaca ggagctgcat atacaaaatt attttctagt   12000
agtcacatta aaaagtaaa aagaaagaac acgattattt ttcttttaa aacagcttta     12060 ttgagagata atttacatac tataaaattt accccttaa agtgtacaat ttgctgttct    12120
tatatattca caatcatgca cgtatcacta ccagctccag acactttca tcaccgtaaa    12180 aagaaacccc gtatccatta gtagccaccc catacttctc ctctgcccag ccctaggaaa   12240
ccaccggttc attttctatt tctatgaatt tgcttattct ggacatttca tataaatgga   12300
atcaaagaat acgtaacggg cttctgtctc ttagcataat gttttcaagg ttgtccacat   12360
tgtagcatgg atcattattt cattccattt tatgattaaa aatatgcctt taagggata    12420 cagggagacc agacgtctat tttatctccc ctccctgatg gggaatccta atttcagcct   12480
ggaaagtcac tgcgaaagtc taaactgcag aggtgatact gttccactg gaagaaactg    12540 tagcacctga ctcaggaagc cagcattaaa accaagaata ttctatatgg atgggatta    12600 cgcactgaaa ggaaaacatg aggaaatgca cttttcagat ttattagatc atagaacttt   12660
tttggagctg gaaaggatgt cggaaaccgt ctagcctacc ccctcatctt accactgagg   12720
taactgaggc ccaggaaggg gaagtggctt gttttgggtc cgggaccact cttcatttct   12780
tatttgagcc aaagcttcct tctggcgtct gtctctgttt cacaagttcc cctcgcatgg   12840
gggctgggta ctgcttggaa gaactggctt cttccttgat acaggggctc gttcaccatc   12900
acctccctcc ctcacgtctc ttctgcctct ctgcagcctc aggccctcct cctgcaccag   12960
gggggcagac tcaacccggg tgggcactgc ctcccagtcc gtggccagag gctggagggc   13020
tagggagact gaacagcccc ggcagctcca gacataacaa cctatgttga ggagtcaggg   13080
caggaagcga acccagctga gaaatctgcg aaggtcagga ccagagccag acgcttatca   13140
agagcaaagt taatggtttt tgtgaaccga gcagtcagct gtttccccga agataataat   13200
agacacatca tgttgggcat tcaggaggca tctgaaaaaa aaaatgtgca gtggaattga   13260
ttggaagctt ttccctaatg cataaaatag gccagaaaag actatcaaat gtaacagcac   13320
cgatcaaacc caatagatca agcaaggact gaaaaacaca attttttttt tctttgccag   13380
tgagtctgaa aagtgatttt caatgacagg cgccttaaa catagacaac ataaacaaca    13440
acatagttgt tctggaagag gcatctttc ccagtaaagc caaagatgca gatctaggct     13500
```

```
gtgcttgtga ctgacagcac agtgaggggt tcacagccag ctggccaggt gcccccccgaa    13560 agcacatttc gaatctactc tatttgagag agactgcctt agccttgttt gggtaagtct    13620
tcctccttca cttcacctgc cacagacttt tccaggcacc atctgctgca gtcttggccc    13680
agcccctgca acagttactg ctcaaggcac ccgggacatg caggacgggg gagcagcctg    13740
aggtctggcg tccggcgagc ttttcccact tggagccgtc tgggagactg tcccggaaag    13800
agaggggctg ccaacacttg gaagtgccaa tgtgtgctgc aagtcgaggc caggctcccg    13860
gctcccccgc ctcttcctcc ttgattcatt aaaaggaaag aaagaggcca cacgaaactc    13920
tcctgaattt catttctttg tttctatgca aagacagag cgtggtcatt catcattcaa     13980
attttagcct ttttaaacaa ataataattc ctgcttgtga attcagtgta ttttaacaag    14040
agtaggtctg agggccgttg gccgtgtctt tccttagatt tgcagacagc ggccctgatg    14100
gtgcataggg tttcaggttt cctttagacc tcagctggct gcctgggcca ccacttagca    14160
atgccattgt cctcctgtg cattttcttt gcagaattcg aggaaatcca gtcgcacagg     14220
cccctctgtg cccatgtccc cggcgccctg gaatgtgcag taccagcagc agcgattaga    14280
atgggggtct ggtttcccgg aatgtgcaag gtctggcttc tgtttctgct gcctccatgc    14340
cccagaccag tgctgggccg ggctctgggc tggagccgtg gctgacaagt tccttggaa     14400 tttaatggag cgggccagac agcatgcagc cactcaaact gaaaacctgg gaaagaaatg    14460
agtgttgtgg ggcagctttg ctgcattcac tgggtcatat atgcttcttt ttcttttcct    14520
caggcaaccc ctcttgcaga caggaggccc cctcccttt cgcttcatgc ctcactggcc     14580
attaggaacc ttttaaaact gatttctctc ctgaccctca gagagaacat agtccaagtt    14640
ccctggagga ggaggaagcg ctctgtgttt ctctgcagtt cacggctcag ttaaatgcag    14700
cctacgtgct gtcttttcccc actcctctgc ctgctcccgt tgtgcttctc atgatcattc    14760
tcaaattcag cgagaaacct cacaaaggga gcttttctta gggaagagtc atccttggcc    14820
tcccgaatgt ggaccagccc ctctccccag ctgcacagca tcaggttagt taaccacctg    14880
cctccatctg ggtcctgtct ggacaggcct actcacacct gctgcaggca tccaacttgc    14940
cctcaggtgc ctgtggctcg tccagagggg tggagcccac attccagtcc tgacaggtaa    15000
agttcagtgg cggggaccct gcatttagtg taaagatcaa tattccaggt cctctcttcc    15060
tgccacccag cgactggccg tttgcaggca ctcggtccca gttgtcctgg gcctgcagcc    15120
cttgcattct ctctgctttg tctctgctat tgcaccctg ccccatcaga aatgcaggtg     15180
ggggggcctt ccgctgggac agtgagagac tgggtagtaa ggggagcgct agagggatgg    15240
ttgcgcttgc atccagccct gactgcattc gctctccccc gcctctctgt gaaggtgctg    15300
agctgtgagt ggaaccaagt ggatgagagt ggccttgggc acctgccgat aaatttcccg    15360
gtgtgtcttc tcctcctggg agtcccatct ggatttgggt ctggatttat ttattcagca    15420
agtagcctct ttatagttac ttttttttt ttttttttt tgagatggag tttcactttg       15480
tcacccaggc tggagtgcac tggcgcaatc ttggctcact gcaagctccg ccttccaggt    15540
tcacgccatt ctcctgcctc agcctcccga gtagctggga ccacaggtgc ctgccaccat    15600
gcctggctaa tttttttgtat ttttagtaga gactgggttt cactgtgtta gccaggacgg    15660
tctcgatctc ctgacctcat gatctgccca ccttggcctc ccaaagcgct gggattacag    15720
gtgtgagcca ccatgcccgg cctgtagtta cttttaattt agccatgctc ggggctgaag    15780
gggatgccaa agaaatataa gatgagcccc tcagacggct aaagatgaag atgaggcctc    15840
```

```
cagtatgtac ctcccacata caccccagga aattctgggt gtcactggat tctggacctc    15900
ccaaaagctg ctggcacctg gaggatgggg ccccgaggct ggacctcact cctgctgggt    15960
tgctggactg ggaaagtact gatggcagct gaggagtgtg tcccagactt cactgagcca    16020
ttcccaaaga ttattccaag ttctcctgac actgcactgg aggcctgctg tgctggcctt    16080
ctttatttac agtttctgac tggtgtctag cagccctgcc agagagagcg gcagtgtgtc    16140
tgcaggcgac caggagaaat gtctcaggct ttagagcagg actttgagca catagctgtg    16200
ggggcccagc aggctgtctc ctgcacggtt acttctcctt gtcctttcat ggtcgagagg    16260
ttgctgcctg gcccttcaag tgaggatggg acatgctatc cattggcctt aatttccaac    16320
ctctgcatga tgcattttat gctcctgcct ttgaaagaac ttttattttc ttgtcattta    16380
tgcccagacc ccacatggca gaaggaaggg aggctgggac aggggaggcg gataagctgc    16440
cgctgacaga cctgcccagt ttcttagctc atcccggcct ccatcctggt gagcagacac    16500
tggcccaatc cagccatatt tttgctgagt ttctgtctt cacatctcat ccttaaccct     16560
gaatcctggc catagttggt actgggttgt attcttattt gtaatcttta aagtaggaat    16620
acctttgctg gtatttaaag tggaagaaat caggtgaaga atcacaagtg atttgcaaac    16680
tggaagagac attagaatgt aaatgtgagg aagcgtcagc atgaggggct tgcctgggct    16740
gcacagcttg ccttggctgg agtatgcact gttctggcat tgcagagagg atgggtacct    16800
tgcctccctg caggtggggg actgtatcag ccccgcaga ctgctcctgg gctcctgagt     16860
ttgacagatt ttttttttt ttttttgaga cggactctca ctctgttgcc caggctggag     16920
tgcagtggtg cgatctcggc tcactgcaag ctccacctcc tgggttcacg ccattctcct    16980
gcctcagcct cccgagtagc tgggactaca ggcgcctgcc accacgcctg gctaattttt    17040
tgtattttta gtagagacag ggtttcaccg tgttagccag gatggtctcg atttcctgac    17100
ctcatgatct gcctgccttg gcctcccaaa gtgctgggat tacaggcttg agccactcgc    17160
ccggctgagt ttgaccagat taaggcagca tctccagtgg cacctgagca gctcctgaga    17220
tgcttttctg tgctaaatct ggatttgggg tattaaatca aatgaatttg aaatgcaggc    17280
acagctggcc ccatgggcat ggacctgtgc agtcacacct tgccccgtgt tcagaagggt    17340
gctgtgcctg ttttaatgct ctgctgttgc tctcttgaga ttcttaataa tttttgaaca    17400
aagggcccca catactcatt ttgtactggg tactgcatat tatgtagcta gtcttgaatc    17460
taggacagtg cattaaaatg ccattgattg gatcaatctg ctcttgcaac tgatttgaat    17520
tttgggaaca tgctgtttcc tgtgaataaa ggaggattca tttcttttcc ctcgaataca    17580
ctgcgttctg ttttccaaat tagctctacg tatcaactca gctgagaaat tggaagcggg    17640
gattgttctg gctggaaggg aaggttagat tgttaatcct gcatcctggc cctgatctca    17700
ccgagtgtga agcatgttcc cacaatggtg tgggctgcgg ggggctggag gctggctgag    17760
aaggtgggga ccaaggaggg aggctagcct gggagccaga cagatggggt taggctcttg    17820
cttttgccac tcgccagctc tgaggcttag ggcaacatga tttaattctc tgatccttgt    17880
ttttttcatc tttctgtaga ctggtgatga gatgcaccct gcaggcttgc aggcttgcag    17940
gagtaattaa aggtaatatt tgtgcctatt attgggcttg acatatagta gatgctctac    18000
aataaataga tcctattatt cttattgata atattatttt attgctaaca ttgaaggttg    18060
ggtgggattt gactagctgg aggcgaggag aatgagatca tccaggccgg aaggaaaaga    18120
gacatgaatg caggggatg gggtggagca ctttggaggt gtgggagag gtctgcaggg      18180 tgggagttgt gcattaagga gtcgtgggga gagtggagga atcagtgcca catggtgaat    18240
```

```
gagagggat  cgtgggcccg  aggagatggc  gatggctgcg  gggatcctgc  aggaagttta   18300
tgtgccccaa  agtggcatta  tcagttaggg  ggagacactg  aagacagagg  tgaggcctgc   18360
ctgaattagc  gtagagtggg  attcttggaa  gcttcagaag  cttgagaaga  gccacttgga   18420
ggtgttgaaa  tgcacctggg  agggacgtgg  ggacccagct  ctgggctgag  agctgggaga   18480
cggaaacgca  ggtgaccttg  gccttgaaga  tggggcatga  tatttagtgc  tttatgtgca   18540
atctcaccta  ggactcccaa  gcccttggga  gtaggtgata  ttagctccgt  gttacagaaa   18600
gggagactga  ggctgaagca  gggacattca  tgatctgaag  tcacacagct  gtacggggca   18660
gaagtgggca  tggaggcatt  aacttagagc  cgaaaggtgt  gacctttctt  agtgtggctg   18720
gccccacggg  gaacgtgtgt  gggttggagt  acaacttggt  gttcctaccc  atcccagatg   18780
ctctgcgttt  gtgaacccca  gttgccacat  cagggcgggc  gagggcagga  agctctgcag   18840
ggagaaggga  caagggacag  agccaagaac  agggggcagtg  ccccagggtc  ctgcaggggc   18900
aatgaagggg  gttggcacac  ctgggttagt  tgctggccag  tgtggggaga  gagctggcct   18960
gggagtctaa  tgggaatgcc  agggaaagct  gccttggtcc  cctaaagtga  agcccccatg   19020
ctggccatgg  agtgttggtg  attgagggtc  cctgctagtt  gtctggccga  ggcagcatgt   19080
cctataggca  tagctctggt  gtcctgctgg  cgtggcgtga  gtgcccctca  tgctgggagc   19140
cagcccgtgg  ctctggaggg  aggtggtggg  aggacaaggg  acagtgggac  ctgccacctg   19200
agcaggaatt  ggcaccttct  cccactggca  ggtccaggtt  ttatggaatc  tgaaacttgt   19260
acaattcagt  ataccctctt  caagaaaaac  acccctcaaa  attatgaata  taacattagg   19320
tatgaaacta  ttattgatat  agattgaaaa  aagaaaatgc  ccaaaatgac  aaacttcaga   19380
aaatagacaa  atactgcaaa  catcacaaaa  tcagaaaaat  aagattaaaa  aaagctaact   19440
gctgaacact  ccgtcatctt  gaaaatgccc  ctctctcctc  ctctatttt  tggctgtgaa   19500 ctctttgctc  acctttcat  gtgacaatgc  ttttgtaata  tttcctacag  agaaaataga   19560
ataatttatt  attactttta  ttgttttgg  attattatta  tgatcaattc  aatatttttc   19620
tgctacccac  acactcactg  tcttctgtcc  aacctctggc  ctgcaccagg  gaaccagca   19680 gtttcccctg  ccataggggtg  tccctggaga  ccacacatat  agcaggatag  atatagcaat   19740
ttaactagac  acagaaggga  cttcaaagcc  acaaatatat  ctcatttaac  ctgaacaaaa   19800
tgattatcca  gttttacttt  tcccttagcc  tcttccccca  aatgctggca  gccaccctga   19860
tgggatagat  gtgtgacaga  gggcaagaga  ccgtggcccc  aaccagctgc  agcttcactc   19920
tttcatttct  gtatactctc  tacaagctgt  gatgatagca  ctttgctagg  gcccctcaca   19980
gggcagatgg  agggctccac  gctgaagctt  tgtggatgtt  tgctgtctat  ccacctctgc   20040
tccttgtgcc  tatgcaggga  ttcaggccca  accactgcag  agagcccaag  agcatcaggc   20100
agaggttccc  aaactgtcat  gattggtggc  acctttagta  gttgatacgg  tttggttgtg   20160
tcctcaccca  aatctcatct  tgaattccca  catgttgtgg  gagggacccg  gttggtggta   20220
attgaatcat  ggggcagat  ctttcccgca  ctgttctcat  gatagtgaat  aagtctccca   20280
agatctgttg  gctttataaa  ggggagtttc  cctgcacaag  ctctctctct  gactgctgcc   20340
atccatgtaa  gacatgacat  gctcctcctt  gcctcccacc  atgattgtga  ggcttcccca   20400
gccacgtgga  actggaagtc  caataaaacc  tccttctttt  gtaaatcacc  cagtctcagg   20460
tatgtcttta  tcagcagtgt  gaaaatggac  taatacagta  gtgcagtcat  ttttcatgg   20520 tccccagtaa  ggccaaaaaa  tacccaacag  ttccatttat  caattagtgg  aggccaaaca   20580
```

```
atttgataag tatttgtgtc cctataacac agtggtcatt aaaaaaagac attttaatttt   20640 cattattcaa taagcatgat tacttatgaa tgggatatgt gcacctgttg ggtgtcacat    20700
gacctttcaa atcttggagt cagattggac accaccatgc ccatttccag ttcaactctg    20760 attttttgtgt ggtacatgct ttttatcaca gtgactgcca gaaatccaac ttcatatgga   20820
atcatgaaaa gggatgtagt gtgatctgat ttcaaaacta tgatcaatct agagctagtt    20880
tacaaggtgt ctaacagtga tcaagtatca ctgtatttcc ctagaaaacc tgaaatatcg    20940
atgaattttc tgtggcactc tggggtccct tggggcacac tatgggaacc atgggattag    21000
gaccataagg atatgatttt ggcttcttcc tgcctcagat ctaatcttta cctggcattt    21060
ttgccttaaa gatgaaagaa gcatacattt tgatgtattt aaagcacata ttcggccagg    21120
tgcggtggct cacacctgta gtcccagcac tttgggtggc tgaggcaggc agatcacaag    21180
gttggaagtt tgagaccagc ctgaccaaca tggtgaaacc ccatctctac taaaaataca    21240
aaaaatagct gggtgtggtg gcatgtgcct gtaatcccag ctactcagga ggctgaggca    21300
ggagaatcac ttgaacccag gaggcagagg ttgcagtgaa ccaagattgc accactgcac    21360
tccagcctgg gctacagagc aagactctgt ctcaaaaaaa aaaaaaaaa aaaaaaagca     21420 catattcatt ttgtgcttat tcttttgaga gaaacacaga taaaagccta tcctttaatt    21480
catactcccc atactgtgat tttcatttt actgcaacaa attttgttca gtgtgataat    21540
gaatgtcaaa cacttaatgc cttgctcttt tcagtaacat gacatattgg agaataatga    21600
ctgaagctta tctacactgc ctacgtctgt tttcttccac cttgaaagaa gttgttgaaa    21660
gtaattaaga agtattatgt gtaaaactcc agggatgatg tgcttcaagg aagcaacatt    21720
tatgaagttg tgtgcttgac tagtagttta taaagaggaa agacgaatca tttattgtct    21780
tgggattgaa tcttggcaat ttttaaacta taaagttaca ggaaatgttg gctgctctta    21840
atgggccatt tgttgtgtta aaaatcagta atgagaaata tttactaggt aagtggaaag    21900
atccatctct ataaattgtt gtaacttacc attttacaaa tcttagttac tcagttttc     21960 tgcttaaaaa tgaaatcatg tagcactgta taagtcattc agttttttat tttggagaat    22020
tactctggat tgtctaggct ctgtgctctc cacatatatt tttgaaatag tttgtgaatt    22080
tctacaaaaa ctcctgctca gaattttcac tgagagtatg cttaatctat gggttaatttt   22140 gtgagaaatt gatagcttaa caatagtgaa tcttctgatc tacaagtgtg gtatttctct    22200
ccatttattt aggtcttctt tattttgata gcgttttgta gctttcaatg tacagatctt    22260
gcaaatatct tgttaaatat ttccctaatt acttgatatt tattttgat gctgttatag     22320 ttatatttta aaaattttga ttccaattgt tgctaataca tagaaatgaa attatttatt    22380
gacctcttat cctgtgacat tgataaacgc agtcatatat tcgtagattt ctagaatttt    22440 tctatatag ctatcatata tatcatctgc aaataaagac ggttttacat tttcctttcc     22500
aatctctatg cctttgttt ctttctcatg cctcattgtg tggtccatta ctgaacggca     22560
gccagttcca gctttctgtt caattaagga gcaggtaaaa tggccaggcc ttgacctttc    22620 aggggggcttc ccgtcctcat tgccttctgc tgcctcagtt ctggcttaac agaacagtgt   22680
ggggaggagg catggtcctt acctactagg gcgttacttg gccttcttca ggttggttgc    22740
ttcgtcaggt ttaagagctc acctgggctg cagttcaggc taggttatct gctgacctgg    22800
ccctgtctcc cttctgtagt gtctgtgggg taccccttgta agctagggag aagagacaca   22860
cgtgaaggcc agaaaaaaca gcctgccaca cagcttccct ggatcatacc ttcgcagtga    22920
catgacgacg tcgttaggag gcgccgaggt ggctgagtgg gtctccagac acctcccttt    22980
```

```
acctctctgc tgtgccactg atgtgtgact tgcttacacc tatgcagagc tgccactgag    23040
cagcactgtg gccagtcctt tggattttct tctttctaaa ttgtatgccg tggcttgatc    23100
aagcatttca tatacagtag atcatgaaat cagcatagaa aacacattga ggtaggtggt    23160
gttaccacat tttatggatg agaggctaac acttggagga gtcaggtaac atgtccaagg    23220
ccacacagct agtgagtacc ctgctgaggg tcacactctg gtccatctga ggccagagcc    23280
tgtgccagcc ttctcctcat gctgatagac gaggaaacag aaagaaggag cagtggacgc    23340
ccccaccctc tgtcccctga acccttggaa gagtaggcag tggcagagcc agcctgggcc    23400
catctatggg aattctccat cgggattgac tcctctggaa ggaagacagt tgacccacag    23460
ttgagatcac agcagatggg ccagccaggg tgtctgtaga ccatcaggca gtggccactc    23520
catgtagttt aatggacaag ccctttaat ggaacaggaa tctaacactg aaccaagctg     23580
cttttagaca cacttttatt cctcactctg aaatggcgtt tggacaagcc aaatatttct    23640
tcttctttca gttgacattt tgtccatctt tgaactgtta gttgatgctt cttctgttta    23700
gttattcctg ttctattttc ctgttgccac tagtccaccc agggatggta agaatggaag    23760
tcaatggttg cttttcatc tgagatgcac cacgaaggct tgtcagtcag ccttgtcata     23820
tggtctgtgc tcccactgct ccttctttct gtttcctcat ctgcagaatt tggagagtcc    23880
tggacctgat ctcaaatttc acatgttatt tatcttcctg cagcacgctg gggagaggaa    23940
gagacaggga catagaaggt tggagctgga acagacttca catctcattc cagaggcatt    24000
tggtccatct tacagatgag gaaatggagg ctgctcagtg gactgaggct ggaactgggc    24060
cttccagtgg ccaggccaga tcctccttga tctcccttgt tgctttcctg gtgggaagac    24120
cctggaacca ctttatgtga ctgtgtgaga agggaactgc ctctcatttt acccagcaaa    24180
atccaccttc aatccatctt cattttgcc cctggtgtgg gcaaattctc ccatacctaa     24240
ttcaggaagc cagaaagagg aagtgagtta atgatcctta gtgggaaggc gctggtaatg    24300
gtccttcttg tgagagtttc tgaaacacca cgctgtctct gtgttctggc ctggctggag    24360
ttaaacctct tcttggcctt tccccaggaa gctggtctga ggaagcccag atgcgtttgt    24420
ttacagctgt ctggtgacat tcgccaggct ctgttttcag aaggaacatt tccattccct    24480
tatttacacc tcccattgga gtgctcgggg ggacacacca attatttgca actacctgga    24540
aacctaggag ggtagcagat ctgtaggagg ccagtgttga agtgagaagc tgtagatctg    24600
gtgacactgt gggcttggga gggcttgccc agatctgtta cttatactct ctattaagaa    24660
acttcagtgt ccatggagaa gttatttaaa gtctgcgagc ctcagtttcc ccatatataa    24720
tatgggaagg atacctgatt ttcctattcc acatgaaggt agaaaaaatt aaattaaggc    24780
agccaatgaa agggttttga aagcaaaaat aataatatga tactgttctg aatttgttaa    24840
attattcttc caagtagttg cagatctttt tctgtacctt agaaaaaaac catgctatgt    24900
aaaaggagat gattccaatc tttaaataaa gcaactcaga ggtcagggc taggacagaa     24960 aacggccctt tgttcacaga agcgctctca cttccaagaa agcaagcgtg ggagaggcag    25020
gtggtcctcc cgatgtccct gtgccccatg gtgtcaagct gggttactat ggcccttcgt    25080
gacccagtgc agcagggatg tgggaaccag tgggtgtgaa gctgtgacgg gtcacaagag    25140
ggctgggacg tctcacagct tttacttata gcctagagcc tggggaaggg ttgccactct    25200
agtgatgaga gaggcgtgtg tgtgtgtgtg tgtatgcgtc tgtatgtatg tgtgcatttg    25260
catgtatata tgtgtgactg tatgtatgtg cacatctgtg agtatatgaa tgtgtgtgga    25320
```

| | | | | |
|---|---|---|---|---|
| agtgtgtata | ggtgtttatg | tgacagtttg | tgtgtaaatg | tgggtgtatg | tgtgggtgtg | 25380
| tttatgcatg | tacatctgtg | ggtgtgtatg | catagtgtgt | atgtgtgagt | ttgtgtgtgt | 25440
| gtgtgcattt | gcatctctgt | gtatatatgc | atgtgtgtta | ggggcaggca | cacaggcctg | 25500
| ttggtaaatg | agacacaaaa | tacctacaaa | atacaaaatg | tgagacagga | aatacaagcc | 25560
| ccagttactc | atttttcagt | gcaacagaca | taagattacc | atgtgaaatt | gctatgaaag | 25620
| tttccgaaag | cttcctgtca | attcgtagtg | agcagctagc | agaggagtgc | gggtccctgg | 25680
| agcctgcttg | tgcaacgctg | agctagtcca | agggggaaga | atggggtgca | tggctctcag | 25740
| ctgcagacca | gcctggaacc | tctccagcct | gctttagcag | agacttgtta | agaggtagca | 25800
| gcaggtggca | agattaggag | ccggagtagt | aggctaaggc | tgcacttcca | gggacacact | 25860
| gcctctgcca | ccacccgtgc | cacgaaaatg | ggagcccagg | accctgaatc | tctagcagtc | 25920
| cgtttctgaa | tcagttacct | tgggtatgtg | cctctggttg | atggaaacta | acttgtagcc | 25980
| ctgctgggtg | agagcctcac | atcgggacat | gtgacagctt | tgttgaaagt | agctttggaa | 26040
| acgcccacca | cgtggggcca | ctcactgtaa | tataaacggt | catgcatcac | tgagcaacag | 26100
| ggatacgttc | tgagaaaatg | gtcgttaggc | gatttcatca | ctgtgggaat | gttacagagt | 26160
| gtgcctacgc | aaacctagat | ggcagagccc | actccacacc | taggccagat | ggcagagcct | 26220
| gttgtttcta | ggatgcacgc | ccgtacagta | ggttactgta | ctgaatactg | taggcagttg | 26280
| taacaatggt | gagtatttgt | gtattcaaac | atagaaaagg | tatagtaaaa | acaatggtgt | 26340
| tatggtccgc | ggctggctga | aacgttatgt | ggtgcatgac | tgtaggtata | aagcattaca | 26400
| gttgtttgat | ttttctcttt | ttctcaccca | cagtcttaag | gcacctctta | tgccttttgt | 26460
| ctgggatgtc | ccgggcaggg | ttggaacgtg | tggttaaggc | atggcggaaa | ctgctttggg | 26520
| gacagacgat | ggcctcagct | tgccttgggg | tgtcagtggg | aaagatagga | gctgcccctt | 26580
| tgccttcgtg | tttcttcgta | ataatctcag | atgtacccgt | ctggtgggcc | tctcctagaa | 26640
| aaagccccgg | tgctctttgc | tcctgcggtg | tttctcagga | gggttgttgc | ttctttgtaa | 26700
| tggtggggac | tcagggaagg | gacgcaggca | gagggtgatg | ccacatcaaa | aagggaccct | 26760
| tggctgggtg | tggtggctta | cgcctgtaat | cctagcactt | tgggaggccg | aggcaggtgg | 26820
| atcacctgag | gtcaggagtt | cgagaccagc | ctggccaacg | tggtgaaacc | cggtccctag | 26880
| taaaaataca | aaaatacaaa | ggtggtgggt | gcctgtaatc | ccagttactc | agtaggctga | 26940
| ggcagaagaa | tcgcttgaac | cggagaggtg | gaggttgtga | tgagccaaga | ttgcgccatt | 27000
| gcactccagc | ctgggtgaca | gagtgcgact | ccatctaaaa | ataaactgaa | aaaaacaaa | 27060
| aaacaaactt | gggccatcag | cttcttggaa | aggctggtgt | gaggttgaag | catttgctgg | 27120
| tgcctctgct | caacgttttt | gtggtgaacc | tgagcaaaga | ggttatcatt | agtggatttt | 27180
| actgccttac | ctgggtgggc | actcccttgg | gaggtggatg | gacatttgca | gctgagccca | 27240
| ggtgggggaa | ttgcgctcac | tccgccttca | gaattccaaa | ggctgggcat | gcatcttggc | 27300
| ttcctctaac | ccatgtcttt | ctctaggtgg | ccacagcaga | gtgtcattaa | gtatctattc | 27360
| tttgcttttg | ttctcagggc | aggaagatcc | caacagtttg | cgccataaat | ataactttat | 27420
| cgcggacgtg | gtggagaaga | tcgccctgc | cgtggttcat | atcgaattgt | ttcgcaagta | 27480
| aagagagcct | tccttttcc | tataacctcc | gaagctttca | ccgccactag | caaaacatga | 27540
| gagctatttt | tgagatacat | taaagtgtca | aagtgtcact | gaatatcttc | ctacttaaga | 27600
| taagtgtgtc | tcccttagaa | catttccct | attcgactat | ataaatctac | attcttgacc | 27660
| cttctgaatg | tttaaagaac | ctcgggctct | gaagagattc | tctaagaata | ttttgtaagt | 27720

```
ggaagttttt gatgcatgca aaaaattggc aggatgttta gtgtttaaat gctaagcccg   27780
atatataaag gagcgatggc taggtgtgtg tggctgttgc acaacccatt aatcaatgcg   27840
ttgaagcgtt cattttaagg tgctacaggc ttaagtgtgt actcctttgg attttaggct   27900
tccgttttct aaacgagagg tgccggtggc tagtgggtct gggtttattg tgtcggaaga   27960
tggactgatc gtgacaaatg cccacgtggt gaccaacaag caccgggtca agttgagct    28020 gaagaacggt gccacttacg aagccaaaat caaggatgtg gatgagaaag cagacatcgc   28080
actcatcaaa attgaccacc aggtaagggt gttctcgcct gcagaggtga gttctcagat   28140
gccccggaac acccttggca aaggcaccag agctctctga ttgcagctga ttctcggggg   28200
gcactgaagc cagtctgagc cagtcacagg agggccttga ggagatgctg agtatggcct   28260
gggggtgtgg gagaggaagg ggctcaggaa aacttctgta aggagccaga taaaagtttt   28320
taaaataatg ttttaaatgt ttgtcaaaga aagcaataga tttgtaaaga aattagtagg   28380
taagtagtga aaattgattc tccttcccat tcccaatcct gtggcaactc ttgttacaga   28440
ttttatttat cctccacaga tacatcatgc gttcacaatg aacatagaat ttactgggtt   28500
ttagactgag ccatccttaa cttgtcaaca gttactttga aaacaaacca gctctcccaa   28560
attggggttt tgcggggtta tgagatgtgt ttcaaaagaa tgtttcgtac tttaaacatc   28620
ttggaaaact tgaattaaaa cagagctaat ggatttcttc tttccagacc ttctcagagc   28680
ttttagtatg ctagtgtgca cgtggcttgc ctacaaaagg gtgttgactg aactatttgc   28740
ccaaattata atcatttgag tatacagctt tttgtggggg caggcagaac tgagacatac   28800
caaaatcagt ttgggaaatg ctgtatttga aaatgctttc tatttaaata ttctctttgc   28860
aatcattttt gctctgttga tttgcttagc aaagtcttca tgtctgggac aatatccatt   28920
tcttactgac tcatcaaaaa ccccccactcg acacgtcgat gagagaggtt ttgtttgctg   28980
tgtggcatgt tcagtgaaag cgtggttcc agtttcttca catccttata attttctaga    29040
cttcagatgg agggaacaat cagaggaggc tggaatcctg cctctgacca aggaaaagac   29100
cagaggctga gccaggtggg gtctcttgtc cagccctctg cttgcctcgc tttacctggg   29160
tgtgggctga gtaattccag acaagcgtgg aattaatctg gctgtttgtg ctgttcagtg   29220
gcacgctggt tacacctcct tctggaaaca actctgcgtg tgctgtttgg gtggtaggat   29280
tccgggtctc cttctccgtc tttttataac atcaagttgc tgcccagctc aggctccttt   29340
acggccagtc ttcagaaaac caccagctaa cacatttact accctccttc cccgatgttc   29400
ctgtagcttc tctatggctg ggtggccagg catggccgaa gaggctctgg gtagatatag   29460
gctctgtgcc cggtgtgtgt aactggcctt gagtgaggct gcagttgtgt gttatttcta   29520
ttaggtcact gtggaatttc tagcgacaac taatctttca aagtgtgttt attggtcaca   29580
ggattattgg gccagcctct gccttcattc ttttcacct aatctgcata atagctgtgt    29640
tatccccatt ttagagaaga agaaacaggg gctcagagaa gtctagtaac ctgtgtgagg   29700
ccacacagca aacacctcat gaccctgccc tcctaaggca gcccatggct actgctggag   29760
ggatagaggc cggccccgtg gtttgatggg acagcttgac cttaaacagc ccatgggaag   29820
gcgggtgcat ctggtttagg aacaggctgc tagaaaggta tccaggatgt ggtagtctca   29880
ccggaaggag ccagtcagaa tagcacagcc tgtggccacg cgtgggacct gttcagcctc   29940
atggagcttt ggaggcagc cagcagcagg gcatgggctg tgtgcaggcg aggcgctggc    30000
ctggacgccg cccccactgc gtaacttcgt gtttggaatg cgtgggcaca taccgtgcgg   30060
```

```
ctgcttctgg ccgggggata ttcttttcca attttgagcc aaggtggaga ctgtctcctc   30120
gtgccatccc tggcatgtcc tggcaagacg tgaacgatct caatagacga gctttgcaga   30180
gtgtgtctga cctgactcct gctgtcttgg gagtttagct cttcagccag cagcatgctg   30240
tttgacatgt gtttcaagcc ccccaagaaa gggtgcttga aatttaaaat tgaactgatg   30300
tggcttttca aaatggaatt ggaaatgaaa ggatattaaa ttgcagacac ccacacaaaa   30360
gactggtttc cactgactaa actgcttttt tttgctgata gtagttgaaa gtagggagag   30420
taacagcatc tcttccagct ttttctcttt tgttcccttg ttttgatgat gggttatttc   30480
gggggaagct ctggctggcc ttgctttgtg tcatcttagg gataacaaag aggatgaaag   30540
agatcaggaa aaccgagaag gcagaacaga accagcagaa actgtgcttg aggaatgaaa   30600
atcacctaca cggctccttg tcatatgaga ctgtggccca gcctcctgca aagccattta   30660
agagtaaccc agtgaagctg gtgagactgc ctgccgcgtc cgtgggccca gtgactaact   30720
cggtggctta tcatctgggc ccagctcctc ccctggcatc ctgatttcac ttggaggggc   30780
ccccgttgtc cttcataaac atgtttattt cattttattt ttatgttttg agacagagtt   30840
ttactgttgc ccaggctgga gtgcagtggc gccatctccg ctcactgcaa cctccacctc   30900
caggactcaa gtgattctcc tgcctcagcc tcctgagtgg ctgggactac aggcgtgcac   30960
caccatgcct ggctactttt tgtattttta gtagagaccg gttttgcca tgttggccag   31020
gctggtctca aactcctgac ctcaggtgat ccacctgcct cagcctccca aagtgctggg   31080
attacaggtg tgagccattg cgcgtggctg taaacgtgat attcttgaga ctttcagtga   31140
aataagaatt gccacggaca tctgtggtca ttgtccactt gccactcacc tacccccttt   31200
tctggcagca acagccggca tttcacatgt ccatcatcgg acagcgtagg tgggaccatc   31260
agtcatggtg tcctaccctc tgtggccaag gagtggacac aggacccagt tagggcaagc   31320
agaggctccc cttggaatcg caaagtgaag ctggatgcca cccacagaga ctaacatggt   31380
gaagctgctg tagcccctgc tgttgagccc cagcactgc ctgagttctt gcactttgtg   31440
agtccagttt aatatctgct tttcctccca ttcttggagc tcccctcaca tctccagtgg   31500
cttgaagttg ccagagatgt ttctgggctt gtgaccaaat gactccttt ctgcttctca   31560
ctgctgagca gacacatgtg cgctcacttt gcctgctgag tcttgggacc cggaagagct   31620
tttgggagac aatcacggac cagccccctc ttgcctgccc tgctgtctcc ctccaagcag   31680
gaggtgagaa ggtgtccacc tgcagccccg gccaggcatc cctttctgtg cttctgccca   31740
aatctgaaat tcccctctcc ttgggaccca cgactgggc cagcctgcct ggggagggaa   31800
tcccagctgc agaaagtcgg gacagtgtgc gtgtaaacat gttaatagaa agcagctttg   31860
agggcagact agttcagctt cagttacaaa ctctttccaa atgcgtttaa catgagccac   31920
tggctgtgcg cagcatatgt caagctttca tccaatggtg gcattttgtc cctgcgggt   31980
ttttttttcc tgagcagttt ggggcagggg tgggacagg gagagagaaa agtaaaaaga   32040
gagcagtttg gtttcttcag gctggagtac aaggcagagg taatgggatg tattgaagaa   32100
ggtaggaggg aaagttactt tagctacagc tatttgtcca gctgtgctga ttaagaaact   32160
tggagaaaag catctttgga atcatgtcct tccatctta tatacagcct ttgcagattt   32220
cctgctgttc tgagagagat ctgaactcct taccaggacc ttgagggccc cacctgattg   32280
ggcacccctc actctctctg cccctcctcc ccttcccctc ctcccctcct ttctccaccc   32340
ccacctgctc tgctcagaca ccccttcctt ggttgcttcc cacaggccag ggctgtcccc   32400
tggggccttg gctgttcccc tcccaggagc gcccctctcc agctcctcat gcagccaacc   32460
```

```
ttcctgtcct tcaggcctct gattaaattc tgccttagac atctctcccc acccgctgt   32520
gtgaggtagc gccccatgcc ccagtcccct caactccact gcctcacttt ggggacacat   32580
caccccaggg acaactgcat tccactcttg gttttccct cctcgtctat ttatcacaat   32640
ttagagtcgc ctcactcatt tgtcaaatga agttcatctc tgcagctgga ctgcggggtt   32700
gggggcacat ccggctgtcg gtcctcaggt aggaggtgct tggcaacctt gttcagagta   32760
ggacgttcac agctgtctgc cccggaggaa gcaagggcac ccgccacatg gatgaattg    32820
aggggaaggc acccggggct cctgcatcga gcttccctcc tatattcaat gaggaaatga   32880
ccctgcagaa ggctggctgc agatgcccct gcctcccggc tttgcctgct ggagtttga    32940
tggacacgtg gtcctgtcag ggctacagca ggtctatggt cttt ggtaac ggaaagcgct   33000
ggtgaaacag tgagctttcc cgtgggtgct tttccctgac gccaacaacc aggtaaatat   33060
ttggaaacgg ccttgttgag gcttgtgagg tggttttcct ccctcccctg taggcctgcg   33120
ccaccccccc aaccccacgg ccaccttggg gccagatggc acccacagac ctgtttgaag   33180
tggccacaga gggagccctc tgggcgctgg ggccgctgtg tttgcagagg gtcctcttac   33240
tgctgagctg gctggtgcag tgagaaggaa ggccgacacc cctgatcctc atcaagttca   33300
gacggggggtc actgcgggtg aggggcctgg ggcctttta c atgtcccggg agctgctgag  33360
caggccactc ttctccaggc caccagaact tggccctgcg catggtgaat cttccctgag   33420
tcagctgagt gaggggggttc aggcagcccc ccgggacatg gcagtggcgg ggagtggact   33480
ggggtggtgc ttgccatgac tcacgccggt tctcctcagg caaccggatg gtcagatgcg   33540
ctgactcagt ggcctgagct cgtccaaaag cgaatcagag aacacagggc ctgggctcac   33600
ccgctgccct cttctggagt catctgtcac tcatcctcat gaaggaagcg cctgggagcc   33660
tggaatgcac atcgcactgc cccagctccc ctcttgtttc tgtgtttttc cattttggat   33720
tctttcccc aacgccttct gtactgggca ttttgtggtc tcttctttt ctccgagaac    33780
tctgagggct accattgcat ttgctaatga tgccacagac ggtgttgacg ttatgaggct   33840
tctattactg tattgatttt taccattttt aggggacgg gaatcaatat tcatgaggg    33900
aatgtgaagc cagacagtga agtagaagct ggcttttatt ttgtgccagg ctttgtccag   33960
aggcgggtgg ggacgtggct cctaagctct tgattgcagc tccttctggc ttgggaaacg   34020
tttcagttcc ccaaactctc agaactggat ccctgtgtg ttctctggcc cggattcaag    34080
aacttagttg attgtcaagg aaattctttg gctatatttt tctcttaata tggtaatgcc   34140
ttttttcact ctggcactct cttttcaggg aattggatta agactattat ttatgggtct   34200
gacaaagcag ttcccaagtt gttgggactg gatttgttta ggaatgtctc ctgtcctctt   34260
cattgagggg ggaatacaaa ttgcttccat ttgacagttt atcaagtgtg tgacagagta   34320
tcagagtcca gggttggcca actacagcca gtagtccaaa gctggccctc tgttgttgta   34380
aataaagttt tattgggaca tggtcatgct cacttattta ggtagagtgt atggctgcat   34440
tcagtctaca ccagcagagt taaatagttg tgatgaagac cacgtggccc gtgaagccaa   34500
aaatatttgc ttcctggccc tttacaggaa aaaaattccc agccccagtg gcaggcaatt   34560
aacaccttgt cctcgaggag ctgaaagtgg ctggaggcag gaatgcttat aagaaccaag   34620
cgaggtgaag cactaggtgg ccgcggcgag caggaagaga agctgatttt gtttgccctt   34680
tcgtttgccca gagattgtgg gttcttttt tttttttttt tttttttttt ttttgcaga    34740
gatgaagctt tgatcttgtc acaatagcag agggaggcct tatttttgtc tatttctctg   34800
```

```
tgacattggt agaaaggact ttgtcagaat tccaagctat ttggcaatta tccaattttg   34860
agatcctaat ggatctttcg aggtctagtt tgttcattct tttagtgatt ccttgttaat   34920
tccctgattt tataaatgtg tgttgaacat ctgtcttggc caaatacttc ttaggtgctg   34980
aggatgcagc aatagtgggc aaagccatgg ggcttaagat ctagtgtggg aaatgggtga   35040
tgtaaagtaa atatggcgat aagtacagtg cacgaagcaa acaagtgaag gggtagaagg   35100
tatcaggctg caaagacagc agatagtgta ggcagggaat cttatctgag ggggtgacat   35160
ctaagctgag atggaaagga cagtgagagc cagccaagga aacaagttgg gtgacaagag   35220
ttgcaggtgg agttgcttaa tttcccactt ctgctcagcc tgcagatcct ggatcttgga   35280
ctaattgcaa actgtcattt cctcgtgagt ttattagaac cctccagaac aagtttctgg   35340
ttagctagtt tctctgtgtg ttgtctcatt tcttgttggt tctggttctt tggggttcct   35400
actcatactc tggaaagctc cagtgtctta agtagtcagt ctcccaagag tctgaaagca   35460
caaagattca caatgatacg atcacctctc aatcatagca gcattgatgc agttccgtag   35520
ctggtttcct aaagccatcc agatctcttt ctgtggcaag agagaaataa gaccttctgg   35580
tgaattgagg actaattatc ctaataaaca tgcgaattaa cagttccttt ggttaaacaa   35640
agcaccagaa tctgataatg ggaacatgtg actcatggta tttccttctt tgctttatct   35700
accaggcagc tcacagaaac cactggcctt ccctgtgttc ccattttatg tcataaaatat  35760 atatttaatt aacttattat aaaaggcccct tgttcattg accatatcaa attattctta   35820
tatagaagag gttatacatg ttttaaacat tttaaaataa atctgaaaag aatgctacat   35880
cctgggcaac ttccctgcat ttggggctca aagaagctct atgtggttat gggtaatgag   35940
gagccagagt gccttcaggg cagttcagca gatgctgaaa ggctgctgtg tgctgttcgc   36000
tgggcccacc aaatagagta ggactgagcc cctgtccacc atgacagccg ggagatacaa   36060
gctgttccct ttgcctccct gagccctgag ctttatagcc tatagacagc tgaaaagcag   36120
gctgcatccg ttacccagtc agttacccag acccaaatgc caggccttgg ctaaccccag   36180
ttattaccta atttaatat cccaatggat gttttaagac ctggctggtt cattctttca    36240
tttatttact tattcattga ttttgtaaat atttctggag catctgccat ggccacatgc   36300
tgttgtagca gcatcagcca ctctgaagtt ggtggatgaa aggggatgca tcaaaggcgc   36360
tgatgtatgg aggagacgca agttagactt gaccaagaca atattattcc tcctctggat   36420
gccccgaata tatacagtca ttagctgtcg ggcccccatg tggcactgtt gacattttgt   36480
ggtttaaaca ctgaagagta agggaatatt ggaaatggca aacatctgat atagtgtaaa   36540
ggagactaaa tattttgatg gtgttcataa acaccgagga ggaaagtctt tcatttttt    36600 tcatttgtgt gctctctctt tctctgttttt tgcacactgt cctctgttct ccttctcctt   36660 ctcttttttcc tttttttctcc cttcatctcc ccatttatct gatctctccc acctgaaccc   36720
cttctaccct gctgccctcc tgtccattct accttctcta ctcccctccc tagacagtag   36780
taatcacatg tcagttggag aaacatgatg gcaacttggt cacaccgttc ttctcagtct   36840
gtatatgtcg gtgatctcag tgcccatctg gcagatcctt cctgccctgg ctcttctgct   36900
cactgcgacc accccttgact ttgtgatcac tgataacctt caccttctct aatctaaatc   36960
ccaagcttct cactcttggt ccaccacctc ccagccttgt ccgttctgaa ccctgaacgg   37020
aagctgaatg gaaccctgaa cggaagggtt ctgaagctgt tcagaaccct gaatggaagc   37080
tgaaatatca atgggccatt gcttttcaca gtcctctgtg aaagattact ggccaagcca   37140
gcatctggag aattcctggt ccaccacctc cctgtctgga gaagctggaa cagccagctg   37200
```

```
catgagcatg tgacccgtgt actcacaggc cctgtgccct gagctcgctg tttttaatttt   37260 atctttgaat ttgtattttt gtgaataaag ccctatgagc taatggagca tgctcaggga   37320
acttggggct ttagctcagg ctggattcct cctgctgcct ccccagtccc tggtcccctg   37380
agaactccag ccccatctga ccttcccttc cctgtctcta tgcaggggtc attgctaccc   37440
tctatccctg gaaaggatgt aggcacaggg cagttctagg ttccagcttg ggcaccgctt   37500
aacatcttgg tggtgcaggg atcaggctga tgataccgtg gttgttctgt gggctactgg   37560
gcagggtcaa gccactccca ccctgatcca ggtacctaat gcacccgaca cagaagcggc   37620
agtgtccttg gggtcatcca ttatccatgt gttggaggag tgggacccta gggaagatgc   37680
ttggctcgac ttccccaccc ctagccaggg cacaatcaga ggtccagggg ctggtgggca   37740
caatgccaag tcgtgaggcc tccagtgtct gcgctcactg tcccataaat aaccacagta   37800
ataactagca aatcaaaaac attgtgatag gtcgagagag acagcatgtg gaagaaagga   37860
aaaagctttc tattttagta cctttaacag tgctttctgt atgctttatg aacaaggagc   37920
ctgcattttt attttgcact gggctctgct aattttgtag ctggtcctgc ccctagtag   37980 ctcaagtcag caaatctttg gttcatctga gtccacagtc cgctgacccg ccctttttca   38040
cagttcctcc cctgcccatg tgctcacttc cctccttacc cagcttggcg cactccctca   38100
agcaagtctt tggatgctga catcccccgt aaacaaccct tctgcggcct ggtttgattt   38160
tccttaggag acatgcaagt tctatagcac tgtttcttgc tgggtatgga ggatgtgcta   38220
ttttgtccat tgcatatttt ttaaagaaaa tgaaaggtta gcataactgt ttccagaagg   38280
cacattgaat cactcagttg agtcccagcc agttgctgca atgttagcct ttgaagcaaa   38340
cttgaaccaa cacaggacca gcctagaagt cccagcctcc agaaatgatg cagtggattc   38400
tgcagattca gcaacaacaa tattttttgta actcaagagc acttagtaat tttcaaagga   38460
gagaaagaag taattgactt ggcttattag gttgaaaaag agttgccaac ttttctcttg   38520
gttttgatgt tattggtttt tttttatttt tcttttctcc aagcttcagg gaatgagatt   38580
gaatgagcac tcaagtgcta ctaggcagaa ccctgaatgg aaggaagctg aaataccgat   38640
gggtcattgc ttttcacagt cctctatgaa agattactgg ccaagccagc atctggaaa   38700 ttctaggaac gccccctcct cttgcagcag tataagtttg cggggatcat ctgacccat   38760 tggggagttg tatgaaaaag gggatttatt ggggaccctg ttgcctgttt ggatcttact   38820
tacatttaac tattgtctgc taatggattt tttggaaagc aaccaggttt tccgtaaaga   38880
atagctaatt gtcagagctg agatgaccat tggagatcac tgggctcaac tccctaattt   38940
tagaggtgct aaaaccgcaa tccagagaag ctaatcaagt ggttcaaggt tgtagactga   39000
gttcatatag gaccaagacc cagcccagat gtcctactgt ctgggacagt gttctctcag   39060
catacgtgga gcctgagggg gtaatgtgtg tgcgtgtgtg tgcatgtatg catatacaca   39120
taggtgtttt gcctaagttt tcacttctgc cccaccttgg ttgatcttgg agaatgagcc   39180
tgaggcgcgc tgtcaacctg ggggcctcat tcagcacagg cccaactttt ctgccctggg   39240
ggagttccag cagttatggt tcatctgtgg ttcagttatg gaactcacac cacacatagt   39300
gcccccaaaa ccgaggctgc gtgcacagac ctcccctccc ttcccgtggt gggcccctgc   39360
ttgggttctt cctaaacttc ccctttgccc tgctctgtgt tataccctct ctggtcccct   39420
gtccctgtgg agtgatccgg ggcacaaggg cagctgtttc cccgctgacc tctgtgtgcc   39480
ctgagcatct gggaggtggg gagcaggctg gtgagaagaa cacctggagt ggaggttggg   39540
```

```
gtcagggagg gtcccagtcc cggtaccacc cccacctgct gtgggacctg cagtcccctc   39600
atcagcagaa cggctatgaa gccatcctgc ccatccacag ggtggtgggt cgtgaaggct   39660
gcatacctgg cagagcggga gaagctctgg gaagatgccg gacacgcgcc gtgggagtga   39720
tttccctgcc ttgcccagat tctgctccca tcacctgaac ctgcctgtca ccaccatgga   39780
actgctgtga ccattgcttt cctttttaagc agattagcag acatctcctg ctccaccctg   39840
ccaaacaaac aaacaaacaa gcaaacaaac aaacaaaaat gtgcatgagg gagtatggac   39900
ttgtagagtc ttttctaaac attgttaggt gcttgtattg ggatcctctc ttaaaatgaa   39960
ccatattccc caggctttgg atgacactca tggttgccca ccctccaact tccttccctg   40020
ctggcagagc cctgggtttg ttttagttcc aaccctgacc ccaccgcatt cctgactcag   40080
gcaaattcgc agggtccaat gcagtcaggg gagccacgtt ccctcctcca acgagtgctg   40140
aggtcgctgc ttgattggat actgccgatg acctacgagg aggagggtgc cagggcgctt   40200
ttgggacttt gcttttctgg agagatgctt ccacagcatg gtcatggaca cagtcacgtc   40260
ttgatgtgat gtctggaatg gtggtggccg tcttgtggct gtgagaacag gctgaggttg   40320
attggatgga gggaaggaag gagccttgtt cttgatgctg tctgtgagcc tttgagttat   40380
cagcctggta ccacccagcc cttggacaga tatctactct acatactcca tttgagtttt   40440
tttttttttt tttttttttt tttttttttt gtcacttgca gttgaaaaca ccctaattga   40500
tacacacaaa ctatttttag tgctggtctg tgtttggccc ttatgaaga ctctgggctg   40560
agctgcccat ggtgagggag gtggactttg tgttttctta ctgctctgtg tcctggtggc   40620
ttgtttgtgt ctctgcccat gagacaaaag ccgagagggc aagggcagat tttcttaatc   40680
atatgttccc tgcaccaagc tcataggaga cactcactga atggttgttg agagagttct   40740
cttttcacgga ggcaatgttt tgtgaaacga tgctgcttgt tgttgtctgt tggttgtaat   40800
atgcatgaac actaagagcc atctttaatc atgctgtggg ccgcctcttc caaggtgtta   40860
gcattactcc cactacctgg tcagcatcct gcctatggct aggactttgc aatttacata   40920
gatatggtgg ggagacctgg agcccatggc caggactctg acaccctcac tggatctgtt   40980
tctacatcta cctggatggc cgtctaggac attagaggat ttgtgtcttc ctaaagtccc   41040
tctgttgaga gacttctggc tctgttaaga ggacactatt tagcattgtg agtccctgca   41100
ggctgggggc cagtgggcgt ttttcttcta gatgccccct ctcttcttct ggcctcccag   41160
gcttcctgct cctgagattg tgagaactgg cctgtgctgg gctcactgca gaaagactgt   41220
cgtcccaaa ggttttgcac caaacttgag ctacaagatc ttttagggggg acctgagatc   41280
tccgcctggg ctctatgaga gcaggcatgg gttgttttttg ccccgtcact gcagtcatgc   41340
ccacacttgc attttctttt cccccagca gtgtgaggat ctggcatgag gagtgggact   41400
cgcgtgccct ctttcttctc ctcttccctc tggccttttc atccgtcagt gggggacaga   41460
tgtttgccct gtttacttct aggcttactg tggggctcca gggagatggt gaagtggcca   41520
aggagaggag ctgccacctt caagacggcc tgtggccggt ccgctttaa agggagactc   41580
agaggtgctt tgctgtgggt ggcgcgggaa ccagcctggg gacagcagtg cagaggcctt   41640
ggactcagag tgcgtgggcc ccgcggggct cacggcgcc tgtggctgtg cacttccagc   41700
catatctgtg ctgcatctct tccacattcc cccatggagc tgatgtctag acagctatgg   41760
aattaaatgc tcaattaccg agtaggaatt tggccagcag aggtatagct gctgagtaga   41820
cagactcgag gtgaggctca cggctgagaa caggccccat ctggctttgg aatgagctga   41880
ggtgcccgat gctcctgcag ccagtggctc ctgtggggag ctggggccgt gaccccaaa    41940
```

```
aggcagcttg acctcatgga ccaccataaa tctggcctgg tcaacatctc tgccagacat   42000
cattcccttg caaagatttc tgcctgtgat tggaattctg gatgaacatg tactgggcgt   42060
gtgggtctga cagctgggaa gcttgttctc ttgtttagcc aggctgccca tcatctgtaa   42120
gcctcagtat ccacatcttt aaaatggggg gaaaatatag ctcaactcct aatggtgcca   42180
tgagaatact ttgtcacctg ccaggcaaaa gcttattcct ttcacagaaa tccagggttt   42240
acaatgtgag accctcccc actccgccgc atgtgtctgc ttgctttttt ctgtcttagg   42300
gttgcccttc atgagctagg aaatgtctga gtggatgaaa acctaaacga gatgatcact   42360
ggtggtgccc attggtgcag cctttgccta aatggctact tacgtagcca catttcctcg   42420
tctgtgttca ggtgaggact ggttcctggg cagactgcct gggtttgcat cacgggtgtc   42480
catcttgtcg aagcccatgt ggtcacccaa gtgtgactga ccaggcttg cccacggggt   42540 gctctgggcc ccattttcgg cagcaggcag cgtcccctgg aggcctggcc ctccccggga   42600
gcatggggag tagcgcctat gggcaagcag cctgcagcct ccatccctgc ctgggggctc   42660
ccccgcccca gcctcacagc ttctccaaaa gtgtttgtct ccttgccgca tcctctaggc   42720
ctgagctcag acggtggaaa agaagagctg gaaggagagt tgcctttcag tctctctgcc   42780
ttctgaggtc tcctgagaca tagagcctgg gcctgcctcc ctttctagga ggcgccaagg   42840
ggtggtaaga ataggggatg agtgagatgt gaattaggat ccccacagca agccctgcct   42900
cgtaactttc tgatgggttt tcaatgtgtg gtgaagcaga cgcctgctgg gccccttcc   42960 tgagttgagt ttgacctcct gcctcctgtc tatctccttg ggcagccagg ccaccccgct   43020
ccattaacct gtgccacccc atcccttac ctgtcgcaag cccagccctg aaggcctcaa   43080
aggcctggtc ttccagccag tccagggcct gaagggatgg cagtgtccct ggtggacctc   43140
ccctggtgtg gcctagtgca catcccagcc ctgcctcctg ccccgcctgc acgccatgag   43200
tgctgaagtc atgcctggca ggggctgctg gcccaggccc agagtaaaca cactgcgctg   43260
agctcgctgg tgtgctgctg gatgctgatg agcttgagga gtgtgggaag tgagcatggg   43320
gctgagtaga gatgcggcag gcctgcacct ccccgcagct gccctgcatg ctccagcctc   43380
aggcagccac acagggaaag ggtcacccac tgtcagggca gacctttacc atggctgggt   43440
gacacgggct ggctgtggaa aggtgtttgg tggttcccgc tgttggattt gcacaggccc   43500
agatgctcac agcaaaacca acacctagat ggtgcttaca ggagccagcg ggtattcaaa   43560
gagctgttca gatcttaagt tgcttcattc tcacagtgga ccattgaggt agctgtacgt   43620
tagtcccatt ttccagatga gaaaactgag gacctgagtg gtcataagct caggccctca   43680
tctaaatcac gcagcctggc cccaggtgtg tgctcttgac catggacagt gctctcctgg   43740
tcctcttggt atctgtgatc tgagggacct tcctcctcct cagtctcgta tagtcagttt   43800
taggtcttgg actctgtctt catatccctt tctcccttcg tgagctttct cacccagcac   43860
cttccttatt tggtgtgtgt tggggatat ttgtggtgtg gcgtggcact gtgtagtgga   43920
tgagagagtc tgttttttccg atcccagtcc caggtttcaa accctgctct gtctcgagtc   43980
acccagaatc ttggaccctc agtttcctca tctgttaaat gggcatggtg gtcaccccac   44040
ctcatcagct agtgtctgct ccatccctgg tggaggagat gactcaagta acccctgggt   44100
tccacctgcc ccaccccact ggtcccctgg ctctttcttt gttgagatag acgaatgtga   44160
ggctctggag ttgcagttcc cacgagggct ggggtggctg tctgatttct gggcctggtc   44220
catgttgttc agggcagctg ctcgttctaa gtgaataaag gctgaaggaa ctcgggaggt   44280
```

```
ctgctcggct ccgaggaagg cagagaggga aagggccccg atgccttccc tgatagagct    44340
agggaggccc ttctgtggtt ccccccagct ccttggcctg ggtgaccctg gagctggctt    44400
ctgttccatt ttgttgtgca gagttgtttg agactcctgg ctttgcctgg cctttgtggg    44460
acgctggaga tcaggcttc tggagttggc caattagcct gcccagacca ggaagcacag     44520
gtggctgaca gagggccgtt tcaggagagg agagacagcc tacctattcg gtcttgctgt    44580
ccccatgctc catccctgcc cctgaccagt gtggccctgt actcagcata ggcgtgcacc    44640
tgagtcagta cagttccctg cccgcagagc accccaaata ttccaggcct caggacggat    44700
gtgcacatga tgagtcgggg caggtttcac tgcctgtagc ttgggatcct tccctggggc    44760
ttggttctct agggccatcc ccagcagtct caccccaaac cctaaattca tgttgtcttc    44820
ctctgtctct tggcctcaag gtttcagagt gagtctgtgc tgatagcttc aagatgtgat    44880
gagaccccga cttggcctcc agttacctcc ccacggtttc cttggtgtgt gtgtggcttc    44940
agtgttcact ggctcccgca cggcttgcaa tgtgtggatt acgggtggga gggaaatcca    45000
gtcctgcccg cagcaaaggg atgttagttg tgagctcagt tccccaccgg gctggtgtt    45060
tccaaatagc ccgtcactgt ccctgcttgg ttttccatga tatctgtgcc tttacctatt    45120
tggttaaatt aaaccaactc agcaacgcca gccattgtgg tttcagggca agctgcctgt    45180
cctgctgctt ggccgctcct cagagctgcg gccgggagag ttcgtggtcg ccatcggaag    45240
cccgttttcc cttcaaaaca cagtcaccac cgggatcgtg agcaccaccc agcgaggcgg    45300
caaagagctg ggctccgca actcagacat ggactacatc cagaccgacg ccatcatcaa     45360
cgtgagcctc tgtccctctg cgggtgggga ttggggcaga gttttgccag gggagagga    45420
gtcagcatag gtcttagccc ctgactttgt tgtagtctgc gtgaagggat ggaactagac    45480
caagccatgt ggattctagt gccagcagca tggcagggt cacatggcgg ggacggtgac     45540
accggagcag gtggacagcc agcctcctcc caggaggaag aagttgtatt gggtgcttta    45600
gggtgattgc agttggcttc tgggcttcag agagaaaatc tccctgttta cggcacctct    45660
aaaactttct gaaaattgtt aaggtcattt ttttccggca aaatattagg ttaatgggaa    45720
tgaatctcag agaagaatcg tgcccccac tctaggcacc gtgctcagga aacgaccagg    45780
cagggacata gattgaacca tgttatgaca cgatttgtaa ccttttcatt tctgtttaat    45840
tgcagtatgg aaactcggga ggcccgttag taaacctggt aaggtctttt aaacctatgt    45900
taggtcattt gttttatct atgtatacgc tgttttttgt ttgtttgttt gttgtttgtt     45960
tgttttgag gcaggggtc ttttcaaaca taaggttgcc aaagtgtatt ataaattcct      46020
ttaaaatggc tctgtaaatg tactgcgtgc ttgcaaatga ccctacggat cttttctgga    46080
aagagtaagg caggccggag gtgagggttg gaaatgttat gccagagaac acacttgtgt    46140
ctcagagtta caggtaaaca ccgtgaaatt cagggccaat gcaggagtaa ggtgaaggtc    46200
actaaaaatg ctggccagtc accgaaagca cctcctccaa attaaatctc ctgggctgct    46260
gaaggagctg gctgggctca tacacatttt ctcttggcca ggaatcctcc cttaaggcct    46320
ggctggaatg aggaggagtt acccacccac aaagatatca cttaagtctt cccttaaata    46380
cttgagcaga aaaagtgaag ccttagaaca cagaccagca gagctagagg gcagctctgg    46440
ggccatttat agagggcagc tctggggcca tttatagagg gcagctctgg ggccatttat    46500
agggggctgtc tttagcaagg cccagtgtga tggcacctcc tagatggtgc cttggcatca    46560
ggtactgaca tctcagcact cctgggaagt gtgcacttgg cagctttctc ttcccagcag    46620
aggggcagct gtgctcccag ctctgtcctc tgcctccccg cgcagcactt ggggatggag    46680
```

```
tggagatggc tttgctggta atgaagcatg acagccctaa gctctagggt tgtttccccc   46740
tgaagtcagc agagtcatct taagatcatt agacatggga gaagcaggaa ggtgtgggca   46800
gccacctaaa ggagtttgag cctttggaaa cgtattcctt gtgaaacagg agcaaatcat   46860
atcgtgcatt ttgaaactat ctgtgcttac cgtgaggtga gcacccagtg ccgacctgga   46920
gtatgtgcga ttcttccaca gctgcgcgtg gctcgcgctg cctgggtgtc ctgatgcctc   46980
tctccctgct gccacgggga tcccctcctt gcatctcccc acttcgatct ctgaaatagc   47040
tcagggactt ctttcaggca tattctctct gggtgtgtac ctgccggtaa agcttcacga   47100
ttcagtaagc cgtgtccttc ttgcttttca ggacggtgaa gtgattggaa ttaacacttt   47160
gaaagtgaca gctggaatct cctttgcaat cccatctgat aagattaaaa agttcctcac   47220
ggagtcccat gaccgacagg ccaaaggtag gcaaggccca cacagccctg gggactccgg   47280
agatggggcc tgaagctcag ctgccctttg ggacttgggg aagggaaaag cggcagcccc   47340
taggactagc caagccgtct ctgatccaga agtgaacggg aatgcacatt actaaatccc   47400
tcgcagaagg tcacagacat ttcaccattt ttgtcctctg atcatggcaa tgtcacttga   47460
gtcagtctaa tatgtaccag gcatgatcct aggtgacttg tgtacattat ttcactttct   47520
ttatgtatgt cacttaattc ttttgcccta tcagttagga attactagtc ccattttgct   47580
gatgagaaaa cggttcaggg agatcattct gcaaacgttt attgccccat ctgctctaag   47640
tcaagcaggg agcttggcag tggacagctc aactggggcc tggggctcaa caggggcctt   47700
tgccggtgtg acttttatgt tctgttgggg gatgggaagg ctgacagtaa ataatcaaac   47760
acataagata ctattagtgc tcccaagaaa acggatcagg gtggccgtca agggagcgac   47820
tggaggggca gctggtggag atggtgtggc caggaaatgc cttccaagct gaggtctgag   47880
tgaggaggaa ccagcgggca gggatgtggg gggaacactc cagaaggaaa gacagaggac   47940
tcagcatagt tgagtgagca caaggcccct gaagtggcct gagggccgga gcacagtgac   48000
agcatggagt tccccggggt ggaaagaggc caaggccggg cgagcaggct cacagcaggc   48060
cgtggtgagg gacctgggtt gcatcctaac gacatttaag aacagggaag tttatgatct   48120
gattgatgtc actgaaagga cactctgatg gctgcgggga gtctgctgga ggggttgctg   48180
gaagttgggg accggttaag gggctctccc agccatctgg atgagacatg ctggggtctc   48240
agacaagggt ggtggcagtg gaggtgggac agaggggtca cattccagat atatatgggg   48300
ggtagagcaa gcttgggaa gggccagctg tcaggatgag gccatgagga attaagggtc   48360
atgcccaggt acctgaccat taattgaaac aatgggactt tcccaaggtc ccccagaggg   48420
gaggggtcca gaccaggatt tgagccgcaa cctcagtgta cccttctgtg gcccttcctg   48480
caacctgggg gattgggccc ccggcccctg tgtccccag cacccccacc aactgggctg    48540
accttctgct gtccctttgt tgtctcacca ggaaaagcca tcaccaagaa gaagtatatt   48600
ggtatccgaa tgatgtcact cacgtccagg tgggtaaaca ggatgcgtgt ctgtgtctta   48660
aattttaata aacctgaact tcagaaggtg ctcacgggca cccctgaaag agaaaccta   48720 tgctgcctta agacgtctca gtttctgctt ataatgaagt agcatcggga aagaggacag   48780
gtcattagcc ttggcccctt tgtttggttt taacctgtgt ttttgcattc tgagctggtt   48840
ttcttcactg gcagcaggcc ctccggtgta gaaggttctg ccctcctctt tgaaggcagg   48900
cctgaacagt gtgtgcgtgg tggggctgtt gattcactct ggctcacgtc ttccttaccc   48960
cacattctgt tgaaacccac attccaggag ggccccaagc ccctcccgca gctctaggca   49020
```

```
ctctgctttc gttgctctgc agctcgtggg ccgcggctcc aggaatgcca gggcaggtcc   49080
agcgcaggga agtgaatgac tgatgtgctt gttttccccg agctggtgga attgcggcct   49140
gtggttggca ggctcatggc atcctggtgt tctaaactgg atgaaaaatt ctggtgtaat   49200
ctcatgagtc ctggtagtag actcacctgg catggctaaa actgtcagag gtaaagtagg   49260
taaagactag aatatagtaa cagatagatt aatgtgttca ttactatgat gaattaatga   49320
ttcactcact gtgaaagtat taatatattt tgatacatgt tatgaatggt ggtcccttc    49380 ttagcactcc agaagatgga gccatttgtc aaggttaaag tgtccctca gttgtttgcc    49440 tttggaacta cgaggtgtag ggaaagatgg taagcccttg gtgcccagct tcctgggttc   49500
ctgtccctgc tctgatatgt cctgccttgt gaccttggga acgatatgac ccctgagtgc   49560
ctcagtttcc tcctcttcag gatagggatg acagcgcagg tgcttctgat gtgtggccag   49620
gctcagatca gggagtggtg gcaggggtca ccagccacag tgatgccagc cactatgtat   49680
cacacgtact gggccaggtg ccttactggg atgatctcat ctgatcctca caactcatgt   49740
tgtagggtac tgttattatc cccatttgc aggtgaggaa atgaaggcac agagaagtta    49800
agcaactgtc cgaggtcaca cagctagcaa atggccgagc tagggctgca aaccaggcca   49860
accactgtac tttactgact ccttagtaat agctactatt aattaagaaa taataacaat   49920
gatgatggct gggtgcggtg gctcacatct gtaatcccag cactttggga ggccaaggcg   49980
ggcagatcac ttgaggccag gagttcgaga ccagcctggc caatttgtga aaccctgttt   50040
ctactaaaaa tataaaaaat tagccgggct tggtggcagg cacctgtaat cccagctact   50100
cgggtggctg aggcaggaga attgcttgaa cccgggatat gtaggttgca gtgaactgag   50160
atcgtaccac tgcactccag cctgggcgac agagcaagac tctgtctcaa aaaaaaaaa   50220 ataaataaaa aaaataaata aataataaag cactttcctt gctgttacca agtaaatctt    50280
tgactctggt agacaggcaa ttttaatttt aaaataggat cagaattcct ggaggaattt    50340
taccttagac ctaaggagaa gacgggaact ggtgagagct gagttttgcg tgaggaaggc   50400
ctggtgtttc ttcacactaa cacgggtgct ttttctctgg agcagcaaag ccaaagagct   50460
gaaggaccgg caccgggact tcccagacgt gatctcagga gcgtatataa ttgaagtaat   50520
tcctgatacc ccagcagaag cgtgagttgg agtcgttttc tcttttccca atattcttgt    50580
tgttcctgtg ggggtagcag gaagagggag cgctgttcct tttctactgg ctcagatgat   50640
tatgttgatc cttgacagac gtggtcggac gttgcttgtc attcctgctg gccaggcctt   50700
ccgacctggc tcggctcggg actcatccat aggagggtgc cttctgtctt caaaagtcct   50760
tgctccacga ggaccctcca gatggacaga gcaatagcag actcgtaatg agtctctgag   50820
atggcccggc tggccagaga gagggtttca ggaacagtgt ccccaagccc tcacttggtg   50880
gtccttttct aggcttcagg acccttctct tcctggagtc ttccagaatg tctctgacaa   50940
ttaggcccat acctgtcaac acctccagaa aaataaccca agtgatatca agtaacatg    51000 acaagaagta gctcaaccat ccatcagggt tgttacctg tattggcgga atatccagag    51060
aaaagtgcga gaccagggac cagcaaatgt gccttggggg ctggatctgg cccactgcct   51120
gcttttatat ggagctgtgg gctaagaata gttttgcat tttatttta ttttacta      51180 ttttttattt tcataggttt tgggggaac aggtggtatt tggttacatg agtaagttct     51240
ttggtggtga tttgtgaggt tttggtgcac ccatcaccca agcagtgtac actgaaccca   51300
atttgtagtc tttatccct catccctgtc ccagcctttc cccttgagtc cccagagtcc    51360
attgtatcat tcttatgcct ttgtgtcctc gtagcttagt tcccacttat gagaacattt    51420
```

```
aaatggttga aaaaatcctg aaataagaat agtattttgt gacatgttaa atttgtatga   51480
aattcaaatt tcagtgtcca ctgtaatttg gtttatgaca tctatggtgg cttttgtgct   51540
ggaacagcag agttgagtag cttcaacaga gaccatatgt actgcaaagc ctaaaatatt   51600
tcctatggag cccttttacag aaaaagtttg cagacccttg tgctagccca tgaaggacca   51660
tgacagcgtt ttgacgctga gctatataag agctacagtt atagtggcaa ccacacaaag   51720
gaagtgcctc ttaacagaaa cattccgccc accctatag gaactgcatt ctgagttgca   51780
atacccatta taagcaagtt ggccagatag tggccaacta tctggcagat atctggccaa   51840
ctacgtggca gatagtacct ggtacatcct tccccacttt ggggtcaatc ttgacctttg   51900
atctccttgg ggtcataaag ccacacaagt gttagtaggc atttctacag tggacacaat   51960
ggatgattta gcctaaaaat ctcaaaagga gcccagcatc ctggcacatg catgtaatcc   52020
cagctactca ggaggctgaa gcagaaggat cccttgagcc caggagttcg agactagctt   52080
gggcaacaat tgagacccca tctcaaaaaa aaaaaaaaa aaaaaaaag agtgggaaa    52140 aaagaacatt attaaaaaaa aaaaccttaa aaagtaatcc aatctaccga tggtttattt   52200
tttattttat tttatttttt ttgagatgga atcccactct gtcacccagg ctggagtgca   52260
gtggcacaat cttggctcac tgcaacctcc acctcctggg ttcaagtgaa tctcttgcct   52320
cagcctctga gtagctggga ttacaggtgc ccaccaccaa acctggctct ttttttttt    52380 tttttgtaa ttttagtaga gacgggggctt caccatgttg gccaggctgg tcttgaactc    52440
ctgacctcag gtgatccacc tgcctcagcc tcccaaagtg ctgggattac aggcatgagc   52500
caccgtgcct gacccactga tggtttgaat tattctaagt tcgccaccgt ccaatcctgt   52560
ttgctctggg cttttaggtt ctaagctgtg cctctgtcca tgtaaagtca gaccaggagg   52620
aatggaaaca cgaaacattg ccattgtgtt tcccttttgtg ttgcagtggt ggtctcaagg   52680
aaaacgacgt cataatcagc atcaatggac agtccgtggt ctccgccaat gatgtcagcg   52740
acgtcattaa aagggaaagc accctgaaca tggtggtccg caggggtaat gaagatatca   52800
tgatcacagt gattcccgaa gaaattgacc cataggcaga ggcatgagct ggacttcatg   52860
tttccctcaa agactctccc gtggatgacg gatgaggact ctgggctgct ggaataggac   52920
actcaagact tttgactgcc attttgtttg ttcagtggag actccctggc caacagaatc   52980
cttcttgata gtttgcaggc aaaacaaatg taatgttgca gatccgcagg cagaagctct   53040
gcccttctgt atcctatgta tgcagtgtgc ttttttcttgc cagcttgggc cattcttgct   53100
tagacagtca gcatttgtct cctcctttaa ctgagtcatc atcttagtcc aactaatgca   53160
gtcgatacaa tgcgtagata gaagaagccc cacgggagcc aggatgggac tggtcgtgtt   53220
tgtgcttttc tccaagtcag cacccaaagg tcaatgcaca gagacccgg gtgggtgagc    53280 gctggcttct caaacggccg aagttgcctc ttttaggaat ctctttggaa ttgggagcac   53340
gatgactctg agtttgagct attaaagtac ttcttacaca ttgc                    53384
```

<210> SEQ ID NO 3
<211> LENGTH: 2012
<212> TYPE: DNA
<213> ORGANISM: Rattus norvegicus

<400> SEQUENCE: 3

```
attttcggct gtggtccagc ccgtggccgt cggagtcgcc atgcagttcc tgcgtaccgc     60
gctcctgtct ttgctactgc tgctgctggc ggctccctct ttggcgttgc cgtcggggat    120
```

| | |
|---|---|
| cagccgctcg gccccgctg ccactgtctg tccggagcac tgcgatccta cccgctgcgc | 180 |
| cccgccaccc acggactgcg agggtggccg cgtccgcgac gcgtgcggct gctgcgaggt | 240 |
| gtgcggcgcg ctcgagggtg cagtgtgcgg cctgcaggag ggtccctgcg gcgagggggct | 300 |
| gcaatgcgta gtgcccttcg gggtgccggc ctccgccaca gtacgacggc gcgcacaggc | 360 |
| cggtctgtgc gtgtgtgcca gcagcgagcc ggtgtgcggc agcgacgcca agacgtacac | 420 |
| caacctgtgc cagctgcgcg ccgccagccg ccgttccgag aagcttcgcc agcctccggt | 480 |
| catcgtcctg cagcgcggcg cctgcggcca agggcaggaa gatcccaaca gtttgcgtca | 540 |
| taagtacaac tttatcgctg atgtggtgga gaagatcgcc cctgctgtgg ttcacattga | 600 |
| actttatcgc aagcttcctt tctcgaagag ggaggtgcca gtggcgagtg ggtcaggatt | 660 |
| cattgtgtcg gaggatggac tgattgtgac aaatgctcac gtggtgacca acaaaaaccg | 720 |
| ggtcaaggtt gagctgaaga atggagcgac ttatgaagcc aaaatcaagg atgtggatga | 780 |
| aaaggccgac attgcgctta tcaagattga ccaccagggt aagctgccag tcctgctgct | 840 |
| tggccgctcc tccgagctgc ggccaggaga atttgtggtt gccatcggaa gcccttctc | 900 |
| tcttcaaaac acggtcacca ctgggatcgt cagcaccacc cagcgaggcg gcaaagaact | 960 |
| ggggctccgg aactccgata tggactacat tcagacagac gccatcatca attatggaaa | 1020 |
| ctccggaggc ccgttagtaa acctggatgg cgaggtgatt gggattaaca ccttgaaggt | 1080 |
| gacggcgggc atctccttcg caattccatc cgataagata aaaagttct tgacagagtc | 1140 |
| ccatgatcga caggccaaag ggaaaactgt caccaagaag aagtatattg ggatacgaat | 1200 |
| gatgtcgctt acatctagca aagccaaaga actgaaggat cgtcaccgag acttcccgga | 1260 |
| tgtaatctcc ggagcatata tcattgaagt catccccgac accccgcag aagctggagg | 1320 |
| gctcaaggaa aatgacgtca tcatcagcat caatggacag tctgtggtca ctgccaatga | 1380 |
| tgtcagtgat gtcatcaaaa aggagaacac cctgaacatg ttgtccgca gagggaatga | 1440 |
| agacattgtg attacggtgg ttcctgaaga aattgatccc taggcagagg caggagctgg | 1500 |
| acttcatgtt tccctcaaag actccaggag atggcgcatg agaactgagc tggtgacgca | 1560 |
| ggacacccag gactttgtcc aacattttgc ttgttcgggg aacacccctg tcgacagaat | 1620 |
| cctccttgat agtttgcggg caaaacaaat gtaatgttgg aggtgcacag gccgaagccc | 1680 |
| tgccctctgt atgctacgca tgcagcctgc ttttcttac aagcttgggc tattcctgct | 1740 |
| taagcagtca acatctgtcc ctgcccttag ccccagttgt ccgactaatg cacttgacag | 1800 |
| acgcatagat ggatgagagg acagtccttg cagccttggt cttgggtgtg tttacacttt | 1860 |
| tactccgagt cagcactcag aggaaattga tgccctgaga ccacaggtgg gtgaccctgg | 1920 |
| cttctgagat ggccaaaaaa tgcctcttag gaatcctgga atcaggagta caatgacttt | 1980 |
| gagtttcagc tattaaaata cttcttcata ct | 2012 |

<210> SEQ ID NO 4
<211> LENGTH: 49442
<212> TYPE: DNA
<213> ORGANISM: Rattus norvegicus

<400> SEQUENCE: 4

| | |
|---|---|
| attttcggct gtggtccagc ccgtggccgt cggagtcgcc atgcagttcc tgcgtaccgc | 60 |
| gctcctgtct ttgctactgc tgctgctggc ggctccctct ttggcgttgc cgtcggggat | 120 |
| cagccgctcg gccccgctg ccactgtctg tccggagcac tgcgatccta cccgctgcgc | 180 |
| cccgccaccc acggactgcg agggtggccg cgtccgcgac gcgtgcggct gctgcgaggt | 240 |

-continued

```
gtgcggcgcg ctcgagggtg cagtgtgcgg cctgcaggag ggtccctgcg gcgaggggct      300
gcaatgcgta gtgcccttcg gggtgccggc ctccgccaca gtacgacggc gcgcacaggc      360
cggtctgtgc gtgtgtgcca gcagcgagcc ggtgtgcggc agcgacgcca agacgtacac      420
caacctgtgc cagctgcgcg ccgccagccg ccgttccgag aagcttcgcc agcctccggt      480
catcgtcctg cagcgcggcg cctgcggcca aggtacccgc cccgccctgc gctgcactcc      540
tgggtggctc cccacccctcg ccaactcagc cggaccagtc gggaccgttg ggaggggatg     600
cagaggggca gagaagcact gcgggctgtt ctaggcatcc cagttagttg gggagagaga      660
tgtgactcgg ggtggtcgtg tttcatgggc tccctcgggc tctatttctt cgccaagcat      720
caggtcgttc tgagaaacac taagcaggtg ctttgtacgc tttggtccag tatcccctgg      780
ctgtggtgac ccaccacgga acttggcatg ttgacgcaca tggccttggg accacaagaa      840
ctcctgtctg tcgccttccc tttcttctcc ctctcggctg ctccctttct tcttggaact      900
atctaggcag tgttttttctt gtagaacgtc ttcgtgaaaa cttttcactt ggggagaggg      960
aacagctctg ctcaatttag caagtaccgt ttctcatctt gcctccaaag cagaaactga     1020
tttagtaacc cgaccttctt ccaccactga tttcaacttt ccaaaaaacc ccacacttgt     1080
cctttggtcc ttttgcttga actcagtcag atagtggacc tcgaagtttg agatagaggg     1140
cccactaggg atgaagaaaa atgcaccctc tttcccctcc acgtgtgacc tttccgtccc     1200
aacaagagtt ggaggtggtg atggtaacag gatgacagag cttggagaac cgcccagctc     1260
catgcaggac cttccagaaa aatgcttcag ttaaatccag agatacccctg tggaaaaaca     1320 gtaaattcag actggccact ccagcggtgt ggggaccagc cagctgggct ccagtgcact     1380
tggcttcagc tactgggctc ctgcccaaac ctagcacctc cccaggggca tgtggtggag     1440
aggataggat agcacaggag agaggggatgg atctagattt ttctttatag gaatatgatc    1500
ccatatgacc acttttggatt tggcaaaact ttactcgaat ggtcaggaaa gtactccggg     1560
tggtgtagga agaggtgggc tgatgtttat attcttacta ccagagcaca gggctggacc     1620
tcagcccagg aaactcggca tcattagaga gaagaaggtt ttttttttc ccccagagag      1680 gactgatcca ggggtaccta ctaagcccca gcccatgcga caggtgagct gtcctgtgac     1740
tctattcggt gtcacagctt ctgcaggggg aagcttctgg ccttgtcgtt gccttagaca     1800
aggtggaact gagagctgga acttgaactc aggcaagttc cttcagaaca ggccagagct     1860
agacctagat gtgggagatg ggcttccagg gggccggact taccatctca ctttggggag     1920
aagtaaagag ctatgcagct gctgagaaga gattggtgtg acaggagtta gttagaaatg     1980
ggcagaagaa gtgacccaca ctggtggccc acagtcccct ggggaggaag tagtgtgtca     2040
cacgtgctga catccttgag tagttcttga acaggcgctg tttggaggag ggctggtgta     2100
ggacaggcct agaggaggag ggcagaaggt aggagtctgg gctactttttg taagaatctg    2160 agtgtgtacc ggtgacattt taaagaaaca cacgtgggaa acaaagtagc tcttactgtt     2220
ggtggcctag ctgcaccagg ccctgggtta ctggcacaag cagaggctga atacttggct     2280
ggttgagttg ctttggggag acaggtcctt ctttggccat cagggccacc aatgtggaga     2340
cagccataga atatagagct gggggggcagc cttctcccct cctttttgtaa atatttgttg   2400 ctctgtatcg tgtctgacac agtgtgtctg tgggcctgat acttagggac taccagttac     2460
atgggtggat ggatagaaag ataggagatg ctaggagtac atcacgggcc cttagccttg     2520
cttcgccctg actcgccatc tgagactgtg tcctaaggta tctcccggag caggatgtgg     2580
```

```
gagacagtca gctcctttga ctcagttcca ttctggctcc tgctttcagc agctggtgct    2640
cagggcagct agctcacttg atgtcacggt tgagtaagaa ttgcttgctt gcttgctccg    2700
gtgcatagta taggtgggga tgctgggagg atacagaggc ctgttttgag aagcacccct    2760
gagtataaca tgaaggggaa tcgactgtga gacacactga ggtcagagag gttctgaggc    2820
agggtctcag cagaaagctc aggagatagg tgggagtgtg gtgggaggga ggcgatgtcc    2880
aaggcgttgc tttgggagtc acgatggctc tttggatgga gaaagtgcca tcattgcata    2940 aaaccttgt ctgcaggtcg gttaatggaa acaccagaga acatgtcttg tttggaaata    3000
gagataaatt tatcagcgca tcagggtttg gctgagacac gtacacgtat accagaggac    3060
aaggacctgt tacttatcac tgaccaggag agtacaagaa gagagtgaga gtgaatgccc    3120
acgagttcga ggctagtttg ggcaacagat tgagaccctg tgtcacgttt taaaacaaaa    3180
aggtatagtc atatagggta gcagcaacaa aggtatcata taattcatac ttctgcttca    3240
ggcgcctttt tacagaacca gtgctgtaat tctcctggta cagctgacta tcacgcagca    3300
gcaccttgag cccatgcgtg gatcatgaac ccgttcgtag cctgtgctgt tgacagagca    3360
acggagatta taaccagat ccagctaagt agagctaaga gccgaaaaac agtgccccag    3420
atggccgtgg ctttgggatg atgacgaagg atgactctcc aacgggcata ggaattggga    3480
cagagttgcc tttagctact ggcccaggag aagcccagag tataagggggt tgtagaaaag    3540 atgtctccca gccagagtcc tagactgtaa attgttttg ggtaggaaag gcccttccgg    3600
atctggagac atttcaaaag agtaatcaac atgtgaggtg ctgcatgtaa aaagccaggg    3660
aaagactctg tggataggag aaactcagtc tacccatcct tactccagca aagccagtcc    3720
tacccaagac atcccaaacc gacaagccca gaggtctcca agcctcatgt gcgggcagag    3780
gtgggctaga ggggacagct agaggttttc agaagttctc cctcctagcc tcaccccaga    3840
gcctctgaag gcagaggcca cggaaccacg cctcttggag gcacggactc tttgttaaat    3900
gggttttatt taggtggctt cttttatgtg agccttgagc aggctgacac tgtgagcgtt    3960
agtacctggt cctgctgaac tcaggagatt caagaggcag cacaaagtcc tccctgagg    4020 aagctcacag ttaacacagt cggggcaaag acagtcattc atattcctgg agacagttag    4080
acagtttctc atctacagtg caagttttgc tattggtagt tggatgcact ttttgtctct    4140
ttaaccaaaa aaaaaaaaa aaaaaaaag agagacgagg gttggtagaa agcatgaatg    4200
gagtttctgc ggtcctaaac cgtttccctg gcatttgtag agcctgcctt actggctggt    4260
gtcttacttt tcttaatgct ctctgatggt ctgctcaagt gttaaatagt aaggctcgat    4320
aaaattagta agttaacagg atcgaaagcc aggcattaag tttactttat cccatcccgg    4380
ggagcaataa atagattgtc ccggaacttg agtgagattg gtcagggacg tcaggatggt    4440
gagctggctg gccagatgcc tcagcgcagc aggatgaatt ctgagtccct ttggagctgg    4500
gtgatcctgg gcaaattctg tgccttggac tcagacatca gactttccgt gagcttacat    4560
ttctcatgga caaagctctg gtcccggaac ctgtgaggga gcagtcactc ttggcagtgc    4620
tttgagtact gaccctggc tctggcctgt gtgggaccag acctgactgg tgccagcctc    4680
cctggccttc agggccatag cagtgaaggg cctgggtcag tggttttgag atcccttgt    4740 tagagctgcc tgtgaggaag gaaaccacca gtctgtgagg agattgtgct cctgtatccc    4800
gctcaaaggc ttggatgccc tggagaggct cccactttaa attatgattt gtaaagccat    4860
gtttggcact gaaggaatgc ctccatcttg accatagcca cccttacttc agctttcagt    4920
cagtttatgt gtctttctgg gagtcagtgg gagtcacatg cccactccta agaaccaatg    4980
```

```
ccacagggta attctttgct cccctctgtg accttggact ttcccctcct ggtccttctg    5040
gttaaggccc tactgagctg tgtcttttgc ttcgacactt tctctgacac cagaaaagaa    5100
aaatgcttgc aacagagaaa ctgaagaggg tagtagacat cttgaatgtt tccctaaaaa    5160
ctcagaagcc cctggaaagt tggtgtgact cagacctgct aagtgacagg tatctagaac    5220
caccgggtta cattagccag gacaacatgc ttcagaaaca gacataagtg gtaagggggg    5280
ggggagttag agcgctggaa gggcagaata catcccaaat ccacccaaac cattccttga    5340
acagtgtctg tgtactcagg agtatggcag gtataggggaa tgagaggtca agttaactga    5400
cctttcttat tgagaagctt tcgcgatgcc tgactgtggg ctaaacttct gtctgagctt    5460 cccttttttga atgtgtgact ggtttcctca cgagtaaaac aataatggaa ataaggtttt    5520 ttttttttttt ctcaccctgc tcagagatat tagcacgaag gacatcgttt cacgaagtgt    5580
tcagcaccat ctggtgtatt tctagataga actctgccct gtcagctgta gtggcaacca    5640
ttgtcatgac catcaaagct ccagcgaggc agtcagttca aagaaaggt ctagaatgtc    5700 tgtcctgtgc aacacttcat gtgggtgagt tgggcgcttt aggaaaggtg cacagaggag    5760
tggaaacgtg gcctgagacg gacatggagt ttgctagtct ggaaaggttc tctgggccaa    5820
gggagttaaa ggctgctttt ctatagcctc tgaccgtcca gtcccaatca ttccccagc    5880 attgagcttc tgaaaagtat gtggcttcct ctgaagtggc tgcatgtgtg gcaccccggg    5940
agtgtgtgtg tgcatgtgtg agtgtgcatg ccgagaccag cgacatatgt tgagcatctc    6000
cgttcatcac gcaccccac cttttgtttt gagacagggt ctctcattga acctagagtc    6060
cataggttca gctagattgc ctagccagcg agccccacag actctcctca gtgctgggat    6120
gatagagata aaacacttac tggcttttcc acatgggtgc aggagatgga actgggactt    6180
catgcttgtg cctcagttta ctgacctgag catttcccta gtccttaaga cttttatacg    6240
cactatctca tttactgggt tagagcttac aggagacggc agttgataga cactctatgt    6300
ccttcttgaa cctggcctgg ttttgttttt atgttctgga aattcctcat agggaaaaat    6360
ttgtcatgtc ttcaggaaag agggggaaaa agaacccaaa caatttggga gtttacaaat    6420
agcctattat tttgattgct aggacagttt gttgagttag catattttgt aaatggttct    6480
gtatagcatt ggttgacagc aactgctccc tagccatggg acagtcacat ctgtgcactg    6540
aattctcgga gggctggtag tcgtggttgg aatttttgat aatttccaaa tttgaataac    6600
ccatgtcttc atgagtcaga gccttgtgca ataatttaga cttcaggaac gtcttcttcc    6660
ctgggttgtg caatgagctc tctagaagga gatgctaggc tgcctgtgca gtgagcatgt    6720
ttgtctcagt gtggatgaga tgtagaattc ccttccacag tcttgggcaa gatgttaccc    6780
gatcatccaa cacttggggc atctcacgcc ctgtgactaa gatgagtttt ctatttggta    6840
cccatactca aagtaggagt catcagtcag taattactct gtagacagat ggatacagac    6900
tgctgccagt tggggttgcc tcagtatatg ccggccggct ggatatggga gagagaggc    6960 tcatccaaaa gttaacacct gcttttcaca gatacacaca cacacacaca cacacacaca    7020
cacacacccg aaagatacag acagtacacg agacatacac agacatacac agacacacac    7080
acagacagac acacagagag acatacacag acacacacac agagacatac acagatacac    7140
agacacacac aggacataca cagacacaca cacagaatac acaaacatac acagacacac    7200
acacagaatc acaaacatac acaggacaca cacacagaca cacacagaca cagacacaca    7260
gacacacaca cagatataac acacacaaca ccaggaccac acagacatac acacacatac    7320
```

```
acacacacac acacacacac acacacacac accagagtga gccacctgga ggtggaatat   7380
tatattcttg ggtcaggatg agggaaatgt caccaaatca cagtgatcta aagagtgacc   7440
actactgttc taattgggcg acaggccttg tcttgttcct ttgtggatat gggaaggtag   7500
tggcattaac cctgctgcct agctatagaa acagaagagg ttccaagagg ttttatctac   7560
ctagggccac ccactaagga gagagctagg atttgaactt ggctccgcct cactatcaga   7620 ctgggggggct tccttaactc aggttgttta aaagcatgct gattaatctt cagacatttg   7680
gagtcttttt caacatcttc cctttttataa gactttcggg tttagttcta tagtggtctt   7740
agaacacctt tggggatttc tgatcttttg aattcattgg agtgtgtttt ctggccttga   7800
atgtggtcag tcttgggaac agctccatat gggctggaga agagcatgtg tttggctgtt   7860
gttgactgga atcttctaga tatcagttag atggtgcagg ctggtggtgc tgtttaacta   7920
gacactgctt ttgcacctgt gttggcaggg tgtgaaggaa ggatgctaaa gcaaccttgg   7980
ctacagtctg tcttctggga ctccatttta gggaactgga cctcctcagc cccaccccca   8040
ccccgcatga gtcactgact ccctgtgctc tgtttcctga ttgtgttgct taaggataat   8100
ggtactggga acaccagcag gggattttt ttttttttt tttttggttc ttttttttccg   8160 gagctgggga ccgaacccag ggcctgcctt gcgcttccta ggtaagcgct ctaccactga   8220
gctaaatccc cagccccacc agcagggat tttaaggtca ggtaaactaa tgggatagtg   8280
aatgagcttt gtcaacgggg aataggaatg attgaccgat acctggactg ctagacagta   8340
ggtccacact cttccagatc tcgtgctagc aaaacaaaca aaaacaaaa caaaacaaaa   8400 ctgaccaggc aaccaaccaa tccccccccc caaaaaaaac cccaaaacac catgactgat   8460
ccagaaaaga tagaaaagta gggtggatct tactgggtca cttctgtcca tggtcacggt   8520
caaagaatcc ctgagactgg gtactttaca aagaagctta ttttgctcac ttttctggag   8580
gtgcaggcat atgcttgact ctggtagaga tgtcatggtg ggtggcacca tgggagtgtg   8640
aactggagag gttgtgagac aatgtggaag tcagaaagag acctacagag gccaggcttg   8700
ttctgtggaa accaccctct cgtaagaact aaccaaggac ccaggagaac tgccttattt   8760
cccgctaaag gccagaccct ccagttatcc agttgcttcc ttataaggcc ctgtctccaa   8820
acgttccaca tcaccccctta acggcaccac atggggacac attctaacca cagaagctca   8880
acattgccac catggaatct gctgtacttt ccactacaca tctgtagcca cacgagctcc   8940
ttgattttgt ctttccttgg tgtttgtgga tcaagacact gccctgtgga gacaccagag   9000
gttggtcaaa gccaccaact aattgtaggg aagacagcat ctcagtacct gaagccgaaa   9060
ggtgctgccg gcctcacagc ccagttcctc acactgtagg tgggaaagct gaggcacccg   9120
aagggaactt ggttctcaca agctgtgtta ttagacttgt tggagtcaga gcctgggccc   9180
tgtcagccct aataaactac attcacgtgc atgtcctcaa caggtcaata aaagacacaa   9240
ttaatagtga gaagcagaaa tgagatattc aatgtgacca cattgggaag gaagacagaa   9300
tagtcccaag tttatctgtg ggaattctga catgaagttt agatttaaac agagggtatg   9360
tggcttaagc agtccaggtc atggtgtggt cccacccatc actgacccat cattgtctcc   9420
gctccagtct cactgaaaag atgtctgat atgtcaggat tgtgtgaaat gtctttccta   9480
aagactagct cctcctctgg ctagcaacag gcgtcaccct ttttatctc tcagcatgag   9540 attcctgggg aaattccaac tccttgggga ccattgtttc aatagaatga tagccaaagg   9600
tgtgtggggg ggggtggggt gtgtgtgtgt gtgtgtgtgt gtgtgtgtgt gtgtgtgtgt   9660
gtgtgtgttc caggagagtc tctttagact atcttcatat ctgaggctgg agggatgctc   9720
```

```
agtcgtatga actgtttttg cagaggaccc aagttgggtt cccaatatgt tgggtaattc   9780
acaactgccc ataactccag tatgggtaat ccagtaccct cctctggccc tcacatgcac   9840 aaacccatg  cgtgggcaaa caagtaagaa taaaaataaa gtcttttaa  aagcacgtat   9900 aaatgtgcag cttggtggtg ggggccgact ctatgaaccc atcttggcag cctccttctc   9960
ctggagcagt taggtgtttg gaggaggctg gggtccacat gggagatttt tcccatgagg  10020
cccgagaaac agtaggtgtt ttcactcagt ctcacttttc aaagtgtcat tgaagagatt  10080 ttttttttc  ctacttgtaa agatgactac atggtagccc gtgtggtaac tggcttttcc  10140
ctgcaagcgt tttgaggctc tggaacacta attgcagtgc acttgcctca gggaaaaatc  10200
tgcgcaaata ttattgcgaa tgattcagtg ccgaggagcc ttggcgcctt aacctatcta  10260
cggtttgaac tttgtcagga tgagcctgtt ttcttctctt cagacaggct tggtttcttt  10320
cttctgtgtt atttagccac tccctctata tgtctgatga tctaaaactg tactctatca  10380 gttttagaa  acccgaagca taatcacgtc aaaatacac  aaggaaagag agtcacgttc  10440
ctacagtctc aagcctcacc tcaggggcc  gtggttgtta gcacttcaag gacagacact  10500
ttatgttcat aggtgttttg gtgtgttgaa ctcttttagg atagacagta ccaagtacag  10560
tagctggaga gaagtggacc ggtttgctgt aacccttggt atttattgtc aaactctgtc  10620
cccaaagggt tgctgaagtc cttttgtcatc agtgatggag attttaaaag tgtttgttgg  10680
gagagagtgt gaatgtatga gtctggggca cgtgtgtgca tacctatttg tggtggtccc  10740
gaatccaggg gtcagtctcg ggtgtctctt ttatttaaag cttttattag gtattttatg  10800
tgtatgagtg ctctgacttc atgtacagac agcacaccag aagagggcat cagatcccat  10860
tgtagatggt tgtgagccac catgtggttg ctgggaattg aactctggac ctctggaaga  10920
gcaacccagt gctcttaacc actgagtcat cttttctagcc ccttgggtgt ttttcctggg  10980
ttctgtcttg gtatttttg  agacctgggt ctccttggcc tggagcttac cgtgtagact  11040
acactggttg gttagttagc cccagggggtc ttctgtctga gcctcctggg tgctgggata  11100
acaggcatct gtcccagcct tcttgtgggt tcttgggctt gaactcagat cctcagtgtt  11160
tgtgtggcaa gcactgtact gaccgagcta tcttcccatc ccagctgtgg aaggtcagcc  11220
tcccatgttg ctgaaaggct acaagaaatt cttcgaagg  aaatccttca tgataaatgg  11280
cagatgtggg tcccaagcca gcagaaccat tcagatgtag attttcctgt tgttgcctg   11340 tcttgtctcc gttcactacg ggtaaaggga agcagtgttt ggggtggaat gagcacttcc  11400
agagattgga attatctggg ttagtgagtt gtgatcatag ctaatctagg ctgaaaaggg  11460
gcttgtgact gccatgtcag ccttctggtt ggtcacttgt ggtttggtga tgtgtttttg  11520
aggggcctgg gtcaagtgaa gggatttgaa ggtccaaaga cattcaccca gtatatgaca  11580
aagaatgcaa atgtccgggt gtctagtcat ggctcactaa atggaacctt ctagatgcta  11640 gctcttttcca aggatgtgga ttgaggccag actgttctg  ttttgaaaag tgaagaatgt  11700
gtttattcag atgttttgga cacatgtaag ggaatatgag ctacataaat ttgattttct  11760
agtctgatag ttccgttcaa aaagaaaata aaaacatgac attattgtta ttaactttga  11820
ttttaatgac aacatattca agatataatt cacatacagg tttttatatg tccttggagc  11880
tgtggactta tcacctgtag ttccagaaca ttcccaccag ctctaaaata aacacagcac  11940
tcactagcag acaccccata tttccctttc cctggctcta gccagccacc agcctacttt  12000
ctatcccaga gaatttgcct tttcaagaca ttttctacaa gtggggtcct ataacgtggt  12060
```

```
ctgttgcgac tggcctctgt cagatggtat catgttatca ttttcataac tgaaaaaaaa   12120
atcttctcat tgtgtggcta tgggaagaca actctccctg ctgaggacac ataatcccag   12180
tcttgaaagt cactttgaaa gtctaaaata ctcaggcagt attaatgtat tagtggttat   12240
gaagccggaa tgaaatattc cataagactg agaatcccac gttgaaaaga tcaggaagtg   12300
tacttttcag atttattaga acacacagct tttttgtaa ttatagaaag gatgtcggaa    12360
atgggcttgc ctctcatctg acaggccaga ggcctagaaa gaggaagggc cttgtttctg   12420
gacccagccc ccgagcccct ttagcagctt gcttgaggca tcatttcctt ctggggtacg   12480
tctcaggttt gtaagccccc cccccccccc cttgctgtct ggcttccat atagaaacgg    12540 cagtacactg gcaagtaaga gggcattggt gcttctccgg gctgagcctc agctctcctg   12600
cctctagaga aacagcctct tggccccacc tccctcccag ccctgccctg gaggttggag   12660
tttcaggggc tgaacaccca ggcagcctca gacaaaacaa ccagaggaat caagagcagg   12720
aagagaactc aattgagaaa tctgtgaagg tcagtgctgg agccagacgg acgcttccca   12780
gagcgagtgg atggagatgg tattgactga gatccccagc attcaccacc cgcacgcgaa   12840
gaaggttact atcattttct ttgttctcat ccttgagaca gaagtaactt tttaaaaatg   12900
aaagcatcat ttaacgtaga cacatgcttt tccaaaggca ccttccccag gaaagccaaa    12960
actacagaat taggtcgagc ttgtgagtca caacacagtt aggggctgtg ggccaactgg   13020
ccagatgccc ccagctgggt cctgagggag acagccttag acttgtttgg gtgacccaac   13080 cccttccct ttacctgctg tgagtgagtg tctgggtacc tggactgcag ccttacccta    13140 gccctgcaa gcagtctctt gcaccatcct cagccctcac agcctgaggt ctggcacagg    13200
gcaagctttt cccacgtgga gccgtctggg agactgtacc ggaaagaggg gctgccagtg   13260
cttggaagtg ccagtgtggg ctgggaacca aggctaaggt ccctggctcc acctcctctt   13320
ccttctctat tcattaggaa gaaagaaaga ggtcacagga aactcaggaa ttttatgcaa   13380 aagataggg cagagtcagt ctctctctct ctctctctct ctctctctct ctctctctcg    13440
gtctctctct ctctctctct cttctttct ttctttcttt ggcagggtct caagtatcca    13500
ggttgtcctt gaactcacaa atctactcat ggttggcctt gaattttga tctcctgcac    13560 ctacttcctg agtgctagga ttacagtgtg tgcattgggg attaaaccca ggactttgtg   13620
catactagat tgtagagaga atatcttgtg tactgtatgg atgcatcacc tgtcaattaa   13680
aaagcctctg gcctatggct taggcaggaa atagaggggg gagattggcc gggaaggtgt   13740
gaggagattg atgcatggtc cctgagcaca ggtgtaggtt agaataaatg gttattttca   13800
gttatgatcc agtcagagga gagcctagct atataaccaa ggtatttgca aatatatttt   13860
gggtctgagt cttacttctg ggagcatggg gctgggagga aggaccagga ctaacttcaa   13920
cattacacac tcagtcaatg cagccacgtc cctagtgccc tcctctaaaa ttttgatgg    13980 taggaaagaa aaatctgagt cagacattgc agaaatttgt taccctagtc aagaagaatc   14040
ccacaggttc agcctggact acatagacga ccccccccc ccacataatg gaaaagaag     14100 gtggtgcagt ggacaaaata gtccttgcat aaacgtcaca cccgatcctc gaggagcgtg   14160 cttctttttct gttcccttct tgtgccgatg atggcacagg gtttcgtttt ttcaggttaa  14220
ccttggacct ccgctggctg tcctgcccgg gccctctctt cttgcttgta tcccgtgctc   14280
agcagcctgg aatgtacagt cgcagcacca ctcagaaaag gggttctggc ttcctggaat   14340
gttcaaggtc ttccttttgt ttctgctgcc ttcccacctc agacccagca gctggctggt   14400
gccaactctg gaatttaaga gagtgggaca cagaacacag ccatttcgac ttgaatgggc   14460
```

```
tcatgggcct ggtgagacat cgttgctgtg attactgggt tatattttct tattttcttt   14520
tccttcaggc acaggaggtc tatctcctac ccactttata cctcatcagc cctacagatt   14580
tctctgatcc tcagagaaag cggtccaagg tcactggcag aggcggagcc ctgcgagctt   14640
cccttacccc cacgcctctc tccttggaac tttccaaccc tcctcccac tctgctcatc    14700
tggactttgg cccttggtct cccaggtcat cccaaattc agtaagaact ctcataaagg    14760
gagcttttcc ttggggacaa atcgtctgtc ccctccatg atggtgcagc accccctcc     14820
ctatctgttc ctctctctgg ctttgtagca cacacctctc cccagacaca ggttctagtc   14880
ctgtctcgac atgccaccca tacctgcttc ggtctcagct gcttgtattc taccctgaca   14940
gggaaagtcc caaggttcgt gagccatgaa ggatttccta gccatggaag gatagcccag   15000
gtgtttgctt cttccttcta gggattggct gcttggtgtg cttggtgcta gttgatttga   15060
taacacagat tgctccttct ctctgctctg taagaactca cttactacac ccctggcaga   15120
gaagtgtggg gatgagtaaa gtgcttgcca gagaagccta aagactgagc tgactctcag   15180
aacctacgtc aaaagccaag cagggcggca tatgcttgca atcccaacac tggggaggga   15240
ggcagggtag gccagccaac ctagcaaaat tggcaagcac caggtcccag tgactccgcc   15300
tcaaaatac aatgtaatga ctgttctgaa ggatactatt cgtggtttat ctctagtggc    15360
tgagcacaca ggcacatgtg aggggaggga gcaggcagtg catgtatggg gactcgcctt   15420
gagttgggag tctggggcct tggctgaagt tgtactccag ccccaggagc cctgttctgc   15480
cctgtctagc acagatggta cgctgtgaac ggagcagaca ggagcacttg cagacaggca   15540
ccttgagtgg ggtgcgtttt tctcctagtc ctgcattgac ttagtagctc tttgtagttc   15600
cttgtcatta ggtcatgctt tggactgatc acactatcaa atataacaca tggctcttgg   15660
gcagctgaaa gatgaagagg acacacccag tgtgtaccct ccacttggct gtgggagggt   15720
gcaggtgaca gctggggact gtgtcctacc ccttcacacc tttcccaaag atctcctcac   15780
ccacagggtg cttgctatgt ttgcctgtgt tgtttatttt ccctcagact cctgggaagg   15840
acttccagct tacaacagcc agggcttcag atggtaatta tttagataac agcttctctt   15900
tgacctcagg tggtcaaggt gccttcccgt aggaatgcac acgtttacca ctggcttcct   15960
ctccaacttc tgtgcaaggc attctggctc ctttgaaagg acttgggtta cttggccagg   16020
tctacatggc agaaggaagc cattctgaac ttgaagtgtc tgggaggaag atgctttccc   16080
ttcatgggcc tgtccagccc cttccgtccc ccttgccttc ctgctgagca ggccttggta   16140
tggtccctgt gtgtttttat cttccttcct aaccctcctt tccttgagtc ctggtttctg   16200
gcaaaactga cctatgcttg tatttttag ttttcagat atgaattcag gtgtgactgg     16260
ctgtgctagc ctttggagtt gaagaaatta ggggaagac cactactgat tttagagctg    16320
agagggacca tcgaggccac ccagtagaac tctctcactg ggaagcagag acccagtct    16380
gagggtcctg cctgtggtcg tatagcttgc ctctgccttt gtgcactgtc ctgacattga   16440
aaatcaccaa ggacaaggaa ggcttctcag ctcccagcag atggatgcgg tgtgagcttt   16500
gtgtgagatg gtccgtgggc tcctggcttc caccttagg aactctagca tgactttaaa    16560
atccgaagaa cttggtgagt tggcagactg actccttcca gcatgggccc gtctagttcc   16620
acagggtccc gtaactatag tcagagggtt ctacctgctt taatgctctg gggtgaccgc   16680
cttgacattt gtaatccttg gaacaaaagc ttcattttca ttttgccctg ggccctgcag   16740
atgatgaagc cagtgttgaa tgtgggtcac tacactaaat gccaagcatt tgatcaattt   16800
```

```
gtacttgcaa ctgatttgaa tttggggaac aggccgttcc ccggggaata aagaaggatt   16860
catttctttt tccctcgaat acactgtgtc ctgttttcca aattctctgt acatatcaac   16920
tctgcagata aattagatgg cggcattgtt cttgctggaa gtgaaggctg gaccattgag   16980
cttgcatcct gccccccctca accccaccca tctttcagtc cagaagtgtg gttcaggatc   17040
ccactgtggt atgggatgta gggagctgaa agctgaggct gaggagggag gctgcagagg   17100
gcagagatga agctgggagt ctctgcacag cccagcttcc cgctgtgcta ctcaccggct   17160
ctgagctttt taggggagg cagggagcaa gcaggtatga aacctcctgt agcccaagct   17220
ggcctcagac ttgataggca gtcaaggatg accttggatt tcagatcctc cttatctcct   17280
gagcactggg attacaggtg cggttcccgt gcctggatta ctgtgtggta cccacagggc   17340
ttcatccatg cacgctaggc caaaactctt ttatctctag tccagttctg ggtctttgag   17400
ccacacactt tcctgctgta tagattcaag tattagggtc accctgaagg ctttgaagaa   17460
aaactagagg aaacatctgt gtctagcatt gtgcttaagc acaaagtctt attggctggt   17520
attgcctagt attttaccgc caatattgaa ggccgactgg ggtctgactg actagctgtt   17580
gggaagaata aagcattcca ggcaggaagc aaaatggtcg tgagtacaca gagagggctg   17640
gagtggagcc ccatcttttt taggaactga ggggaggag cctaaagttc tcagaagcac   17700
aggatgagcc ccatagggtt gttgcgaggc aatggccaca gagttgggct aagcaagagc   17760
tcggaaatgg tagcagggac ttcgggctga ggcgctctct gtgcagtccg tcacttggga   17820
tagctgccat gtgggagaag acagagtct gtggcagaag acagagcct gtggcatctg   17880 ttagtgtttt tatcactgtg acaaaacact ggatatgagg ggttgggat ttagctcagt   17940 ggtagagtgc ttgcctagca agcgcaaggc cctgggttcg gtccccagct ccggaaaaaa   18000
caaacaaaca aacaaacaaa caaacaaaaa aaaaccact ggatatgaat aacttaagcg   18060
aggagagtgg cttttgttct attttgtttt tctagacagg gttttagga gtctcaagct   18120 agtattggtc tcagtattgt agccaaggat gacttgagtt tctggtcctg cctctgcggg   18180
atgctgtgat taccagctac gctatacca gtaactctgc cagctgagtt acgtccctcc   18240
tggccaaggg agggaagatt tgtgattcca tttcagtggg cttgtgaggc acatgcaggt   18300
actggtggca gaggggtctg ctcatctcat gtctgctaag gaggggatgg gtggaagggc   18360
atggagggag ggggaaggaa agatctggag accagacacc cttttaaaag acacacccca   18420
gcaatttcct ctcagccagg acctatctgc taccacctag tgatgtcatc gtgtgattat   18480
gtcatcagtg gattggccca ttggtgaggc cagagtcttc agtgttcgga tccaccaaca   18540
ctgatgagat caaggcttca acacaaaagc ctatgggagg atacatcatg tccagccctg   18600
tagcttgtct ttgctacttt gtggattctt cttttcccta ccctaacatc ccctcccac    18660 accctgtctc acccctctca ctaggtagga gaaaaggaag gatagagggg agagagataa   18720
agattcttgg atttaatttc ttcttttgcgc atgattatta acacacccct aacaacccc    18780 ctttcaacag ccgtcaacca ccaaccctgc ctattgaggc tctagcattt atagtccctc   18840
tgaaaagttc ccagaattcc aaacgtcaca caattgcaga aactctgcag ctggcaaaac   18900
cacgcctcta ctagagcacg aggcaagtca tagccactgc tgcggatgat cagaagcagc   18960
cccatatccc tgcacctgga gttaacttga aaacatagtc ttccgatgtt tctgtgtttt   19020
aaaaatgaaa caaaatccca gaattattac tacacagccc ataacactga agcaactgca   19080
tccgatgaac tgttttacct ctgtaagttt tccacgtgct gatgccttgt tacagctctt   19140
gtcagagaca tgggccctgt tgggctgact ttcgctatac accgtctgct ctgcatcttt   19200
```

```
cgcactggtg tagggattca gtagcatccg aggtccctaa ctgccttggc ttctgatagt   19260
cttagcacat cctctccttc cttccaggag acagttgtat cacagcaaag ttttcatgac   19320
attcccaggc caaaagaaca ccgaagagtt ccaattgcca agagtgttat cctaacaact   19380
tatttgtgtc cttacgacat agtagtcatc agggaaaaaa caattacctt tcacttcacc   19440
ttaccactgt tgccactgaa tggaacacac acacacacac acacacacac acacacacac   19500
acacacaccc ctctttggtg gcttttcctgg ttagctttca tatacaggaa ggacccagat  19560
tacctgagag agtctcactt gggggattac tagtcagact ggttaatggg gcattttctt   19620
aattgctaat tggtaagaat gtcccatcca ctgtgggcaa taccattcct aggcaagggg   19680
tcctggacag tgtaaggaaa ctagggagag catgccagaa accagtgtcc ttccatcgtt   19740
tttttgcttg attcccgccc tgatttccct gaatgatgga ctggaaatct aagacagaat   19800
aaaccatttc ctcctcaagt tgcttttggc cgcgctattt atcacagcaa aaggaaaaca   19860
gataagacta gtgacctttg accttttccag tactacagac aaattcagta caacttccac   19920
catttccagt gttgagtaat ttttctgtgg tccggttctt ttatcaaagc aactgtcagc   19980
agcctcacct tgtggagata ggggggtcat ccaaagaatg tggtgacaca aaagttttga   20040
gactgtcatc ccttttctct cacttccaca tatatatgta tgaaagacac cttgcccctc   20100
acttaaggaa ggtaagcatt tacagacaga tttgggcatc tgctaaggac ctggaaaccg   20160
tcaggttgtt gaaccagaga tctttccagt aagcattctg tataagggga gctgtgtgtt   20220
tctctctttg ttcctaaaag gtagttgttg aaaatgctta atttaaaaag gaaaggaaag   20280
aaacaaatgg tggtttagat ggtgcacacc tttaatcgcg gcactcagaa gacagaggca   20340
aacgtatctc tgtgagttca aggtcagcct ggtctacata gtgagtttcg ggacagccat   20400
ggctatgcag agagatcttg tctgaaaaaa aaaataataa taaagaaata aagaaagtg   20460 attaatgata ccgtctgtga acccccagag atgatgagtt ctaagggttt gacatttatg   20520
aagtggtgtg cctattagtt tataacagac aaaggcgggt catttgcctt ttgggattga   20580
agtctggcag ccattagctc ataaaacgat aagaaatagt tggctgtgct taatgggcca   20640
tttgtggtgt taaaatcagt aatactaaat atttattagc caagcggaaa gatttatctc   20700
tgtaaattgc tgtgactcat cttttccgcgg gccgattctg gttatttaga ttaattttg    20760 tttaaaaatg aagtcctgtt gtaggtcctt cagtgcttcc tgtgtgagac tcgcatgtat   20820
ggtaccagtc tttaatgtcg acatacattt tagaagtagg cttctacta aaactcctga   20880 ggttttctgt ggaagtgtgt tttaatctac acatccactg ggggaaattg aaaacttagc   20940
agcgctgagc ctcgaaactg caagtctggt attttctgc atttatttag gtctagttta    21000
acttgtttgg acacttgttc tggagcattc gagggggcagt tcttacacaa ccttgttaat   21060
gttttcccca ggtattttt taatactttt gatgtcgtta tgatatttgt aagttttttt   21120
tgctgtcatt gttcattgat aaacatacaa agtctaatgc attctgcgta ttgacctgct   21180
ttcctacggc accactaaac tcatgtatcc gggtatttta tttttatatt ccctaagagt   21240
tttctagaag gaccatcagt tcatatcaaa gcaatgttta tgttttcttt tccaatcccc   21300
atgtctctag ttttcctctc ctgcctcatt gtatgtgggc cactactata gggcagccag   21360
ttccagcttt gtgctctgtt tagccatggg acaattagga agggccagcc tcagccccac   21420
agacttcctt ctcccccagc taagggagca gacggaatgg ggagtggggg atggggtcct   21480
gctccttagg gtgtggcggg cttgccttcg ggtgggtctc tccgtagagt gcccgtctgg   21540
```

```
gttgcagtgt ggttagatcg gtgctgactc aacctctggc ttcttctgca aagccgtggg   21600
gtgactgtga gctggttcag gttgtgatca gaaaaatgag cctcttctcc tagactctac   21660
ccatcagcca atgcaggagt ggccatagcg atgctgttgg aagcttcaga acccacttga   21720
gtttgcatag cttggacctc tgcctccctc ctctccctgt tgtttcattg atgtcggaag   21780
tgctcacatc tgcccagcca tctcattctt actatactct gtggcttcat cgggcgcttc   21840 ctggggtga gtgctacatt ctcattctgt gaagcaagcg cccgagcttt gtgcctttat    21900
cctcacattc ttttctgaca tgggattagg agtagaggag tagggtctgg ggtatgactg   21960
aggtcacaca gtagtaggtg cggtgccccg agccctcagt gaccatcaga ggtcagagct   22020
agtgtttggt gttcttccct tgatggggc tctagatgca gcaccctcca tctctctgca    22080
ttccctggga gagcagggct tggcagagcc agcctggctt cacctatgga gtgagtgtct   22140
ctgtttgggc tgaccattct atacggaggt cagaagcagg gccaccaggg actgcagaca   22200
caaggaggct ctaatagtca ctccctccag ttaaatgaaa cagggatggg cccccaacca   22260
ttctgccttt acatctaaag gtgctgtgaa actacagggg caggaatcac gcatctcttc   22320
tctttgggtt gacgtctggc catctttgag gagtgggcat tcctgggttt agttgtctgt   22380
gtttggtttt tctgtggata tctatcaggt gacagcaatg gaagtcagca gctagcttgt   22440
cactgtcctc ttctctgttc cttctgcccc aactagccaa tgggagagcc ccgtacccat   22500
ccccagagcc acactttgtt ttgatgcttc ctgatatgct gatagttaca gtcgggactc   22560
aaaccatatg gagcagacca cacacacaca caactcatcc ccattttgct ggtgaggaaa   22620
tggagactaa cctgtgttct gaggaggggc ctcaggcctt catgtgccta ggccagatcc   22680
ttcttgtagt tttcctggtg gacagacatt ggaaccactt tccctactct gtctgagaaa   22740
gattcctgct ttctcattcg aacctgaaaa tcctatattt atgttcaccc cggtgtgggc   22800
agaccatctt aagcctaatt cagaagccga agaagtgagt taattattct tcagggcagg   22860
agtctggcag ctggtggttt cggaatacca tgtgtcttct ggttgctggc cagatggagt   22920
taaacatcca cttggtccca ggaagcccag agacacttgt ttacagctgt ctctggtgat   22980
gtttgccaga ctctgtttag gaggaacatt tccactccat agttcgttcc gtctttatt    23040 tgggtgtcca gggggacacg cctattaatc ataactacct aagaacctgg gagaactgtg   23100
gtggtttaaa tgaccccta accccaccc cttatgctgt ggtacttagc acttggttcc     23160
cagttgctgg ccctgcttgg gaagacttcg gtggtatagt cttgtaggaa gtacggtact   23220
gggtgtaggg aggctctgag atgaaaaagct tctcaccact cccaattcac tctcactggt  23280
tcgcacttgt ggttaaggat tcgagctctc agttcctgat tctgcccccc ccccccggc   23340 ccccgacaga ctcttatctc cctaaatgtt tccttctata agttgccttg gtcatggcgt   23400
cttttcacag caacagaagg tgattgatgc agggacaagc tctgtgtgat gccgatacag   23460
aggtggaaaa gctgtgcatt tgatgaccac agagttaggg gcagttccca gattttcctg   23520
ttatttatat ttgttattaa gaccacttag tatacatgga gaaatcctcc cctcagtttc   23580
cccaaatata acatggtaac aatgctcatt ttcaaagtct gcaacaaagt agagaattaa   23640
aggctttata agtagatgta ataaggtatt tatgccacga gtttgtctcc ctaaaagtaa   23700
cagctctttt cctgaaccca agaacatcat cacaccatgg gatcagattt catggctgta   23760
tcaagcaatt cagggtgggg aactaggcgg atgaggctc ccttcctttcc tgcataggaa    23820 gctggtccct gtgcccagtt acgtccactt ggagcactgc agaccctgat ggaacccaca   23880 gatacctgg aactttttgg gggagcctgg ggacatgcag ctgtgatggg tcacaagagg    23940
```

```
actggaaagg tcccagttct tactcatagc ccagagccta gggagtgatt gtttctcttc   24000
cacagagaag cgtgtgtgtg tgtgtgtgtg tgtgtgtgtg tgtgtgtgtg tgtgtgtgtg   24060
tatgtgtgtg tgcatatact tgttatgcac gattacatag atgtgcatat gtgttcctat   24120
gtttatgtat gttctataca tgtgagtata cacatgtgta tgtaagtgca tgtatgtgta   24180
tgagtttgtg tgtttgagtg ggcacacata tatgtaatgt gttttttggct ccctctatcc   24240 tataccttgt tgcaggcccc ctgcacaggc tcagtagcac taaactgtct cattgccttt   24300
gtccccaggg caggaagatc ccaacagttt gcgtcataag tacaacttta tcgctgatgt   24360
ggtggagaag atcgccctg ctgtggttca cattgaactt tatcgcaagt aaagaggcct   24420
tcctttcccc tcagtaataa atggcaccag agctgctttt gaagcacatt aaagtgtcag   24480
gaatgtcacc gggcagactc ctgtactaca ctcaagttct ctgccttagg aaaagtcctc   24540
tatttagacc gacactcttg gcccctttaag cgttttaata acttctagct ctgaagtgat   24600
tcctagggaa tatttcctaa gtggaaatat ttttggtgca ttccaaaaag tagctcggtg   24660
ttattttaag acatcaaacg ctcgctagat gtgtgcgagc tgcgcttgcg gggtcattca   24720
cttgtgtgtg caaatgaggc ttggtcaagc tcaaccaatg tctgttccag gcttcctttc   24780
tcgaagaggg aggtgccagt ggcgagtggg tcaggattca ttgtgtcgga ggatggactg   24840
attgtgacaa atgctcacgt ggtgaccaac aaaaaccggg tcaaggttga gctgaagaat   24900
ggagcgactt atgaagccaa aatcaaggat gtggatgaaa aggccgacat tgcgcttatc   24960
aagattgacc accaggtgag atgcttctga ggcccaagtg ccttctgggc ctgcagcacc   25020
cagctctcag aaggtgaggt ggagatggtg aggacatcag ctccctggta ctcggagaac   25080
gttcagcaac aacacagaag ctgcaggacc agacaggtct catcaaagag agacctgaga   25140
aaaggaggag ggaggaagga ggagggagcc gggaggagag aagcccttgg aagaaactca   25200
ctctcagatc agaggttttt aaagtagcat tttatctta taaagcaaca agctacaaag   25260
aagttactgg gtagctggtg agaatggaaa ctctggtcct tgagatgaaa catgtattac   25320
aaagttatgt ttcttccac tgaggtgaac ctggagtctc tgtggctaaa gaatgggctt   25380 taaattttt aaaaatttt tttaattgta tgttgtgttt gtaagtgggt gtgtacacag   25440
agatgttgga tacccttggc tggggttaca gggttataaa ccactggaca ctgagtctct   25500
gcaaaactag tatgtcctct taactaccga gtcatttctc cagctccttg ttaatgtatg   25560
tatgtatgta tgtatgtatg tatgtatgta tgtatgtatg tgtatatata tatatatata   25620
tatatatata tatatatata tatatatata tatatgtatg agtacaatgt agctatcttc   25680
agacacacca gaagaaggta ttgtgtccca ttacagatgg ttgtgagcca ccatgtgatt   25740
gctggacttt gaactcctga cctgtggaag agcagtcagt gctcttaacc actgagccat   25800
ctctccagct cattaagctt tttatactca aggttttggg aaccttaaga cgaaattaac   25860
acctcttcct tgagtcccctt agaatcctta gtatgatgtc atggtcatag tccccttaaa   25920
agggctgccg tgctctatct acccaaatta tagccttcca tggtggggaa cttagaatca   25980
gggccagtac aaaactaagt cacagtgaga gtgagctcca tttgaaaaat gcttgtatgg   26040
aattgctttg tgggttattg gggtaactac ttctagtcct atctgaattt tattatttta   26100 tttactttt ggagattgtg agacaaggtc tcaagttcta gctgtcttag aactcacttt   26160
atagaccagg ctggccttga cctcacagag gtcctcctgg ctttgcctcc caagtgctac   26220
cacacccaac aaaaaaattt attaaaagaa aagaaagaaa ataattttaa tttaatattc   26280
```

```
tgtttatggt tacttttgc tcagcagagc ctttattttt attttaggt ctcgagtagc    26340
acaggttgcc ttcatttata atctgtggat agctttgaac ctttgactcc cttgcctcta    26400
tcttgtgtat gtgaggatta tgggcatgta ggaccaagcc gggctcacac agtattgtgg    26460
accaaaccag ggctttgtga gagctagcca agcactctgc cacacctccc acacttgttt    26520
agcgaggcct tcatgcccga aactgaatac agttcttact ggatcaccag caaaaattcc    26580
tagtcctcct catggtgatg tgatgtctgt ttgcacttct ggtgagattg gagtttctgt    26640
tttcttcctg ccattggaaa ttccttcaga aagaaggtag aagggtcagt gggaattttg    26700
tggttggtgc agaaaaagac gtgggtgggg cgggtaatga agcgtagcat tttcttgtga    26760
agctctagct tgcttctcat ctgactgagc tatgaagtca gctaggtgtg aagtcctact    26820
atgaaagctc agggtactgt tgggcagtag gactctgggt cccttttattt cttttatagc    26880
gccaggcagc ctttcagaac ccctttcaca cccagcttgt tcccttacct tctcagaggc    26940
tggggtggtg agggctgggg ctgaagtttg caggaacagg ctctgggccc atgtaggtga    27000
ctgactttag tgtgatcaca aatgtgtgtt atttctgcta agttgctgtg aaatttctac    27060
caacagctca tctttctaaa tgtgtttatt ggtaccaaaa cagttggtcc aggctctgac    27120
ttcacatcta accgttctct aatacacaga atagctgtgt tattcccatt ttataagaga    27180
agaaagaatg ctcagagacc acttctctat cttttcaccc ctagcttcct gggagccagg    27240
ctgcagattc caggcaccca actccactgc acaggcccag agcctggcct tcacagggat    27300
ggactagcat gaccttaaat agcccatgga aaggttggcg tgtccccatt tgggaatgct    27360
gcgagcaagg tgtctagagt ctggtggtag caccggaagg aaggaggttg ccagaatag    27420
cacagccagt gaccacaggt aggaccttca gactcagttc ctggaaggca gccagcgctg    27480
ggagcctcct ggccatctgc aggcagagct ctggcctgtg tggttcgtga gctgtctcct    27540
caagtaattt catgtttgga atgcgtgggt gcataccacg tgattgcttc cagtccgggg    27600
atattctttt ctgatttcga gccaatgtgg agatgggagg agccccatgt cacctctggt    27660
atatccaggc aaaatgtgaa ggcgctcaac agaggatctg tgtgaagggt ttcaggcagg    27720
cgggccctaa gagtctcttc agccagaagc ctgctatttg acatgtgccg cacacatcct    27780
cctgccccccc caagtttgga aatgtaaatc ggactgatgt agcttttgaa aatggaattg    27840
gaaacgaaag gcttttgtat tgcagacacc cacattgaag cctgatttct gatgactagc    27900
ctgaccccgc ccctcttttc tctctgtccc tgttctgatg cgagttgttg tagggagagt    27960
ctggcttgta ataaagcttg acttggaagg aatgggccgg ccacccaggt gaatggtgtt    28020
cgagcagaat ttaccctgta gttcgtggtg tgatcagggt gtggtgtgtg tggtgtgagg    28080
tgtgtggtgg gcagtgatgg gctaggtgct tgcttgcttg gtgctgggtc atcttagggg    28140
cagcaagaaa aggaacgtgt cagagaaggt cagagaagac tgtgggtgtg gtggtgcata    28200
cctaccctcc tagcatttga gggagggggg gatgtgaagg caggaagatc aggagtttaa    28260
gcccagtgac taattcaacg gttggtcatc taggccgggc ttcctatcag catgagattg    28320
cttgagttgt ctgtgactca cattgaaact gttttccgtg aaatgaaagt gcaattttta    28380
tccctcctcc tcttttttttt ttcctgaga gcatcagcca tctttctttt ggggagaccc    28440
accagtgtac agcttgtgtg tgtgtgtgtg tgtgtgtgtg tgtgtgtgtg tgtgtgtgtg    28500
tgtgtatgtg tgtgtgtgtg tatgtgtgta tgggagggg tcctatgcct caacccataa    28560
ggcccaatct gatgagtgca tgctgcccct taaaattgca aaccatcacg ggaaagtaca    28620
cgtgtgtaaa ggcctctgta attagcacca cagagcaggc ccttcccaag ttccttcact    28680
```

```
tcctccctct cacagagagg ccgcacatct ctaagggctt gaagctgctt ggcttgcagt    28740
tgccagagag ctttctgggc tggtgaccaa aagcctctct tttgtttctc tctgctgagc    28800
agacacatgt gcactcactc tgcctgttgc attttgagac cctgaagaac tcagtgggaa    28860
tggcctacac ggggaagcct acgtggtcct gactcctgtt ccaccccctg gacgagagag    28920
gatgacccct gtgggtcttc cctctagcct cacggaatgc tcctgtccta gagctgaaac    28980
taagggtcct caatgggatc agtgctggtc tggaggtggg gggtggggct cacacatgta    29040
aacattttaa tggaaagcag ttttgagggc aaactagttc agcttgggat acaaactact    29100
tccaaatgtg tctaacacga gccactggcc atgtatgcag aatatttta actttcatcc     29160 aaaagcagtt tttgttctcc cccttccccc tccagtagtt taagaggagg atagagccac    29220
aagagctgga gggaaatgta aaacgtcaac ctatcaggtg tcttttagtc tggaacagag    29280
gcatgggcag acatatgggc aagtattaag aaagtacaag ggaaatgttg tcacgcggtt    29340 gttttttccag ctgttgtact gattcctcca gatgctttcc cacctatgct atggaaatcc    29400
tctctttcag agaagccatt ctcaacctat ggttgcaac ccccttgggg gtcgcacagc     29460
aggtatttac attaggattc ataacggtag caaaattaca gttatggagt agcaatgaaa    29520
taactctatg gttgggaggg tcaccacaac acgagggacg gtatcacagg gtcttagcat    29580
taggaaggtt gaggagccct atttcagagt gtcctgacaa ctccttcctg ggaccacctg    29640
acttgatctg gagccccttc cctcacgctc ctactcctta ccatctctgc acagctctct    29700
gaggcttaga gtggtctttc ttcctggcct tcccttttcc ttcaggtatg cagtcacatc    29760
ctgctttaga ccccagggac attccgtgtc tgactcactg cacaaaatag tttcccacat    29820
atgagtcctc aaccgcccca catcacgaga cggacaagac cggagacgcc atacattctg    29880
tatttgccct ccttcctcat ttaaatagga atttgttgct gtttaatttt tcattatttg    29940
tgtgtgtgtg tgtgtgtgtg tgtgtgtgtg tgtgtgtgtg tgtatgtgcg cgcacgttaa    30000
tatgccgctc agaatagtct aaaactgctg ggctcaagta atcttctcag cttctcaaat    30060
acctaggatt tttggcatgt aacctgaact cagcctcact tgattccgat ttctctatct    30120
gtctctccct gtctctctgt ctctgtctgt ctatctgcct ccctgtcatc tgtctctctc    30180
tgtttaggtg acagctgctg tccaccttat tctttgagac acggtcactt gccaaaccgg    30240
gagcttattg acatgtttac actggctggc cagcaagctc caaggatccc tttagctctg    30300
cctctccagt gctgggacca caggtgtgcc tggccttttc atgggttcag agaatcaaac    30360
ttaggctctc atgattgtga gacaagcact tcactgaccg agccatctcc ccagcgcctc    30420
atctctgttc agactccaca ttcttctgct agagtataaa ggatgcattt cttttggcct    30480
tctgatcagg tcatgggtac tggacaagcc aggctggcca gtcttaggtc aagttgacat    30540
acaagttaga attatctgga aggagggaat cttaattgag aaaatatctc cataagatcc    30600
agctataagg cattttctta atattgatgg aggagggctc agcccattgt gggtggggcc    30660
atccccaagc tgatgggcct gggttccata agaaagcagg ctgtgggagt catgaggact    30720
aagccagtaa gcggcatccc tccatggcct ctgcatcagc tcctgtatcc aggttcctcc    30780
cctgagtgag tttatgtcct gacttccttc gatgatgaac agtggaagtg taagccaaat    30840 aaacctttc ttctccaact tgttttttgg tcatggtgta gaccacgacc aatcaaaacc      30900
ctgatggaga caatagcatc tgcttagagg ttagccagac ccacagctcc ccagtgtgat    30960
ggagagagag agagagagag agagagagag agagagagag agagagagag agagagagaa    31020
```

```
catggctagt acctagctcc tttgaaccag cttcaggtga agaggactgt gtagcaggca    31080
gactgcgccc tcttgtcttc cactgttggc tttggccaga tacagcccga gtcagggcta    31140
cactgagcct gtggtcttgg tacctcagag tgctgaggaa gcaaggagac ttcctgtggg    31200
ttcttttccc tgacaccaac aaccaggtaa atatttggac acagcctgta tccaggcttg    31260
aggtggtttt ctttctcccc ttaggcctac catggcaggt aggtgcctgg ccacctttag    31320
cccaccagtc ccacagacct gtttgaattg gctgaggcat tgcctctggg taccgttggt    31380
tttgcttacc gagggggtcct cttacagctg agcttgctga gagggcctga agtctgatgc    31440
ttcaccgtgg agttcagagc agggtcacct aggggtgggg gttgtgggga ctggggcttt    31500
catatctaaa cctcccataa tttggccttg tacgtggaga gtcagcctct ggtggccggc    31560
cgctggggat gactcactcg ggttctcctc aggccacttg actgttagag gatgctgact    31620
aagcccctgg gctcctccaa aagcaaatca gataaccaaa gcctgtgcat cctctggacg    31680
ttttcctctt cccctgaagc aggctggagc ctggagtaga cacgcactgc cccaaacctt    31740
cccatccggc ttttgtgtat gtccattttg gatgcctttc tggggttctt cttgctgctc    31800
tttttgtggt cttctctctg agaactagaa gggcttctgc tgcagttgtc agagatgcta    31860
cagatcatgt tgatgtgcaa agctcctatt actggattga ttttttacctt tttttatagg    31920
gaggtgagca tcaatatttc aggaaggaag aagtgcagac agggacgtgg aaggtggctt    31980
ttactttgca gtgcaagtcc tcggtccaga agcgaatggc tgcctggctc ctctttgttc    32040
tgactgtagt cattttggca tgtgaaaata tttcacttcc ccaaactcag aactggagcc    32100
ctgtgtgttc tctggcccca tttcaagaac ttcgttgatg gttgaggaaa ttctttggct    32160
ccatttttct cttaatatgg ccatgccttt tttttctttt ggcaccctt  gcaaggaatc    32220
agaaggagga tatgatggtt caggcaaaac aagtctcagg tcactgggag tctctcctgt    32280
ccttctcatc tgggggagac atcatgggaa gttatttgac tgttgtaagc atgtcttgtg    32340
ttagtctaga ttggccagcg gtagcctccg gttcgtatct gaccccccatc tttttttgta    32400
aacagtttta tcagatcaca cccatgcctg ttcatttgcg tagtctatga ccgctttcat    32460
tctgtaccaa agaagttgca tacttggcct ggagaccata cagcgaggca agccagacat    32520
ttggttttca atgcttcata gtgagatttt accagcacca gtgatgaatc cttattctga    32580
gggagcagca agtgtctggg aggaatgtgc gagaaagttc aaagctcagc gaagcaccaa    32640
gggaccagaa atgaggatgg tgatgctgac ttcatttgtc ttttttctgg gaggtgtttg    32700
cctctgtgaa aacgaggctt tggtcttgcc agactgagca gagagaggcc ttaagcctgt    32760
cacttctctg tggtgttggt aaacaggaac ttactagaat tacaagacgt tttccaggtt    32820
acgatccaac tttgagtcct ttcattggct tgtgtcatat gtgctattga acaccggtct    32880
tggccagaca ttgtgaggtc tgcttagaca tccagggtaa accgaggtgt ggggtgcaga    32940
gttggtgatt ggtcactcag caggctttcc tctgagggga caaagcttga ttctgtgggg    33000
ctgataagac gctccctggg gctgctggga agggtgaggg aaatcaagta tgtgtgcaca    33060
tccacggtgg atgagcaagt ttcaacgagc tccaaccact ttacatatat acatacgtac    33120
acatacatac acatacacac atttagtaga tggagcaaag ctccaaccac tttacgtata    33180
cacatataca catatacata taaacacata tacgcataaa cgcatataca catacataca    33240
tgcatacaca catatgcaca catgcacaca cacatacaca catatacaca tatacacatt    33300
cacacattca cacatgtaca catgcacaca tacacacaca tacacacata cacacatata    33360
cacatataca catatacact tacacatgtc tgcacatagc aatagtgggc acaagttatg    33420
```

```
gagctgaaga ttagtgttgg ggacagaagt gaaatggagg aaaggagaca aagagaaaaa    33480
gggcaagaac ctgcccgagg ctggaaggct tccataaatg ctgtgttcag aagcttatct    33540
gcagaaggga cagttgggtg agatgagatg ccttgagcca gccatgtgga caggtaggaa    33600
atgattggtg aagcttctta cttctccctt tctccccagc ctggatgatc tgtatcgtgg    33660
actatgtgca aacaggcatt ttccagcaag tttatgataa cttctaaaat gcaaggccag    33720
cgtttctcct cagctgctat ctctttgtat tgtttaagcg ccttgctggc ctgctcctcc    33780
tctgggacct tccgaggcct tcaaggcact taatttcctg agaggctcaa atgaaaagg     33840
gttcttaatt atctggacat agaacacagt ttcccctaac tcattgctga atcctccaga    33900
cctctgtggg aatggaaagg taaggccttg tggtggattg aggaccgatt ggtctactaa    33960
acacactaat tgacaagaca tgagttacac acaacactga agtctcataa caaggacact    34020
ttagagataa ttgcaaacca aggcatttca agtctgttac catggccaaa atgctaggcc    34080
ttagctaata tgagaattgc cccaccccac cccaactcct ttgctaaggg tctaatggat    34140
tttttttat cttgttcatt gattttttcta aatatttatt gagcatcctt cacgacggga    34200
cactgccgta gcagccatgc tgaggttggt ggttaaatgg gttgatgcat ctagaagatt    34260
caatcaacgt cctgtttctt ctcctgtggg tgacacagaa tatgtatggc tgttggctcc    34320
catatagagc tgttgacatt ttgtggtcaa aaacagaaca agaggatatt tgaaatagca    34380
aacatttctt gatatatctc acaggagact aaatatttatg atgtgttcat aaacagtgag    34440
gaggaaggag gttgcacttc agagtttaca ttctttctct tcttttgcct cctgccttct    34500
ccttctcctg tttccctcca ttgctctcac ttcttccacc tcccttctaa ccagcttctc    34560
atgtgtccgg catctctaga caccaatagc atgtccaatg gggaaaaaat caatctcatg    34620
agcctgtata cattggtggt cagtacccat ggagcaggcc cttcctgccc tagcctctcg    34680
gttattagtt acatctttcc attcaccaca gccatcctgg gctctgtcaa agttctatac    34740
ctgactgtgc catcattcat ggcctctttg gtcaagaaaa aatatgagag cagtctgtcg    34800
agcccttttg taaagatgac atgttctgct ctgtagcagt ttcttctgaa tccacatctt    34860
actgctgttg aattcgggtt gaaaggttga agtaggaatt ggcagaaaag agtcgcatag    34920
gaaaaatcta gacttgggta agctacctgg gcccagactg atgagagtcc ctcagggtcc    34980
tctgacagac ataggacaaa gttaaagtga ggatagtctc ataaagatga gcccatgtta    35040
attataaaaa ttgtgaaagt ggaggaggaa gaccatcact tcaataaact aaattctagc    35100
atctcactct tggtccactt ggcagatgac tttatgtgca tgtgaacccc tgggctcaga    35160
gaggtcctat tctctgaggc cattgtttca atttgatctt ggaatttgtg tcttgtccta    35220
gattctcaat gggacaatgg tatgtgctca gtgggcttgg agccttggat caggtgattc    35280
tttctcctca ttcctcctca ggatagctcc tggtcttccc agtattgtgc tacagggacc    35340
tctgaccctg cctgtcctct tcctttgtct gtgtggtgat tgtaactata tcccatgcct    35400
ggaagacatc ccatgcccaa aggagacatg gggattggag ttagtgttac acttcacaga    35460
tcttagggca gggagttaca cagggcttgg agtgacagac taaaggcttg ttccatggat    35520
caccaggcaa gggaaagctt ctaatttgat ctaggtcccc aatatgtccc acagatacgt    35580
ataggatggt aatgccagag cccttgaagt cgtccatcat ctctgggttg gaccttggga    35640
aggagaggtg ccaggctttt cttccttacc ccagttggta cagtgtggag attatatacc    35700
ttggtggcaa agtactgggt tatgaggtca attggctgtc tgcacttgcc agtctgcgga    35760
```

```
tttctttgtt cttcaaggac caaagtaaat acggaccatt aagatgtggg aagagtatgt    35820
acaaaaagaa aagaacctat gaacctggga ccatgtttta tttcacattg ccctgcagat    35880
gctatatccg gtcctcagaa aagcttaggc tcacctggtc cacagcccac agtcctatgc    35940
cagcacactc tccctatgc tttaggcaag ttcttggatg gtaacgtccc cttccccaag    36000
gtccctctgc tttcttcttt ctgggcatgg gggatacaca cttcccccta ctgcatagtt    36060
ttaaagaaaa cgagcgtttg tcataactgt ttccagaagg catgttgaat cactcaattg    36120
agttgcagcc agtggctgca acattagtct ttgatgagaa cttgagccaa catgaggccc    36180
agcctgaaag ccccagccct aaacaggagc gtgccgggcg ggcagctggc agacacagaa    36240
aactgcaggc tcagcaacaa aaatattttt gtagctgagg aacctgttgt acttctccaa    36300
ggagatgatc aacttggctc attagttttt tgttttgttt ttttttttt taaaagaaga    36360
tgggcaactt tcccttcctc ttggctttgt tggttcactt cattgctctt ctctttaagc    36420
ttaaggggat gaggtgagtg catagactgg tagctgcaac tgagctggtg aagggacctg    36480
gctttctgct gtctttgctg gaggatgact ggtcaaacga ccacctcaca aattccagac    36540
atctgtccac gtgatgcttc agatgctgca gtgatcttga gatctccttg ggggttgtat    36600
gcagtttgag gcccccgtcc ccttcctgat tttacccatt taagtactgc taatggagtt    36660
ttcagcaaca ggcacatctg gaaagagccc ttaatcatca taaccaactc tagacgcgac    36720
gtctttattc ttggagaaag taaaactaag atccagggaa atcaatcaag taacacactg    36780
aggtagtata agacccagga ccagagagat ggctcagtgg ggaaaggcat ttgccacaca    36840
agcctaatga tctgagtatg attccagagc ccatgtaaag gtaggagaga actgactaca    36900
aagatggcct ctgaccagca tatatatgcg ctctctctct ctctgtctct ctctgtcttt    36960
ctctgtctct ctgtctctct ctctctcaca cacagataca cacacacaca gacactcaca    37020
cacacacaca tacacacaca cacacacaca cacacacaca cacacacaca cattaaagtt    37080
ttaaaactac aggatttcat ccaaatatgt aacatactag aagtgtgtgt gcatgtgaga    37140
atgttttgc ctcatctttc tttggcacca gcttgtttga tgttggcacc tcatgtccaa    37200
atgagccatc atttagcagg gactcagctc tcccgatctg cagagttctg gcagttagaa    37260
ttcatcctct gtttacaaat gaaacctaca gcacatgaga ccctgaagct aaggacaagc    37320
ttaccagggc ttggctgagg ataagacaga ctctccaaaa gataccatgg gataaacagt    37380
aagaccagcc cttcacttga gaaccactgg cccagctcct gttggctggt ccatctgatg    37440
gctttgtttt ttaaatttcc ttgtgctggg gatagaacac aaggtctcgc acatgctagg    37500
taagactacc cctgaggtcc acctagtctc tctgtcatgg ttcttaaact cctctgtcat    37560
tgctttgctc tgttacactg gctgctgtcc cctccctctg tgcatagatc attccttcc    37620
tcattggtca gttgtgtgct ctgagaatct tcgttgtccc acagacacaa ttcctgtgca    37680
gccaagcaga aggaagcaat tgtgtgaggg agtgagtttc tcgacagtgg ccaggtttca    37740
ctcagtcacc tgcatcttga ctcagctgag acacatgttg ccgtccagac cttgtgggac    37800
ctttcatggg gatggagctc ggttgctttt gcctgatgag ctatcttatc ggctctctct    37860
gttcttctga ggagtcatgt tgctggcagg caccttcttg cctttggttg gtgtctacag    37920
tggtagtggc tgtcttctga ctgtgagagc acactgaagt tgacagagta gagaggatgt    37980
gcttggttct tactgttgcc cttcagcttt tgaagccggg ccacagtaga cagcccactc    38040
ctagtgcacc tcagaaagtg cttctccttt ttctcagtcc tggtacaacc ctggcctcag    38100
tcacatagct gtgtccgatt ggatttggct tgcatgtgag acagacacag agccttacag    38160
```

```
tgttattctg tgctcagtat tatacacaat cctgtgccca gttacctgca gcaagggga    38220
tgaacttcat tcttctttac tcttgagccc cgtggttcat ccatgctctg cccaccagac    38280
aggaagcctg gagaactgga ctggatatgt tggtccttga agtcttatgc caggcactgg    38340
aaagacaatt tgttgagact gtccctctc agattcactt tttatcctga aagtgactcc    38400
tgggattgtt tgggacggtg tgataatttt aaccaactag gaagacccttt ataaaaccat    38460
tctatggacc aaaccctcac cctacttcac aattagcatc taacctatgg atggtactta    38520
gtgattttttg tggacattga aacctggagt ccatgttcag gccactgac actgtcctt    38580
gggctcattc tccacctact caggtgacat tgggtctata acttgggaat tatgggctct    38640
tttttttct taaattgtgc atgtgtggtc acatgcatgc acatgtgtgc aagtgtgcat    38700
atggagatta gaggacaact ttttggtgtc tgttctttca ccttgtggtg atttgaatga    38760
aaatgccctc ccaccctcct agagtgtcaa tattggagat gtggagcagg tgtgaccttg    38820
ctggagtatg tcacaggagg taggcttttga ggtttcagaa actcaagcca ggcccagtgt    38880
cactctctct tcctgctgcc tgtggatcca gatgtagacg tctcagctat ctctccagca    38940
ccaggtctga ctacatgccg ccatgcttcc caccatgatg atgatggact aaacctctaa    39000
agtgtaagcc agccccgatt aaattttttag ttttcatata agagtttcca gggtcatggt    39060
gtatttcac agcactagaa acgtaagaca gattttcttg tttctgccac tgccctgcat    39120
ataattatcc aggctaactg gtctgtgagc ttatgctgta ttctgttttcc catcttgaag    39180
taggagatat gtgccaccgc atgcggcatt taaaaataag gttctaggag tggaactcag    39240
gtcatctggc tgcctggctg agccatcttc ccagccccta ggaatccttc tctttctcta    39300
gtctctctct catgactctg tggtgccat tttgccttag gcagtgccct gaagatatgg    39360
tggttttaca ttgtcctcct tcacagctgt ctcttctgct ggcctctcag gctgctgttc    39420
cttttcagtc tggtgagaac tcactgtgag agactgactg catatcctac gtcctaaaaa    39480
gctgctagcc ctcctggtag aagttgggg ttccttctgg gctttatgat atgggcttca    39540
gagccatttt ttcctgatgt catctcatga ctttattatg ccttttttgtg tccccccct    39600
caaccctcca gctttgaggc catagtagcg gtgggtccct tccttcccct cagactttgc    39660
accaatcagg actaatgttt gccctgtttc cttcttaggg aactttgag ttgatggatg    39720
gggggggggg ggatatggat gtggctgttg ggaaaagagt tggtctctta gatggcctgt    39780
ggctggcatt gcttcaaagg gagccccaga cagagcgtct acagcaggag cctggagatg    39840
gctttgatgt gggcacacgg gaagcagcct gcatgtggac acagagcagg gaccctgaag    39900
tgtggcaggg tgcccgcagg tcaaggctgc agtgtggctg tgccttccag ctatgtacgt    39960
atatttcgtt tcctctgtcc ccccaagagt gtggctgtct agacagggat agaattaaaa    40020
gctcaattac tgagcaggaa tttggccagt gaaagctcag ctactgagca gacaggcctg    40080
ggtgaggatt gtggctgaga ttgagcccca tttggaccta agtaaggcta gagagcctga    40140
ggctcctagc cagccagcac ctgcagggcc ccttaaggca gcttgacctc atggagctgt    40200
aaatctggct tggccgccac ctcggcacca cctccctctc ccatacaggg atttctgctt    40260
atagttggag tccagcaatt agaattcctg cctttgggga tggaggcctg cagctgggaa    40320
ctggttctcc agctcaccca ggctcttctt atggctgaga gaagctcttc catggtgtgt    40380
gtgtgtgtgt gtgtgtgtgt gtgtgtgtgt gtgtgtgtgt gtgtgtgtgt gtgtgttgtt    40440
atgcccctga atcatcagag tgtcctgaaa gtactttgtc atctggcaga gaagggtttg    40500
```

```
ttcctttcgt ataaatggag aatctagact gtgatatccc cttctttacc ctgccatcgt    40560
gcgtcttcct gtttagtgtt tgtgtcacag tcatccttca tgatctgtaa catgtattta    40620
aggaggcatg ctcactggga ctgcccacct gggcgggcgt gacagggtag tttcatggca    40680
tccctatgga ttctcatcat tggtgtcctt gtctaaaccc aatatgggca tcttggtgac    40740
agaggatgag accttttgttc ttgagcctgg catgtcctct cggtgtttta tagcatagag    40800
gcctctatct cctgccactg tggaggtctc tattgtcttt ccatacagct ttctctcaaa    40860
catttatctc ctttctagcg ttctctgggc ctgagctcag actttggaca gaagcactgg    40920
acagggtgtt gttaggtccc tgctctctaa ggactgtggg gcttaaagcc taaatctctg    40980
gctctcctcc tagtaggcag gggcagtggc tggagggtgt tatagccaga tgctgataaa    41040
gattctcatg tcggatctta cctcagccct gatatagctc ccgccgtgta ggtgccccca    41100
ctgtcccatg cctaagcttg attctttttt tttttttttt tttttttttgg gtctttttt    41160 cagagctggg gaccgaactc agggccctgc gcttcctagg caagcgctct accactgagc    41220
taaatcccca accccctaag cttgattctt atctgtgtag ttctgtttct tcggatgtcc    41280
aggccgacct gctgcaggct gtagccacct ctcttgcctg tccttcacag ttatccctga    41340
agattcaaag ataggatttc cagccagccc caggccccaa aggaatggta ctgtcctggt    41400
gggcctcccc cagtgtggcc agcactcatc agcagccaga ctctgcccca ccctgcctcg    41460
atggctgagg tcattcttgg cagagcttgc tggcaggac tgttggcgcc cacccaggat    41520
aaacatgtca cactgagctt gctgcgtgcc attggatgcc gagtgggtct gcgtagggaa    41580
tgccataggc cccggcctca ggtgaccttta aagtgaaagg gtcatagcca gtgtggaact    41640
gtgtctggaa aggtgacaca ccctggcttg tcacagcaca gttgctggaa tccttcaatg    41700 gatttttcagg gatttgaaaa ctagtaaaca gccgagtagg ctctttccag agaaccgttc    41760
aggctcctaa ttcatcgtta tcctaaatca ccatcataac agaccagtgc gattggtggg    41820
ctctcttatc ccacttctca ggcgaggcgt ccgtgcttgt catgcagagt ttcagtttgg    41880
cagcctgtgc cacagatggc tggtgccctg tggggtgtgt ggtatctgag agtagaggtg    41940
cggcttctca ggctcctggc tggtgagagc ttgtgctgtg tcttccgaca tgttttcgta    42000
ggcagtgcta gtcttactgg ccatgtgcat gcgtgcatga gtgcatgtgt gcgtgcaggg    42060
agtgtgtgtg tttcaaatct gtatcatggt gctgtggggt aagtgagtac agtgaaatct    42120
ctgttgtatc tcaggtcacc cagggtctgg ggcctcccctt atctgctagt caattgtccg    42180
agctcatcag cagttccatt tctctttgca gagaggatga taaagtctct tgtctgggct    42240
acccatccca ccatcccacc tccacccact ggatttttttt ttttttttgt agcttatcct    42300
ttctcaaatt gaatgactat aaagagttcc cttagcaggc atccaggact aacttttttt    42360
tttttttttt tttttttttt tttggtattc catgagcaat gcatagaaaa ttcaggaatt    42420
ctgggcaatg tgggaagaag aaagcaggat ctggggccat ctcagtggaa gaaggcagcc    42480
tccagtcatt ttccccagcc cttttaacctc catggtccta tcttgttatg aggagttatt    42540
tagggcttcg gactctgccc agtatcagga gggagtggga cataggacgt gggacatagg    42600
atgtcttcag ctgaatcctc agtctgcatc ggctgggggc agatgcagtg atagggattt    42660
tcccagtgtg cacaggagag acagtccgcc attgggtcct gggtgctgcc agcctttgct    42720
tgtccttgtg ccttaccacc actgggctgc acaagaaagt cagtgcgagt ttctgcctca    42780
gggctcccca catcccaggc ctcaggaagg ttattcatgt gggagagtag acccatggtt    42840
ccttgcttcc cctaaggcac acggactcag gatccctgtc tgggactttg atctttaagc    42900
```

```
cttaaaccaa agttgtctcc tcttgtcctc tctccagctg cacagatcgt tccaaaatgt   42960
gaggcctaga aactgtctat cacctttcc cattttccc tggtacaagc gcttccattt     43020
cattgactcg ctaagggcct gtgtgtggat tatggcaggg gcttggccct caggagagga   43080
gtgtccaccc caagctcagt ccctaggac tgctcttcgc tctctgtatt tgaattgtgc    43140
agcaatgact ccctttgtgc ttacagggta agctgccagt cctgctgctt ggccgctcct   43200
ccgagctgcg gccaggagaa tttgtggttg ccatcggaag ccccttctct cttcaaaaca   43260
cggtcaccac tgggatcgtc agcaccaccc agcgaggcgg caaagaactg gggctccgga   43320
actccgatat ggactacatt cagacagacg ccatcatcaa tgtgagccct ctgctccctc   43380
tgcctgctgg gctggggacg agtttttccc agaggaagtt gggcttcttc ctattcccaa   43440
accgtctcac agactgcatg aattcccaga acatctgaga tgttctggtg ttaggcatta   43500
ggtgttaatg ttcctctcgg agctgttcag agttgaacta tggggtcctg aagccagtgg   43560
gtggccagtc tcatcggagg aggaggtaaa agtggggtta gctgcttacc gtggtctcag   43620
aactaaacca tttcactatg gcacacccca agcttcgtga aaagtggtca aggtcctttt   43680
cttcagttaa aattaggtga tcctagacaa agcctaggga agcccagcct gctggctgct   43740
tcatcagcgc tttgaaatct gggtagagac attgattagg tgttggtatg acacagagcc   43800
aacctttgcc ttctgtttcg tttcagtatg gaaactccgg aggcccgtta gtaaacctgg   43860
taaggctctc cagtacctac gccgtgtttc tttcttctgt gggcacacct ttgctttccc   43920
cttgcatgtg agcttgtcag aacaagcagt cagttgatag ccatgtgagc gtttctttgc   43980
acctttcccc accagcccctt tccggaagca gtaaggtcag aggacacgtt ggtgtttcaa   44040
gccatgggtg gatgctaagg agctcaaacc cagtctaggc agaaagggga ctgaaagtcc   44100
acatggcact gccagctgca gaaagttacc ttcagccctg agggcgactg agtggagacg   44160
agctggcctg gctcgtgccc atgccaaaac tctccctgaa tgcctgtggg tatgacgggg   44220
agccacctgt ttgctcacag atgtctcact caaccgagac ttcagtataa agctgaaggc   44280
ttcaggtcat agaatgccag agcttggggg ttgtttgaga gagtataagt tgaggctacc   44340
caatagtatg tcctcctggg tcccctgggt gtcaggagct gatatgtaca gagcacatca   44400
ggaacaattt atactgaaag tttacagagt ccttttttgtc agcacagcat cgggccacca   44460
gaaacttctt agggaagagc cacatctttta acttgctcca gccatacct ggggcagatg    44520 ctgggagtaa ggcctgtggc tcaagccagc atctacggtc attggaaata ggggaggaag   44580
ggagggtgga tagtcaccctt agcaattcag agattctgga aacatccttc ctatgaaaag   44640
agaagatagg gtggactttg atatatgcaa tatatgcaat aagcaacta ttagcttcca    44700 ctgaggcttc tttgttccat ccacacctga gcgtgggtgg cactacccag gtgccccaac    44760
aaatgtctct ccttttatcc ctgaccttc tcttccagc cctcctgatt ctcagacaca     44820
gcccaaatac tgctctcccc catgtgcctg tatatatgag tatttgcatg catgtggccc   44880
caagtgtgtg tgtgtgtgtg tgtgtgtgtg tgtgtgtgtg tgtgtgtgcg cgcactggag   44940 ggggaggtg ttgcctgtgc acatgtgtgt atttgtggag gccctgtgga ggcccggggt    45000
tgatgagggg ctgtcttcat tcccttttct ccttattcag tgaggcaggg tctctcagtt   45060
gaacccagag ctaggtgtga cagctggtcc ctctagccag cttttctcctg ggatcctacc  45120 tctgcctctg aggctggaat tacaggcagg tcaccacaca cacccaggat aagcttggct   45180 cggggggatcc caacctctag agctttcatt tgcaaggcag acatttaacc acgttgttgt  45240
```

```
cttctcagcc cacactttt ttttattac tatttaatt atacacattt gtggggtaga    45300
gcgtgggatg accagtcagg taagatagca tcttcctctc aatcttttt ttttttttga   45360 aactaggcct caaatggtgg ctcaggctgg ccaggatctc acagtgatcc tatctcggat   45420
actctagaat gctggtcttg ccagtgtgag gcgttacacc tggcgccaca ttttaaagac   45480
tcctgtccta tagattctct gctcccttcc aacctgtgcc tgcctctgac ctcctggagt   45540
tagtgagcat gccccttgct tttcaggatg gcgaggtgat tgggattaac accttgaagg   45600
tgacggcggg catctccttc gcaattccat ccgataagat aaaaaagttc ttgacagagt   45660
cccatgatcg acaggccaaa ggtaagtaga tccgggcatc ctggggacct tcgtaggttc   45720
acaccagagg cctcgatacc ccttgaggac ttgggagagg ggaagatgac agtctctaag   45780
atcaggcctc tcaagctgag agtgaatatg ttaccagggt ggtggtggtg gtggagactg   45840
aacaaaggga gtctcgttcc agacacccaa aaaggttagc aacaaagggt cacaccacgg   45900
gtctggaatc caggccagga ctgaagtaca gttttggggg cccctcttg tgcctcatgc    45960 tacaaggtgg agctttagaa ctctggatcc tatgtcccca caccccagag gactaggctg   46020 acttttttt tcccttgtt gacacaccag ggaaaactgt caccaagaag aagtatattg     46080
ggatacgaat gatgtcgctt acatctaggt gggtaaacag gacacattac tatataaata   46140
taaatgtcag gcctatgttt atataaactt gggctttgca agacttcatg ggcattcttg   46200
aagggaaact atttccttca gtcatcatag tttctgctta caagtaagca ctggggaaag   46260
ggaagggtgt gggctgggc ctggttttg tatttctgac cacctggaag actccactct     46320
cctccctgaa ggcacgcctg agcatctaaa ggctggctag ccggcacact tttgtgcttg   46380
cctctctcca cgcatcctgt tgaaacttac attccaggag tgccccagtg cccgccccag   46440
ggcttgcccc agcctggagc acccacctcc cctgcatgct ggtgtgaggg gtgtggctgc   46500
aggaatgcag gccgaggacc tgcctccggg gactggtgac tgatggactt gtttccctga   46560
gtgtagaagt tgcagcttgg gtttaccagg ctcctgacat ccctgaaaga gttggggggg   46620
gggaagtggg gagggagcct tcatgaaata caggaaaccg aagtgactgg catgtctgag   46680
tcattcgaga gcttgacatt tattgatggt actgttttat ccaactgtta aaatattaag   46740
acattccaca caggttatga acactggtac ttagtgttgc caagcatagg atggcaagct   46800
gagactgaaa tcacacaggt tgtctttgga agcagaagag atacaagtgt tggggaggga   46860
agctaggcta agggtcacct tcctgagtca ttccccaagc tcctatgctt ctagcttact   46920
gagtgctctg tacccttccc ttcagggtga ggctgatgct gtaggcatgc ctactgtata   46980
gccagcagca gttctgtgct gatgcttgga gtagtttctt actactacac agagcactgt   47040
tgatgctggc aggcaggcca ttttaaagca gaatcagggg ctaggagct ggctcagtgg    47100 gtaaagtgct tactatgcta gtatgaagat ctaagttcaa atccccagga cctgtgtaaa   47160
gcccggcata aagaatgtg tcttctaaac tcccagtgct ttctctgtgg taaacaggag    47220
attcctctag caggccagct agcctagtgt atacagcagc aaacaagaga tcctcatctc   47280
aagtaaggca ggtactgagc ttgtcctcag acctctatat acatgttttg ctgtgccaaa   47340
gcctctatag gtgtcacgaa gacttgaagt tgagactcag gggggatt ggtgagagct     47400 gagtgttggc ctgaggaggc catgggaggt taatatcaac acaagcactt tttctcctaa   47460
gcagcaaagc caaagaactg aaggatcgtc accgagactt cccggatgta atctccggag   47520
catatatcat tgaagtcatc cccgacaccc ccgcagaagc gtgagtgtga cattatatcc   47580
ctcttcatga aatctatgtg gttcgtgggc caggggcag tgtaggtatt tgagctgtct    47640
```

```
ctcatggccc cgagtaccca tcctttccta tcagccaggg ctcctgactg ctttgggttc   47700
agggcttgtc cacagaagga tgtttcttct cttgggtcat ctccagggtc atccacatag   47760
ggagagcact cactaatggc ctcactggga atccctagga agcctggctg ttgagagagc   47820
ttcacagagc aggattcatc ctttgaggaa cctctgtagt tgtacttgtg actcgtgaag   47880
tcatagctgc caatacctaa agggaaacaa tccgatgaca tcgcaatagt agtagttcat   47940
ccagaactga ggcttgtttc caggacccca tgacatctag agagtaacac gcactgaaga   48000
gctgcgcatg aggccctagg ccagacctg gcctgatgcc tctcggtgga tgacccgtga    48060
gctgagaaaa atcagttttc gcatgatttt tatggttgga aaaaaaaatc caagtggctg   48120
tattttgtga tactgtaaat tctcgaaatg caaatatgca cacgtgtttt attagaccac   48180
agtcgtgtcc cctgacaaga tgacatcttg tctggaacaa gttttatgct gccgcagcag   48240
aaatgaatag ctgagacaaa gagaccagat gctctgtgaa gcttaagcta tttcccatct   48300
ggccctttgt ggaaaaagtc tgtagacttg tattagaaca aggaggacct cggtagcata   48360
gtgatcctgt cacgtatgaa ctaaggttcc aaccgcggca cagaggaata gaggcatcca   48420
acattcctgg aagaatcact ttctaaatta cagtcccatt tatgtgcaaa ttggctgtgg   48480
tcatcagacc tggtgtttcc ttgtcccctc tgaggataat tgatcatagt tcacataaaa   48540
atttcgtaaa gcatttctac aagaaatatt attgatttgg cttaaaaaga atctcgacag   48600
gaaatatcat cttctctcct tgaagtcatt ccatcaccat ttcctataac ccccatttgt   48660
tctgtttggg ttctaagatg tgccttttt gatgactgtg aggaatggaa atgttaacag    48720
tgtgtgtttc cctttgtgtt tcagtggagg gctcaaggaa aatgacgtca tcatcagcat   48780
caatggacag tctgtggtca ctgccaatga tgtcagtgat gtcatcaaaa aggagaacac   48840
cctgaacatg gttgtccgca gagggaatga agacattgtg attacggtgg ttcctgaaga   48900
aattgatccc taggcagagg caggagctgg acttcatgtt tccctcaaag actccaggag   48960
atggcgcatg agaactgagc tggtgacgca ggacacccag gactttgtcc aacattttgc   49020
ttgttcgggg aacacccctg tcgacagaat cctccttgat agtttgcggg caaaacaaat   49080
gtaatgttgg aggtgcacag gccgaagccc tgccctctgt atgctacgca tgcagcctgc   49140 ttttcttac aagcttgggc tattcctgct taagcagtca acatctgtcc ctgcccttag    49200
ccccagttgt ccgactaatg cacttgacag acgcatagat ggatgagagg acagtccttg   49260
cagccttggt cttgggtgtg tttacacttt tactccgagt cagcactcag aggaaattga   49320
tgccctgaga ccacaggtgg gtgaccctgg cttctgagat ggccaaaaaa tgcctcttag   49380
gaatcctgga atcaggagta caatgacttt gagtttcagc tattaaaata cttcttcata   49440
ct                                                                  49442
```

```
<210> SEQ ID NO 5
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 5
gaaagggaaa tatggg                                                   16

<210> SEQ ID NO 6
<211> LENGTH: 16
```

```
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 6
gatgaggtat aaagtg                                                     16

<210> SEQ ID NO 7
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 7
ggtgtgttaa taatca                                                     16

<210> SEQ ID NO 8
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 8
cttatgacgc aaactg                                                     16

<210> SEQ ID NO 9
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 9
tttgtctcct ttcctc                                                     16

<210> SEQ ID NO 10
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 10
gaatggaaag atgtaa                                                     16

<210> SEQ ID NO 11
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 11
gttctttggc tttgct                                                     16

<210> SEQ ID NO 12
<211> LENGTH: 16
<212> TYPE: DNA
```

```
<213> ORGANISM: Artificial
<220> FEATURE:
<223> OTHER INFORMATION: Reference Sequence or Oligonucleoitde Motif
      Sequence

<400> SEQUENCE: 12
ttcaatgata tatgct                                                    16

<210> SEQ ID NO 13
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 13
agtatgaaga agtatt                                                    16

<210> SEQ ID NO 14
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 14
cccaatcacc tcgcca                                                    16

<210> SEQ ID NO 15
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 15
gcagtagcaa agacagg                                                   17

<210> SEQ ID NO 16
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 16
aagttgaaat cagtggt                                                   17

<210> SEQ ID NO 17
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 17
tctggtagta agaatata                                                  18

<210> SEQ ID NO 18
<211> LENGTH: 18
<212> TYPE: DNA
<213> ORGANISM: Artificial
```

```
<220> FEATURE:
<223> OTHER INFORMATION: Reference Sequence or Oligonucleoitde Motif
      Sequence

<400> SEQUENCE: 18
aacagtaaga gctacttt                                                        18

<210> SEQ ID NO 19
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 19
tcagacacga tacagag                                                         17

<210> SEQ ID NO 20
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 20
tggtcagtga taagtaa                                                         17

<210> SEQ ID NO 21
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 21
gcactgtaga tgagaaac                                                        18

<210> SEQ ID NO 22
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 22
ataaagtaaa cttaatgcc                                                       19

<210> SEQ ID NO 23
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 23
attggttctt aggagtgggc                                                      20

<210> SEQ ID NO 24
<211> LENGTH: 19
<212> TYPE: DNA
<213> ORGANISM: Artificial
<220> FEATURE:
```

<223> OTHER INFORMATION: Reference Sequence or Oligonucleoitde Motif
      Sequence

<400> SEQUENCE: 24
attattgttt tactcgtga                                              19

<210> SEQ ID NO 25
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 25
atgctggggt aatgattg                                               18

<210> SEQ ID NO 26
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 26
agtctaaatt attgcacaa                                              19

<210> SEQ ID NO 27
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 27
ccaattagaa cagtagtgg                                              19

<210> SEQ ID NO 28
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 28
agtgtctagt taaacagcac                                             20

<210> SEQ ID NO 29
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 29
taccagagtc aagcatatg                                              19

<210> SEQ ID NO 30
<211> LENGTH: 20
<212> TYPE: DNA
<213> ORGANISM: Artificial
<220> FEATURE:
<223> OTHER INFORMATION: Reference Sequence or Oligonucleoitde Motif -continued

```
       Sequence

<400> SEQUENCE: 30
atctaaactt catgtcagaa                                                 20

<210> SEQ ID NO 31
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 31
ttcatacgac tgagcatc                                                   18

<210> SEQ ID NO 32
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 32
gtacagtttt agatcatc                                                   18

<210> SEQ ID NO 33
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 33
atcctaaaag agttcaaca                                                  19

<210> SEQ ID NO 34
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 34
cattctttgt catatact                                                   18

<210> SEQ ID NO 35
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 35
ttcaaagtga ctttcaag                                                   18

<210> SEQ ID NO 36
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence
```

<400> SEQUENCE: 36
tcctttctat aattacaaa                                    19

<210> SEQ ID NO 37
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 37
ctaattctgt agttttgg                                     18

<210> SEQ ID NO 38
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 38
actgagtgtg taatgttga                                    19

<210> SEQ ID NO 39
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 39
agagaaatct gtagggc                                      17

<210> SEQ ID NO 40
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 40
ttatcaaatc aactagcac                                    19

<210> SEQ ID NO 41
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 41
ttatatttga tagtgtgatc                                   20

<210> SEQ ID NO 42
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

```
<400> SEQUENCE: 42
aagagaagct gttatctaaa                                          20

<210> SEQ ID NO 43
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 43
aagtcatgct agagttcc                                            18

<210> SEQ ID NO 44
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 44
acacagtgta ttcgaggg                                            18

<210> SEQ ID NO 45
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 45
gacacagtgt attcgaggg                                           19

<210> SEQ ID NO 46
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 46
gacacagtgt attcgagg                                            18

<210> SEQ ID NO 47
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 47
aggacacagt gtattcgagg                                          20

<210> SEQ ID NO 48
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 48
```
aggacacagt gtattcgag                    19

<210> SEQ ID NO 49
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 49
caggacacag tgtattcgag                   20

<210> SEQ ID NO 50
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 50
aggacacagt gtattcg                      17

<210> SEQ ID NO 51
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 51
aacaggacac agtgtattcg                   20

<210> SEQ ID NO 52
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 52
tgaatctata cagcaggaa                    19

<210> SEQ ID NO 53
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 53
cttaagttat tcatatcca                    19

<210> SEQ ID NO 54
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 54
taggtggtag cagatag                                                17

<210> SEQ ID NO 55
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 55
gtagtaataa ttctggga                                               18

<210> SEQ ID NO 56
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 56
agtggtaagg tgaagtgaa                                              19

<210> SEQ ID NO 57
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 57
ttttgctgtg ataaatagc                                              19

<210> SEQ ID NO 58
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 58
tttcttatcg ttttatga                                               18

<210> SEQ ID NO 59
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 59
ggaaaacatt aacaaggttg                                             20

<210> SEQ ID NO 60
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 60
tgggtagagt ctaggag                                                17

<210> SEQ ID NO 61
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 61
agggagtgac tattagag                                                  18

<210> SEQ ID NO 62
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 62
cagagtaggg aaagtggttc                                                20

<210> SEQ ID NO 63
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 63
accatgttat atttggg                                                   17

<210> SEQ ID NO 64
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 64
tttattactg aggggaaagg                                                20

<210> SEQ ID NO 65
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 65
acttgagtgt agtacag                                                   17

<210> SEQ ID NO 66
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 66
catactagtt ttgcagaga                                                 19

```
<210> SEQ ID NO 67
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 67
ggactagaag tagttac                                                    17

<210> SEQ ID NO 68
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 68
agggagtcaa aggttcaa                                                   18

<210> SEQ ID NO 69
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 69
tctgtgtatt agagaacg                                                   18

<210> SEQ ID NO 70
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 70
tcaaaagcta catcagtc                                                   18

<210> SEQ ID NO 71
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 71
accgttgaat tagtcac                                                    17

<210> SEQ ID NO 72
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 72
tttccattaa aatgtttaca                                                 20
```

```
<210> SEQ ID NO 73
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 73
gagatggtaa ggagtaggag                                               20

<210> SEQ ID NO 74
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 74
agttttagac tattctg                                                  17

<210> SEQ ID NO 75
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 75
gtcaggacat aaactcac                                                 18

<210> SEQ ID NO 76
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 76
ttgttggtgt cagggaaaag                                               20

<210> SEQ ID NO 77
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 77
tcctgaaata ttgatgc                                                  17

<210> SEQ ID NO 78
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 78
tgccaaaatg actacagt                                                 18

<210> SEQ ID NO 79
```

```
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 79
ctcaaagttg gatcgtaac                                                19

<210> SEQ ID NO 80
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 80
ttgcatttta gaagttat                                                 18

<210> SEQ ID NO 81
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 81
tgtcaattag tgtgtttag                                                19

<210> SEQ ID NO 82
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 82
cataatattt agtctcct                                                 18

<210> SEQ ID NO 83
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 83
tatagttaca atcacca                                                  17

<210> SEQ ID NO 84
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 84
ttttgtacat actcttcc                                                 18

<210> SEQ ID NO 85
<211> LENGTH: 18
```

```
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 85
tagcagtact taaatggg                                                       18

<210> SEQ ID NO 86
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 86
tatgttacat atttggatga                                                     20

<210> SEQ ID NO 87
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 87
catggtatct tttggagag                                                      19

<210> SEQ ID NO 88
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 88
caacatatcc agtccag                                                        17

<210> SEQ ID NO 89
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 89
taattgtgaa gtagggtg                                                       18

<210> SEQ ID NO 90
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 90
actttagagg tttagtcc                                                       18

<210> SEQ ID NO 91
<211> LENGTH: 18
<212> TYPE: DNA
```

```
<213> ORGANISM: Artificial
<220> FEATURE:
<223> OTHER INFORMATION: Reference Sequence or Oligonucleoitde Motif
      Sequence

<400> SEQUENCE: 91 gagctttaa ttctatcc                                                  18

<210> SEQ ID NO 92
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 92
ctccttaaat acatgttac                                                19

<210> SEQ ID NO 93
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 93
gagataaatg tttgagaga                                                19

<210> SEQ ID NO 94
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 94
atgatggtga tttaggat                                                 18

<210> SEQ ID NO 95
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 95
agtcattcaa tttgagaaa                                                19

<210> SEQ ID NO 96
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 96
cagtggtggt aaggcac                                                  17

<210> SEQ ID NO 97
<211> LENGTH: 18
<212> TYPE: DNA
<213> ORGANISM: Artificial
```

```
<220> FEATURE:
<223> OTHER INFORMATION: Reference Sequence or Oligonucleoitde Motif
      Sequence

<400> SEQUENCE: 97
tgaaatggtt tagttctg                                              18

<210> SEQ ID NO 98
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 98
tgccatagtg aaatggttt                                             19

<210> SEQ ID NO 99
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 99
caggaggaca tactatt                                               17

<210> SEQ ID NO 100
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 100
atatatacag gcacatgg                                              18

<210> SEQ ID NO 101
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 101
gacaggagtc tttaaaatg                                             19

<210> SEQ ID NO 102
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 102
tatttatata gtaatgtgtc                                            20

<210> SEQ ID NO 103
<211> LENGTH: 17
<212> TYPE: DNA
<213> ORGANISM: Artificial
<220> FEATURE:
```

```
<223> OTHER INFORMATION: Reference Sequence or Oligonucleoitde Motif
      Sequence

<400> SEQUENCE: 103
ggataaaaca gtaccat                                                    17

<210> SEQ ID NO 104
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 104
ggagtttaga agacacat                                                   18

<210> SEQ ID NO 105
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 105
gtacaactac agaggtt                                                    17

<210> SEQ ID NO 106
<211> LENGTH: 19
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 106
aggaaatggt gatggaatg                                                  19

<210> SEQ ID NO 107
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 107
tcggagtaaa agtgtaaaca                                                 20

<210> SEQ ID NO 108
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 108
agatgggtgt gaaagg                                                     16

<210> SEQ ID NO 109
<211> LENGTH: 16
<212> TYPE: DNA
<213> ORGANISM: Artificial
<220> FEATURE:
<223> OTHER INFORMATION: Reference Sequence or Oligonucleoitde Motif
```

Sequence

<400> SEQUENCE: 109
atgttgtcta tgttta                                                        16

<210> SEQ ID NO 110
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 110
tatgttgtct atgttt                                                        16

<210> SEQ ID NO 111
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 111
gatgtttgca gtattt                                                        16

<210> SEQ ID NO 112
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 112
tatatagtcg aatagg                                                        16

<210> SEQ ID NO 113
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 113
tttggcttcg taagtg                                                        16

<210> SEQ ID NO 114
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 114
tgaggcagtg gagttg                                                        16

<210> SEQ ID NO 115
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 115
tggacaggag ggcagc                                                   16

<210> SEQ ID NO 116
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 116
tagagaaggt agaatg                                                   16

<210> SEQ ID NO 117
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 117
atttagatta gagaag                                                   16

<210> SEQ ID NO 118
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 118
gttcttaaat gtcgtt                                                   16

<210> SEQ ID NO 119
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 119
aagggcttac catctt                                                   16

<210> SEQ ID NO 120
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 120
tacttcaatt atatac                                                   16

<210> SEQ ID NO 121
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

```
<400> SEQUENCE: 121
gcaatgtgta agaagt                                                          16

<210> SEQ ID NO 122
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 122
aaactgttgg gatctt                                                          16

<210> SEQ ID NO 123
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 123
caaactgttg ggatct                                                          16

<210> SEQ ID NO 124
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 124
gcaaactgtt gggatc                                                          16

<210> SEQ ID NO 125
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 125
gatgtttgca gtattt                                                          16

<210> SEQ ID NO 126
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 126
attgggtttg atcggt                                                          16

<210> SEQ ID NO 127
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 127
```
ctattgggtt tgatcg                                                     16

<210> SEQ ID NO 128
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 128
tattgggttt gatcgg                                                     16

<210> SEQ ID NO 129
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 129
cgaatatgtg ctttaa                                                     16

<210> SEQ ID NO 130
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 130
gctgattatg acgtcg                                                     16

<210> SEQ ID NO 131
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 131
tgctgattat gacgtc                                                     16

<210> SEQ ID NO 132
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 132
attgggtttg atcggt                                                     16

<210> SEQ ID NO 133
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 133
ctattgggtt tgatcg                                                        16

<210> SEQ ID NO 134
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 134
tgctgattat gacgtc                                                        16

<210> SEQ ID NO 135
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 135
tattgggttt gatcgg                                                        16

<210> SEQ ID NO 136
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 136
cgaatatgtg ctttaa                                                        16

<210> SEQ ID NO 137
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 137
gctgattatg acgtcg                                                        16

<210> SEQ ID NO 138
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 138
caaatattta cctggttg                                                      18

<210> SEQ ID NO 139
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 139
tttacctggt tgttgg                                                        16

```
<210> SEQ ID NO 140
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 140
ccaaatattt acctggtt                                                 18

<210> SEQ ID NO 141
<211> LENGTH: 20
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 141
ccaaatattt acctggttgt                                               20

<210> SEQ ID NO 142
<211> LENGTH: 18
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 142
atatttacct ggttgttg                                                 18

<210> SEQ ID NO 143
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 143
tatttacctg gttgtt                                                   16

<210> SEQ ID NO 144
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 144
atatttacct ggttgt                                                   16

<210> SEQ ID NO 145
<211> LENGTH: 17
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 145
atatttacct ggttgtt                                                  17
```

<210> SEQ ID NO 146
<211> LENGTH: 11
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 146
tttacctggt t                                                          11

<210> SEQ ID NO 147
<211> LENGTH: 22
<212> TYPE: DNA
<213> ORGANISM: Homo Sapiens

<400> SEQUENCE: 147
ccaacaacca ggtaaatatt tg                                              22

<210> SEQ ID NO 148
<211> LENGTH: 16
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 148
aacaaccagg taaata                                                     16

<210> SEQ ID NO 149
<211> LENGTH: 18
<212> TYPE: DNA
<213> ORGANISM: Homo sapiens

<400> SEQUENCE: 149
caaccaggta aatatttg                                                   18

<210> SEQ ID NO 150
<211> LENGTH: 16
<212> TYPE: DNA
<213> ORGANISM: Homo sapiens

<400> SEQUENCE: 150
ccaacaacca ggtaaa                                                     16

<210> SEQ ID NO 151
<211> LENGTH: 18
<212> TYPE: DNA
<213> ORGANISM: Homo sapiens

<400> SEQUENCE: 151
aaccaggtaa atatttgg                                                   18

<210> SEQ ID NO 152
<211> LENGTH: 20
<212> TYPE: DNA
<213> ORGANISM: Homo sapiens

```
<400> SEQUENCE: 152
acaaccaggt aaatatttgg                                              20

<210> SEQ ID NO 153
<211> LENGTH: 18
<212> TYPE: DNA
<213> ORGANISM: Homo sapiens

<400> SEQUENCE: 153
caacaaccag gtaaatat                                                18

<210> SEQ ID NO 154
<211> LENGTH: 16
<212> TYPE: DNA
<213> ORGANISM: Homo sapiens

<400> SEQUENCE: 154
acaaccaggt aaatat                                                  16

<210> SEQ ID NO 155
<211> LENGTH: 17
<212> TYPE: DNA
<213> ORGANISM: Homo sapiens

<400> SEQUENCE: 155
aacaaccagg taaatat                                                 17

<210> SEQ ID NO 156
<211> LENGTH: 22
<212> TYPE: DNA
<213> ORGANISM: Artificial
<220> FEATURE:
<223> OTHER INFORMATION: Reference Sequence or Oligonucleoitde Motif
      Sequence

<400> SEQUENCE: 156
caaatattta cctggttgtt gg                                           22
```

ANTISENSE OLIGONUCLEOTIDES FOR MODULATING HTRA1 EXPRESSION

FIELD OF INVENTION

The present invention relates to antisense oligonucleotides (oligomers) that are complementary to HTRA1, leading to modulation of the expression of HTRA1. Modulation of HTRA1 expression is beneficial for a range of medical disorders, such as macular degeneration, e.g. age-related macular degeneration.

BACKGROUND

The human high temperature requirement A (HTRA) family of serine proteases are ubiquitously expressed PDZ-proteases that are involved in maintaining protein homeostasis in extracellular compartments by combining the dual functions of a protease and a chaperone. HTRA housekeeping proteases are implicated in organization of the extracellular matrix, cell proliferation and ageing. Modulation of HTRA activity is connected with severe diseases, including Duchenne muscular dystrophy (Bakay et al. 2002, Neuromuscul. Disord. 12: 125-141), arthritis, such as osteoarthritis (Grau et al. 2006, JBC 281: 6124-6129); cancer, familial ischemic cerebral small-vessel disease and age-related macular degeneration, as well as Parkinson's disease and Alzheimer's disease. The human HTRA1 contains an insulin-like growth factor (IGF) binding domain. It has been proposed to regulate IGF availability and cell growth (Zumbrunn and Trueb, 1996, FEES Letters 398:189-192) and to exhibit tumor suppressor properties. HTRA1 expression is down-regulated in metastatic melanoma, and may thus indicate the degree of melanoma progression. Overexpression of HTRA1 in a metastatic melanoma cell line reduced proliferation and invasion in vitro, and reduced tumor growth in a xenograft mouse model (Baldi et al., 2002, Oncogene 21:6684-6688). HTRA1 expression is also down-regulated in ovarian cancer. In ovarian cancer cell lines, HTRA1 overexpression induces cell death, while antisense HTRA1 expression promoted anchorage-independent growth (Chien et al., 2004, Oncogene 23:1636-1644).

In addition to its effect on the IGF pathway, HTRA1 also inhibits signaling by the TGFβ family of growth factors (Oka et al., 2004, Development 131:1041-1053). HTRA1 can cleave amyloid precursor protein (APP), and HTRA1 inhibitors cause the accumulation of Aβ peptide in cultured cells. Thus, HTRA1 is also implicated in Alzheimer's disease (Grau et al., 2005, Proc. Nat. Acad. Sci. USA. 102: 6021-6026).

On the other hand HTRA1 upregulation has been observed and seems to be associated to Duchenne muscular dystrophy (Bakay et al. 2002, Neuromuscul. Disord. 12: 125-141) and osteoarthritis (Grau et al. 2006, JBC 281: 6124-6129) and AMD (Fritsche, et al. Nat Gen 2013 45(4): 433-9.)

A single nucleotide polymorphism (SNP) in the HTRA1 promoter region (rs11200638) is associated with a 10 fold increased risk of developing age-related macular degeneration (AMD). Moreover the HTRA1 SNPs are in linkage disequilibrium with the ARMS2 SNP (rs10490924) associated with increased risk of developing age-related macular degeneration (AMD). The risk allele is associated with 2-3 fold increased HTRA1 mRNA and protein expression, and HTRA1 is present in drusen in patients with AMD (Dewan et al., 2006, Science 314:989-992; Yang et al., 2006, Science 314:992-993). Different animal models have confirmed that over-expression of HtrA1 Induces AMD-like phenotype in mice. The hHTRA transgenic mouse (Veierkottn, PlosOne 2011) reveals degradation of the elastic lamina of Bruch's membrane, determines choroidal vascular abnormalities (Jones, PNAS 2011) and increases the Polypoidal choroidal vasculopathy (PCV) lesions (Kumar, IOVS 2014). Additionally it has been reported Bruch's membrane damage in hHTRA1 Tg mice, which determines upon exposure to cigarette smoke 3 fold increases CNV (Nakayama, IOVS 2014)

Age-related macular degeneration (AMD) is the leading cause of irreversible loss of vision in people over the age of 65. With onset of AMD there is gradual loss of the light sensitive photoreceptor cells in the back of the eye, the underlying pigment epithelial cells that support them metabolically, and the sharp central vision they provide. Age is the major risk factor for the onset of AMD: the likelihood of developing AMD triples after age 55. Smoking, light iris color, gender (women are at greater risk), obesity, and repeated exposure to UV radiation also increase the risk of AMD. There are two forms of AMD: dry AMD and wet AMD. In dry AMD, drusen appear in the macula of the eye, the cells in the macula die, and vision becomes blurry. Dry AMD can progress in three stages: 1) early, 2) intermediate, and 3) advanced dry AMD. Dry AMD can also progress into wet AMD during any of these stages. Wet AMD (also known as exudative AMD), is associated with pathologic posterior segment neovascularization. The posterior segment neovascularization (PSNV) found in exudative AMD is characterized as pathologic choroidal neovascularization. Leakage from abnormal blood vessels forming in this process damages the macula and impairs vision, eventually leading to blindness. Treatment strategies for wet AMD are few and palliative at best. There is therefore an unmet medical need in the provision of effective drugs to treat macular degenerative conditions such as wet and dry AMD. WO 2008/013893 claims a composition for treating a subject suffering from age related macular degeneration comprising a nucleic acid molecules comprising an antisense sequence that hybridizes to HTRA1 gene or mRNA: No antisense molecules are disclosed. WO2009/006460 provides siRNAs targeting HTRA1 and their use in treating AMD.

OBJECTIVE OF THE INVENTION

The present invention provides antisense oligonucleotides which modulate HTRA1 in vivo or in vitro. The invention identified cryptic target sequence motifs present in the human HTRA1 mRNA (including pre-mRNA) which may be targeted by antisense oligonucleotides to give effective HTRA1 inhibition. The invention also provides effective antisense oligonucleotide sequences and compounds which are capable of inhibiting HTRA1, and their use in treatment of diseases or disorders where HTRA1 is indicated.

SUMMARY OF INVENTION

The present invention relates to oligonucleotides targeting a mammalian HTRA1 nucleic acid, i.e. are capable of inhibiting the expression of HTRA1 and to treat or prevent diseases related to the functioning of the HTRA1. The oligonucleotides targeting HTRA1 are antisense oligonucleotides, i.e. are complementary to their HTRA1 nucleic acid target.

The oligonucleotide of the invention may be in the form of a pharmaceutically acceptable salt, such as a sodium salt or a potassium salt.

Accordingly, the invention provides antisense oligonucleotides which comprise a contiguous nucleotide sequence of 10-30 nucleotides in length with at least 90% complementarity, such as fully complementary to a mammalian HTRA1 nucleic acid, such as SEQ ID NO 1, SEQ ID NO 2, SEQ ID NO 3 or SEQ ID NO 4.

In a further aspect, the invention provides pharmaceutical compositions comprising the oligonucleotides of the invention and pharmaceutically acceptable diluents, carriers, salts and/or adjuvants.

The invention provides LNA antisense oligonucleotides, such as LNA gapmer oligonucleotides, which comprise a contiguous nucleotide sequence of 10-30 nucleotides in length with at least 90% complementarity, such as fully complementary to a HTRA1 nucleic acid, such as a sequence selected from the group consisting of SEQ ID NO 1, SEQ ID NO 2, SEQ ID NO 3 or SEQ ID NO 4.

The invention provides for an antisense oligonucleotide comprising a contiguous nucleotide region of 10-22, such as 12-22 nucleotides which are at least 90% such as 100% complementarity to SEQ ID NO 147:

```
SEQ ID NO 147:
5' CCAACAACCAGGTAAATATTTG 3'
```

The invention provides for an antisense oligonucleotide comprising a contiguous nucleotide region of 10-17, such as 11, 12, 13, 14, 15, 16, such as 12-16 or 12-17 nucleotides which are complementarity to a sequence selected from the group consisting of SEQ ID NO 148-155.

The invention provides for an antisense oligonucleotide comprising a contiguous nucleotide region of 10-17, such as 11, 12, 13, 14, 15, 16, such as 12-16 or 12-17 nucleotides which are complementarity to SEQ ID NO 148 or 155.

The invention provides for an antisense oligonucleotide of 10-30 nucleotides in length, wherein said antisense oligonucleotide comprises a contiguous nucleotide region of 10-22 nucleotides which are at least 90% such as 100% complementarity to SEQ ID NO 147:

```
SEQ ID NO 147:
5' CCAACAACCAGGTAAATATTTG 3'
```

The invention provides for an antisense oligonucleotide of 10-30 nucleotides in length, wherein said antisense oligonucleotide comprises a contiguous nucleotide region of at least 10, such as at least 12 contiguous nucleotides which are complementary to a sequence present in a sequence selected from SEQ ID NO 148-155.

The invention provides for an antisense oligonucleotide of at least 12 nucleotides in length, wherein said antisense oligonucleotide comprises the contiguous sequence of SEQ ID NO 146

```
SEQ ID NO 146:
5' TTTACCTGGTT 3'.
```

The invention provides for the oligonucleotides provided in the examples. The invention provides for the oligonucleotide, such as an antisense oligonucleotide, which comprises at least 10, such as at least 12, present in a sequence selected from the group consisting of SEQ ID NO 5-145.

The invention provides for a conjugate comprising the oligonucleotide according to the invention, and at least one conjugate moiety covalently attached to said oligonucleotide.

The invention provides for a pharmaceutically acceptable salt of the oligonucleotide or conjugate of the invention.

In a further aspect, the invention provides methods for in vivo or in vitro method for modulation of HTRA1 expression in a cell which is expressing HTRA1, by administering an oligonucleotide, conjugate or composition of the invention in an effective amount to said cell.

In a further aspect the invention provides methods for treating or preventing a disease, disorder or dysfunction associated with in vivo activity of HTRA1 comprising administering a therapeutically or prophylactically effective amount of the oligonucleotide of the invention, or conjugate thereof, to a subject suffering from or susceptible to the disease, disorder or dysfunction.

In a further aspect the oligonucleotide or composition of the invention is used for the treatment or prevention of macular degeneration, and other disorders where HTRA1 is implicated.

The invention provides for the oligonucleotide or conjugate of the invention, for use in the treatment of a disease or disorder selected from the list comprising of Duchenne muscular dystrophy, arthritis, such as osteoarthritis, familial ischemic cerebral small-vessel disease, Alzheimer's disease and Parkinson's disease.

The invention provides for the oligonucleotide or conjugate of the invention, for use in the treatment of macular degeneration, such as wet or dry age related macular degeneration (e.g. wAMD, dAMD, geographic atrophy, intermediate dAMD) or diabetic retinopathy.

The invention provides for the use of the oligonucleotide, conjugate or composition of the invention, for the manufacture of a medicament for the treatment of macular degeneration, such as wet or dry age related macular degeneration (e.g. wAMD, dAMD, geographic atrophy, intermediate dAMD) or diabetic retinopathy.

The invention provides for the use of the oligonucleotide, conjugate or composition of the invention, for the manufacture of a medicament for the treatment of a disease or disorder selected from the group consisting of Duchenne muscular dystrophy, arthritis, such as osteoarthritis, familial ischemic cerebral small-vessel disease, Alzheimer's disease and Parkinson's disease.

The invention provides for a method of treatment of a subject suffering from a disease or disorder selected from the group consisting of Duchenne muscular dystrophy, arthritis, such as osteoarthritis, familial ischemic cerebral small-vessel disease, Alzheimer's disease and Parkinson's disease, said method comprising the step of administering an effective amount of the oligonucleotide, conjugate or composition of the invention to the subject.

The invention provides for a method of treatment of a subject suffering from an ocular disease, such as macular degeneration, such as wet or dry age related macular degeneration (e.g. wAMD, dAMD, geographic atrophy, intermediate dAMD) or diabetic retinopathy, said method comprising the step of administering an effective amount of the oligonucleotide, conjugate or composition of the invention to the subject.

The invention provides for a method of treatment of a subject suffering from an ocular disease, such as macular degeneration, such as wet or dry age related macular degeneration (e.g. wAMD, dAMD, geographic atrophy, intermediate dAMD) or diabetic retinopathy, said method comprising administering at least two dosages of the oligonucleotide of the invention, or pharmaceutically acceptable salt thereof, in an intraocular injection in a dosage of from about 10

μg-200 μg, wherein the dosage interval between administration consecutive is at least 4 weeks or at least monthly.

DEFINITIONS

Oligonucleotide

Figure 1:
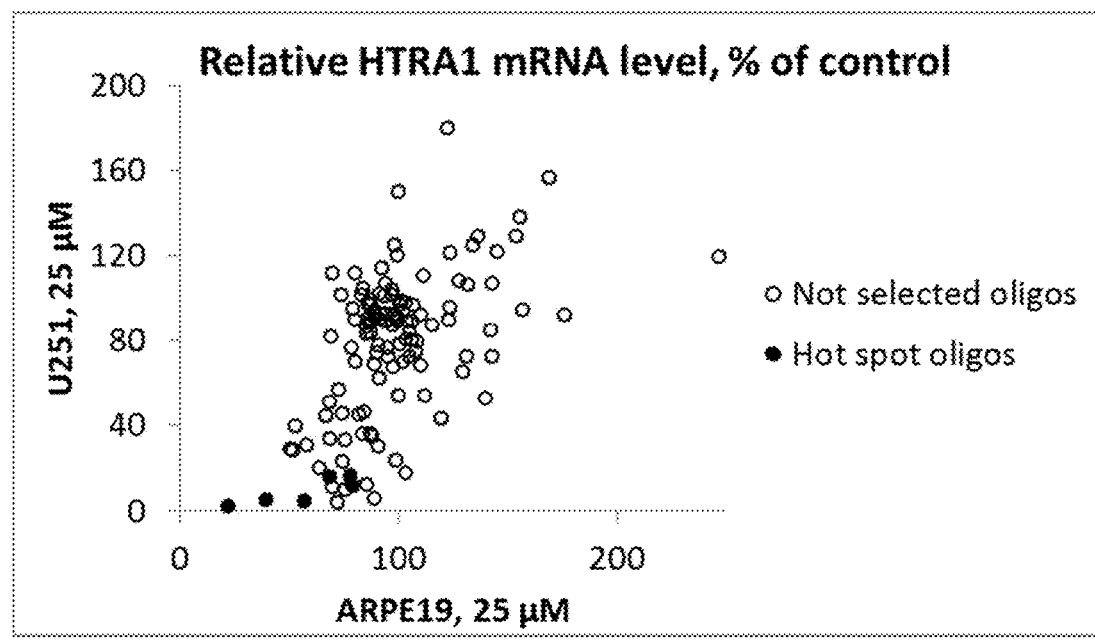
FIG. 1. A library of n=129 HTRA1 LNA oligonucleotides were screened in U251 and ARPE19 cell lines at 25 μM. Read out: HTRA1 qPCR. n=6 oligos located between position 33042-33064 were relatively active.

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs. Preferably, the antisense oligonucleotides of the present invention are single stranded.

Contiguous Nucleotide Region

The term "contiguous nucleotide region" refers to the region of the oligonucleotide which is complementary to the target nucleic acid. The term may be used interchangeably herein with the term "contiguous nucleotide sequence" or "contiguous nucleobase sequence" and the term "oligonucleotide motif sequence". In some embodiments all the nucleotides of the oligonucleotide are present in the contiguous nucleotide region. In some embodiments the oligonucleotide comprises the contiguous nucleotide region and may, optionally comprise further nucleotide(s), for example a nucleotide linker region which may be used to attach a functional group to the contiguous nucleotide sequence. The nucleotide linker region may or may not be complementary to the target nucleic acid. In some embodiments the inter-nucleoside linkages present between the nucleotides of the contiguous nucleotide region are all phosphorothioate inter-nucleoside linkages. In some embodiments, the contiguous nucleotide region comprises one or more sugar modified nucleosides.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers".

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region of a gapmer oligonucleotide, as well as in regions of modified nucleosides.

In an embodiment, the oligonucleotide comprises one or more internucleoside linkages modified from the natural phosphodiester to a linkage that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

In some embodiments the modified internucleoside linkages may be phosphorothioate internucleoside linkages. In some embodiments, the modified internucleoside linkages are compatible with the RNaseH recruitment of the oligonucleotide of the invention, for example phosphorothioate.

In some embodiments the internucleoside linkage comprises sulphur (S), such as a phosphorothioate internucleoside linkage.

A phosphorothioate internucleoside linkage is particularly useful due to nuclease resistance, beneficial pharmakokinetics and ease of manufacture. In some embodiments all of the internucleoside linkages of the oligonucleotide, or contiguous nucleotide sequence thereof, are phosphorothioate.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used. In some embodiments, the cytosine nucleobases in a 5'cg3' motif is 5-methyl cytosine.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term complementarity describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide region or sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences, dividing by the total number of nucleotides in the oligonucleotide and multiplying by 100. In such a comparison a nucleobase/nucleotide which does not align (form a base pair) is termed a mismatch.

It will be understood that when referring to complementarity between two sequences, the determination of complementarity is measured across the length of the shorter of the two sequences, such as the length of the contiguous nucleotide region or sequence.

The term "fully complementary", refers to 100% complementarity. In the absence of a % term value or indication of a mismatch, complementary means fully complementary.

Identity

The term "Identity" as used herein, refers to the number of nucleotides in percent of a contiguous nucleotide sequence in a nucleic acid molecule (e.g. oligonucleotide) which, at a given position, are identical to (i.e. in their ability to form Watson Crick base pairs with the complementary nucleoside) a contiguous nucleotide sequence, at a given position of a separate nucleic acid molecule (e.g. the target nucleic acid). The percentage is calculated by counting the number of aligned bases that are identical between the two sequences, including gaps, dividing by the total number of nucleotides in the oligonucleotide and multiplying by 100.

Percent Identity=(Matches×100)/Length of aligned region (with gaps).

When determining the identity of the contiguous nucleotide region of an oligonucleotide, the identity is calculated across the length of the contiguous nucleotide region. In embodiments where the entire contiguous nucleotide sequence of the oligonucleotide is the contiguous nucleotide region, identity is therefore calculated across the length of the nucleotide sequence of the oligonucleotide. In this respect the contiguous nucleotide region may be identical to a region of the reference nucleic acid sequence, or in some embodiments may be identical to the entire reference nucleic acid. Unless otherwise indicated a sequence which has 100% identity to a reference sequence is referred to as being identical. For example, the reference sequence may be selected from the group consisting of any one of SEQ ID NOs 5-146 and 156. However, if the oligonucleotide comprises additional nucleotide(s) flanking the contiguous nucleotide region, for example region D' or D", these additional flanking nucleotides may be disregarded when determining identity. In some embodiments, identity may be calculated across the entire oligonucleotide sequence.

In some embodiments, the antisense oligonucleotide of the invention comprises a contiguous nucleotide region of 10-22 contiguous nucleotides which are identical to SEQ ID NO 156:

SEQ ID NO 156:
5' CAAATATTTACCTGGTTGTTGG 3'

In some embodiments, the contiguous nucleotide region consists or comprises of at least 10 contiguous nucleotides, such as 11, 12, 13, 14, 15, 16, 17, 18, 19, 20, 21, 22, contiguous nucleotides, such as from 12-22, such as from 14-18 contiguous nucleotides of SEQ ID NO 156. In some embodiments, the entire contiguous sequence of the oligonucleotide consists or comprises of at least 10 contiguous nucleotides, such as 11, 12, 13, 14, 15, 16, 17, 18, 19, 20, 21, 22, contiguous nucleotides, such as from 12-22, such as from 14-18 contiguous nucleotides of SEQ ID NO 156.

In some embodiments, the contiguous nucleotide region is at least 12 contiguous nucleotides of SEQ ID NO 156. In some embodiments, the contiguous nucleotide region is at least 14 contiguous nucleotides of SEQ ID NO 156. In some embodiments, the contiguous nucleotide region is at least 16 contiguous nucleotides SEQ ID NO 156.

In some embodiments, the contiguous nucleotide region is at least 10, 12, 14 or 16 contiguous nucleotides which are identical to SEQ ID NO 143.

In some embodiments, the contiguous nucleotide region is at least 10, 12, 14 or 16 contiguous nucleotides which are identical to SEQ ID NO 145.

In some embodiments, the contiguous nucleotide region is at least 10, 11, 12, 13, 14, 15 or 16 contiguous nucleotides which are identical to SEQ ID NO 143.

In some embodiments, the contiguous nucleotide region is at least 10, 11, 12, 13, 14, 15, 16 or 17 contiguous nucleotides which are identical to SEQ ID NO 145.

In some embodiments, the contiguous nucleotide consists or comprises SEQ ID NO 143.

In some embodiments, the contiguous nucleotide region consists or comprises SEQ ID NO 145.

In some embodiments, the contiguous nucleotide region is at least 10, 12, 14 or 16 contiguous nucleotides which are identical to a sequence selected from the group consisting of SEQ ID NO 138, 139, 140, 141, 142, 143, 144 and 145. In some embodiments, the contiguous nucleotide region comprises or consists of a sequence selected from the group consisting of SEQ ID NO 138, 139, 140, 141, 142, 143, 144 and 145.

In some embodiments the contiguous nucleotide region comprises the sequence SEQ ID NO 146: TTTACCTGGTT.

The invention provides for an antisense oligonucleotide 11-30 nucleotides in length, such as 12-20 nucleotides in length, which comprises the sequence SEQ ID NO 146: TTTACCTGGTT.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy $\Delta G°$ is a more accurate representation of binding affinity and is related to the dissociation constant ($K_d$) of the reaction by $\Delta G°=-RT \ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for $\Delta G°$ measurements. $\Delta G°$ can also be estimated numerically by using the nearest neighbor model as described by SantaLucia, 1998, *Proc Natl Mad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated $\Delta G°$ values below −10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Target Sequence

The oligonucleotide comprises a contiguous nucleotide region which is complementary to or hybridizes to a sub-sequence of the target nucleic acid molecule. The term "target sequence" as used herein refers to a sequence of nucleotides present in the target nucleic acid which comprises the nucleobase sequence which is complementary to the contiguous nucleotide region or sequence of the oligonucleotide of the invention. In some embodiments, the target sequence consists of a region on the target nucleic acid which is complementary to the contiguous nucleotide region or sequence of the oligonucleotide of the invention. In some embodiments the target sequence is longer than the complementary sequence of a single oligonucleotide, and may, for example represent a preferred region of the target nucleic acid which may be targeted by several oligonucleotides of the invention.

The oligonucleotide of the invention comprises a contiguous nucleotide region which is complementary to the target nucleic acid, such as a target sequence.

The oligonucleotide comprises a contiguous nucleotide region of at least 10 nucleotides which is complementary to or hybridizes to a target sequence present in the target nucleic acid molecule. The contiguous nucleotide region (and therefore the target sequence) comprises of at least 10 contiguous nucleotides, such as 11, 12, 13, 14, 15, 16, 17, 18, 19, 20, 21, 22, contiguous nucleotides, such as from 12-22, such as from 14-18 contiguous nucleotides.

In some embodiments the target sequence is, or is present within SEQ ID NO 147.

In some embodiments the target sequence is selected from the group consisting of SEQ ID NO 148, 149, 150, 151, 152, 153, 154 and 155:

```
SEQ ID NO 148:
AACAACCAGGTAAATA

SEQ ID NO 149:
CAACCAGGTAAATATTTG

SEQ ID NO 150:
CCAACAACCAGGTAAA

SEQ ID NO 151:
AACCAGGTAAATATTTGG

SEQ ID NO 152:
ACAACCAGGTAAATATTTGG

SEQ ID NO 153:
CAACAACCAGGTAAATAT

SEQ ID NO 154:
ACAACCAGGTAAATAT

SEQ ID NO 155:
AACAACCAGGTAAATAT
```

The invention provides for an antisense oligonucleotide of 10-30 nucleotides in length, wherein said antisense oligonucleotide comprises a contiguous nucleotide region of at least 10, contiguous nucleotides which are complementary to a sequence present in a sequence selected from SEQ ID NO 147 & 148-155.

The invention provides for an antisense oligonucleotide of 12-30 nucleotides in length, wherein said antisense oligonucleotide comprises a contiguous nucleotide region of at least 12 contiguous nucleotides which are complementary to a sequence present in a sequence selected from SEQ ID NO 147 & 148-155.

The invention provides for an antisense oligonucleotide of 14-30 nucleotides in length, wherein said antisense oligonucleotide comprises a contiguous nucleotide region of at least 14 contiguous nucleotides which are complementary to a sequence present in a sequence selected from SEQ ID NO 147 & 148-155.

The invention provides for an antisense oligonucleotide which consists or comprises a contiguous nucleotide region which is complementary to a sequence selected from SEQ ID NO 148-155.

The target sequence may be a sub-sequence of the target nucleic acid. In some embodiments the oligonucleotide or contiguous nucleotide region is fully complementary to, or only comprises one or two mismatches to an HTRA1 sub-sequence, such as a sequence selected from the group consisting of SEQ ID NO 148-154. In some embodiments the oligonucleotide or contiguous nucleotide region is fully complementary to, or only comprises one or two mismatches to an HTRA1 sub-sequence SEQ ID NO 147.

Target Cell

The term a target cell as used herein refers to a cell which is expressing the target nucleic acid. In some embodiments the target cell may be in vivo or in vitro. In some embodiments the target cell is a mammalian cell such as a rodent cell, such as a mouse cell, or a rat cell, or a primate cell such as a monkey cell or a human cell. In some embodiments, the cell may be a pig cell, a dog cell or a rabbit cell. In some embodiments the target cell may be a retinal cell, such as a retinal pigment epithelium (PRE) cell. In some embodiments the cell is selected from the group consisting of RPE cells, Bipolar Cell, Amacrine cells, Endothelial cells, Ganglion cells and Microglia cells. For in vitro assessment, the target cell may be a primary cell or an established cell line, such as U251, ARPE19, HEK293, or rat C6 cells.

Target Nucleic Acid

According to the present invention, the target nucleic acid is a nucleic acid which encodes mammalian HTRA1 and may for example be a gene, a RNA, a mRNA, and pre-mRNA, a mature mRNA or a cDNA sequence. The target may therefore be referred to as an HTRA1 target nucleic acid.

Suitably, the target nucleic acid encodes an HTRA1 protein, in particular mammalian HTRA1, such as human HTRA1 (See for example tables 1 & 2 which provides the mRNA and pre-mRNA sequences for human and rat HTRA1).

In some embodiments, the target nucleic acid is selected from the group consisting of SEQ ID NO: 1, 2, 3, and 4, or naturally occurring variants thereof (e.g. sequences encoding a mammalian HTRA1 protein.

A target cell is a cell which is expressing the HTRA1 target nucleic acid. In preferred embodiments the target nucleic acid is the HTRA1 mRNA, such as the HTRA1 pre-mRNA or HTRA1 mature mRNA. The poly A tail of HTRA1 mRNA is typically disregarded for antisense oligonucleotide targeting.

If employing the oligonucleotide of the invention in research or diagnostics the target nucleic acid may be a cDNA or a synthetic nucleic acid derived from DNA or RNA.

The target sequence may be a sub-sequence of the target nucleic acid. In some embodiments the oligonucleotide or contiguous nucleotide region is fully complementary to, or only comprises one or two mismatches to an HTRA1 sub-sequence, such as a sequence selected from the group consisting of SEQ ID NO 148, 149, 150, 151, 152, 153, 154 and 155.

Complementarity to the target or sub-sequence thereof is measured over the length of the oligonucleotide, or contiguous nucleotide region thereof.

For in vivo or in vitro application, the oligonucleotide of the invention is typically capable of inhibiting the expression of the HTRA1 target nucleic acid in a cell which is expressing the HTRA1 target nucleic acid. The contiguous sequence of nucleobases of the oligonucleotide of the invention is typically complementary to the HTRA1 target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides (e.g. region D). The target nucleic acid may, in some embodiments, be a RNA or DNA, such as a messenger RNA, such as a mature mRNA or a pre-mRNA. In some embodiments the target nucleic acid is a RNA or DNA which encodes mammalian HTRA1 protein, such as human HTRA1, e.g. the human HTRA1 mRNA sequence, such as that disclosed as SEQ ID NO 1 (NM_002775.4, GI:190014575). Further information on exemplary target nucleic acids is provided in tables 1 & 2.

sufficient complementary sequence to the oligonucleotide, the oligonucleotide of the invention may therefore target the target nucleic acid and naturally occurring variants thereof. In some embodiments, the naturally occurring variants have at least 95% such as at least 98% or at least 99% homology to a mammalian HTRA1 target nucleic acid, such as a target nucleic acid selected form the group consisting of SEQ ID NO 1, 2, 3, or 4.

Modulation of Expression

The term "modulation of expression" as used herein is to be understood as an overall term for an oligonucleotide's ability to alter the amount of HTRA1 when compared to the amount of HTRA1 before administration of the oligonucleotide. Alternatively modulation of expression may be determined by reference to a control experiment where the oligonucleotide of the invention is not administered. One type of modulation is an oligonucleotide's ability to inhibit, down-regulate, reduce, suppress, remove, stop, block, prevent, lessen, lower, avoid or terminate expression of HTRA1, e.g. by degradation of mRNA or blockage of transcription. The antisense oligonucleotide of the invention are capable of inhibiting, down-regulating, reduce, suppress, remove, stop, block, prevent, lessen, lower, avoid or terminate expression of HTRA1.

High Affinity Modified Nucleosides

A high affinity modified nucleoside is a modified nucleotide which, when incorporated into the oligonucleotide enhances the affinity of the oligonucleotide for its complementary target, for example as measured by the melting temperature (Tm). A high affinity modified nucleoside of the

TABLE 1

Genome and assembly information for human and rat HTRA1.

| Species | Chr. | Strand | Genomic coordinates Start | End | Assembly | NCBI reference sequence* accession number for mRNA |
|---------|------|--------|--------------------------|-----|----------|---------------------------------------------------|
| Human | 10 | fwd | 122461525 | 122514908 | GRCh38.p2 release 107 | NM_002775.4 |
| Rat | 1 | fwd | 201499067 | 201548508 | Rnor_6.0 release 105 | NM_031721.1 |

Fwd = forward strand.
The genome coordinates provide the pre-mRNA sequence (genomic sequence).
The NCBI reference provides the mRNA sequence (cDNA sequence).
*The National Center for Biotechnology Information reference sequence database is a comprehensive, integrated, non-redundant, well-annotated set of reference sequences including genomic, transcript, and protein. It is hosted at www.ncbi.nlm.nih.gov/refseq.

TABLE 2

Sequence details for human and rat HTRA1.

| Species | RNA type | Length (nt) | SEQ ID NO |
|---------|----------|-------------|-----------|
| Human | mRNA | 2138 | 1 |
| Human | premRNA | 53384 | 2 |
| Rat | mRNA | 2012 | 3 |
| Rat | premRNA | 49442 | 4 |

Naturally Occurring Variant

The term "naturally occurring variant" refers to variants of HTRA1 gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms, and allelic variants. Based on the presence of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

2' Modified Nucleosides.

A 2' sugar modified nucleoside is a nucleoside which has a substituent other than H or —OH at the 2' position (2' substituted nucleoside) or comprises a 2' linked biradicle, and includes 2' substituted nucleosides and LNA (2'-4' biradicle bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

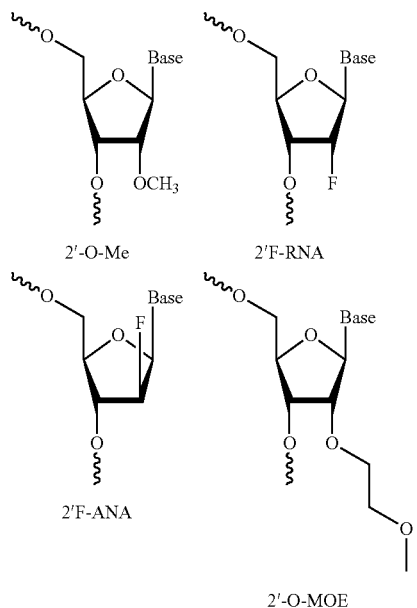

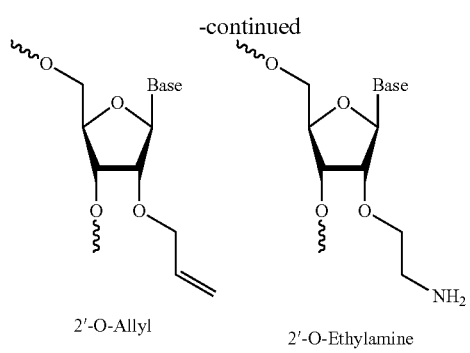

Locked Nucleic Acid Nucleosides (LNA).

LNA nucleosides are modified nucleosides which comprise a linker group (referred to as a biradicle or a bridge) between C2' and C4' of the ribose sugar ring of a nucleotide. These nucleosides are also termed bridged nucleic acid or bicyclic nucleic acid (BNA) in the literature.

In some embodiments, the modified nucleoside or the LNA nucleosides of the oligomer of the invention has a general structure of the formula I or II:

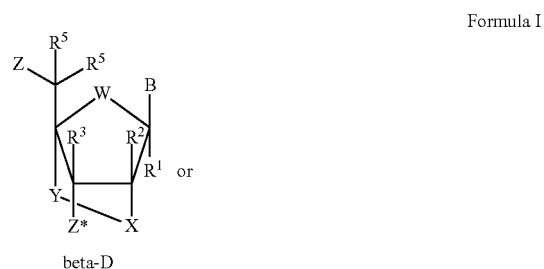

Formula I

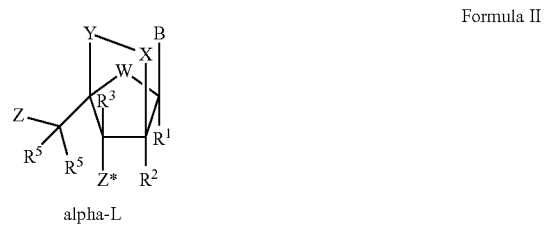

Formula II wherein W is selected from —O—, —S—, —N($R^a$)—, —C($R^a R^b$)—, such as, in some embodiments —O—; B designates a nucleobase moiety;

Z designates an internucleoside linkage to an adjacent nucleoside, or a 5'-terminal group;

Z* designates an internucleoside linkage to an adjacent nucleoside, or a 3'-terminal group;

X designates a group selected from the list consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, N$R^a R^b$, —CH$_2$—, C$R^a R^b$, —C(=CH$_2$)—, and —C(=C$R^a R^b$)—

In some embodiments, X is —O—

Y designates a group selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, Y is selected from the group consisting of: —CH$_2$—, —C($R^a R^b$)—, —CH$_2$CH$_2$—, —C($R^a R^b$)—C($R^a R^b$)—, —CH$_2$CH$_2$CH$_2$—, —C($R^a R^b$)C($R^a R^b$)C($R^a R^b$)—, —C($R^a$)=C($R^b$)—, and —C($R^a$)=N—

In some embodiments, Y is selected from the group consisting of: —CH$_2$—, —CHR$^a$—, —CHCH$_3$—, CR$^a$R$^b$— or —X—Y— together designate a bivalent linker group (also referred to as a radicle) together designate a bivalent linker group consisting of 1, 2, or 3 groups/atoms selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z, In some embodiments, —X—Y— designates a biradicle selected from the groups consisting of: —X—CH$_2$—, —X—CR$^a$R$^b$—, —X—CHR$^a$—, —X—C(HCH$_3$)—, —O—Y—, —O—CH$_2$—, —S—CH$_2$—, —NH—CH$_2$—, —O—CHCH$_3$—, —CH$_2$—O—CH$_2$, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —NR$^a$—CH$_2$—, N—O—CH$_2$, —S—CR$^a$R$^b$— and —S—CHR$^a$—.

In some embodiments —X—Y— designates —O—CH$_2$— or —O—CH(CH$_3$)—.

wherein Z is selected from —O—, —S—, and —N($R^a$)—, and $R^a$ and, when present $R^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation.

wherein $R^1$, $R^2$, $R^3$, $R^5$ and $R^{5*}$ are independently selected from the group consisting of: hydrogen, optionally substituted C$_{1-6}$-alkyl, optionally substituted C$_{2-6}$-alkenyl, optionally substituted C$_{2-6}$-alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted, and where two geminal substituents together may designate oxo, thioxo, imino, or optionally substituted methylene.

In some embodiments $R^1$, $R^2$, $R^3$, $R^5$ and $R^{5*}$ are independently selected from C$_{1-6}$ alkyl, such as methyl, and hydrogen.

In some embodiments $R^1$, $R^2$, $R^3$, $R^5$ and $R^{5*}$ are all hydrogen.

In some embodiments $R^1$, $R^2$, $R^3$, are all hydrogen, and either $R^5$ and $R^{5*}$ is also hydrogen and the other of $R^5$ and $R^{5*}$ is other than hydrogen, such as C$_{1-6}$ alkyl such as methyl.

In some embodiments, $R^a$ is either hydrogen or methyl. In some embodiments, when present, $R^b$ is either hydrogen or methyl.

In some embodiments, one or both of $R^a$ and $R^b$ is hydrogen

In some embodiments, one of $R^a$ and $R^b$ is hydrogen and the other is other than hydrogen In some embodiments, one of $R^a$ and $R^b$ is methyl and the other is hydrogen In some embodiments, both of $R^a$ and $R^b$ are methyl.

In some embodiments, the biradicle —X—Y— is —O—CH$_2$—, W is O, and all of $R^1$, $R^2$, $R^3$, $R^5$ and $R^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—CH$_2$—, W is O, and all of $R^1$, $R^2$, $R^3$, $R^5$ and $R^{5*}$ are all hydrogen. Such thio LNA nucleosides are disclosed in WO99/014226 and WO2004/046160 which are hereby incorporated by reference.

In some embodiments, the biradicle —X—Y— is —NH—CH$_2$—, W is O, and all of $R^1$, $R^2$, $R^3$, $R^5$ and $R^{5*}$ are all hydrogen. Such amino LNA nucleosides are disclosed in WO99/014226 and WO2004/046160 which are hereby incorporated by reference.

In some embodiments, the biradicle —X—Y— is —O—CH$_2$—CH$_2$— or —O—CH$_2$—CH$_2$—CH$_2$—, W is O, and all of $R^1$, $R^2$, $R^3$, $R^5$ and $R^{5*}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2'-O-4'C-ethylene bridged nucleic acids (ENA).

In some embodiments, the biradicle —X—Y— is —O—CH$_2$—, W is O, and all of $R^1$, $R^2$, $R^3$, and one of $R^5$ and $R^{5*}$ are hydrogen, and the other of $R^5$ and $R^{5*}$ is other than hydrogen such as C$_{1-6}$ alkyl, such as methyl. Such 5' substituted LNA nucleosides are disclosed in WO2007/134181 which is hereby incorporated by reference.

In some embodiments, the biradicle —X—Y— is —O—CR$^a$R$^b$—, wherein one or both of $R^a$ and $R^b$ are other than hydrogen, such as methyl, W is O, and all of $R^1$, $R^2$, $R^3$, and one of $R^5$ and $R^{5*}$ are hydrogen, and the other of $R^5$ and $R^{5*}$ is other than hydrogen such as C$_{1-6}$ alkyl, such as methyl. Such bis modified LNA nucleosides are disclosed in WO2010/077578 which is hereby incorporated by reference.

In some embodiments, the biradicle —X—Y— designate the bivalent linker group —O—CH(CH$_2$OCH$_3$)— (2' O-methoxyethyl bicyclic nucleic acid—Seth at al., 2010, J. Org. Chem. Vol 75(5) pp. 1569-81). In some embodiments, the biradicle —X—Y— designate the bivalent linker group —O—CH(CH$_2$CH$_3$)— (2'O-ethyl bicyclic nucleic acid—Seth at al., 2010, J. Org. Chem. Vol 75(5) pp. 1569-81). In some embodiments, the biradicle —X—Y— is —O—CHR$^a$—, W is O, and all of $R^1$, $R^2$, $R^3$, $R^5$ and $R^{5*}$ are all hydrogen. Such 6' substituted LNA nucleosides are disclosed in WO10036698 and WO07090071 which are both hereby incorporated by reference.

In some embodiments, the biradicle —X—Y— is —O—CH(CH$_2$OCH$_3$)—, W is O, and all of $R^1$, $R^2$, $R^3$, $R^5$ and $R^{5*}$ are all hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)—. —in either the R- or S- configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH(CH$_3$)—, W is O, and all of $R^1$, $R^2$, $R^3$, $R^5$ and $R^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—CR$^a$R$^b$—, wherein in neither R$^a$ or R$^b$ is hydrogen, W is O, and all of $R^1$, $R^2$, $R^3$, $R^5$ and $R^{5*}$ are all hydrogen. In some embodiments, R$^a$ and R$^b$ are both methyl. Such 6' di-substituted LNA nucleosides are disclosed in WO 2009006478 which is hereby incorporated by reference.

In some embodiments, the biradicle —X—Y— is —S—CHR$^a$—, W is O, and all of $R^1$, $R^2$, $R^3$, $R^5$ and $R^{5*}$ are all hydrogen. Such 6' substituted thio LNA nucleosides are disclosed in WO11156202 which is hereby incorporated by reference. In some 6' substituted thio LNA embodiments R$^a$ is methyl.

In some embodiments, the biradicle —X—Y— is —C(=CH2)-C(R$^a$R$^b$)—, such as —C(=CH$_2$)—CH$_2$—, or —C(=CH$_2$)—CH(CH$_3$)—W is O, and all of $R^1$, $R^2$, $R^3$, $R^5$ and $R^{5*}$ are all hydrogen. Such vinyl carbo LNA nucleosides are disclosed in WO08154401 and WO09067647 which are both hereby incorporated by reference.

In some embodiments the biradicle —X—Y— is —N(—OR$^a$)—, W is O, and all of $R^1$, $R^2$, $R^3$, $R^5$ and $R^{5*}$ are all hydrogen. In some embodiments R$^a$ is $C_{1-6}$ alkyl such as methyl. Such LNA nucleosides are also known as N substituted LNAs and are disclosed in WO2008/150729 which is hereby incorporated by reference. In some embodiments, the biradicle —X—Y— together designate the bivalent linker group —O—NR$^a$—CH$_3$— (Seth at al., 2010, J. Org. Chem). In some embodiments the biradicle —X—Y— is —N(R$^a$)—, W is O, and all of $R^1$, $R^2$, $R^3$, $R^5$ and $R^{5*}$ are all hydrogen. In some embodiments R$^a$ is $C_{1-6}$ alkyl such as methyl.

In some embodiments, one or both of $R^5$ and $R^{5*}$ is hydrogen and, when substituted the other of $R^5$ and $R^{5*}$ is $C_{1-6}$ alkyl such as methyl. In such an embodiment, $R^1$, $R^2$, $R^3$, may all be hydrogen, and the biradicle —X—Y— may be selected from —O—CH2- or —O—C(HCR$^a$)—, such as —O—C(HCH3)-.

In some embodiments, the biradicle is —CR$^a$R$^b$—O—CR$^a$R$^b$—, such as CH$_2$—O—CH$_2$—, W is O and all of $R^1$, $R^2$, $R^3$, $R^5$ and $R^{5*}$ are all hydrogen. In some embodiments R$^a$ is $C_{1-6}$ alkyl such as methyl. Such LNA nucleosides are also known as conformationally restricted nucleotides (CRNs) and are disclosed in WO2013036868 which is hereby incorporated by reference.

In some embodiments, the biradicle is —O—CR$^a$R$^b$—O—CR$^a$R$^b$—, such as O—CH$_2$—O—CH$_2$—, W is O and all of $R^1$, $R^2$, $R^3$, $R^5$ and $R^{5*}$ are all hydrogen. In some embodiments R$^a$ is $C_{1-6}$ alkyl such as methyl. Such LNA nucleosides are also known as COC nucleotides and are disclosed in Mitsuoka et al., Nucleic Acids Research 2009 37(4), 1225-1238, which is hereby incorporated by reference.

It will be recognized than, unless specified, the LNA nucleosides may be in the beta-D or alpha-L stereoisoform.

Examples of LNA nucleosides are presented in Scheme 1.

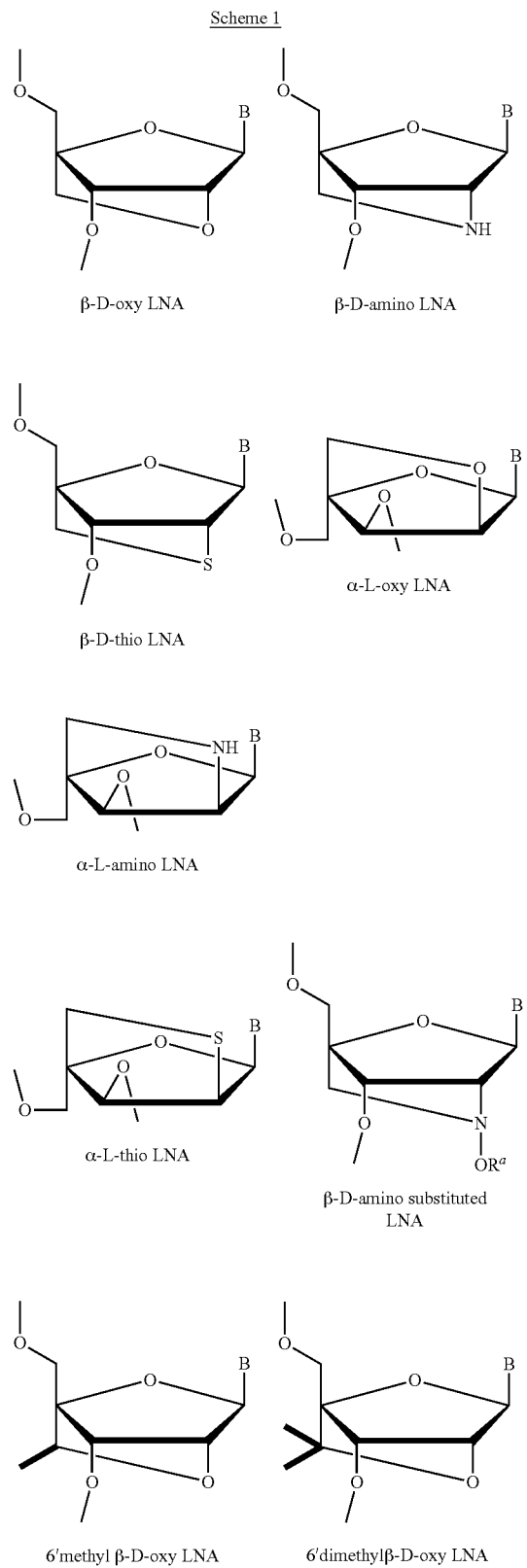

Scheme 1

β-D-oxy LNA

β-D-amino LNA

β-D-thio LNA

α-L-oxy LNA

α-L-amino LNA

α-L-thio LNA

β-D-amino substituted LNA

6'methyl β-D-oxy LNA

6'dimethylβ-D-oxy LNA

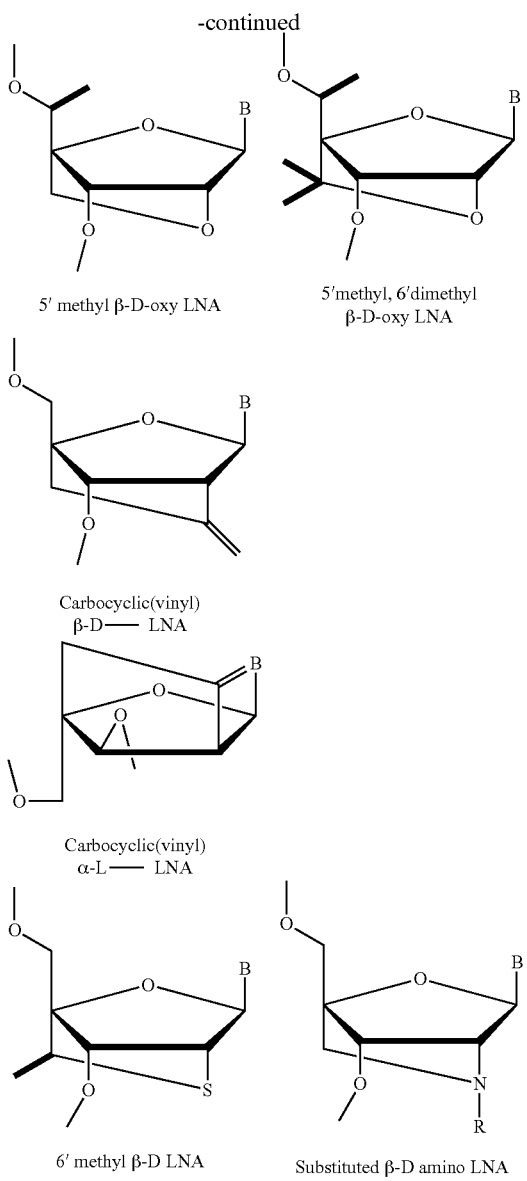

5' methyl β-D-oxy LNA

5'methyl, 6'dimethyl β-D-oxy LNA

Carbocyclic(vinyl) β-D— LNA

Carbocyclic(vinyl) α-L— LNA

6' methyl β-D LNA

Substituted β-D amino LNA

As illustrated in the examples, in some embodiments of the invention the LNA nucleosides in the oligonucleotides are beta-D-oxy-LNA nucleosides.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers, with phosphorothioate linkages between all monomers in the oligonucleotide, and using the methodology provided by Example 91-95 of WO01/23613 (hereby incorporated by reference).

Gapmer

The term gapmer as used herein refers to an antisense oligonucleotide which comprises a region of RNase H recruiting oligonucleotides (gap) which is flanked 5' and 3' by regions which comprise one or more affinity enhancing modified nucleosides (flanks or wings). Various gapmer designs are described herein. Headmers and tailmers are oligonucleotides capable of recruiting RNase H where one of the flanks is missing, i.e. only one of the ends of the oligonucleotide comprises affinity enhancing modified nucleosides. For headmers the 3' flank is missing (i.e. the 5' flank comprises affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one DNA nucleoside or at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA and 2'-F-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Conjugate

The term conjugate as used herein refers to an oligonucleotide which is covalently linked to a non-nucleotide moiety (conjugate moiety or region C or third region).

The term conjugate as used herein refers to an oligonucleotide which is covalently linked to a non-nucleotide moiety (conjugate moiety or region C or third region).

In some embodiments, the non-nucleotide moiety selected from the group consisting of a protein, such as an enzyme, an antibody or an antibody fragment or a peptide; a lipophilic moiety such as a lipid, a phospholipid, a sterol; a polymer, such as polyethyleneglycol or polypropylene glycol; a receptor ligand; a small molecule; a reporter molecule; and a non-nucleosidic carbohydrate.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety to an oligonucleotide (e.g. the termini of region A or C).

In some embodiments of the invention the conjugate or oligonucleotide conjugate of the invention may optionally, comprise a linker region which is positioned between the oligonucleotide and the conjugate moiety. In some embodiments, the linker between the conjugate and oligonucleotide is biocleavable.

Biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference), and may be referred to as region D herein.

Conjugates may also be linked to the oligonucleotide via non bioclevable linkers, or in some embodiments the conjugate may comprise a non-cleavable linker which is covalently attached to the biocleavable linker. Linkers that are not necessarily biocleavable but primarily serve to covalently connect a conjugate moiety to an oligonucleotide or biocleavable linker. Such linkers may comprise a chain structure or an oligomer of repeating units such as ethylene glycol, amino acid units or amino alkyl groups. In some embodiments the linker (region Y) is an amino alkyl, such as a $C_2$-$C_{36}$ amino alkyl group, including, for example $C_6$ to $C_{12}$ amino alkyl groups. In some embodiments the linker (region Y) is a $C_6$ amino alkyl group. Conjugate linker groups may be routinely attached to an oligonucleotide via use of an amino modified oligonucleotide, and an activated ester group on the conjugate group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

DETAILED DESCRIPTION OF THE INVENTION

The Oligonucleotides of the Invention

The invention relates to oligonucleotides capable of inhibiting the expression of HTRA1. The modulation is may achieved by hybridizing to a target nucleic acid encoding HTRA1 or which is involved in the regulation of HTRA1. The target nucleic acid may be a mammalian HTRA 1 sequence, such as a sequence selected from the group consisting of SEQ ID 1, 2, 3 or 4.

The oligonucleotide of the invention is an antisense oligonucleotide which targets HTRA1, such as a mammalian HTRA1.

In some embodiments the antisense oligonucleotide of the invention is capable of modulating the expression of the target by inhibiting or down-regulating it. Preferably, such modulation produces an inhibition of expression of at least 20% compared to the normal expression level of the target, such as at least 30%, 40%, 50%, 60%, 70%, 80%, or 90% inhibition compared to the normal expression level of the target. In some embodiments compounds of the invention may be capable of inhibiting expression levels of HTRA1 mRNA by at least 60% or 70% in vitro using ARPE-19 cells. In some embodiments compounds of the invention may be capable of inhibiting expression levels of HTRA1 mRNA by at least 60% or 70% in vitro using ARPE-19 cells. In some embodiments compounds of the invention may be capable of inhibiting expression levels of HTRA1 protein by at least 50% in vitro using ARPE-19 cells. Suitably, the examples provide assays which may be used to measure HTRA1 RNA or protein inhibition (e.g. example 3). The target modulation is triggered by the hybridization between a contiguous nucleotide sequence of the oligonucleotide and the target nucleic acid. In some embodiments the oligonucleotide of the invention comprises mismatches between the oligonucleotide and the target nucleic acid. Despite mismatches hybridization to the target nucleic acid may still be sufficient to show a desired modulation of HTRA1 expression. Reduced binding affinity resulting from mismatches may advantageously be compensated by increased number of nucleotides in the oligonucleotide and/or an increased number of modified nucleosides capable of increasing the binding affinity to the target, such as 2' modified nucleosides, including LNA, present within the oligonucleotide sequence.

An aspect of the present invention relates to an antisense oligonucleotide which comprises a contiguous nucleotide region of 10 to 30 nucleotides in length with at least 90% complementarity to HTRA1 target sequence, such as fully complementary to an HTRA1 target sequence, e.g. a nucleic acid selected from the group consisting SEQ ID NO 1, 2, 3 & 4.

In some embodiments, the oligonucleotide comprises a contiguous sequence which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid.

In some embodiments, the oligonucleotide of the invention, or a contiguous nucleotide sequence thereof is fully complementary (100% complementary) to a region of the target nucleic acid, or in some embodiments may comprise one or two mismatches between the oligonucleotide and the target nucleic acid.

In some embodiments the oligonucleotide, or a contiguous nucleotide sequence of at least 12 nucleotides thereof, is at least 90% complementary, such as fully (or 100%) complementary to a region of SEQ ID NO 147.

In some embodiments the oligonucleotide, or a contiguous nucleotide sequence of at least 12 nucleotides thereof, is at least 90% complementary, such as fully (or 100%) complementary to a region of a sequence selected from the group consisting of SEQ ID NOs 148, 149, 150, 151, 152, 153, 154 and 155.

In some embodiments the oligonucleotide, or a contiguous nucleotide sequence of at least 14 nucleotides thereof, is fully (or 100%) complementary to SEQ ID 147, or a sequence selected from the group consisting of SEQ ID NOs 148, 149, 150, 151, 152, 153, 154 and 155.

In some embodiments the oligonucleotide, or a contiguous nucleotide sequence of at least 16 nucleotides thereof, is fully (or 100%) complementary to SEQ ID 147, or a sequence selected from the group consisting of SEQ ID NOs 148, 149, 150, 151, 152, 153, 154 and 155.

In some embodiments the oligonucleotide, or contiguous nucleotide region thereof is fully (or 100%) complementary to a sequence selected from the group consisting of SEQ ID NOs 148, 149, 150, 151, 152, 153, 154 and 155.

In some embodiments the oligonucleotide or contiguous nucleotide region thereof comprises or consists of a sequence selected from the group consisting of SEQ ID NOs 143, 138, 139, 140, 141, 142, 144 and 145:

SEQ ID NO 143:
TATTTACCTGGTTGTT

SEQ ID NO 138:
CAAATATTTACCTGGTTG

SEQ ID NO 139:
TTTACCTGGTTGTTGG

SEQ ID NO 140:
CCAAATATTTACCTGGTT

SEQ ID NO 141:
CCAAATATTTACCTGGTTGT

SEQ ID NO 142:
ATATTTACCTGGTTGTTG

SEQ ID NO 144:
ATATTTACCTGGTTGT

SEQ ID NO 145:
ATATTTACCTGGTTGTT

It is understood that the oligonucleotide motif sequences can be modified to for example increase nuclease resistance and/or binding affinity to the target nucleic acid. Modifications are described in the definitions and in the "Oligonucleotide design" section.

In some embodiments, the oligonucleotide of the invention, or contiguous nucleotide region thereof is fully complementary (100% complementary) to a region of the target nucleic acid, or in some embodiments may comprise one or two mismatches between the oligonucleotide and the target nucleic acid. In some embodiments the oligonucleotide, or contiguous nucleotide sequence of at least 12 nucleotides thereof, is at least 90% complementary, such as fully (or 100%) complementary to the target nucleic acid sequence.

In some embodiments the oligonucleotide, or a contiguous nucleotide sequence of at least 12 nucleotides thereof, has 100% identity to a sequence selected from the group consisting of SEQ ID NOs 5-107, or SEQ ID NOs 108-137.

In some embodiments the oligonucleotide, or a contiguous nucleotide sequence of at least 14 nucleotides thereof, has 100% identity to a sequence selected from the group consisting of SEQ ID NOs 5-107, or SEQ ID NOs 108-137.

In some embodiments the oligonucleotide, or contiguous nucleotide sequence of at least 16 nucleotides thereof, has 100% identity to a sequence selected from the group consisting of SEQ ID NOs 5-107, or SEQ ID NOs 108-137.

In some embodiments the oligonucleotide, or contiguous nucleotide region thereof, comprises or consists of a sequence selected from SEQ ID NOs 5-107, or SEQ ID NOs 108-137.

In some embodiments the compound of the invention is selected from the group consisting of:

| SEQ ID NO | Compound ID # | |
|---|---|---|
| 138 | 138,1 | $^{m}C_sA_sA_sA_st_sa_st_st_sa_sc_sc_st_sg_sG_sT_sT_sG$ |
| 139 | 139,1 | $T_sT_st_sa_sc_sc_st_sg_sg_st_st_sg_st_sT_sG_sG$ |
| 140 | 140,1 | $^{m}C_s{}^{m}C_sA_sA_sa_st_sa_st_st_sa_sc_sc_st_sg_sG_sT_sT$ |
| 141 | 141,1 | $^{m}C_s{}^{m}C_sA_sa_sa_st_sa_st_st_sa_sc_sc_st_sg_sg_st_sG_sT$ |
| 142 | 142,1 | $A_sT_sA_st_st_st_sa_sc_sc_st_sg_sg_st_sg_sT_sT_sG$ |
| 143 | 143,1 | $T_sA_sT_st_st_sa_sc_sc_st_sg_sg_st_sT_sG_sT_sT$ |
| 143 | 143,2 | $T_sA_st_st_st_sa_sc_sc_st_sg_sG_st_sT_sg_sT_sT$ |
| 143 | 143,3 | $T_sA_sT_st_st_sa_sc_sc_st_sg_sg_sT_sT_sg_sT_sT$ |
| 144 | 144,1 | $A_sT_sA_sT_st_st_sa_sc_sc_st_sg_sg_sT_sT_sG_sT$ |
| 144 | 144,2 | $A_st_sA_sT_sT_sa_sc_sc_st_sg_sg_st_sT_sG_sT$ |
| 145 | 145,1 | $A_st_sA_sT_st_st_sa_sc_sc_st_sg_sG_sT_sT_sg_sT_sT$ |
| 145 | 145,2 | $A_sT_sA_st_st_st_sa_sc_sc_st_sg_sG_sT_sT_sg_sT_sT$ |
| 145 | 145,3 | $A_st_sA_sT_st_st_sa_sc_sc_st_sg_sg_st_sT_sG_sT_sT$ |

Wherein capital letters represent beta-D-oxy LNA nucleosides, all LNA cytosines are 5-methyl cytosine (as indicated by the superscript m), lower case letters represent DNA nucleosides. All internucleoside linkages are phosphorothioate internucleoside linkages (as indicated by the subscript $_s$).

Oligonucleotide Design

Oligonucleotide design refers to the pattern of nucleoside sugar modifications in the oligonucleotide sequence. The oligonucleotides of the invention comprise sugar-modified nucleosides and may also comprise DNA or RNA nucleosides. In some embodiments, the oligonucleotide comprises sugar-modified nucleosides and DNA nucleosides. Incorporation of modified nucleosides into the oligonucleotide of the invention may enhance the affinity of the oligonucleotide for the target nucleic acid. In that case, the modified nucleosides can be referred to as affinity enhancing modified nucleotides.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. In an embodiment, the oligonucleotide of the invention may comprise modifications, which are independently selected from these three types of modifications (modified sugar, modified nucleobase and modified internucleoside linkage) or a combination thereof. Preferably the oligonucleotide comprises one or more sugar modified nucleosides, such as 2' sugar modified nucleosides. Preferably the oligonucleotide of the invention comprise the one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. Even more preferably the one or more modified nucleoside is LNA.

In some embodiments, at least 1 of the modified nucleosides is a locked nucleic acid (LNA), such as at least 2, such as at least 3, at least 4, at least 5, at least 6, at least 7, or at least 8 of the modified nucleosides are LNA. In a still further embodiment all the modified nucleosides are LNA.

In a further embodiment the oligonucleotide comprises at least one modified internucleoside linkage. In a preferred embodiment the internucleoside linkages within the contiguous nucleotide sequence are phosphorothioate or boranophosphate internucleoside linkages. In some embodiments all the internucleotide linkages in the contiguous sequence of the oligonucleotide are phosphorothioate linkages.

In some embodiments, the oligonucleotide of the invention comprise at least one modified nucleoside which is a 2'-MOE-RNA, such as 2, 3, 4, 5, 6, 7, 8, 9 or 10 2'-MOE-RNA nucleoside units. In some embodiments, at least one of said modified nucleoside is 2'-fluoro DNA, such as 2, 3, 4, 5, 6, 7, 8, 9 or 10 2'-fluoro-DNA nucleoside units.

In some embodiments, the oligonucleotide of the invention comprises at least one LNA unit, such as 1, 2, 3, 4, 5, 6, 7, or 8 LNA units, such as from 2 to 6 LNA units, such as from 3 to 7 LNA units, 4 to 8 LNA units or 3, 4, 5, 6 or 7 LNA units. In some embodiments, all the modified nucleosides are LNA nucleosides. In some embodiments, all LNA cytosine units are 5-methyl-cytosine. In some embodiments the oligonucleotide or contiguous nucleotide region thereof has at least 1 LNA unit at the 5' end and at least 2 LNA units at the 3' end of the nucleotide sequence. In some embodiments all cytosine nucleobases present in the oligonucleotide of the invention are 5-methyl-cytosine.

In some embodiments, the oligonucleotide of the invention comprises at least one LNA unit and at least one 2' substituted modified nucleoside.

In some embodiments of the invention, the oligonucleotide comprise both 2' sugar modified nucleosides and DNA units.

In an embodiment of the invention the oligonucleotide of the invention is capable of recruiting RNase H.

In some embodiments, the oligonucleotide of the invention or contiguous nucleotide region thereof is a gapmers oligonucleotide.

Gapmer Design

In some embodiments the oligonucleotide of the invention, or contiguous nucleotide region thereof, has a gapmer design or structure also referred herein merely as "Gapmer". In a gapmer structure the oligonucleotide comprises at least three distinct structural regions a 5'-flank, a gap and a 3'-flank, F-G-F' in '5->3' orientation. In this design, flanking regions F and F' (also termed wing regions) comprise at least one sugar modified nucleoside which is adjacent to region G, and may in some embodiments comprise a contiguous stretch of 2-7 sugar modified nucleoside, or a contiguous stretch of sugar modified and DNA nucleosides (mixed wings comprising both sugar modified and DNA nucleosides). Consequently, the nucleosides of the 5' flanking region and the 3' flanking region which are adjacent to the gap region are sugar modified nucleosides, such as 2' modified nucleosides. The gap region, G, comprises a contiguous stretch of nucleotides which are capable of recruiting RNase H, when the oligonucleotide is in duplex with the HTRA1 target nucleic acid. In some embodiments, region G comprises a contiguous stretch of 5-16 DNA nucleosides. The gapmer region F-G-F' is complementary to the HTRA1 target nucleic acid, and may therefore be the contiguous nucleotide region of the oligonucleotide.

Regions F and F', flanking the 5' and 3' ends of region G, may comprise one or more affinity enhancing modified nucleosides. In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. In other embodiments, the flanking regions may comprise both LNA nucleosides and other nucleosides (mixed flanks), such as DNA nucleosides and/or non-LNA modified nucleosides, such as 2' substituted nucleosides. In this case the gap is defined as a contiguous sequence of at least 5 RNase H recruiting nucleosides (such as 5-16 DNA nucleosides) flanked at the 5' and 3' end by an affinity enhancing modified nucleoside, such as an LNA, such as beta-D-oxy-LNA.

Region F

Region F (5' flank or 5' wing) attached to the '5 end of region G comprises, contains or consists of at least one sugar modified nucleoside such as at least 2, at least 3, at least 4, at least 5, at least 6, at least 7 modified nucleosides. In some embodiments region F comprises or consists of from 1 to 7 modified nucleosides, such as from 2 to 6 modified nucleosides, such as from 2 to 5 modified nucleosides, such as from 2 to 4 modified nucleosides, such as from 1 to 3 modified nucleosides, such as 1, 2, 3 or 4 modified nucleosides.

In an embodiment, one or more or all of the modified nucleosides in region F are 2' modified nucleosides.

In a further embodiment one or more of the 2' modified nucleosides in region F are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In one embodiment of the invention all the modified nucleosides in region F are LNA nucleosides. In a further embodiment the LNA nucleosides in region F are independently selected from the group consisting of oxy-LNA, thio-LNA, amino-LNA, cET, and/or ENA, in either the beta-D or alpha-L configurations or combinations thereof. In a preferred embodiment region F has at least 1 beta-D-oxy LNA unit, at the 5' end of the contiguous sequence.

Region G

Region G (gap region) may comprise, contain or consist of at 5-16 consecutive DNA nucleosides capable of recruiting RNaseH. In a further embodiment region G comprise, contain or consist of from 5 to 12, or from 6 to 10 or from 7 to 9, such as 8 consecutive nucleotide units capable of recruiting RNaseH.

In a still further embodiment at least one nucleoside unit in region G is a DNA nucleoside unit, such as from 4 to 20 or 6 to 18 DNA units, such as 5 to 16, In some embodiments, all of the nucleosides of region G are DNA units.

In further embodiments the region G may consist of a mixture of DNA and other nucleosides capable of mediating RNase H cleavage. In some embodiments, at least 50% of the nucleosides of region G are DNA, such as at least 60%, at least 70% or at least 80%, or at least 90% DNA.

Region F'

Region F' (3' flank or 3' wing) attached to the '3 end of region G comprises, contains or consists of at least one sugar modified nucleoside such as at least 2, at least 3, at least 4, at least 5, at least 6, at least 7 modified nucleosides. In some embodiments region F' comprises or consists of from 1 to 7 modified nucleosides, such as from 2 to 6 modified nucleosides, such as from 2 to 5 modified nucleosides, such as from 2 to 4 modified nucleosides, such as from 1 to 3 modified nucleosides, such as 1, 2, 3 or 4 modified nucleosides.

In an embodiment, one or more or all of the modified nucleosides in region F' are 2' modified nucleosides.

In a further embodiment one or more of the 2' modified nucleosides in region F' are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In one embodiment of the invention all the modified nucleosides in region F' are LNA nucleosides. In a further embodiment the LNA nucleosides in region F' are independently selected from the group consisting of oxy-LNA, thio-LNA, amino-LNA, cET, and/or ENA, in either the beta-D or alpha-L configurations or combinations thereof. In a preferred embodiment region F' has at least 1 beta-D-oxy LNA unit, at the 5' end of the contiguous sequence.

Region D, D' and D"

The oligonucleotide of the invention comprises a contiguous nucleotide region which is complementary to the target nucleic acid. In some embodiments, the oligonucleotide may further comprise additional nucleotides positioned 5' and/or 3' to the contiguous nucleotide region, which are referred to as region D herein. Region D' and D" can be attached to the 5' end of region F or the 3' end of region F', respectively. The D regions (region D' or D") may in some embodiments form part of the contiguous nucleotide sequence which is complementary to the target nucleic acid, or in other embodiments the D region(s) may be non-complementary to the target nucleic acid.

In some embodiments the oligonucleotide of the invention consists or comprises of the contiguous nucleotide region and optionally 1-5 additional 5' nucleotides (region D').

In some embodiments the oligonucleotide of the invention consists or comprises of the contiguous nucleotide region and optionally 1-5 additional 3' nucleotides (region D").

Region D' or D" may independently comprise 1, 2, 3, 4 or 5 additional nucleotides, which may be complementary or non-complementary to the target nucleic acid. In this respect the oligonucleotide of the invention, may in some embodiments comprise a contiguous nucleotide sequence capable of modulating the target which is flanked at the 5' and/or 3' end by additional nucleotides. Such additional nucleotides may serve as a nuclease susceptible biocleavable linker, and may therefore be used to attach a functional group such as a conjugate moiety to the oligonucleotide of the invention. In some embodiments the additional 5' and/or 3' end nucleotides are linked with phosphodiester linkages, and may be DNA or RNA. In another embodiment, the additional 5' and/or 3' end nucleotides are modified nucleotides which may for example be included to enhance nuclease stability or for ease of synthesis. In some embodiments the oligonucleotide of the invention comprises a region D' and/or D" in addition to the contiguous nucleotide region.

In some embodiments, the gapmer oligonucleotide of the present invention can be represented by the following formulae:

F-G-F'; in particular $F_{1-7}$-$G_{4-12}$-$F'_{1-7}$

D'-F-G-F', in particular $D'_{1-3}$-$F_{1-7}$-$G_{4-12}$-$F'_{1-7}$

F-G-F'-D", in particular $F_{1-7}$-$G_{4-12}$-$F'_{1-7}$-$D''_{1-3}$

D'-F-G-F'-D", in particular $D'_{1-3}$-$F_{1-7}$-$G_{4-12}$-$F'_{1-7}$-$D''_{1-3}$ Method of Manufacture In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand). In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Salts

For use as a therapeutic, the oligonucleotide of the invention may be provided as a suitable pharmaceutical salt, such as a sodium or potassium salt. In some embodiments the oligonucleotide of the invention is a sodium salt.

Pharmaceutical Composition

In a further aspect, the invention provides pharmaceutical compositions comprising any of the aforementioned oligonucleotides and/or oligonucleotide conjugates and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline. In some embodiments the oligonucleotide is used in the pharmaceutically acceptable diluent at a concentration of 50-300 µM solution. In some embodiments, the oligonucleotide of the invention is administered at a dose of 10-1000 µg.

WO 2007/031091 provides suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Oligonucleotides or oligonucleotide conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In some embodiments, the oligonucleotide or oligonucleotide conjugate of the invention is a prodrug. In particular with respect to oligonucleotide conjugates the conjugate moiety is cleaved of the oligonucleotide once the prodrug is delivered to the site of action, e.g. the target cell.

Applications

The oligonucleotides of the invention may be utilized as research reagents for, for example, diagnostics, therapeutics and prophylaxis.

In research, such oligonucleotides may be used to specifically modulate the synthesis of HTRA1 protein in cells (e.g. in vitro cell cultures) and experimental animals thereby facilitating functional analysis of the target or an appraisal of its usefulness as a target for therapeutic intervention. Typically the target modulation is achieved by degrading or inhibiting the mRNA producing the protein, thereby prevent protein formation or by degrading or inhibiting a modulator of the gene or mRNA producing the protein.

In diagnostics the oligonucleotides may be used to detect and quantitate HTRA1 expression in cell and tissues by northern blotting, in-situ hybridisation or similar techniques.

For therapeutics, an animal or a human, suspected of having a disease or disorder, which can be treated by modulating the expression of HTRA1.

The invention provides methods for treating or preventing a disease, comprising administering a therapeutically or prophylactically effective amount of an oligonucleotide, an oligonucleotide conjugate or a pharmaceutical composition of the invention to a subject suffering from or susceptible to the disease.

The invention also relates to an oligonucleotide, a composition or a conjugate as defined herein for use as a medicament.

The oligonucleotide, oligonucleotide conjugate or a pharmaceutical composition according to the invention is typically administered in an effective amount.

The invention also provides for the use of the oligonucleotide or oligonucleotide conjugate of the invention as described for the manufacture of a medicament for the treatment of a disorder as referred to herein, or for a method of the treatment of as a disorder as referred to herein.

The disease or disorder, as referred to herein, is associated with expression of HTRA1. In some embodiments disease or disorder may be associated with a mutation in the HTRA1 gene or a gene whose protein product is associated with or interacts with HTRA1. Therefore, in some embodiments, the target nucleic acid is a mutated form of the HTRA1 sequence and in other embodiments, the target nucleic acid is a regulator of the HTRA1 sequence.

The methods of the invention are preferably employed for treatment or prophylaxis against diseases caused by abnormal levels and/or activity of HTRA1.

The invention further relates to use of an oligonucleotide, oligonucleotide conjugate or a pharmaceutical composition as defined herein for the manufacture of a medicament for the treatment of abnormal levels and/or activity of HTRA1.

In one embodiment, the invention relates to oligonucleotides, oligonucleotide conjugates or pharmaceutical compositions for use in the treatment of diseases or disorders selected from eye disorders, such as macular degeneration, including age related macular degeneration (AMD), such as dry AMD or wet AMD, and diabetic retinopathy. In some embodiments the oligonucleotide conjugates or pharmaceutical compositions of the invention may be for use in the treatment of geographic atrophy or intermediate dAMD. HTRA1 has also been indicated in Alzheimer's and Parkinson's disease, and therefore in some embodiments, the oligonucleotide conjugates or pharmaceutical compositions of the invention may be for use in the treatment of Alzheimer's or Parkinson's. HTRA1 has also been indicated in Duchenne muscular dystrophy, arthritis, such as osteoarthritis, familial ischemic cerebral small-vessel disease, and therefore in some embodiments, the oligonucleotide conjugates or pharmaceutical compositions of the invention may be for use in the treatment of Duchenne muscular dystrophy, arthritis, such as osteoarthritis, or familial ischemic cerebral small-vessel disease.

Administration

The oligonucleotides or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intra-muscular, intracerebral, intracerebroventricular or intrathecal).

In some embodiments the oligonucleotide, conjugate or pharmaceutical compositions of the present invention are administered by a parenteral route including intravenous, intraarterial, subcutaneous, intraperitoneal or intramuscular injection or infusion, intrathecal or intracranial, e.g. intracerebral or intraventricular, administration. In some embodiments the active oligonucleotide or oligonucleotide conjugate is administered intravenously. In another embodiment the active oligonucleotide or oligonucleotide conjugate is administered subcutaneously.

For use in treating eye disorders, such as macular degeneration, e.g. AMD (wet or dry), intraocular injection may be used.

In some embodiments, the compound of the invention, or pharmaceutically acceptable salt thereof, is administered via an intraocular injection in a dose from about 10 µg to about 200 µg per eye, such as about 50 µg to about 150 µg per eye, such as about 100 µg per eye. In some embodiments, the dosage interval, i.e. the period of time between consecutive dosings is at least monthly, such as at least bi monthly or at least once every three months.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above Embodiments of the Invention 1. An antisense oligonucleotide of 10-30 nucleotides in length, wherein said antisense oligonucleotide comprises a contiguous nucleotide region of 10-22 nucleotides which are at least 90% such as 100% complementarity to SEQ ID NO 147:

```
SEQ ID NO 147:
5' CCAACAACCAGGTAAATATTTG3'
```

2. The antisense oligonucleotide according to embodiment 1, wherein the antisense oligonucleotide is capable of inhibiting the expression of HTRA1 mRNA.
3. The antisense oligonucleotide according to embodiment 1 or 2, wherein the contiguous nucleotide region is identical to a sequence present in a sequence selected from the group consisting of SEQ ID NO 138, 139, 140, 141, 142, 143, 144 and 145:

```
SEQ ID NO 138:
CAAATATTTACCTGGTTG

SEQ ID NO 139:
TTTACCTGGTTGTTGG

SEQ ID NO 140:
CCAAATATTTACCTGGTT

SEQ ID NO 141:
CCAAATATTTACCTGGTTGT

SEQ ID NO 142:
ATATTTACCTGGTTGTTG

SEQ ID NO 143:
TATTTACCTGGTTGTT

SEQ ID NO 144:
ATATTTACCTGGTTGT

SEQ ID NO 145:
ATATTTACCTGGTTGTT
```

4. The antisense oligonucleotide according to any one of embodiments 1-3, wherein the contiguous nucleotide region comprises the sequence SEQ ID NO 146: SEQ ID NO 146: TTTACCTGGTT 5. The antisense oligonucleotide according to any one of embodiments 1-4, wherein the contiguous nucleotide region of the oligonucleotide consists or comprises of a sequence selected from any one of SEQ ID NO 138, 139, 140, 141, 142, 143, 144 and 145.

6. The antisense oligonucleotide according to any one of embodiments 1-5 wherein the contiguous nucleotide region of the oligonucleotide comprises one or more 2' sugar modified nucleosides.

7. The antisense oligonucleotide according to embodiment 6, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

8. The antisense oligonucleotide according to any one of embodiments 5-7, wherein the one or more modified nucleoside is a LNA nucleoside.

9. The antisense oligonucleotide according to any one of embodiments 1-8, where the contiguous nucleotide region of the oligonucleotide comprises at least one modified internucleoside linkage, such as one or more phosphorothioate internucleoside linkages.

10. The antisense oligonucleotide according to embodiment 9, wherein all the internucleoside linkages within the contiguous nucleotide region are phosphorothioate internucleoside linkages.

11. The antisense oligonucleotide according to any one of embodiments 1-10, wherein the oligonucleotide is capable of recruiting RNase H.

12. The antisense oligonucleotide according to any one of embodiments 1-11, wherein the oligonucleotide or contiguous nucleotide sequence thereof is or comprises a gapmer.

13. The antisense oligonucleotide of embodiment 11 or 12, wherein the oligonucleotide or contiguous nucleotide sequence thereof is a gapmer of formula 5'-F-G-F'-3', where region F and F' independently comprise 1-7 sugar modified nucleosides and G is a region 6-16 nucleosides which is capable of recruiting RNaseH, wherein the nucleosides of regions F and F' which are adjacent to region G are sugar modified nucleosides.

14. The antisense oligonucleotide according to embodiment 13, wherein region G consists or comprises 6-16 DNA nucleosides.

15. The antisense oligonucleotide according to embodiment 13 or 14, wherein region F and F' each comprise at least one LNA nucleoside.

16. The antisense oligonucleotide according to any one of embodiments 1-15, selected from the group selected from:

(SEQ ID NO 138, Comp # 138,1)
$C_sA_sA_sA_st_sa_st_st_st_sa_sc_sc_st_sg_sG_sT_sT_sG$ (SEQ ID NO 139, Comp # 139,1)
$T_sT_st_sa_sc_sc_st_sg_sg_st_st_sg_st_sT_sG_sG$ (SEQ ID NO 140, Comp # 140,1)
$C_sC_sA_sA_sa_st_sa_st_st_st_sa_sc_sc_st_sg_sG_sT_sT$ (SEQ ID NO 141, Comp # 141,1)
$C_sC_sA_sa_sa_st_sa_st_st_st_sa_sc_sc_st_sg_sg_st_st_sG_sT$ (SEQ ID NO 142, Comp # 142,1)
$A_sT_sA_st_st_st_sa_sc_sc_st_sg_sg_st_st_sg_sT_sT_sG$ (SEQ ID NO 143, Comp # 143,1)
$T_sA_sT_st_st_sa_sc_sc_st_sg_sg_st_sT_sG_sT_sT$ (SEQ ID NO 143, Comp # 143,2)
$T_sA_st_st_st_sa_sc_sc_st_sg_sG_st_sT_sg_sT_sT$ (SEQ ID NO 143, Comp # 143,3)
$T_sA_sT_st_st_sa_sc_sc_st_sg_sg_sT_sT_sg_sT_sT$ (SEQ ID NO 144, Comp # 144,1)
$A_sT_sA_sT_st_st_sa_sc_sc_st_sg_sg_sT_sT_sG_sT$ (SEQ ID NO 144, Comp # 144,2)
$A_st_sA_sT_sT_st_sa_sc_sc_st_sg_sg_st_sT_sG_sT$ (SEQ ID NO 145, Comp # 145,1)
$A_st_sA_sT_st_st_sa_sc_sc_st_sg_sG_sT_sT_sg_sT_sT$ (SEQ ID NO 145, Comp # 145,2)
$A_sT_sA_st_st_st_sa_sc_sc_st_sg_sG_st_sT_sg_sT_sT$ (SEQ ID NO 145, Comp # 145,3)
$A_st_sA_sT_st_st_sa_sc_sc_st_sg_sg_st_sT_sG_sT_sT$ Wherein a capital letter represents an LNA nucleoside unit, a lower case letter represents a DNA nucleoside unit, subscript s represents a phosphorothioate internucleoside linkage, wherein all LNA cytosines are 5-methyl cytosine.

17. The antisense oligonucleotide according to embodiment 16, wherein the LNA nucleosides are all beta-D-oxy LNA nucleosides.

18. A conjugate comprising the oligonucleotide according to any one of embodiments 1-17, and at least one conjugate moiety covalently attached to said oligonucleotide.

19. A pharmaceutical composition comprising the oligonucleotide of embodiment 1-17 or the conjugate of embodiment 18 and a pharmaceutically acceptable diluent, solvent, carrier, salt and/or adjuvant.

20. An in vivo or in vitro method for modulating HTRA1 expression in a target cell which is expressing HTRA1, said method comprising administering an oligonucleotide of any one of embodiments 1-17 or the conjugate according to embodiment 18 or the pharmaceutical composition of embodiment 19 in an effective amount to said cell.

21. A method for treating or preventing a disease comprising administering a therapeutically or prophylactically effective amount of an oligonucleotide of any one of embodiments 1-17 or the conjugate according to embodiment 18 or the pharmaceutical composition of embodiment 19 to a subject suffering from or susceptible to the disease.

22. The method of embodiment 21, wherein the disease is selected from the group consisting of macular degeneration (such as wetAMD, dryAMD, geographic atrophy, intermediate dAMD, diabetic retinopathy), Parkinson's disease, Alzhiemer's disease, Duchenne muscular dystrophy, arthritis, such as osteoarthritis, and familial ischemic cerebral small-vessel disease.

23. The oligonucleotide of any one of embodiments 1-17 or the conjugate according to embodiment 18 or the pharmaceutical composition of embodiment 19 for use in medicine.

24. The oligonucleotide of any one of embodiments 1-17 or the conjugate according to embodiment 18 or the pharmaceutical composition of embodiment 19 for use in the treatment or prevention of a disease is selected from the group consisting of macular degeneration (such as wetAMD, dryAMD, geographic atrophy, intermediate dAMD, diabetic retinopathy), Parkinson's disease, Alzhiemer's disease, Duchenne muscular dystrophy, arthritis, such as osteoarthritis, and familial ischemic cerebral small-vessel disease.

25. Use of the oligonucleotide of embodiment 1-17 or the conjugate according to embodiment 18 or the pharmaceutical composition of embodiment 19, for the preparation of a medicament for treatment or prevention of a disease is selected from the group consisting of macular degeneration (such as wetAMD, dryAMD, geographic atrophy, intermediate dAMD, diabetic retinopathy), Parkinson's disease, Alzhiemer's disease, Duchenne muscular dystrophy, arthritis, such as osteoarthritis, and familial ischemic cerebral small-vessel disease.

EXAMPLES

Materials and Methods
Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 µmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), LNA-T) is performed by using a solution of 0.1 M of the 5'-O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THF/Pyridine/water 7:2:1. The rest of the reagents are the ones typically used for oligonucleotide synthesis.

For post solid phase synthesis conjugation a commercially available C6 aminolinker phorphoramidite can be used in the last cycle of the solid phase synthesis and after deprotection and cleavage from the solid support the amino-linked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C18 10µ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations
DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay:

Oligonucleotide and RNA target (phosphate linked, PO) duplexes are diluted to 3 mM in 500 ml RNase-free water and mixed with 500 ml 2× $T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Example 1

Testing In Vitro Efficacy of Antisense Oligonucleotides Targeting Rat Htra1 in C6 Cell Lines at Single Dose Concentration Rat C6 cell line was purchased from ATCC and maintained as recommended by the supplier in a humidified incubator at 37° C. with 5% $CO_2$. For assays, 1500 C6 cells/well were seeded in a 96 multi well plate in culture media. Cells were incubated for 2 hours before addition of oligonucleotides dissolved in PBS. Concentration of oligonucleotides: 25 µM. 4 days after addition of oligonucleotides, the cells were harvested. RNA was extracted using the PureLink Pro 96 RNA Purification kit (Ambion, according to the manufacturer's instructions). cDNA was then synthesized using M-MLT Reverse Transcriptase, random decamers RETROscript, RNase inhibitor (Ambion, according the manufacturer's instruction) with 100 mM dNTP set PCR Grade (Invitrogen) and DNase/RNase free Water (Gibco). For gene expressions analysis, qPCR was performed using TaqMan Fast Advanced Master Mix (2×) (Ambion) in a doublex set up. Following TaqMan primer assays were used for qPCR: Htra1, Rn00581870_m1 (FAM-MGB) and house keeping gene, Tbp, Rn01455646_m1 (VIC-MGB). All primer sets were purchase from Life Technologies. The relative Htra1 mRNA expression level in the table is shown as % of control (PBS-treated cells).

Oligonucleotides Used:

| SEQ ID NO | Motif | CMP ID NO | Compound | mRNA level |
|---|---|---|---|---|
| 5 | gaaagggaaatatggg | 5,1 | GAAagggaaatatGGG | 51 |
| 6 | gatgaggtataaagtg | 6,1 | GATgaggtataaaGTG | 54 |

-continued

| SEQ ID NO | Motif | CMP ID NO | Compound | mRNA level |
|---|---|---|---|---|
| 7 | ggtgtgttaataatca | 7,1 | GGTgtgttaataaTCA | 60 |
| 8 | cttatgacgcaaactg | 8,1 | CTTatgacgcaaaCTG | 26 |
| 9 | tttgtctcctttcctc | 9,1 | TTTgtctcctttccTC | 70 |
| 10 | gaatggaaagatgtaa | 10,1 | GAATggaaagatGTAA | 27 |
| 11 | gttctttggctttgct | 11,1 | GTtctttggctttgCT | 63 |
| 12 | ttcaatgatatatgct | 12,1 | TTCaatgatatatGCT | 15 |
| 13 | agtatgaagaagtatt | 13,1 | AGTatgaagaagtATT | 27 |
| 14 | cccaatcacctcgcca | 14,1 | CCCaatcacct$^m$cgCCA | 72 |
| 15 | gcagtagcaaagacagg | 15,1 | GCagtagcaaagacAGG | 28 |
| 16 | aagttgaaatcagtggt | 16,1 | AAGttgaaatcagTGGT | 12 |
| 17 | tctggtagtaagaatata | 17,1 | TCTGgtagtaagaaTATA | 73 |
| 18 | aacagtaagagctacttt | 18,1 | AACAgtaagagctaCTTT | 62 |
| 19 | tcagacacgatacagag | 19,1 | TCAgaca$^m$cgatacAGAG | 39 |
| 20 | tggtcagtgataagtaa | 20,1 | TGGtcagtgataaGTAA | 34 |
| 21 | gcactgtagatgagaaac | 21,1 | GCACtgtagatgagAAAC | 37 |
| 22 | ataaagtaaacttaatgcc | 22,1 | ATAAgtaaacttaaTGCC | 32 |
| 23 | attggttcttaggagtgggc | 23,1 | Attggttcttaggagtggcc | 56 |
| 24 | attattgttttactcgtga | 24,1 | ATTattgttttact$^m$cgTGA | 32 |
| 25 | atgctggggtaatgattg | 25,1 | ATGctggggtaatgaTTG | 58 |
| 26 | agtctaaattattgcacaa | 26,1 | AGTCtaaattattgcACAA | 72 |
| 27 | ccaattagaacagtagtgg | 27,1 | CCAAttagaacagtagtGG | 58 |
| 28 | agtgtctagttaaacagcac | 28,1 | AGtgtctagttaaacagCAC | 84 |
| 29 | taccagagtcaagcatatg | 29,1 | TACcagagtcaagcataTG | 33 |
| 30 | atctaaacttcatgtcagaa | 30,1 | ATCtaaacttcatgtcAGAA | 86 |
| 31 | ttcatacgactgagcatc | 31,1 | TTCAta$^m$cgactgagcATC | 26 |
| 32 | gtacagttttagatcatc | 32,1 | GTAcagttttagatCATC | 18 |
| 33 | atcctaaaagagttcaaca | 33,1 | ATCCtaaaagagttcaACA | 77 |
| 34 | cattctttgtcatatact | 34,1 | CATtctttgtcataTACT | 49 |
| 35 | ttcaaagtgactttcaag | 35,1 | TTCAaagtgactttCAAG | 11 |
| 36 | tcctttctataattacaaa | 36,1 | TCCTttctataattaCAAA | 35 |
| 37 | ctaattctgtagttttgg | 37,1 | CTaattctgtagttTTGG | 31 |
| 38 | actgagtgtgtaatgttga | 38,1 | ACtgagtgtgtaatgtTGA | 59 |
| 39 | agagaaatctgtagggc | 39,1 | AGAgaaatctgtaggGC | 56 |
| 40 | ttatcaaatcaactagcac | 40,1 | TTAtcaaatcaactaGCAC | 84 |
| 41 | ttatatttgatagtgtgatc | 41,1 | TTATatttgatagtgtgATC | 55 |
| 42 | aagagaagctgttatctaaa | 42,1 | AAGAgaagctgttatcTAAA | 42 |
| 43 | aagtcatgctagagttcc | 43,1 | AAgtcatgctagagtTCC | 37 |
| 44 | acacagtgtattcgaggg | 44,1 | ACAcagtgtatt$^m$cgagGG | 38 |

-continued

| SEQ ID NO | Motif | CMP ID NO | Compound | mRNA level |
|---|---|---|---|---|
| 45 | gacacagtgtattcgaggg | 45,1 | GAcacagtgtatt${}^m$cgagGG | 52 |
| 46 | gacacagtgtattcgagg | 46,1 | GACacagtgtatt${}^m$cgaGG | 26 |
| 47 | aggacacagtgtattcgagg | 47,1 | AGgacacagtgtatt${}^m$cgaGG | 38 |
| 48 | aggacacagtgtattcgag | 48,1 | AGgacacagtgtatt${}^m$cgAG | 32 |
| 49 | caggacacagtgtattcgag | 49,1 | CAggacacagtgtatt${}^m$cgAG | 53 |
| 50 | aggacacagtgtattcg | 50,1 | AGgacacagtgtaTTCG | 11 |
| 51 | aacaggacacagtgtattcg | 51,1 | AAcaggacacagtgtaTTCG | 28 |
| 52 | tgaatctatacagcaggaa | 52,1 | TGAAtctatacagcagGAA | 46 |
| 53 | cttaagttattcatatcca | 53,1 | CTTaagttattcatatCCA | 39 |
| 54 | taggtggtagcagatag | 54,1 | TAGgtggtagcagatAG | 48 |
| 55 | gtagtaataattctggga | 55,1 | GTAgtaataattctgGGA | 7 |
| 56 | agtggtaaggtgaagtgaa | 56,1 | AGtggtaaggtgaagTGAA | 45 |
| 57 | ttttgctgtgataaatagc | 57,1 | TTttgctgtgataaaTAGC | 65 |
| 58 | tttcttatcgttttatga | 58,1 | TTTCttat${}^m$cgttttATGA | 24 |
| 59 | ggaaaacattaacaaggttg | 59,1 | GGAAacattaacaagGTTG | 38 |
| 60 | tgggtagagtctaggag | 60,1 | TGggtagagtctaggAG | 58 |
| 61 | agggagtgactattagag | 61,1 | AGggagtgactattaGAG | 45 |
| 62 | cagagtagggaaagtggttc | 62,1 | CAgagtagggaaagtggtTC | 76 |
| 63 | accatgttatatttggg | 63,1 | ACCAtgttatatttgGG | 54 |
| 64 | tttattactgaggggaaagg | 64,1 | TTTAttactgaggggaaaGG | 67 |
| 65 | acttgagtgtagtacag | 65,1 | ACTtgagtgtagtACAG | 21 |
| 66 | catactagttttgcagaga | 66,1 | CAtactagttttgcagAGA | 54 |
| 67 | ggactagaagtagttac | 67,1 | GGActagaagtagTTAC | 58 |
| 68 | agggagtcaaaggttcaa | 68,1 | AGggagtcaaaggtTCAA | 13 |
| 69 | tctgtgtattagagaacg | 69,1 | TCTGtgtattagagAACG | 44 |
| 70 | tcaaaagctacatcagtc | 70,1 | TCAaaagctacatcAGTC | 7 |
| 71 | accgttgaattagtcac | 71,1 | ACCGttgaattagtCAC | 39 |
| 72 | tttccattaaaatgtttaca | 72,1 | TTTCcattaaaatgttTACA | 28 |
| 73 | gagatggtaaggagtaggag | 73,1 | GAgatggtaaggagtaggAG | 60 |
| 74 | agttttagactattctg | 74,1 | AGTTttagactattCTG | 37 |
| 75 | gtcaggacataaactcac | 75,1 | GTCaggacataaacTCAC | 18 |
| 76 | ttgttggtgtcagggaaaag | 76,1 | TTGttggtgtcagggaaaAG | 20 |
| 77 | tcctgaaatattgatgc | 77,1 | TCCtgaaatattgaTGC | 51 |
| 78 | tgccaaaatgactacagt | 78,1 | TGCcaaaatgactacAGT | 54 |
| 79 | ctcaaagttggatcgtaac | 79,1 | CTCaaagttggat${}^m$cgTAAC | 37 |
| 80 | ttgcattttagaagttat | 80,1 | TTGCattttagaagTTAT | 49 |
| 81 | tgtcaattagtgtgtttag | 81,1 | TGTCaattagtgtgtttAG | 20 |

| SEQ ID NO | Motif | CMP ID NO | Compound | mRNA level |
|---|---|---|---|---|
| 82 | cataatatttagtctcct | 82,1 | CATaatatttagtctCCT | 40 |
| 83 | tatagttacaatcacca | 83,1 | TATAgttacaatcaCCA | 30 |
| 84 | ttttgtacatactcttcc | 84,1 | TTttgtacatactcTTCC | 11 |
| 85 | tagcagtacttaaatggg | 85,1 | TAGcagtacttaaatGGG | 28 |
| 86 | tatgttacatatttggatga | 86,1 | TATgttacatatttggaTGA | 41 |
| 87 | catggtatcttttggagag | 87,1 | CATggtatcttttggagAG | 36 |
| 88 | caacatatccagtccag | 88,1 | CAAcatatccagtcCAG | 22 |
| 89 | taattgtgaagtagggtg | 89,1 | TAattgtgaagtagGGTG | 33 |
| 90 | actttagaggtttagtcc | 90,1 | ACTttagaggtttagtCC | 55 |
| 91 | gagcttttaattctatcc | 91,1 | GAgcttttaattctATCC | 56 |
| 92 | ctccttaaatacatgttac | 92,1 | CTCcttaaatacatgTTAC | 49 |
| 93 | gagataaatgtttgagaga | 93,1 | GAGAtaaatgtttgagAGA | 41 |
| 94 | atgatggtgatttaggat | 94,1 | ATGAtggtgatttagGAT | 22 |
| 95 | agtcattcaatttgagaaa | 95,1 | AGTCattcaatttgaGAAA | 35 |
| 96 | cagtggtggtaaggcac | 96,1 | CAGtggtggtaaggcAC | 53 |
| 97 | tgaaatggtttagttctg | 97,1 | TGAAatggtttagttCTG | 41 |
| 98 | tgccatagtgaaatggttt | 98,1 | TGCcatagtgaaatggtTT | 57 |
| 99 | caggaggacatactatt | 99,1 | CAGgaggacatacTATT | 77 |
| 100 | atatatacaggcacatgg | 100,1 | ATAtatacaggcacaTGG | 71 |
| 101 | gacaggagtctttaaaatg | 101,1 | GACAggagtctttaaAATG | 80 |
| 102 | tatttatatagtaatgtgtc | 102,1 | TATTtatatagtaatgTGTC | 57 |
| 103 | ggataaaacagtaccat | 103,1 | GGAtaaaacagtaCCAT | 77 |
| 104 | ggagtttagaagacacat | 104,1 | GGAgtttagaagacaCAT | 33 |
| 105 | gtacaactacagaggtt | 105,1 | GTACaactacagagGTT | 65 |
| 106 | aggaaatggtgatggaatg | 106,1 | AGGaaatggtgatggAATG | 58 |
| 107 | tcggagtaaaagtgtaaaca | 107,1 | TCGGagtaaaagtgtaaACA | 81 |

For Compounds: Capital letters represent LNA nucleosides (beta-D-oxy LNA nucleosides were used), all LNA cytosines are 5-methyl cytosine, lower case letters represent DNA nucleosides, DNA cytosines preceded with a superscript $^m$ represents a 5-methyl C-DNA nucleoside. All internucleoside linkages are phosphorothioate internucleoside linkages.

Example 2

Testing In Vitro Potency and Efficacy of Selected Oligonucleotides Targeting Rat Htra1 in C6 Cell Line in a Dose Response Curve Rat C6 cell line was described in Example 1. The assay was performed as described in Example 1. Concentration of oligonucleotides: from 50 µM, half-log dilution, 8 points. 4 days after addition of oligonucleotides, the cells were harvested. RNA extraction, cDNA synthesis and qPCR were performed as described in Example 1. n=2 biological replicates. $EC_{50}$ determinations were performed in GraphPad Prism6. The relative Htra1 mRNA level at treatment with 50 µM oligonucleotide is shown in the table as % of control (PBS). Additional primer sets (Htra1, Rn00668987_m1 [FAM-MGB] vs. Ppia, Rn006900933_m1 [VIC-MGB] and Hprt, Rn01527840_m1 [VIC-MGB]) were also tested and the same trends were observed using those primers (data not shown).

| SEQ ID NO | CMP ID NO | $EC_{50}$ | mRNA level at Max KD |
|---|---|---|---|
| 12 | 12.1 | 3.3 | 14 |
| 16 | 16.1 | 3.2 | 11 |
| 32 | 32.1 | 4.3 | 27 |
| 35 | 35.1 | 2.6 | 8 |
| 50 | 50.1 | 1.9 | 9 |
| 55 | 55.1 | 2.0 | 6 |
| 58 | 58.1 | 4.4 | 25 |
| 65 | 65.1 | 3.1 | 14 |

| SEQ ID NO | CMP ID NO | EC$_{50}$ | mRNA level at Max KD |
|---|---|---|---|
| 68 | 68.1 | 4.1 | 8 |
| 70 | 70.1 | 1.5 | 2 |
| 75 | 75.1 | 3.7 | 16 |
| 76 | 76.1 | 4.9 | 21 |
| 81 | 81.1 | 3.0 | 18 |
| 84 | 84.1 | 2.2 | 9 |
| 88 | 88.1 | 6.8 | 20 |
| 94 | 94.1 | 2.9 | 15 |

Example 3

Testing In Vitro Efficacy of Oligonucleotides Targeting Human HTRA1, in U251 Cell Line at Single Dose Concentration Human glioblastoma U251 cell line was purchased from ECACC and maintained as recommended by the supplier in a humidified incubator at 37° C. with 5% $CO_2$. For assays, 15000 U251 cells/well were seeded in a 96 multi well plate in starvation media (media recommended by the supplier with the exception of 1% FBS instead of 10%). Cells were incubated for 24 hours before addition of oligonucleotides dissolved in PBS. Concentration of oligonucleotides: 5 µM. 3-4 days after addition of compounds, media was removed and new media (without oligonucleotide) was added. 6 days after addition of oligonucleotides, the cells were harvested. RNA was extracted using the PureLink Pro 96 RNA Purification kit (Ambion, according to the manufacturer's instructions). cDNA was then synthesized using M-MLT Reverse Transcriptase, random decamers RETROscript, RNase inhibitor (Ambion, according the manufacturer's instruction) with 100 mM dNTP set PCR Grade (Invitrogen) and DNase/RNase free Water (Gibco). For gene expressions analysis, qPCR was performed using TaqMan Fast Advanced Master Mix (2×) (Ambion) in a doublex set up. Following TaqMan primer assays were used for qPCR: HTRA1, Hs01016151_m1 (FAM-MGB) and house keeping gene, TBP, Hs4326322E (VIC-MGB) from Life Technologies. The relative HTRA1 mRNA expression level in the table is shown as % of control (PBS-treated cells).

| SEQ ID NO | Motif | CMP ID NO | Compound | mRNA level |
|---|---|---|---|---|
| 108 | agatgggtgtgaaagg | 108,1 | AGAtgggtgtgaaAGG | 35 |
| 109 | atgttgtctatgttta | 109,1 | ATGttgtctatgtTTA | 5 |
| 110 | tatgttgtctatgttt | 110,1 | TATgttgtctatgTTT | 5 |
| 111 | gatgtttgcagtattt | 111,1 | GATgtttgcagtaTTT | 17 |
| 112 | tatatagtcgaatagg | 112,1 | TATatagtcgaatAGG | 18 |
| 113 | tttggcttcgtaagtg | 113,1 | TTTggcttcgtaaGTG | 1 |
| 114 | tgaggcagtggagttg | 114,1 | TGaggcagtggagtTG | 32 |
| 115 | tggacaggagggcagc | 115,1 | TGgacaggagggcaGC | 92 |
| 116 | tagagaaggtagaatg | 116,1 | TAGagaaggtagaATG | 78 |
| 117 | atttagattagagaag | 117,1 | ATTTagattagaGAAG | 50 |
| 118 | gttcttaaatgtcgtt | 118,1 | GTTcttaaatgtcGTT | 10 |
| 119 | aagggcttaccatctt | 119,1 | AAGggcttaccatCTT | 62 |
| 120 | tacttcaattatatac | 120,1 | TACttcaattatatAC | 25 |
| 121 | gcaatgtgtaagaagt | 121,1 | GCAatgtgtaagaAGT | 15 |
| 122 | aaactgttgggatctt | 122,1 | AAACtgttgggaTCTT | 11 |
| 123 | caaactgttgggatct | 123,1 | CAAActgttgggATCT | 50 |
| 124 | gcaaactgttgggatc | 124,1 | GCAaactgttgggATC | 11 |
| 125 | gatgtttgcagtattt | 125,1 | GAtgtttgcagtaTTT | 22 |
| 126 | attgggtttgatcggt | 126,1 | ATTgggtttgat$^m$cgGT | 15 |
| 127 | ctattgggtttgatcg | 127,1 | CTAttgggtttgatCG | 16 |
| 128 | tattgggtttgatcgg | 128,1 | TATtgggtttgatCGG | 10 |
| 129 | cgaatatgtgctttaa | 129,1 | CGAatatgtgcttTAA | 8 |
| 130 | gctgattatgacgtcg | 130,1 | GCTgattatga$^m$cgTCG | 13 |
| 131 | tgctgattatgacgtc | 131,1 | TGCtgattatga$^m$cGTC | 10 |

-continued

| SEQ ID NO | Motif | CMP ID NO | Compound | mRNA level |
|---|---|---|---|---|
| 132 | attgggtttgatcggt | 132,1 | ATTgggtttgatCGGT | 18 |
| 133 | ctattgggtttgatcg | 133,1 | CTAttgggtttgATCG | 49 |
| 134 | tgctgattatgacgtc | 134,1 | TGCtgattatgaCGTC | 46 |
| 135 | tattgggtttgatcgg | 135,1 | TATTgggtttgaTCGG | 58 |
| 136 | cgaatatgtgctttaa | 136,1 | CGAAtatgtgctTTAA | 13 |
| 137 | gctgattatgacgtcg | 137,1 | GCTGattatga$^m$cGTCG | 39 |

For Compounds: Capital letters represent LNA nucleosides (beta-D-oxy LNA nucleosides were used), all LNA cytosines are 5-methyl cytosine, lower case letters represent DNA nucleosides, DNA cytosines preceded with a superscript $^m$ represents a 5-methyl C-DNA nucleoside. All internucleoside linkages are phosphorothioate internucleoside linkages.

Example 4

Testing In Vitro Efficacy of a Library of Oligonucleotides Targeting Human HTRA1 mRNA in ARPE19 and U251 Cell Lines at 2 Concentrations Identification of promising "hot spot" region for HTRA1. A library of n=129 human/cyno/rat HTRA1 LNA oligonucleotides were screened in U251 and ARPE19 cell lines. From this library we identified a series of active oligonucleotides targeting human HTRA1 pre-mRNA (SEQ ID NO 2) between position 33042-33064 as shown in FIG. 1.

Human retinal pigmented epithelium ARPE19 cell line was purchased by from ATCC and maintained in DMEM-F12 (Sigma, D8437), 10% FBS, 1% pen/strep in a humidified incubator at 37° C. with 5% $CO_2$. The U251 cell line was described in example 3. For assays, 5000 ARPE19 cells/well were seeded in a 96 multi well plate in culture media (with the exception of 5% FBS instead of 10%). Cells were incubated for 1 hour before addition of oligonucleotides dissolved in PBS. 4 days after addition of oligonucleotides, the cells were harvested. The assay with the U251 cell line was performed as described in example 3. Concentration of oligonucleotides: 25 and 2.5 µM. RNA was extracted using the RNeasy 96 Biorobot 8000 kit (Qiagen, according to the manufacturer's instructions). cDNA was then synthesized using Retroscript cDNA synthesis kit (ThermoFisher, according the manufacturer's instruction).

For gene expressions analysis, qPCR was performed using the Fluidigm Biomark system. Following TaqMan primer assays were used for qPCR: HTRA1, Hs01016151_m1 and house-keeping genes, TBP, Hs99999910_m1 and PPIA, Hs99999904_m1, from Life Technologies. n=2 biologial replicates. The relative HTRA1 mRNA expression level is shown in the table as % of control (PBS). Additional HTRA1 primer set (Hs00170197_m1) was also tested and the same trends were observed (data not shown).

| SEQ ID NO | Comp # | Compound | ARPE19 mRNA level 25 µM | ARPE19 mRNA level 2.5 µM | U251 mRNA level 25 µM | U251 mRNA level 2.5 µM |
|---|---|---|---|---|---|---|
| 138 | 138,1 | $^m$CAAAtatttacctgGTTG | 79 | 97 | 11 | 60 |
| 139 | 139,1 | TTtacctggttgaGG | 39 | 73 | 5 | 37 |
| 140 | 140,1 | $^mC^m$CAAatatttacctgGTT | 68 | 100 | 16 | 70 |
| 141 | 141,1 | $^mC^m$CAaatatttacctggttGT | 78 | 87 | 16 | 78 |
| 142 | 142,1 | ATAtttacctggttgTTG | 56 | 78 | 4 | 23 |
| 143 | 143,1 | TATttacctggaGTT | 22 | 77 | 3 | 23 |

For Compounds: Capital letters represent LNA nucleosides (beta-D-oxy LNA nucleosides were used), all LNA cytosines are 5-methyl cytosine, lower case letters represent DNA nucleosides. All internucleoside linkages are phosphorothioate internucleoside linkages.

Example 5

Testing In Vitro Efficacy of Selected Human/Rat HTRA1 Targeting LNA Oligonucleotides in Rat C6 Cell Lines at Single Dose Concentration Rat C6 cell line was described in Example 1. The assay was performed as described in Example 1. Concentration of oligonucleotides: 25 µM. n=2 biologial replicates. The relative Htra1 mRNA expression level in the table is shown as % of control (PBS-treated cells).

| SEQ ID NO | CMP ID NO | mRNA level |
|---|---|---|
| 139 | 139.1 | 24 |
| 140 | 140.1 | 6 |
| 142 | 142.1 | 26 |
| 143 | 143.1 | 16 |

Example 6

Testing In Vitro Potency and Efficacy of Selected Human/Cyno/Rat LNA Oligonucleotides in ARPE19, U251 and C6 Cell Lines in a Dose Response ARPE19, U251 and C6 cell lines were described in example 4, 3 and 1, respectively. For assays, 2000 U251 or ARPE19 cells/well were seeded in a 96 multi well plate in culture media recommended by the supplier. Cells were incubated for 2 hours before addition of oligonucleotides dissolved in PBS. The C6 cell line assay was performed as described in example 1-2. Concentration of oligonucleotides: from 50 µM, half-log dilution, 8 points. 4 days after addition of oligonucleotides, the cells were harvested. RNA extraction, cDNA synthesis and qPCR were performed for all cell lines as described in Example 1. Following TaqMan primer assays were used for U251 and ARPE19 cells: HTRA1, Hs01016151_m1 (FAM-MGB) and house-keeping gene, TBP, Hs4326322E (VIC-MGB). All primer sets were purchased from Life Technologies. n=2 biologial replicates. EC50 determinations were performed in Graph Pad Prism6. The relative HTRA1 mRNA level at treatment with 50 µM oligonucleotide is shown in the table as % of control (PBS).

| | | ARPE19 | | U251 | | C6 | |
|---|---|---|---|---|---|---|---|
| SEQ ID NO | CMP ID NO | EC50 (µM) | mRNA level at max KD | EC50 (µM) | mRNA level at max KD | EC50 (µM) | mRNA level at max KD |
| 138 | 138.1 | 10 | 63 | 6.2 | 36 | ND | ND |
| 139 | 139.1 | 10 | 38 | 3.2 | 18 | ND | ND |
| 140 | 140.1 | 7.9 | 57 | 4.5 | 29 | 1.3 | 2 |
| 141 | 141.1 | 9.3 | 64 | 4.5 | 44 | ND | ND |
| 142 | 142.1 | 5.8 | 40 | 3.9 | 25 | ND | ND |
| 143 | 143.1 | 3.3 | 25 | 1.7 | 6.0 | 3.5 | 5 |

Example 7

Figure 2:
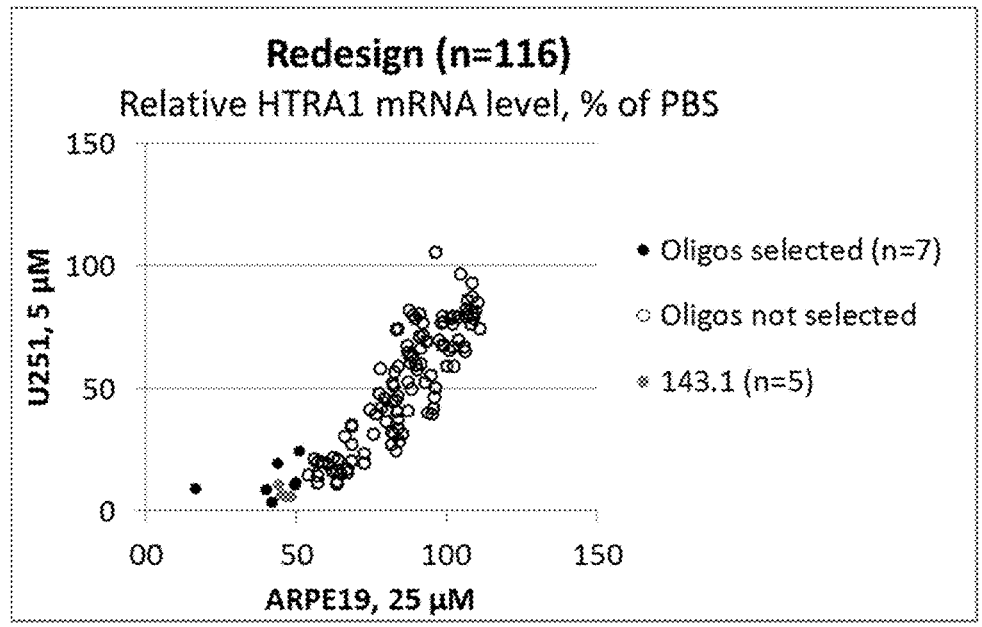
FIG. 2. A library of n=116 HTRA1 LNA oligonucleotides in the 33042-33064 hot spot were screened in U251 and ARPE19 cell lines at 5 and 25 μM, respectively. n=7 oligos were selected for further analysis. Read out: HTRA1 qPCR.

Testing In Vitro Efficacy of Selected Human HTRA1 Targeting Oligonucleotides in ARPE19 and U251 Cell Lines at Single Dose Concentration ARPE19 and U251 cell lines and assays were described in example 6. RNA extraction was performed as described in example 1, cDNA synthesis and qPCR were performed using qScript XLT one-step RT-qPCR ToughMix Low ROX, 95134-100 (Quanta Biosciences). Following TaqMan primer assays were used for U251 and ARPE19 cells in a douplex set up: HTRA1, Hs01016151_m1 (FAM-MGB) and housekeeping gene, GAPDH, Hs4310884E (VIC-MGB). All primer sets were purchased from Life Technologies. n=1 biological replicate. The relative HTRA1 mRNA expression level in the table is shown as % of control (PBS-treated cells). Additional primer sets (HTRA1, Hs00170197_m1 [FAM-MGB] vs. TBP Hs4326322E [VIC-MGB]) were also tested for U251 and the same trends were observed using those primers (data not shown). See FIG. 2.

| SEQ ID NO | CMP ID NO | ARPE19 mRNA level | U251 mRNA level |
|---|---|---|---|
| 143 | 143.1 | 46 | 7 |
| 143 | 143.2 | 49 | 10 |
| 143 | 143.3 | 50 | 11 |
| 144 | 144.1 | 44 | 19 |
| 144 | 144.2 | 16 | 9 |
| 145 | 145.1 | 51 | 24 |
| 145 | 145.2 | 40 | 9 |
| 145 | 145.3 | 42 | 4 |

Example 8

Testing In Vitro Efficacy and Potency in Human Primary RPE Cells

Human primary Retinal Pigmented Epithelium (hpRPE) cells are purchased from Sciencell (Cat#6540). For assays, 5000 hpRPE cells/well are seeded in a Laminin (Laminin 521, BioLamina Cat# LN521-03) coated 96 multi well plate in culture media (EpiCM, Sciencell Cat#4101). They are expanded with this media for one week and differentiated using the following media for 2 weeks: MEM Alpha media (Sigma Cat# M-4526) supplemented with N1 supplement (Sigma Cat# N-6530), Glutamine-Penicillin-Streptomycin (Sigma Cat# G-1146), Non-Essential Amino Acid (NEAA, Sigma Cat# M-7145), Taurine (Sigma Cat# T-0625), Hydrocortisone (Sigma Cat# H-03966), Triiodo-thyronin (Sigma Cat# T-5516) and Bovine Serum Albumin (BSA, Sigma Cat# A-9647). Cells are cultured in a humidified incubator at 37° C. with 5% $CO_2$.

Figure 3:
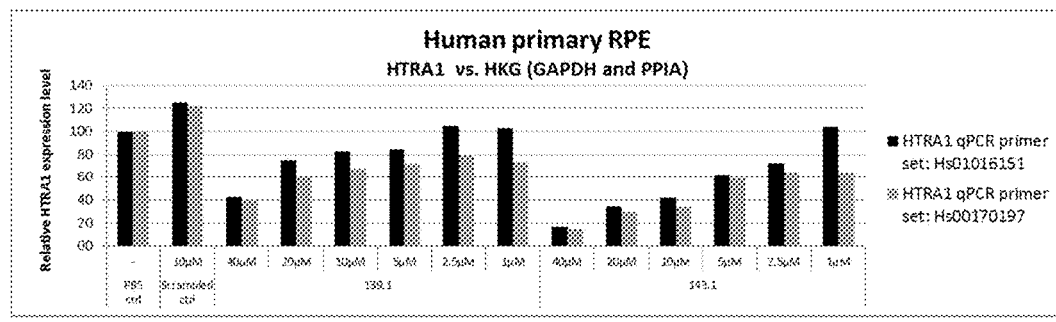
FIG. 3. Dose response of HTRA1 mRNA level upon treatment of human primary RPE cells with LNA oligonucleotide 139,1 and 143,1.

On the day of the experiment, cells are incubated for 1 hour with fresh differentiation media before addition of oligonucleotides. These are dissolved in PBS and applied on cells at day 0 and day 4. On day 7, cells are harvested with 50 µl of RLT buffer with β-mercapto-ethanol (Qiagen Cat#79216). The extraction of the RNA is performed according to the user's manual of the Qiagen RNeasy Mini Kit (Cat#74104; Lot 151048073) including DNase I treatment (Cat#79254; Lot 151042674). RNA quality control is performed with the Agilent Bioanalyzer Nano Kit (Agilent; Cat#5067-1511; Lot 1446). Reverse transcription of total RNA into cDNA (cDNA synthesis) is performed using the High Capacity cDNA Reverse Transcription Kit which is based on random hexamer oligonucleotides, according to the manufacturer's instructions (Thermo Fisher Scientific, Cat#4368814; Lot 00314158). The measurement of the cDNA samples is carried out in triplicates, in a 384-well plate format on the 7900HT real-time PCR instrument (Thermo Fisher Scientific). The following TaqMan primer assays are used for qPCR: HTRA1, Hs01016151_m1 and Hs00170197_m1, housekeeping genes, GAPDH, Hs99999905_m1 and PPIA, Hs99999904_m1, from Life Technologies. n=3 biological replicates. The relative HTRA1 mRNA expression level is shown in the table as % of control (PBS). See FIG. 3.

Example 9

Rat In Vivo Efficacy Study, 7 Days of Treatment, Intravitreal (IVT) Injection, 30 µg/Eye Animals Experiment was performed on pigmented male Brown Norway rats. Five animals were included in each group of the study, 15 in total.

Compounds and Dosing Procedures

To start the experiment, the animals were anesthetized with isoflurane, eyes were disinfected and dilated before an intravitreal injection of 30 μg (in 3 μl) per eye.

Euthanasia

At the end of the in-life phase (Day 7) all rats were euthanized with $CO_2$ before eyes were harvested for dissection. Retina, sclera and vitreous fluid were taken for further analysis.

Quantification of HTRA1 RNA Expression

Figure 4:
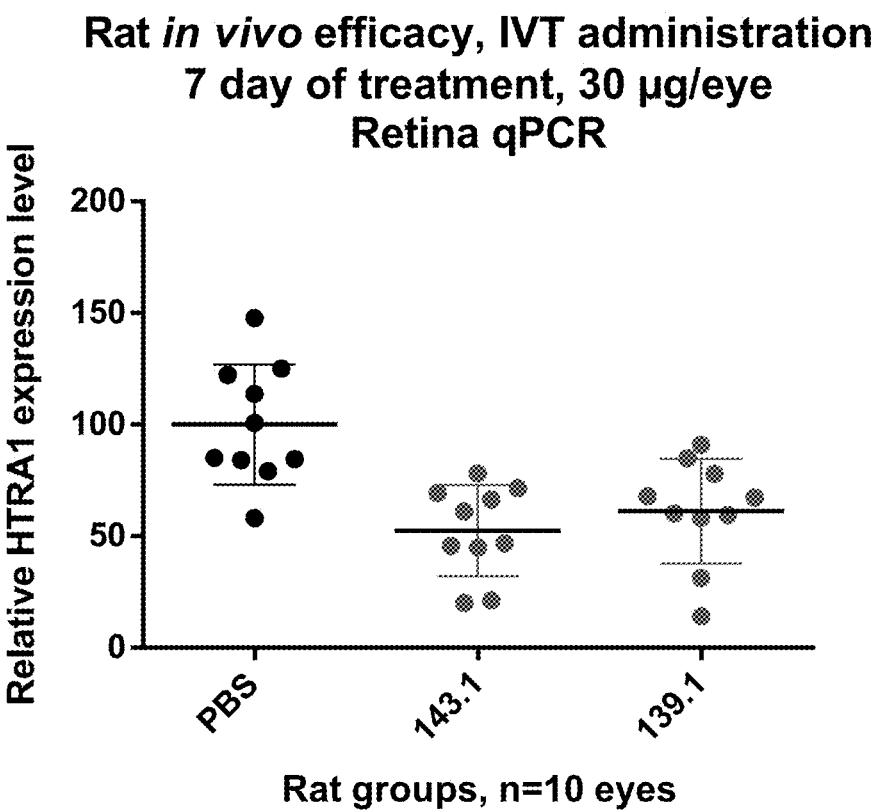
FIG. 4. Results of analysis of in vivo expression of HTRA1.
Figure 5A:
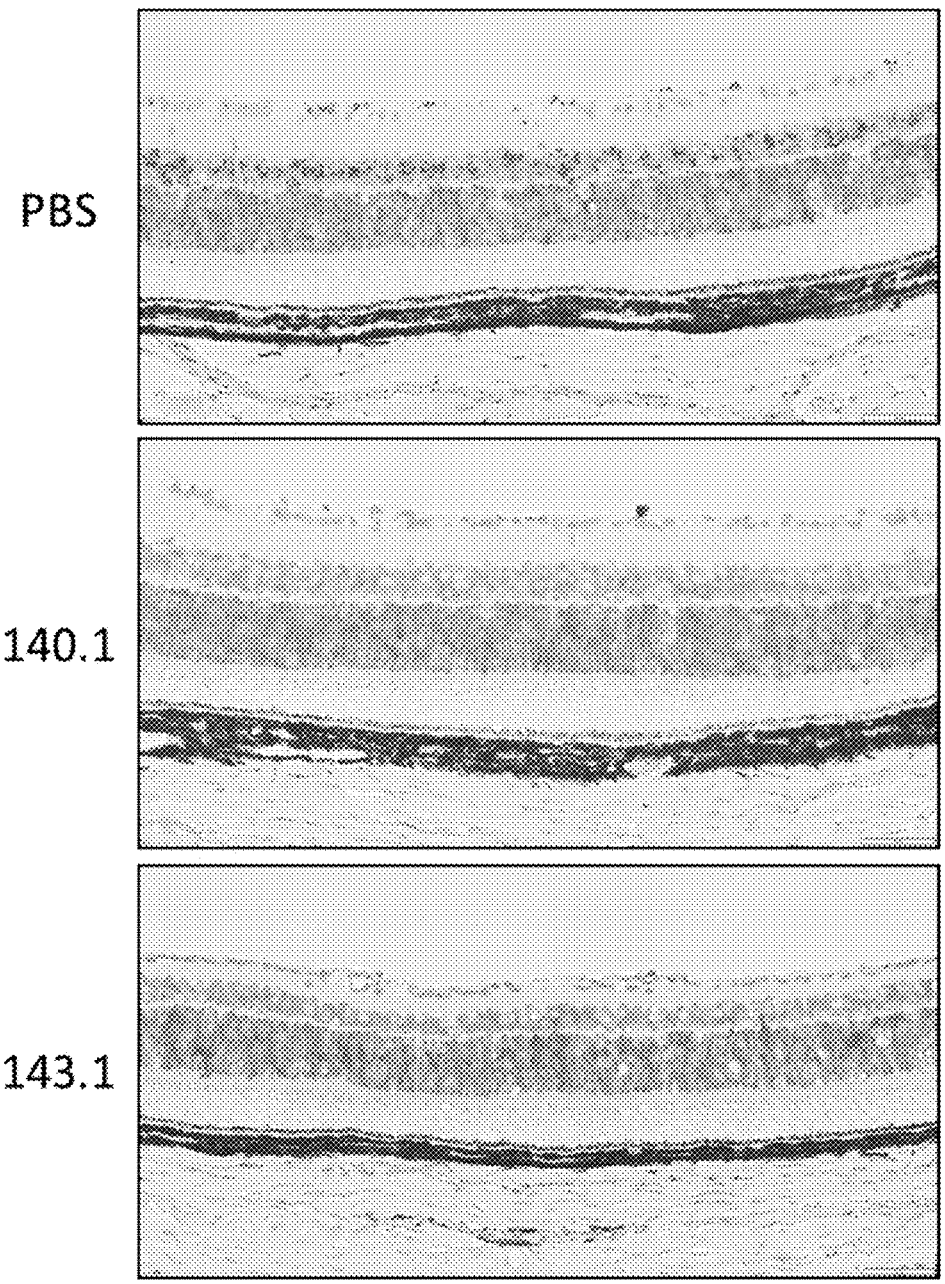
FIG. 5. Rat in vivo efficacy study, 7 days of treatment, IVT administration, dose response. Retina samples from rat eyes treated with PBS, 140.1 or 143.1 were analyzed. Htra1 ISH RNAscope was performed, in A) representative samples and in B) an overview table of results are shown. GFAP IHC was also performed, GFAP is a marker for reactive gliosis and reticular fibrosis. C) Retina samples subjected to Htra1 qPCR. RE: right eye, LE: left eye. D) Oligo content bioanalysis was performed and dose response curves for bioanalysis plotted versus relative mRNA expression is shown. $EC_{50}$ determinations was made in Graph Pad Prims. For PBS treated samples, the oligo content were set to 0.01 μg/g tissue.
Figures 5B, 5C:
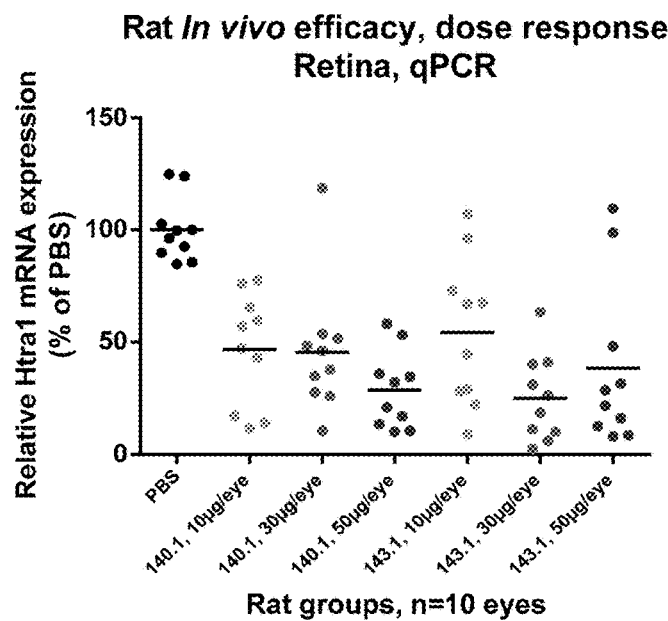
Figure 5D:
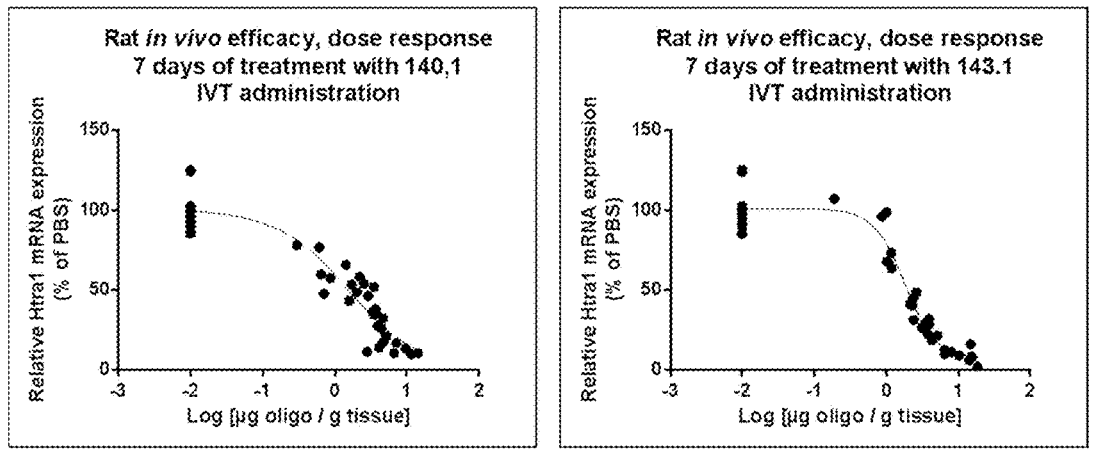
Figure 6A:
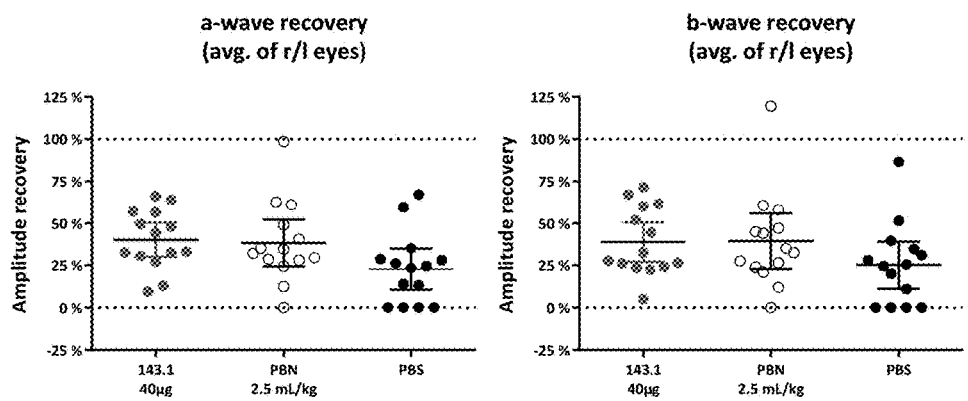
FIG. 6. Poc study, Blue light-induced retinal degeneration in albino rats A) Recovery of electroretinogram a-wave and b-wave amplitudes 14 days after blue light exposure (%). The bars indicate group means and 95% Cl. Each data point indicates mean of right and left eye values for each study animal. B) ISH RNA scope, examples from 2 different areas of the retina. C) Htra1 qPCR of retina samples. D) PK PD correlation.
Figure 6B:
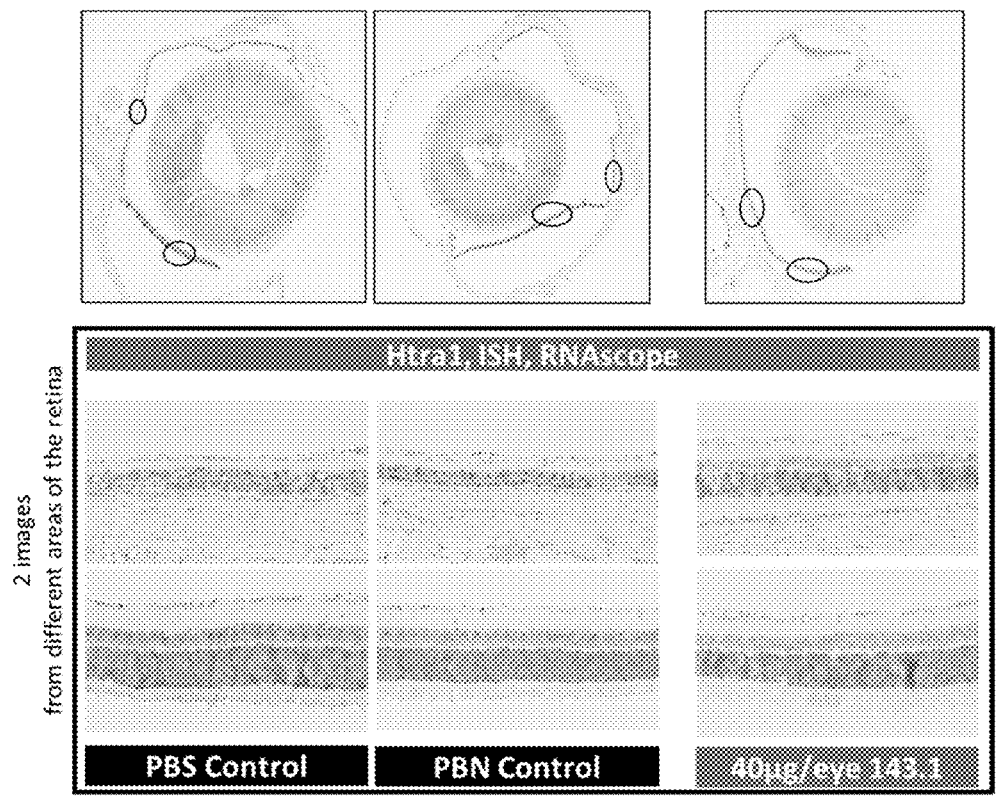
Figure 6C:
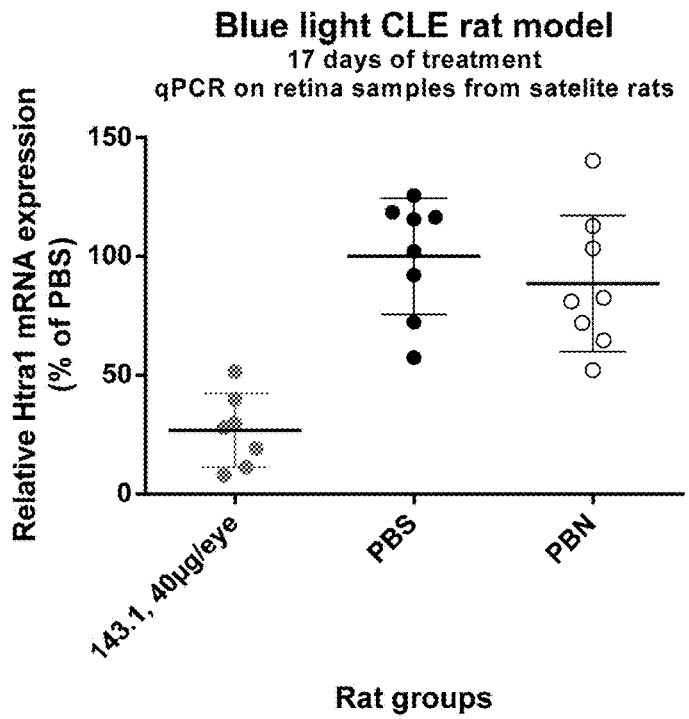
Figure 6D:
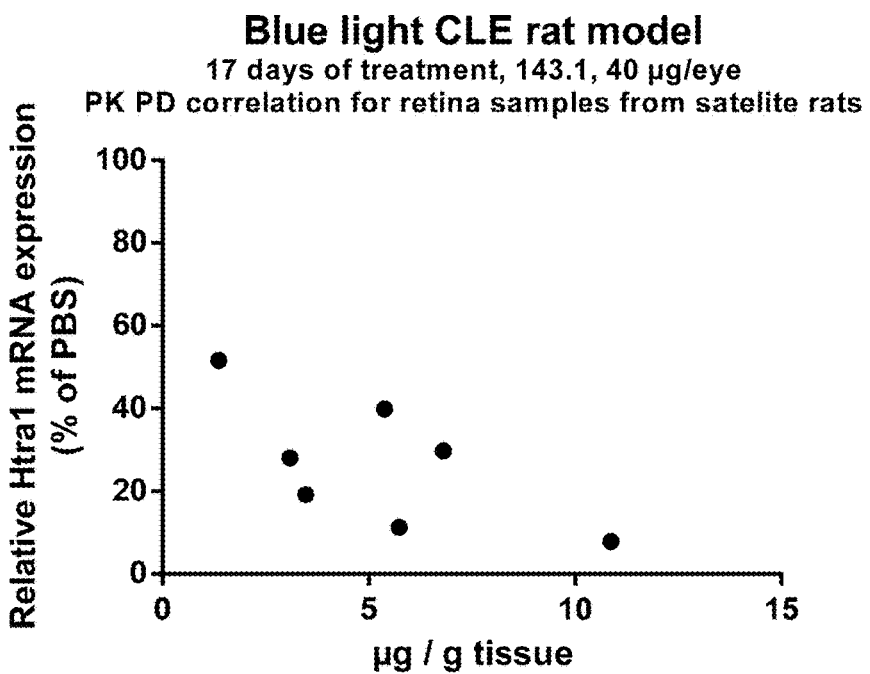

Retina samples were dissected. Rat retina snap frozen tissue was kept frozen and was lysed in the testing facility in RLT lysis buffer (Qiagen RNeasy Mini Kit) and RNA extraction was continued according to the user's manual of the Qiagen RNeasy Mini Kit (Cat#74104; Lot 151039852) including DNase I treatment (Cat#79254; Lot 151048613). RNA quality control was performed with the Agilent Bioanalyzer Nano Kit (Agilent; Cat#5067-1511; Lot 1446). Reverse transcription of total RNA into cDNA (cDNA synthesis) was performed using the High Capacity cDNA Reverse Transcription Kit which is based on random hexamer oligonucleotides, according to the manufacturer's instructions (Thermo Fisher Scientific, Cat#4368814, Lot 00314158). The measurement of the cDNA samples was carried out in triplicates, in a 384-well plate format on the 7900HT real-time PCR instrument (Thermo Fisher Scientific). Following TaqMan primer assays were used for qPCR: Htra1, Rn00581870_m1 and housekeeping genes, Gapdh, Rn01775763_g1 and Tbp, Rn01455646_m1, from Life Technologies. Rats/group: 5, n=10 eyes. Each eye was treated as an individual sample. The relative Htra1 mRNA expression level is shown as % of control (PBS). See FIG. 4.

Example 10

Rat In Vivo Efficacy Study, 7 Days of Treatment, Intravitreal (IVT) Injection, Dose Response Animals All experiments were performed on pigmented Brown Norway rats. 17 animals were included in each group of the study, 34 in total.

Compounds and Dosing Procedures

The animals were anesthetized with an intramuscular injection of a mix of xylazine and ketamine. The test item and negative control (PBS) were administered intravitreally in both eyes of anesthetized animals (3 μL per administration) on study day 1.

Euthanasia

At the end of the in-life phase (Day 8) were euthanized by intraperitoneal an overdose injection of pentobarbital.

Oligo Content Measurement and Quantification of Htra1 RNA Expression

Both eyeballs of all animals in low-dose and mid-dose group as well as from 5 first animals from high-dose and PBS groups were used for bioanalysis. Immediately after euthanasia, Vitreous (V), Retina (R) and Choroid (CH) were quickly and carefully dissected out on ice and stored at −80° C. until shipment. Retina sample was lysed in 700 μL MagNa Pure 96 LC RNA Isolation Tissue buffer and homogenized by adding 1 stainless steel bead per 2 ml tube 2×1.5 min using a precellys evolution homogenizer followed by 30 min incubation at RT. The samples were centrifuges, 13000 rpm, 5 min. half was set aside for bioanalysis and for the other half, RNA extraction was continued directly For bioanalysis, the samples were diluted 10-50 fold for oligo content measurements with a hybridization ELISA method. A biotinylated LNA-capture probe and a digoxigenin-conjugated LNA-detection probe (both 35 nM in 5×SSCT, each complementary to one end of the LNA oligonucleotide to be detected) was mixed with the diluted homogenates or relevant standards, incubated for 30 minutes at RT and then added to a streptavidine-coated ELISA plates (Nunc cat. no. 436014).

The plates were incubated for 1 hour at RT, washed in 2×SSCT (300 mM sodium chloride, 30 mM sodium citrate and 0.05% v/v Tween-20, pH 7.0) The captured LNA duplexes were detected using an anti-DIG antibodies conjugated with alkaline phosphatase (Roche Applied Science cat. No. 11093274910) and an alkaline phosphatase substrate system (Blue Phos substrate, KPL product code 50-88-00). The amount of oligo complexes was measured as absorbance at 615 nm on a Biotek reader.

For RNA extraction, cellular RNA large volume kit (05467535001, Roche) was used in the MagNA Pure 96 system with the program: Tissue FF standard LV3.1 according to the instructions of the manufacturer, including DNAse treatment. RNA quality control and concentration were measured with an Eon reader (Biotek). The RNA concentration was normalized across samples, and subsequent cDNA synthesis and qPCR was performed in a one-step reaction using qScript XLT one-step RT-qPCR ToughMix Low ROX, 95134-100 (Quanta Biosciences). The following TaqMan primer assays were used in a duplex reaction: Htra1, Rn00581870_m1 and Rn00668987_m1 and housekeeping genes, HPRT, Rn01527840_m1 and Tbp, Rn01455646_m1, from Life Technologies. The qPCR analyses were run on a ViiA7 machine (Life Technologies). Rats/group: 5, n=10 eyes. Each eye was treated as an individual sample. The relative Htra1 mRNA expression level is shown as % of control (PBS).

Histology

Both eyeballs of the 2 remaining animals of high dose and PBS animals were removed and fixed in 10% neutral buffered formalin for 24 hours, trimmed and embedded in paraffin. For ISH analysis, sections of formalin-fixed, paraffin-embedded rat retina tissue 4 um thick were processed using the fully automated Ventana Dicovery ULTRA Staining Module (Procedure: mRNA Discovery Ultra Red 4.0—v0.00.0152) using the RNAscope 2.5 VS Probe-Rn-HTRA1 (Cat No. 440959, Advanced Cell Diagnostic). Chromogen used is Fasted, Hematoxylin H counterstain.

Example 11

PoC Study, Blue Light-Induced Retinal Degeneration in Albino Rats

Animals

All experiments were performed on albino Sprague-Dawley rats. Sixteen animals were included in each group of the study, 42 in total.

Compounds and Dosing Procedures

The animals were anesthetized with an intramuscular injection of a mix of xylazine and ketamine. The test item and negative control (PBS) were administered intravitreally in both eyes of anesthetized animals (3 μL per administration) on study day −3.

The positive control item (PBN) was injected intraperitoneally on Day 0, 4 times (0.5 h before starting light exposure, 2 h and 4 h after starting light exposure and just after the end of light exposure), at a dose volume of 2.5 mL/kg, using a 25-gauge needle mounted on a 1 mL-plastic syringe, protected from light.

Light Exposure

The rats were dark adapted for 36 hours and then exposed to a continuous blue fluorescent light (400-540 nm) in clear plastic cages for 6 hours. After exposure, the rats were placed in dark room for 24 hours before returning to standard cyclic light conditions.

Electroretinogram (ERG)

Electroretinograms (ERGs) were be recorded at baseline and on Day 14 on both eyes after overnight darkadaption. A-wave and b-wave amplitudes were measured for each ERG recording Euthanasia At the end of the in-life phase (Day 14), the animals were anesthetized and euthanized by intraperitoneal an overdose injection of pentobarbital.

Outer Nuclear Layer (ONL) Thickness Measurements

From the 10 main animals of each group, both eyeballs were enucleated, fixed in Bouin Hollande solution and embedded in paraffin. Thin sections (5 to 7 µm thick) were cut along the vertical meridian and stained with Trichrome-Masson. ONL thickness was measured at seven points (every 250 µm) from the optic nerve to the peripheral retina in each part (superior and inferior) of the retina. The thickness of the outer nuclear layer was measured at each point and the area under the curve (AUC) calculated.

Oligo Content Measurement and Quantification of Htra1 RNA Expression

Both eyeballs of 4 satellite animals from test article and PBS groups were used for bioanalysis. Immediately after euthanasia, Vitreous (V), Retina (R) and Choroid (CH) were quickly and carefully dissected out on ice and stored at −80° C. until shipment. Retina sample was lysed in 700 µL MagNa Pure 96 LC RNA Isolation Tissue buffer and homogenized by adding 1 stainless steel bead per 2 ml tube 2×1.5 min using a precellys evolution homogenizer followed by 30 min incubation at RT. The samples were centrifuges, 13000 rpm, 5 min. half was set aside for bioanalysis and for the other half, RNA extraction was continued directly.

For bioanalysis, the samples were diluted 10-50 fold for oligo content measurements with a hybridization ELISA method. A biotinylated LNA-capture probe and a digoxigenin-conjugated LNA-detection probe (both 35 nM in 5×SSCT, each complementary to one end of the LNA oligonucleotide to be detected) was mixed with the diluted homogenates or relevant standards, incubated for 30 minutes at RT and then added to a streptavidine-coated ELISA plates (Nunc cat. no. 436014).

The plates were incubated for 1 hour at RT, washed in 2×SSCT (300 mM sodium chloride, 30 mM sodium citrate and 0.05% v/v Tween-20, pH 7.0) The captured LNA duplexes were detected using an anti-DIG antibodies conjugated with alkaline phosphatase (Roche Applied Science cat. No. 11093274910) and an alkaline phosphatase substrate system (Blue Phos substrate, KPL product code 50-88-00). The amount of oligo complexes was measured as absorbance at 615 nm on a Biotek reader.

For RNA extraction, cellular RNA large volume kit (05467535001, Roche) was used in the MagNA Pure 96 system with the program: Tissue FF standard LV3.1 according to the instructions of the manufacturer, including DNAse treatment. RNA quality control and concentration were measured with an Eon reader (Biotek). The RNA concentration was normalized across samples, and subsequent cDNA synthesis and qPCR was performed in a one-step reaction using qScript XLT one-step RT-qPCR ToughMix Low ROX, 95134-100 (Quanta Biosciences). The following TaqMan primer assays were used in a duplex reaction: Htra1, Rn00581870_m1 and Rn00668987_m1 and housekeeping genes, HPRT, Rn01527840_m1 and Tbp, Rn01455646_m1, from Life Technologies. The qPCR analyses were run on a ViiA7 machine (Life Technologies). Rats/group: 5, n=10 eyes. Each eye was treated as an individual sample. The relative Htra1 mRNA expression level is shown as % of control (PBS).

Histology

Both eyeballs of the remaining 2 satellite animals from test article and PBS groups were removed and fixed in 10% neutral buffered formalin for 24 hours, trimmed and embedded in paraffin. ISH RNAscope was performed as described in example 10.

Example 12

Figure 7A:
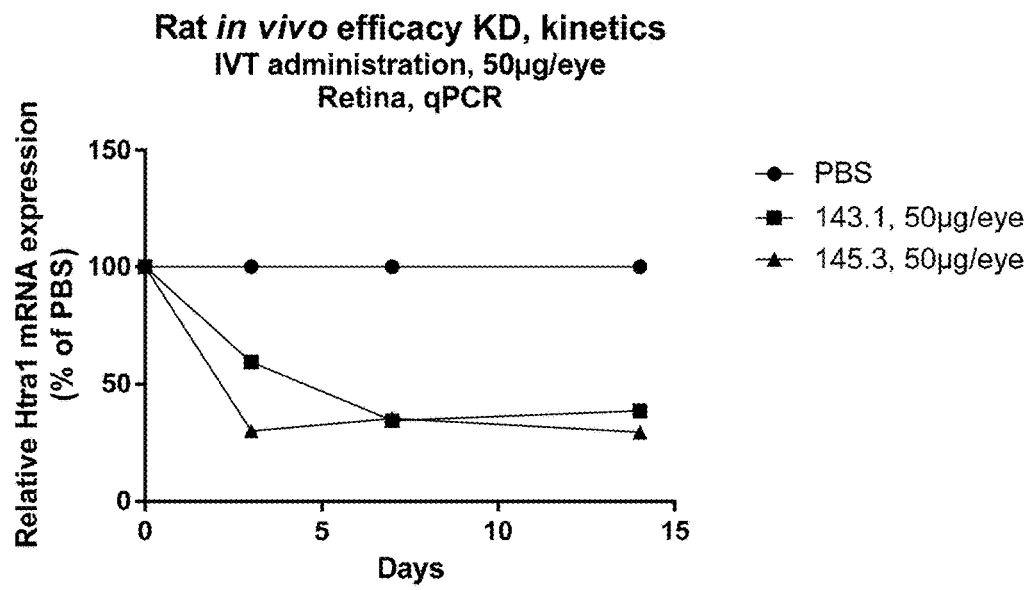
FIG. 7. Rat in vivo efficacy kinetic study, IVT administration, 50 μg/eye, 3, 7, 14 days of treatment. A) HTRA1 mRNA level measured in the retina by qPCR. B) HTRA1 mRNA level quantified by ISH. The residual HTRA1 mRNA expression level is shown as % of control (PBS-treated cells) in A and B & C) Dose response curves of oligo content vs. qPCR data for individual time points.
Figure 7B:
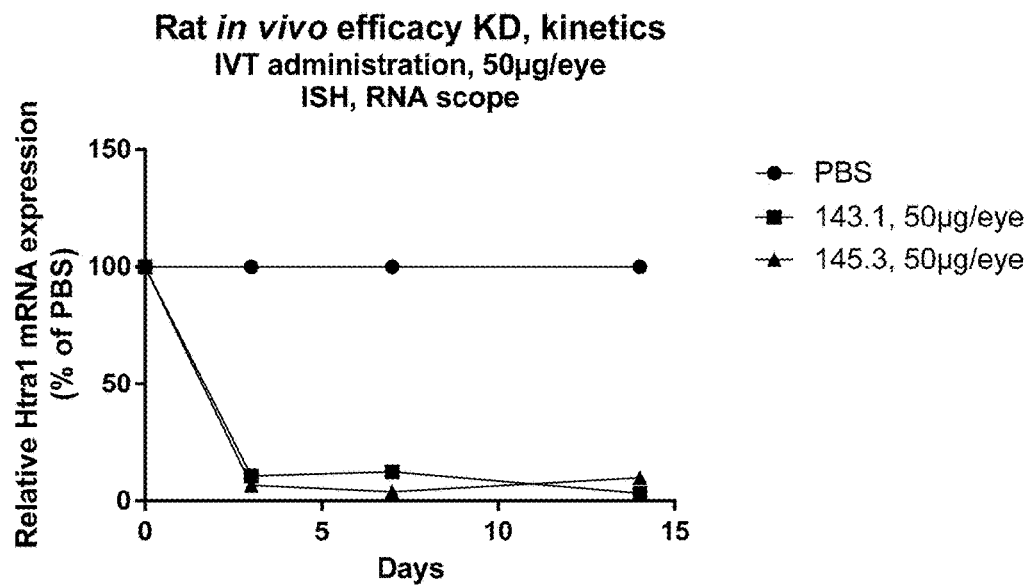

Rat In Vivo Efficacy Kinetic Study, 3, 7 and 14 Days of Treatment, Intravitreal (IVT) Injection, Single Dose Knockdown (KD) at mRNA level was observed in the retina for 2 selected HTRA1 LNA oligonucleotides targeting the "hotspot" in human HTRA1 pre-mRNA between position 33042-33064 (SEQ ID NO 147). This was observed both with qPCR and ISH readouts (see FIGS. 7A and /B and the following table).

| Compound ID | Days of Treatment | qPCR Residual mRNA level | Stdev | n | ISH Residual mRNA level | Stdev | N |
|---|---|---|---|---|---|---|---|
| 143.1 | 3 | 59 | 31 | 12 | 11 | 14 | 4 |
|  | 7 | 34 | 28 | 12 | 12 | 8 | 4 |
|  | 14 | 39 | 35 | 12 | 3 | 5 | 4 |
| 145.3 | 3 | 30 | 29 | 12 | 7 | 5 | 4 |
|  | 7 | 35 | 32 | 12 | 4 | 3 | 4 |
|  | 14 | 30 | 21 | 12 | 10 | 9 | 4 |

Figure 7C:
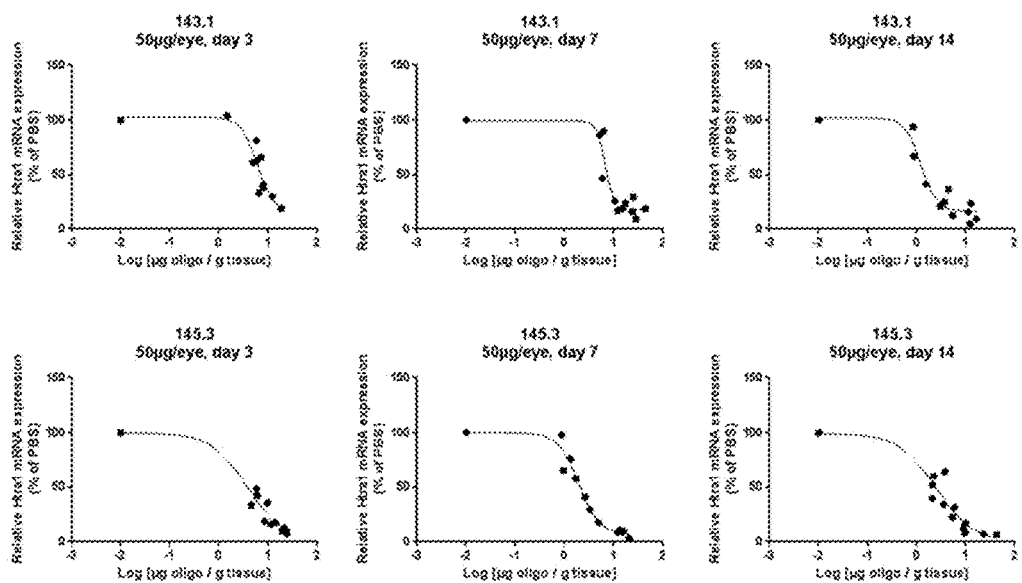
Figure 8A:
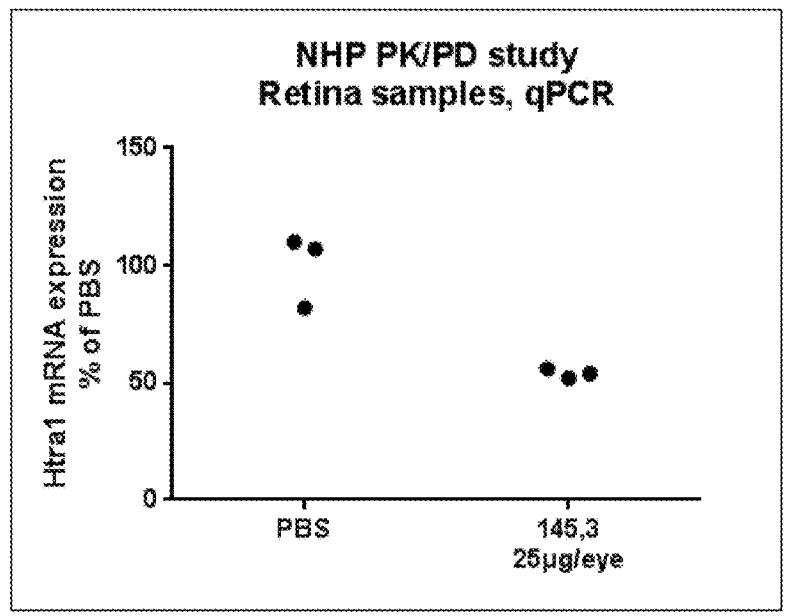
FIG. 8. Non Human Primate (NHP) PK/PD study, IVT administration, 25 μg/eye. A) HTRA1 mRNA level measured in the retina by qPCR. B) HTRA1 mRNA level illustrated by ISH. C-D) Quantification of HTRA1 protein level in retina and vitreous, respectively, by IP-MS. Dots show data for individual animals. Error bars show standard deviations for technical replicates (n=3).
Figure 8B:
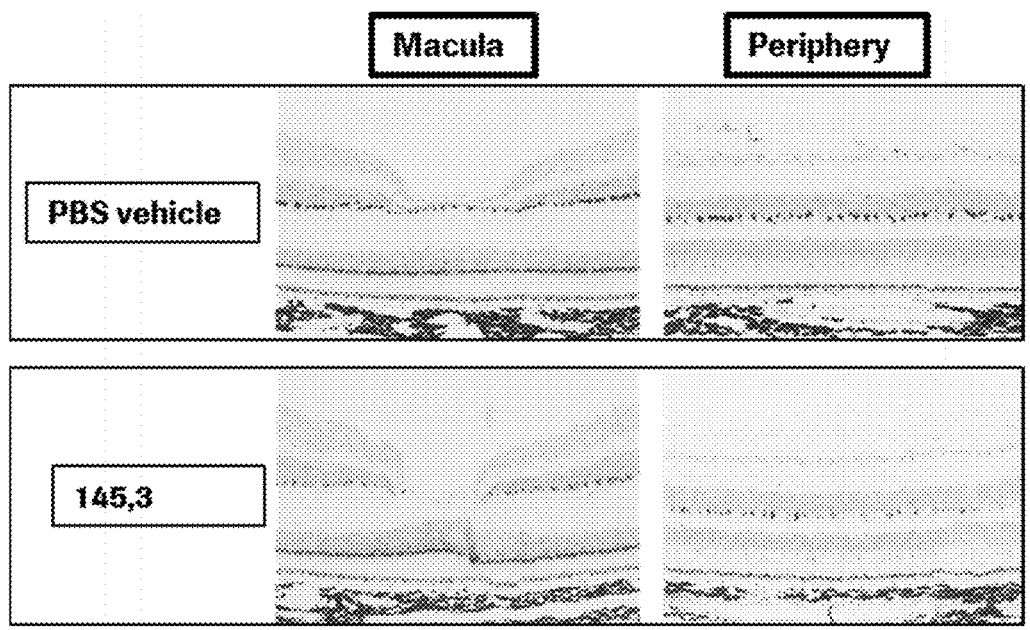
Figure 8C:
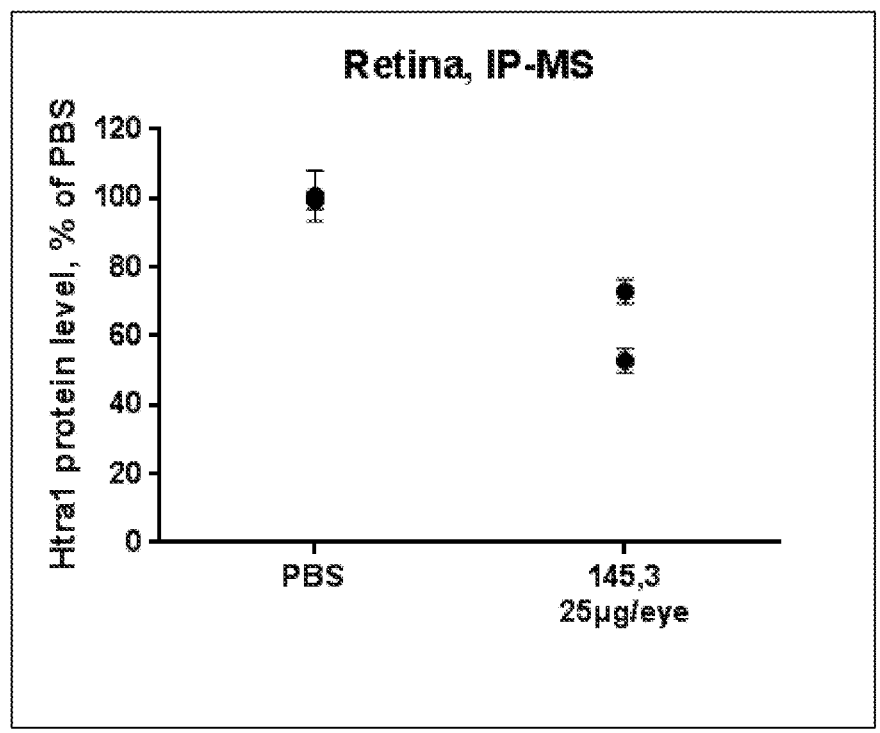
Figure 8D:
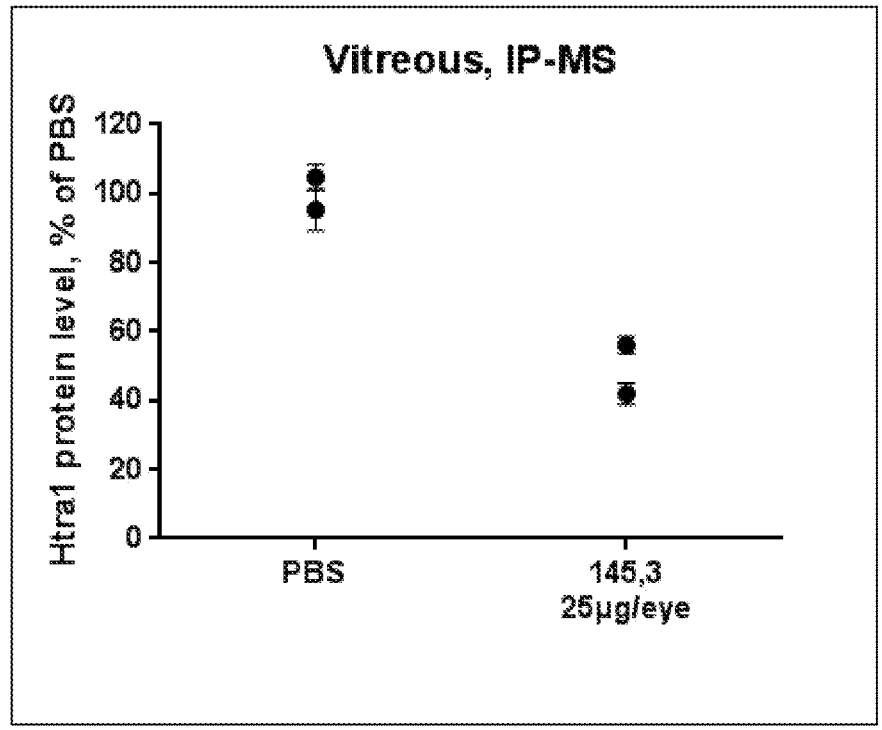
Figure 9:
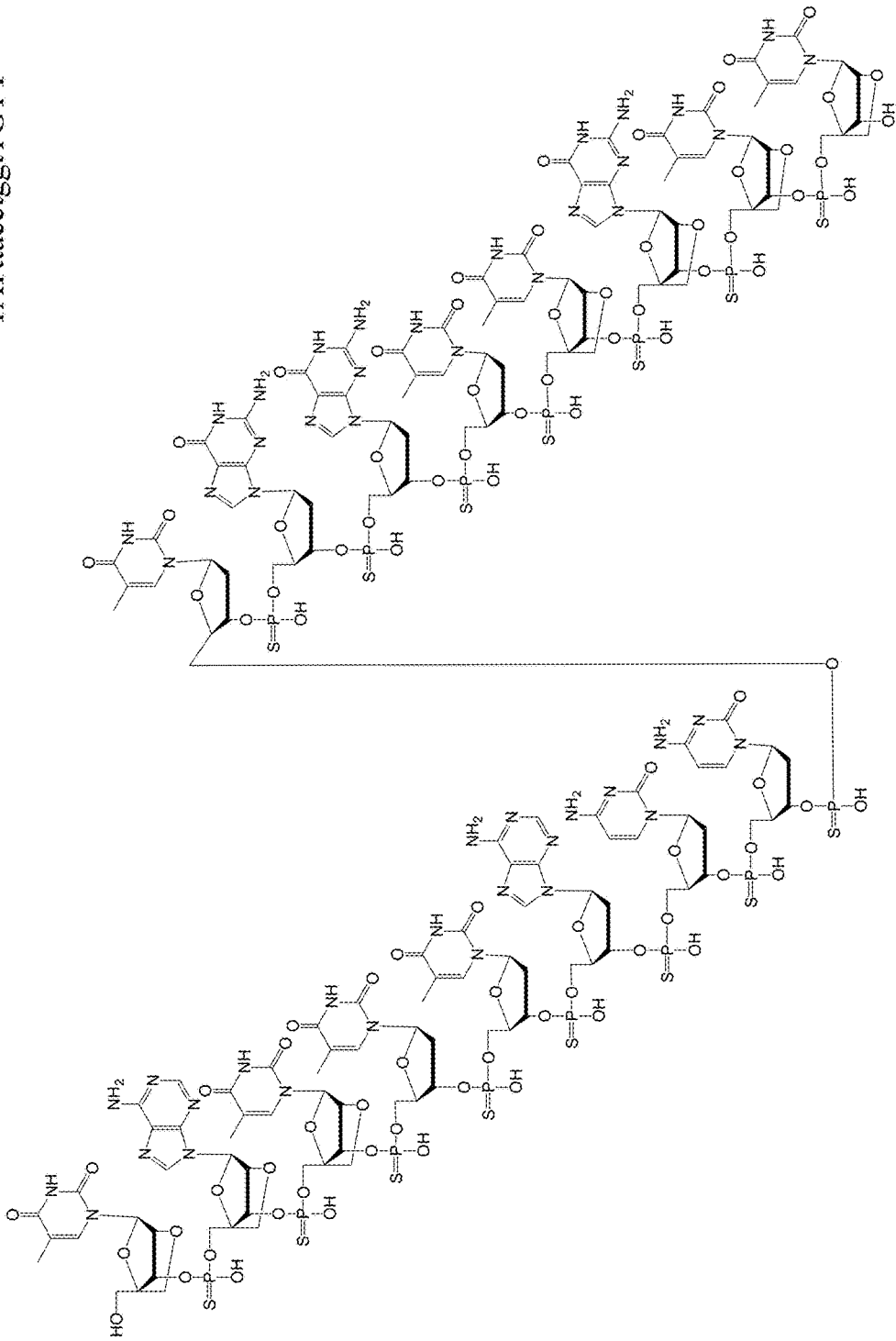
FIG. 9. A Compound of the invention (SEQ ID NO:143; Compound ID NO 143,1). The compound may be in the form of a pharmaceutical salt, such as a sodium salt or a potassium salt.
Figure 10:
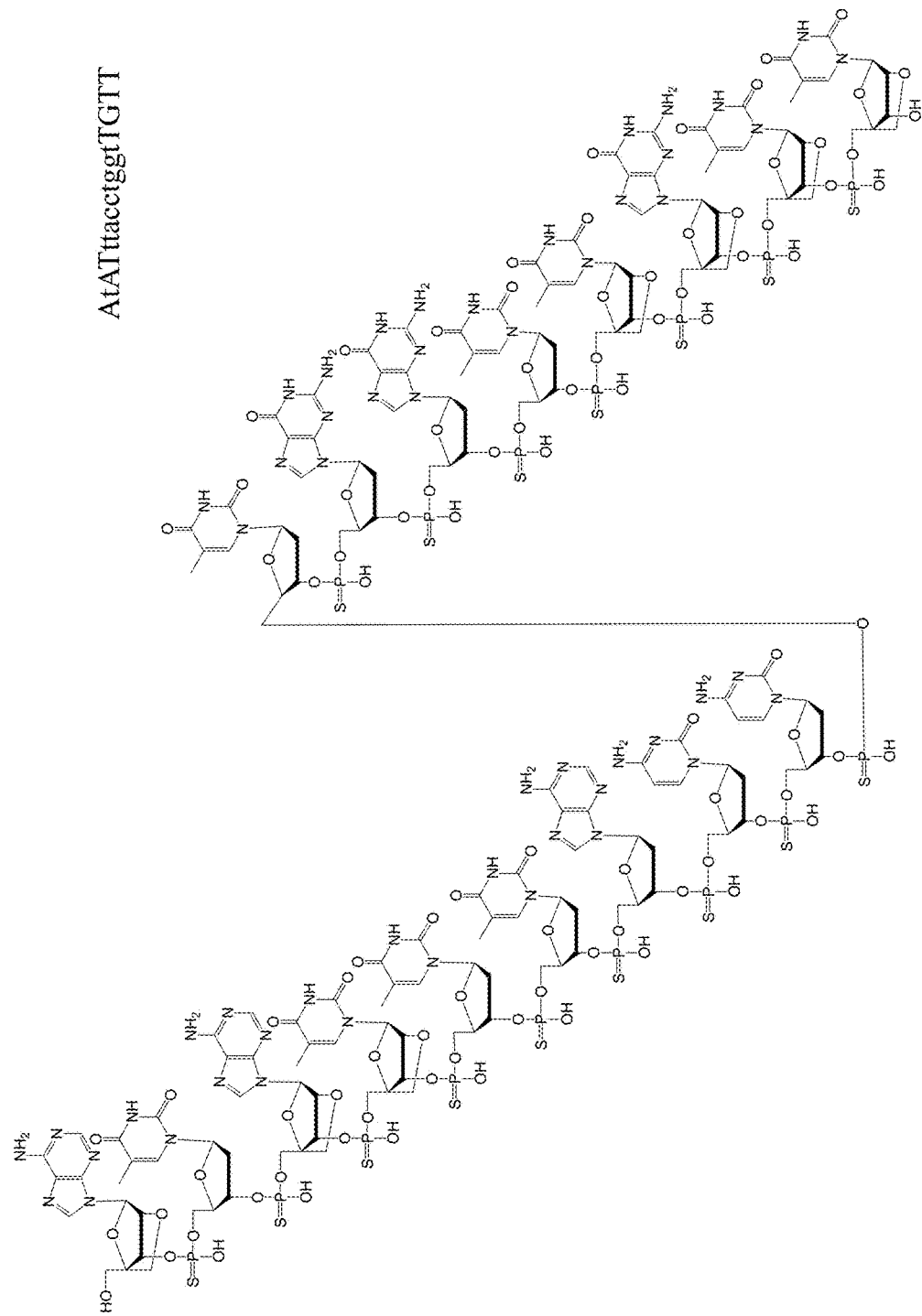
FIG. 10. A Compound of the invention (SEQ ID NO:145; Compound ID No 145,3). The compound may be in the form of a pharmaceutical salt, such as a sodium salt or a potassium salt.
Figure 11:
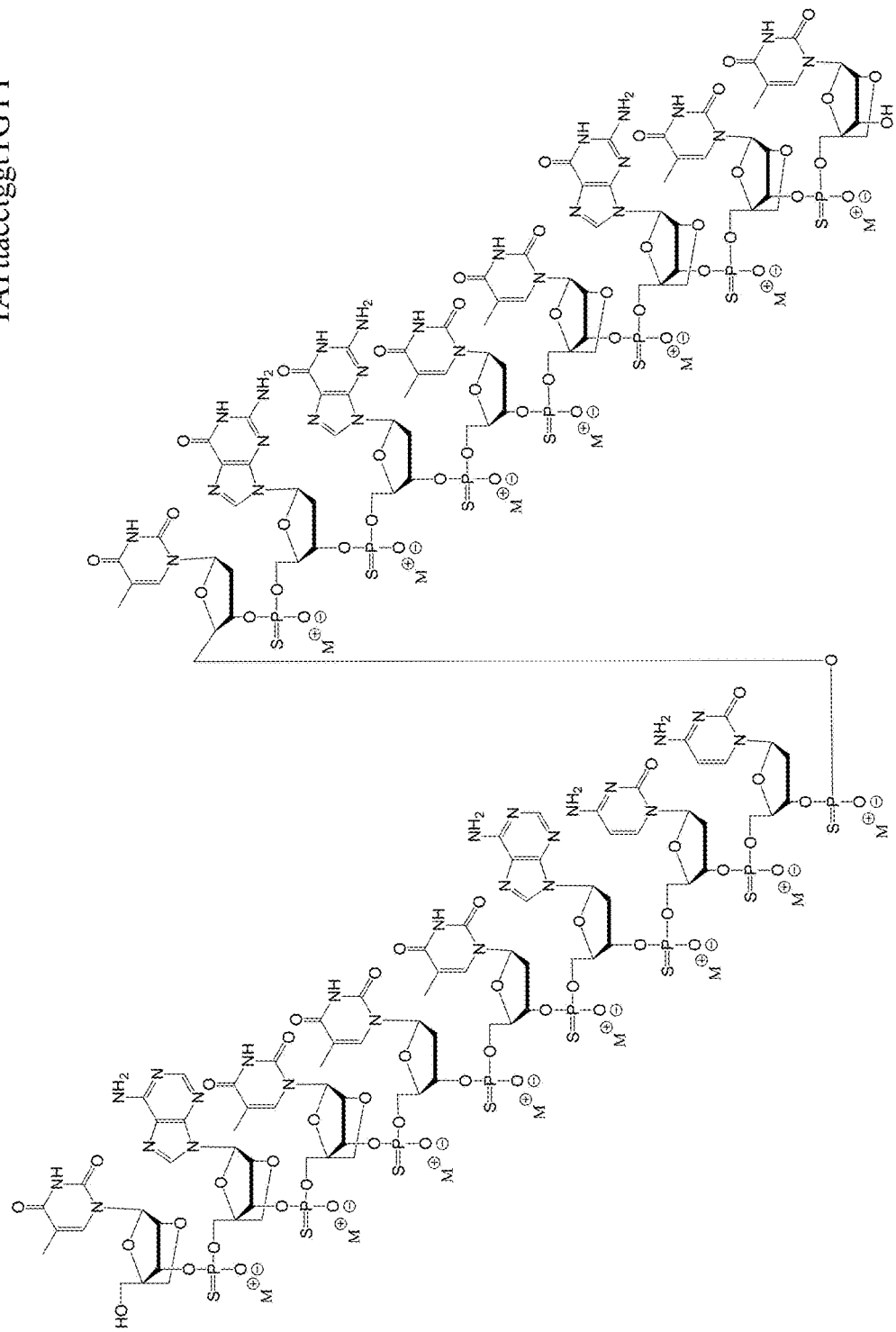
FIG. 11. An example of a pharmaceutical salt of compound 143.1 (SEQ ID NO:143). M+is a suitable cation, typically a positive metal ion, such as a sodium or potassium ion. The stoichiometric ratio of the cation to the oligonucleotide anion will depend on the charge of the cation used. Suitably, cations with one, two or three positive charge (M+, M++, or M+++, may be used). For illustrative purpose, twice as many single +charged cations (monovalent), such as Na+or K+are needed as compared to a divalent cation such as Ca2+.
Figure 12:
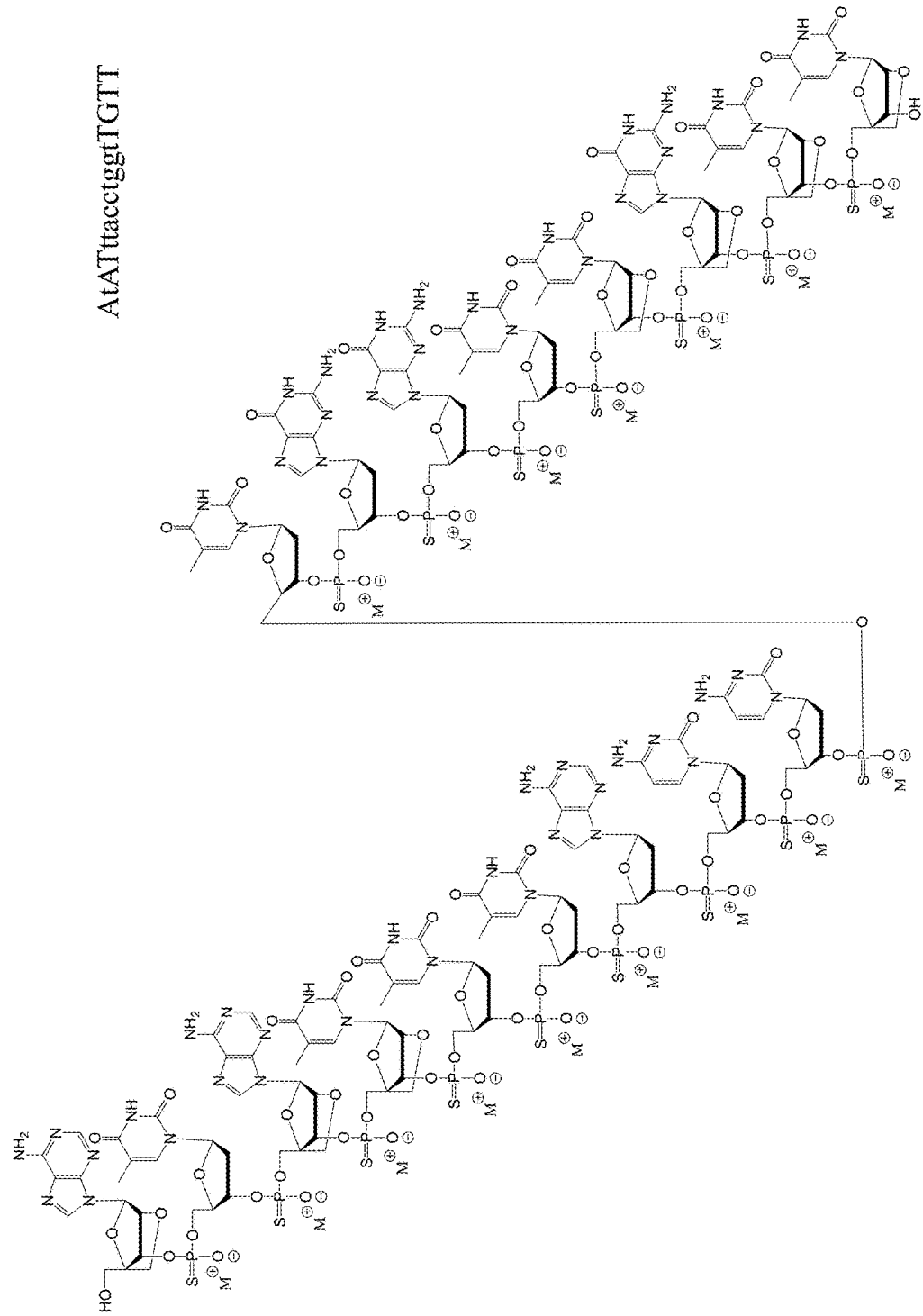
FIG. 12. An example of a pharmaceutical salt of compound 145.3 (SEQ ID NO:145). See the figure legend for FIG. 11 for the description of the cation W.

The variation of the knockdown is relatively large, see the standard deviations listed in the table. The variation seems to be at the administration level which can be seen when plotting a dose response curve for oligo content vs. residual HTRA1 mRNA level (see FIG. 7C).

Animals

All experiments were performed on albino Sprague-Dawley rats.

Compounds and Dosing Procedures

The animals were anesthetized in isofluran. The test item and negative control (PBS) were administered intravitreally in both eyes of anesthetized animals (3 µL per administration) on study day 1.

Euthanasia

At the end of the in-life phase (study day 4, 8 or 15) the rats were anesthetized and euthanized by decapitation.

Oligo Content Measurement and Quantification of Htra1 RNA Expression

Oligo content measurement and quantification of Htra1 mRNA expression was performed as described in Example 10.

The relative residual Htra1 mRNA expression level is shown as % of control (PBS).
Histology
Histology was performed as described in Example 10.

Example 13

Cynomolgus Monkey (Non-Human Primate, NHP) In Vivo Pharmacokinetics and Pharmacodynamics (PK/PD) Study, 21 Days of Treatment, Intravitreal (IVT) Injection, Single Dose Knockdown was observed for 1 selected HTRA1 LNA oligonucleotide, 145.3, targeting the "hotspot" in human HTRA1 pre-mRNA between position 33042-33064 both at mRNA in the retina and at protein level in the retina and in the vitreous (see FIG. 8).
Animals
All experiments were performed on Cynomolgus monkeys (*Macaca fascicularis*).
Compounds and Dosing Procedures
Buprenorphine analgesia was administered prior to, and two days after test compound injection. The animals were anesthetized with an intramuscular injection of ketamine and xylazine. The test item and negative control (PBS) were administered intravitreally in both eyes of anesthetized animals (50 µL per administration) on study day 1 after local application of tetracaine anesthetic.
Euthanasia
At the end of the in-life phase (Day 22) all monkeys were euthanized by intraperitoneal an overdose injection of pentobarbital.
Oligo Content Measurement and Quantification of Htra1 RNA Expression by qPCR
Immediately after euthanasia, eye tissues were quickly and carefully dissected out on ice and stored at −80° C. until shipment. Retina sample was lysed in 700 µL MagNa Pure 96 LC RNA Isolation Tissue buffer and homogenized by adding 1 stainless steel bead per 2 ml tube 2×1.5 min using a precellys evolution homogenizer followed by 30 min incubation at RT. The samples were centrifuged, 13000 rpm, 5 min. Half was set aside for bioanalysis and for the other half, RNA extraction was continued directly.
For bioanalysis, the samples were diluted 10-50 fold for oligo content measurements with a hybridization ELISA method. A biotinylated LNA-capture probe and a digoxigenin-conjugated LNA-detection probe (both 35 nM in 5×SSCT, each complementary to one end of the LNA oligonucleotide to be detected) was mixed with the diluted homogenates or relevant standards, incubated for 30 minutes at RT and then added to a streptavidine-coated ELISA plates (Nunc cat. no. 436014).
The plates were incubated for 1 hour at RT, washed in 2×SSCT (300 mM sodium chloride, 30 mM sodium citrate and 0.05% v/v Tween-20, pH 7.0) The captured LNA duplexes were detected using an anti-DIG antibodies conjugated with alkaline phosphatase (Roche Applied Science cat. No. 11093274910) and an alkaline phosphatase substrate system (Blue Phos substrate, KPL product code 50-88-00). The amount of oligo complexes was measured as absorbance at 615 nm on a Biotek reader.
For RNA extraction, cellular RNA large volume kit (05467535001, Roche) was used in the MagNA Pure 96 system with the program: Tissue FF standard LV3.1 according to the instructions of the manufacturer, including DNAse treatment. RNA quality control and concentration were measured with an Eon reader (Biotek). The RNA concentration was normalized across samples, and subsequent cDNA synthesis and qPCR was performed in a one-step reaction using qScript XLT one-step RT-qPCR ToughMix Low ROX, 95134-100 (Quanta Biosciences). The following TaqMan primer assays were used in singplex reactions: Htra1, Mf01016150_, Mf01016152_m1 and Rh02799527_m1 and housekeeping genes, ARFGAP2, Mf01058488_g1 and Rh01058485_m1, and ARL1, Mf02795431_m1, from Life Technologies. The qPCR analyses were run on a ViiA7 machine (Life Technologies). Eyes/group: n=3 eyes. Each eye was treated as an individual sample. The relative Htra1 mRNA expression level is shown as % of control (PBS).
Histology
Eyeballs were removed and fixed in 10% neutral buffered formalin for 24 hours, trimmed and embedded in paraffin.
For ISH analysis, sections of formalin-fixed, paraffin-embedded retina tissue 4 µm thick were processed using the fully automated Ventana Dicovery ULTRA Staining Module (Procedure: mRNA Discovery Ultra Red 4.0—v0.00.0152) using the RNAscope 2.5 VS Probe-MmU-HTRA1, REF 486979, Advanced Cell Diagnostics, Inc. Chromogen used is Fastred, Hematoxylin H counterstain.
HTRA1 Protein Quantification Using a Plate-based Immunoprecipitation Mass Spectrometry (IP-MS) Approach
Sample Preparation, Retina
Retinas were homogenized in 4 volumes (w/v) of RIPA buffer (50 mM Tris-HCl, pH 7.4, 150 mM NaCl, 0.25% deoxycholic acid, 1% NP-40, 1 mM EDTA, Millipore) with protease inhibitors (Complete EDTA-free, Roche) using a Precellys 24 (5500, 15 s, 2 cycles). Homogenates were centrifuged (13,000 rpm, 3 min) and the protein contents of the supernatants determined (Pierce BCA protein assay)
Sample Preparation, Vitreous
Vitreous humors (300 µl) were diluted with 5× RIPA buffer (final concentration: 50 mM Tris-HCl, pH 7.4, 150 mM NaCl, 0.25% deoxycholic acid, 1% NP-40, 1 mM EDTA) with protease inhibitors (Complete EDTA-free, Roche) and homogenized using a Precellys 24 (5500, 15 s, 2 cycles). Homogenates were centrifuged (13,000 rpm, 3 min) and the protein contents of the supernatants determined (Pierce BCA protein assay)
Plate-based HTRA1 Immunoprecipitation and Tryptic Digest
A 96 well plate (Nunc MaxiSorp) was coated with anti-HTRA1 mouse monoclonal antibody (R&D MAB2916, 500 ng/well in 50 µl PBS) and incubated overnight at 4° C. The plate was washed twice with PBS (200 µl) and blocked with 3% (w/v) BSA in PBS for 30 min at 20° C. followed by two PBS washes. Samples (75 µg retina, 100 µg vitreous in 50 µl PBS) were randomized and added to the plate followed by overnight incubation at 4° C. on a shaker (150 rpm). The plate was then washed twice with PBS and once with water. 10 mM DTT in 50 mM TEAB (30 µl) were then added to each well followed by incubation for 1 h at 20° C. to reduce cysteine sulfhydryls. 150 mM iodoacetamide in 50 mM TEAB (5 µl) were then added to each well followed by incubation for 30 min at 20° C. in the dark in order to block cysteine sulfhydryls. 10 µl Digestion solution were added to each well (final concentrations: 1.24 ng/µl trypsin, 20 fmol/µl BSA peptides, 26 fmol/µl isotope-labeled HTRA1 peptides, 1 fmol/µl iRT peptides, Biognosys) followed by incubation overnight at 20° C.
HTRA1 Peptide Quantification by Targeted Mass Spectrometry (Selected Reaction Monitoring, SRM)
Mass spectrometry analysis was performed on an Ultimate RSLCnano LC coupled to a TSQ Quantiva triple quadrupole mass spectrometer (Thermo Scientific). Samples (20 pL) were injected directly from the 96 well plate used for IP and loaded at 5 µL/min for 6 min onto a Acclaim Pepmap 100 trap column (100 µm×2 cm, C18, 5 µm, 100 Å, Thermo Scientific) in loading buffer (0.5% v/v formic acid, 2% v/v ACN). Peptides were then resolved on a PepMap Easy-SPRAY analytical column (75 µm×15 cm, 3 µm, 100 Å, Thermo Scientific) with integrated electrospray emitter heated to 40° C. using the following gradient at a flow rate of 250 nL/min: 6 min, 98% buffer A (2% ACN, 0.1% formic acid), 2% buffer B (ACN+0.1% formic acid); 36 min, 30% buffer B; 41 min, 60% buffer B; 43 min, 80% buffer B; 49 min, 80% buffer B; 50 min, 2% buffer B. The TSQ Quantiva was operated in SRM mode with the following parameters: cycle time, 1.5 s; spray voltage, 1800 V; collision gas pressure, 2 mTorr; Q1 and Q3 resolution, 0.7 FWHM; ion transfer tube temperature 300° C. SRM transitions were acquired for the HTRA1 peptide "LHRPPVIVLQR" and an isotope labelled (L-[U-13C, U-15N]R) synthetic version, which was used an internal standard. Data analysis was performed using Skyline version 3.6.

The invention claimed is:

1. An antisense oligonucleotide of 10-30 nucleotides in length, wherein said antisense oligonucleotide targets a human high temperature requirement A 1 (HTRA1) nucleic acid and comprises a contiguous nucleotide region of 10-22 nucleotides which is perfectly complementarity (SEQ ID NO 147)
    5' CCAACAACCAGGTAAATATTTG 3' and wherein the nucleotides are linked by phosphorothioate linkages.

2. The antisense oligonucleotide according to claim 1, wherein the contiguous nucleotide region is identical to a sequence present in a sequence selected from the group consisting of:

(SEQ ID NO 138)
    CAAATATTTACCTGGTTG;

(SEQ ID NO 139)
    TTTACCTGGTTGTTGG;

(SEQ ID NO 140)
    CCAAATATTTACCTGGTT;

(SEQ ID NO 141)
    CCAAATATTTACCTGGTTGT;

(SEQ ID NO 142)
    ATATTTACCTGGTTGTTG;

(SEQ ID NO 143)
    TATTTACCTGGTTGTT;

(SEQ ID NO 144)
    ATATTTACCTGGTTGT;
    and (SEQ ID NO 145)
    ATATTTACCTGGTTGTT.

3. The antisense oligonucleotide according to claim 1, wherein the contiguous nucleotide region comprises the sequence TTTACCTGGTT (SEQ ID NO: 146).

4. The antisense oligonucleotide according to claim 1, wherein the contiguous nucleotide region of the oligonucleotide consists of or comprises a sequence selected from the group consisting of SEQ ID NO: 138, SEQ ID NO: 139, SEQ ID NO: 140, SEQ ID NO: 141, SEQ ID NO: 142, SEQ ID NO: 143, SEQ ID NO: 144, and SEQ ID NO: 145.

5. The antisense oligonucleotide according to claim 1, wherein the contiguous nucleotide region of the oligonucleotide comprises one or more 2' sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and locked nucleic acid (LNA) nucleosides.

6. The antisense oligonucleotide according to claim 1, wherein the oligonucleotide or contiguous nucleotide sequence thereof comprises gapmer of formula 5'-F-G-F'-3', where region F and F' independently comprise 1-7 sugar modified nucleosides and G is a region of 6-16 nucleosides which is capable of recruiting RNaseH, wherein the nucleosides of regions F and F' that are adjacent to region G are sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

7. The antisense oligonucleotide according to claim 6, wherein at least one of or both of region F and F' each comprise at least one LNA nucleoside.

8. The antisense oligonucleotide according to claim 1, selected from the group consisting of:

```
                                (SEQ ID NO 138, Comp # 138,1)
CsAsAsAstsastststsascscstsgsGsTsTsG (SEQ ID NO 139, Comp # 139,1)
TsTstsascscstsgsgststsgstsTsGsG (SEQ ID NO 140, Comp # 140,1)
CsCsAsAsastsastststsascscstsgsGsTsT (SEQ ID NO 141, Comp # 141,1)
CsCsAsasastsastststsascscstsgsgststsGsT (SEQ ID NO 142, Comp # 142,1)
AsTsAstststsascscstsgsgststsgsTsTsG (SEQ ID NO 143, Comp # 143,1)
TsAsTststsascscstsgsgstsTsGsTsT (SEQ ID NO 143, Comp # 143,2)
TsAststststsascscstsgsGstsTsgsTsT (SEQ ID NO 143, Comp # 143,3)
TsAsTststsascscstsgsgsTsTsgsTsT (SEQ ID NO 144, Comp # 144,1)
AsTsAsTststsascscstsgsgsTsTsGsT (SEQ ID NO 144, Comp # 144,2)
AstsAsTsTstsascscstsgsgstsTsGsT (SEQ ID NO 145, Comp # 145,1)
AstsAsTststsascscstsgsGsTsTsgsTsT (SEQ ID NO 145, Comp # 145,2)
AsTsAststststsascscstsgsGstsTsgsTsT (SEQ ID NO 145, Comp # 145,3)
AstsAsTststsascscstsgsgstsTsGsTsT
``` wherein a capital letter represents an LNA nucleoside unit, a lower case letter represents a DNA nucleoside unit, s represents a phosphorothioate internucleoside linkage, and all LNA cytosines are 5-methyl cytosine.

9. The antisense oligonucleotide according to claim 8, wherein the LNA nucleosides are all beta-D-oxy LNA nucleosides.

10. A conjugate comprising the oligonucleotide according to claim 1 or claim 8, and at least one conjugate moiety covalently attached to said oligonucleotide.

11. A pharmaceutical composition comprising the oligonucleotide of claim 1 or claim 8 and a pharmaceutically acceptable diluent, solvent, carrier, salt and/or adjuvant.

12. An in vivo or in vitro method for modulating HTRA1 expression in a target cell which is expressing HTRA1, said method comprising administering the pharmaceutical composition of claim 11 in an effective amount to said cell.

13. A compound having the formula:

SEQ ID NO: 143

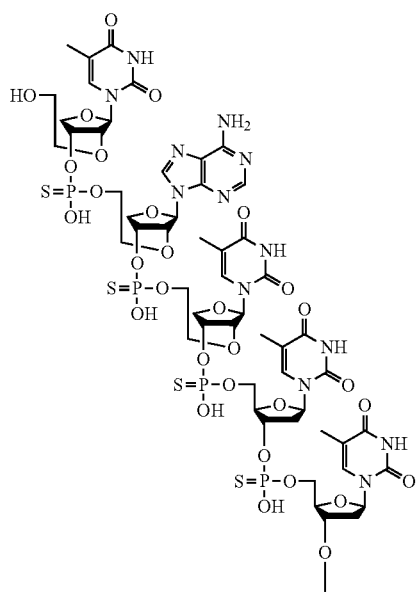
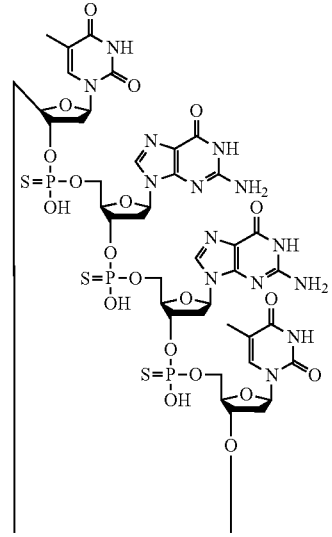

-continued

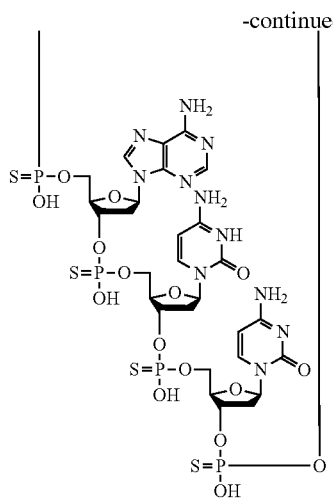 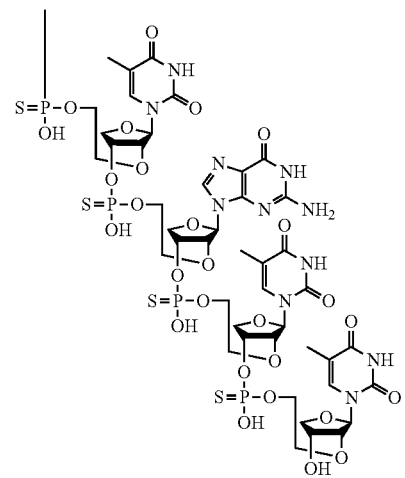

or a pharmaceutically acceptable salt thereof.

14. The antisense oligonucleotide according to claim 2, wherein the contiguous nucleotide region of the oligonucleotide comprises one or more 2' sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

15. The antisense oligonucleotide according to claim 3, wherein the contiguous nucleotide region of the oligonucleotide comprises one or more 2' sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

16. The antisense oligonucleotide according to claim 4, wherein the contiguous nucleotide region of the oligonucleotide comprises one or more 2' sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

17. The antisense oligonucleotide according to claim 2, wherein the oligonucleotide or contiguous nucleotide sequence thereof comprises gapmer of formula 5'-F-G-F'-3', where region F and F' independently comprise 1-7 sugar modified nucleosides and G is a region of 6-16 nucleosides which is capable of recruiting RNaseH, wherein the nucleosides of regions F and F' that are adjacent to region G are sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

18. The antisense oligonucleotide according to claim 3, wherein the oligonucleotide or contiguous nucleotide sequence thereof comprises gapmer of formula 5'-F-G-F'-3', where region F and F' independently comprise 1-7 sugar modified nucleosides and G is a region of 6-16 nucleosides which is capable of recruiting RNaseH, wherein the nucleosides of regions F and F' that are adjacent to region G are sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

19. The antisense oligonucleotide according to claim 4, wherein the oligonucleotide or contiguous nucleotide sequence thereof comprises gapmer of formula 5'-F-G-F'-3', where region F and F' independently comprise 1-7 sugar modified nucleosides and G is a region of 6-16 nucleosides which is capable of recruiting RNaseH, wherein the nucleosides of regions F and F' that are adjacent to region G are sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

20. The antisense oligonucleotide according to claim 5, wherein the oligonucleotide or contiguous nucleotide sequence thereof comprises gapmer of formula 5'-F-G-F'-3', where region F and F' independently comprise 1-7 sugar modified nucleosides and G is a region of 6-16 nucleosides which is capable of recruiting RNaseH, wherein the nucleosides of regions F and F' that are adjacent to region G are sugar modified nucleosides independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

21. The antisense oligonucleotide of formula:
CsAsAsAstsastststsascscstsgsGsTsTsG (SEQ ID NO 138, Comp # 138,1), wherein a capital letter represents an LNA nucleoside unit, a lower case letter represents a DNA nucleoside unit, s represents a phosphorothioate internucleoside linkage, and all LNA cytosines are 5-methyl cytosine.

22. The antisense oligonucleotide of formula:
TsTstsascscstsgsgststsgstsTsGsG (SEQ ID NO 139, Comp # 139,1), wherein a capital letter represents an LNA nucleoside unit, a lower case letter represents a DNA nucleoside unit, s represents a phosphorothioate internucleoside linkage, and all LNA cytosines are 5-methyl cytosine.

23. The antisense oligonucleotide of formula:
CsCsAsAsastsaststststsascscstsgsGsTsT (SEQ ID NO 140, Comp # 140,1),wherein a capital letter represents an LNA nucleoside unit, a lower case letter represents a DNA nucleoside unit, s represents a phosphorothioate internucleoside linkage, and all LNA cytosines are 5-methyl cytosine.

24. The antisense oligonucleotide of formula:
CsCsAsasastsaststststsascscstsgsgststsGsT (SEQ ID NO 141, Comp # 141,1), wherein a capital letter represents an LNA nucleoside unit, a lower case letter represents a DNA nucleoside unit, s represents a phosphorothioate internucleoside linkage, and all LNA cytosines are 5-methyl cytosine.

25. The antisense oligonucleotide of formula:
AsTsAststststsascscstsgsgststsgsTsTsG (SEQ ID NO 142, Comp # 142,1), wherein a capital letter represents an LNA nucleoside unit, a lower case letter represents a DNA nucleoside unit, s represents a phosphorothioate internucleoside linkage, and all LNA cytosines are 5-methyl cytosine.

26. The antisense oligonucleotide of formula:
TsAsTststsascscstsgsgstsTsGsTsT (SEQ ID NO 143, Comp # 143,1), wherein a capital letter represents an LNA nucleoside unit, a lower case letter represents a DNA nucleoside unit, s represents a phosphorothioate internucleoside linkage, and all LNA cytosines are 5-methyl cytosine.

27. The antisense oligonucleotide of formula:
TsAststststsascscstsgsGstsTsgsTsT (SEQ ID NO 143, Comp # 143,2), wherein a capital letter represents an LNA nucleoside unit, a lower case letter represents a DNA nucleoside unit, s represents a phosphorothioate internucleoside linkage, and all LNA cytosines are 5-methyl cytosine.

28. The antisense oligonucleotide of formula:
TsAsTststsascscstsgsgsTsTsgsTsT (SEQ ID NO 143, Comp # 143,3), wherein a capital letter represents an LNA nucleoside unit, a lower case letter represents a DNA nucleoside unit, s represents a phosphorothioate internucleoside linkage, and all LNA cytosines are 5-methyl cytosine.

29. The antisense oligonucleotide of formula:
AsTsAsTststsascscstsgsgsTsTsGsT (SEQ ID NO 144, Comp # 144,1), wherein a capital letter represents an LNA nucleoside unit, a lower case letter represents a DNA nucleoside unit, s represents a phosphorothioate internucleoside linkage, and all LNA cytosines are 5-methyl cytosine.

30. The antisense oligonucleotide of formula:
AstsAsTsTststsascscstsgsgstsTsGsT (SEQ ID NO 144, Comp # 144,2), wherein a capital letter represents an LNA nucleoside unit, a lower case letter represents a DNA nucleoside unit, s represents a phosphorothioate internucleoside linkage, and all LNA cytosines are 5-methyl cytosine.

31. The antisense oligonucleotide of formula:
AstsAsTststsascscstsgsGsTsTsgsTsT (SEQ ID NO 145, Comp # 145,1), wherein a capital letter represents an LNA nucleoside unit, a lower case letter represents a DNA nucleoside unit, s represents a phosphorothioate internucleoside linkage, and all LNA cytosines are 5-methyl cytosine.

32. The antisense oligonucleotide of formula:
AsTsAststststsascscstsgsGstsTsgsTsT (SEQ ID NO 145, Comp # 145,2), wherein a capital letter represents an LNA nucleoside unit, a lower case letter represents a DNA nucleoside unit, s represents a phosphorothioate internucleoside linkage, and all LNA cytosines are 5-methyl cytosine.

33. The antisense oligonucleotide of formula:
AstsAsTststsascscstsgsgststsTsGsTsT (SEQ ID NO 145, Comp # 145,3), wherein a capital letter represents an LNA nucleoside unit, a lower case letter represents a DNA nucleoside unit, s represents a phosphorothioate internucleoside linkage, and all LNA cytosines are 5-methyl cytosine.

34. A conjugate comprising the oligonucleotide according to claim 2 and at least one conjugate moiety covalently attached to said oligonucleotide.

35. A conjugate comprising the oligonucleotide according to claim 3 and at least one conjugate moiety covalently attached to said oligonucleotide.

36. A conjugate comprising the oligonucleotide according to claim 4 and at least one conjugate moiety covalently attached to said oligonucleotide.

37. A conjugate comprising the oligonucleotide according to claim 5 and at least one conjugate moiety covalently attached to said oligonucleotide.

38. The pharmaceutical acceptable salt of the compound of claim 13, wherein the salt is sodium.

39. A pharmaceutical composition comprising the compound of claim 13 or the compound of claim 38 and phosphate buffered saline.

40. The pharmaceutical composition according to claim 39 wherein the concentration of the oligonucleotide salt in the phosphate buffered saline diluent is 50-300 µM.

41. A pharmaceutical composition comprising the oligonucleotide of claim 26 and phosphate buffered saline diluent.

42. The pharmaceutical composition according to claim 41 wherein the concentration of the oligonucleotide in the phosphate buffered saline diluent is 50-300 µM.

* * * * *